US012090198B2

(12) United States Patent
Zhang et al.

(10) Patent No.: US 12,090,198 B2
(45) Date of Patent: Sep. 17, 2024

(54) COMBINED VACCINE AGAINST MYCOBACTERIUM TUBERCULOSIS

(71) Applicant: THE CHILDREN'S MEDICAL CENTER CORPORATION, Boston, MA (US)

(72) Inventors: Fan Zhang, Chestnut Hill, MA (US); Richard Malley, Beverly, MA (US); Yingjie Lu, Chestnut Hill, MA (US)

(73) Assignee: THE CHILDREN'S MEDICAL CENTER CORPORATION

( * ) Notice: Subject to any disclaimer, the term of this patent is extended or adjusted under 35 U.S.C. 154(b) by 570 days.

(21) Appl. No.: 16/616,258

(22) PCT Filed: May 18, 2018

(86) PCT No.: PCT/US2018/033380
§ 371 (c)(1),
(2) Date: Nov. 22, 2019

(87) PCT Pub. No.: WO2018/217564
PCT Pub. Date: Nov. 29, 2018

(65) Prior Publication Data

US 2020/0121777 A1 Apr. 23, 2020

Related U.S. Application Data

(60) Provisional application No. 62/509,368, filed on May 22, 2017.

(51) Int. Cl.

| | |
|---|---|
| ***A61K 39/04*** | (2006.01) |
| ***A61P 31/06*** | (2006.01) |
| ***C07K 14/35*** | (2006.01) |
| ***C07K 14/465*** | (2006.01) |
| *A61K 39/00* | (2006.01) |

(52) U.S. Cl.
CPC .............. *A61K 39/04* (2013.01); *A61P 31/06* (2018.01); *C07K 14/35* (2013.01); *C07K 14/465* (2013.01); *A61K 2039/545* (2013.01); *A61K 2039/55* (2013.01); *A61K 2039/552* (2013.01); *A61K 2039/6087* (2013.01); *A61K 2039/625* (2013.01); *A61K 2039/70* (2013.01); *C07K 2319/40* (2013.01)

(58) Field of Classification Search
CPC ................ A61K 39/04; A61K 2039/70; A61K 2039/625; A61K 2039/627; A61P 31/06; C07K 14/35
See application file for complete search history.

(56) References Cited

U.S. PATENT DOCUMENTS

| | | | | |
|---|---|---|---|---|
| 10,766,932 B2 * | 9/2020 | Malley | A61K 47/61 | |
| 11,013,793 B2 * | 5/2021 | Malley | A61K 47/55 | |
| 11,305,001 B2 * | 4/2022 | Malley | A61K 39/085 | |
| 2003/0147897 A1 * | 8/2003 | Andersen | C12N 1/205 | 435/69.3 |
| 2006/0024332 A1 | 2/2006 | Waters et al. | | |
| 2013/0101614 A1 | 4/2013 | Horwitz et al. | | |
| 2014/0154287 A1 * | 6/2014 | Malley | A61K 47/543 | 424/192.1 |
| 2015/0374811 A1 * | 12/2015 | Malley | A61K 39/092 | 424/190.1 |
| 2016/0090404 A1 | 3/2016 | Malley et al. | | |

* cited by examiner

*Primary Examiner* — Mary Maille Lyons
(74) *Attorney, Agent, or Firm* — NIXON PEABODY LLP; David S. Resnick; Jeanne N. Jodoin

(57) ABSTRACT

The present embodiments provide for a *Mycobacterium tuberculosis* (*M. tuberculosis*) Multiple Antigen Presenting System (MAPS) immunogenic composition comprising an immunogenic polysaccharide which induces an immune response, where at least one *M. tuberculosis* peptide or polypeptide antigen is associated to the immunogenic polysaccharide by complementary affinity molecules. In some embodiments, the immunogenic polysaccharide can be an antigenic capsular polysaccharide of a *Mycobacterium tuberculosis*, Type 5 (CP5) or Type 8 (CP8), or a combination of Type 5 or Type 8 capsular polysaccharide from *Staphylococcus aureus*, or alternatively, a different immunogenic capsular or noncapsular polysaccharide, and where the protein or peptide *M. tuberculosis* antigens are indirectly linked via an affinity binding pair. The present *M. tuberculosis*-MAPS immunogenic compositions can elicit both humoral and cellular immune responses to the immunogenic polysaccharide and one or multiple *M. tuberculosis* antigens at the same time.

30 Claims, 11 Drawing Sheets

Specification includes a Sequence Listing.

FIG. 1A
| Vaccines | Composition | Adjuvant | Dosage |
|---|---|---|---|
| MAPS1 | BCPS1-rhavi-ESAT6/CFP10 | AlOH | 10 μg |
| | BCPS1-rhavi-TB9.8/TB10.4 | | 10 μg |
| | BCPS1-rhavi-MPT64 | | 10 μg |
| | BCPS1-rhavi-MPT83 | | 10 μg |
| MAPS2 | BCPS1-lipidated rhavi | AlOH | 5 μg |
| | BCPS1-rhavi-ESAT6/CFP10 | | 10 μg |
| | BCPS1-rhavi-TB9.8/TB10.4 | | 10 μg |
| | BCPS1-rhavi-MPT64 | | 10 μg |
| | BCPS1-rhavi-MPT83 | | 10 μg |
FIG. 1B
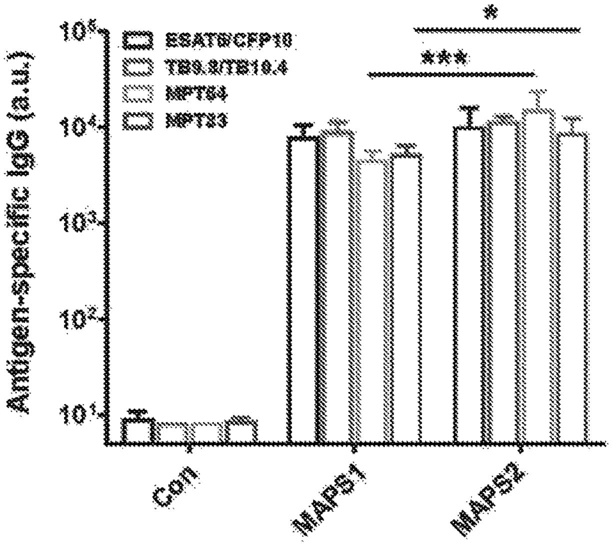
FIG. 1C
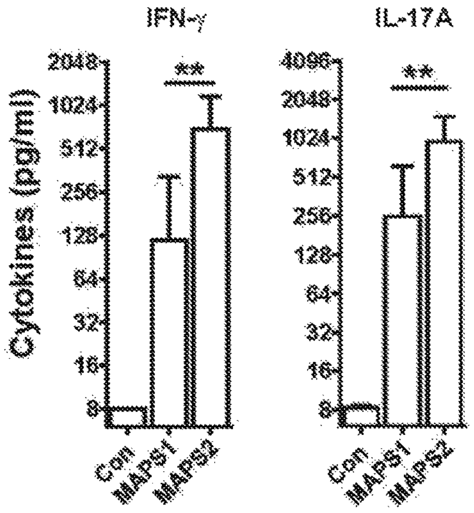

| Vaccines | Composition | Adjuvant | Dosage |
|---|---|---|---|
| MAPS3 | BCPS1-lipidated rhavi | AlOH | 2.5 μg |
| | BCPS1-rhavi-TB9.8/TB10.4-MPT83 | | 12.5 μg |
| MAPS4 | BCPS1-lipidated rhavi | AlOH | 2.5 μg |
| | BCPS1-rhavi-MPT51 | | 5 μg |
| | BCPS1-rhavi-ESAT6/CFP10-MPT64 | | 12.5 μg |
| | BCPS1-rhavi-TB9.8/TB10.4-MPT83 | | 12.5 μg |
| BCG | BCG | None | $1\times10^5$ CFU |

| Immunizations | Con | BCG | BCG/MAPS3 | BCG/MAPS4 |
|---|---|---|---|---|
| 1st dose | Saline | BCG | BCG | BCG |
| 2nd dose | Alum | Alum | MAPS3 | MAPS4 |
| 3rd dose | Alum | Alum | MAPS3 | MAPS4 |

FIG. 2D

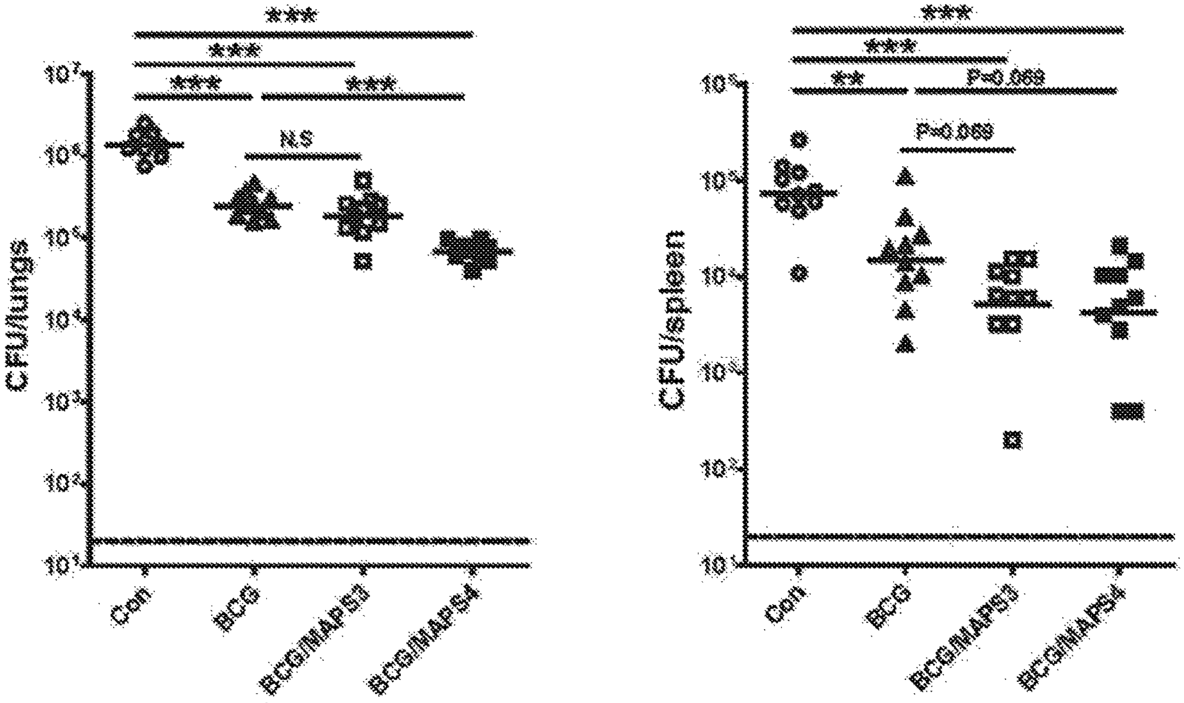

FIG. 3A

| Vaccines | Composition | Adjuvant | Dosage |
|---|---|---|---|
| MAPS4 | BCPS1-lipidated rhavi | AlOH | 2.5 μg |
| | BCPS1-rhavi-MPT51 | | 5 μg |
| | BCPS1-rhavi-ESAT6/CFP10-MPT64 | | 12.5 μg |
| | BCPS1-rhavi-TB9.8/TB10.4-MPT83 | | 12.5 μg |
| MAPS5 | BCPS1-lipidated rhavi | AlOH | 2.5 μg |
| | BCPS1-rhavi-MPT51 | | 5 μg |
| | BCPS1-rhavi-ESAT6/CFP10-MPT64 | | 12.5 μg |
| | BCPS1-rhavi-TB9.8/TB10.4-MPT83 | | 12.5 μg |
| | BCPS1-rhavi-PPE41/PE25 | | 5 μg |
| BCG | BCG | None | 1×10⁵ CFU |

FIG. 3B

| Immunizations | Con | BCG | BCG/MAPS4 Strategy 1 | BCG/MAPS4 Strategy 2 | BCG/MAPS4 Strategy 3 | MAPS4 | MAPS5 |
|---|---|---|---|---|---|---|---|
| 1st dose | Saline | BCG | BCG | BCG+MAPS4 | BCG+MAPS4 | MAPS4 | MAPS5 |
| 2nd dose | Alum | Alum | MAPS4 | Alum | MAPS4 | MAPS4 | MAPS5 |
| 3rd dose | Alum | Alum | MAPS4 | MAPS4 | MAPS4 | MAPS4 | MAPS5 |

1 = Alum
2 = BCG
3 = BCG -> MAPS 4 (2X)
4 = BCG+MAPS 4 -> MAPS 4 (1X)
5 = BCG+MAPS 4 -> MAPS 4 (2X)
6 = MAPS 4 (3X)
7 = MAPS 5 (3X)

1 = Alum
2 = BCG
3 = BCG -> MAPS 4 (2X)
4 = BCG+MAPS 4 -> MAPS 4 (1X)
5 = BCG+MAPS 4 -> MAPS 4 (2X)
6 = MAPS 4 (3X)
7 = MAPS 5 (3X)

| | |
|---|---|
| 1 = Alum | 5 = BCG+MAPS 4 -> MAPS 4 (2X) |
| 2 = BCG | 6 = MAPS 4 (3X) |
| 3 = BCG -> MAPS 4 (2X) | 7 = MAPS 5 (3X) |
| 4 = BCG+MAPS 4 -> MAPS 4 (1X) | |

1 = Alum
2 = BCG
3 = BCG -> MAPS 4 (2X)
4 = BCG+MAPS 4 -> MAPS 4 (1X)
5 = BCG+MAPS 4 -> MAPS 4 (2X)
6 = MAPS 4 (3X)
7 = MAPS 5 (3X)

COMBINED VACCINE AGAINST MYCOBACTERIUM TUBERCULOSIS

CROSS-REFERENCE TO RELATED APPLICATION

This Application is a 371 National Phase Entry of International Patent Application No. PCT/US2018/033380 filed on May 18, 2018 which claims benefit under 35 U.S.C. § 119(e) of the U.S. Provisional Application No. 62/509,368 filed May 22, 2017, the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Apr. 11, 2018, is named 701039-089410WOPT_SL.txt and is 34,167 bytes in size.

FIELD OF THE INVENTION

The present invention relates to molecular genetics, immunology, and microbiology. The present application is generally directed to compositions and methods for preparation of immunogenic compositions. More specifically, an embodiment of the present invention provides for an immunogenic composition comprising at least one immunogenic *Mycobacterium tuberculosis* protein or peptide antigen attached to an immunogenic polysaccharide. In some embodiments, this complex can be used as an immunogenic composition, such as a vaccine, to confer a synergistic humoral and cellular immune response; and in some embodiments, elicits synergistic antibody and/or B-cell response and also in some embodiments, a T-cell mediated protection against *M. tuberculosis* infection and colonization and carriage.

BACKGROUND OF INVENTION

Tuberculosis (TB) is a major cause of morbidity and mortality worldwide, with approximately 9 million new cases per year resulting in at least 1.5 million deaths annually (1). Although the incidence of TB has declined in the U.S. for the past several years, the rate of decline has slowed, and the number of TB cases appears to be reaching a plateau (2). In contrast to the U.S., in many parts of the developing world TB rates remain high, fueled in part by the HIV pandemic and the lack of resources and infrastructure to combat these two deadly infectious diseases. In areas where Mtb and HIV are both prevalent, it has been estimated that 50% of persons with HIV will develop TB, and TB is the leading cause of death among HIV-infected persons (3). Drug-resistant Mtb is also increasing with multidrug-resistant strains (MDR) accounting for 4% of new cases and extensively drug-resistant (XDR) strains that are essentially untreatable becoming a serious threat in many parts of the world (4). Novel means to combat TB are urgently needed, including effective vaccines.

Infection with *Mycobacterium Tuberculosis* (Mtb) does not usually result in active TB disease; and while over ⅓ of the world's population are infected, most remain symptom-free (i.e. clinically latent infection). Because exposure does not lead to sterilizing immunity, about 10% of these individuals will develop disease.

The current vaccine against TB, Bacille Calmette-Guerin (BCG), has an excellent safety track record (given to over 4 billion individuals) but offers little protection against adult pulmonary TB. Its main efficacy lies in the prevention of severe disseminated disease in infancy, and to a lesser extent, pulmonary disease at that age. BCG-induced protection is short-lived; at the same time, studies do not support any role for revaccination in adolescence or adulthood. Importantly, the underlying immunological mechanisms whereby BCG protects infants are not well understood, a major limitation that affects the prospects for improving BCG-based vaccine strategies. Despite this, most countries in TB endemic areas have universal immunization programs that include BCG vaccination at birth.

Although BCG vaccinations have helped millions of people, the effectiveness of the vaccine greatly varies. One major reason for BCG's varying efficacy is due to the vast amount of different BCG strains. When BCG was first distributed around the world in 1924, several different distinct daughter strains developed because BCG is a live vaccine (1). As early as the 1950s, scientists realized BCG substrains contained unique biochemical and immunological phenotypes. Researchers have now discovered that different strains vary in the amount of protein antigens which affect the immunogenicity of current BCG strains (1). One example of the vast differences in BCG strains can be seen through examination of phthiocerol dimycocerosates (PDIMs) and phenolic glycolipids (PGLs). Both molecules play an important role in modulation of the immune response, and dysfunctional PDIMs and PGLs can lead to increased attenuated virulence (1). Many of the strains contain variations of PDIMs and PGLs due to mutations; therefore, different BCG strains have varied effectiveness because of their unique biochemical characteristics. Researchers are currently looking for ways to improve the efficacy of the BCG vaccine as well as looking at alternative methods for a vaccine against tuberculosis.

Given BCG provides little protection against adult pulmonary TB, there remains a need to improve the efficacy of vaccines against Mtb and prevention of TB, particularly to prevent infection and/or colonization and carriage as well as TB later in life (TB reactivation), and reduce the risk of reinfection. While replacement of the BCG vaccine with another vaccine is one strategy, with 9 different TB vaccine candidates currently undergoing clinical trials in non-HIV infected individuals. Each of these are subunit vaccines that are used in combination with a vaccination with BCG

SUMMARY OF THE INVENTION

The disclosure herein relates to composition and methods for vaccination against *Mycobacterium tuberculosis* (Mtb). In particular, the inventors have discovered that administration of a TB-MAPS composition as disclosed herein, at substantially the same time at separate sites, or after, a BCG vaccine, increases the humorial response to the Mtb antigens. More specifically, the inventors have surprisingly discovered that BCG administered before administration of TB-MAPS composition in a subject reduces the Th17 response to TB-MAPS composition, and surprisingly, when a BCG composition and a TB-MAPS composition is administered at separate sites at substantially the same time, the Th17 response is produced.

Accordingly, the present invention provides for an immunogenic multiple antigen presenting system (MAPS) comprising an immunogenic polysaccharide, and attached to the immunogenic polysaccharide via an affinity binding pair, at least two *Mycobacterium tuberculosis* (Mtb) antigens. Such a *Mycobacterium tuberculosis* (Mtb)-MAPS (TB-MAPS) composition as disclosed herein is useful for the production of immunogenic compositions, such as those useful in vaccines against TB, as well as for treatment of TB.

In some embodiments, the TB-MAPS immunogenic composition as disclosed herein generates an immune response in a subject, preferably an antibody response and a B-cell and/or T-cell response. In some embodiments, the TB-MAPS immunogenic composition as disclosed herein generates a CD8+ T-cell response, a CD4+ T-cell response or a CD8+/CD4+ T-cell response. The inventors demonstrate that mice immunized with or administered a TB-MAPS immunogenic composition as disclosed, alone or when administered with BGC at a separate site, responded to TB antigens and produced significant amount of IFN-γ and IL-17A demonstrating that the TB-MAPS composition can generate of Th1, Th2 and Th17 responses and in some embodiments, a Th22 response.

Accordingly, in some embodiments, a TB-MAPS immunogenic composition as disclosed herein generates a T-cell response and, more specifically, any one or more of a Th1, Th2, Th17 response and, in some embodiments, a Th22 response to a Mtb peptide or protein present in the TB-MAPS composition. In some embodiments, a TB-MAPS immunogenic composition as disclosed herein generates an anti-polysaccharide antibody response and/or a B-cell and/or T-cell, e.g., Th1/Th2/Th17/Th22 response. In some embodiments, the immune response elicited by the TB-MAPS immunogenic composition as disclosed herein is an antibody or B cell response to at least one antigenic polysaccharide, and an antibody or B cell response and a CD4+ and/or CD8+ T cell response, including Th1, Th2, Th17 or Th22 responses, or a CD8+ T cell response.

In some embodiments, a TB-MAPS immunogenic composition as disclosed herein elicits an immune response that results in activation of any of, or a combination of INF-γ, IL-17A, IL-17F, or IL-22 producing cells, or produces INF-γ and/or IL-17A producing cells, and in some embodiments, also IL-22 producing cells. This is important in that the TB-MAPS immunogenic composition presents a major advantage by eliciting two forms of immunity—that is, a conventional humoral (B-cell dependent) immune response to an immunogenic polysaccharide and Mtb-antigens, as well as a T-cell response and, more specifically, any one or more of Th17, Th1, Th2 and/or Th22 responses to a Mtb peptide or protein present in the TB-MAPS composition. Moreover, in some embodiments, the TB-MAPS immunogenic composition as disclosed herein can enhance specific B-cell or T-cell responses by modifying the protein/polysaccharide ratio, complex size, or by incorporating specific co-stimulatory factor, such as TLR2/4 ligands, etc., into the composition.

In particular, the present invention is relates to compositions comprising an immunogenic polysaccharide, at least one *Mycobacterium tuberculosis* (Mtb) protein or peptide antigen; and at least one complementary affinity-molecule pair comprising (i) a first affinity molecule that associates with the immunogenic polysaccharide, and (ii) a complementary affinity molecule that associates with the Mtb protein or peptide antigen, such that the first and complementary affinity molecules serve as an indirect link between the immunogenic polysaccharide and Mtb protein or peptide antigens. Such a system allows for a modular immunogenic composition, where one or more Mtb protein or peptide antigens can be attached to the immunogenic polysaccharide in a modular fashion, allowing for flexibility in the number and type of Mtb antigens attached to immunogenic polysaccharide. Accordingly, the immunogenic polysaccharide can attach at least 1, or at least 2, or a plurality of the same, or different Mtb protein or peptide antigens. In some embodiments, the immunogenic polysaccharide is antigenic, and in some embodiments, the immunogenic polysaccharide is a polysaccharide from *Mycobacterium tuberculosis* (Mtb), such as, for example, alpha glucan, lipoarabinomannan, arabinomannan, or a Mtb polysaccharide comprising either arabinomannan and/or glucan, or any of the polysaccharides selected from: Type 5 (CP5) or Type 8 (CP8), or a combination of Type 5 or Type 8 capsular polysaccharide from *Staphylococcus aureus*, or can be a pneumococcal capsular polysaccharide, e.g., Type 1 (CP1) capsular polysaccharide from *S. pneumoniae*.

The TB-MAPS immunogenic composition as disclosed herein can elicit both humoral and cellular responses to one or multiple Mtb antigens at the same time. The TB-MAPS immunogenic compositions provide for a long-lasting memory response, potentially protecting a subject from future infection. This allows for a single TB-MAPS immunogenic composition that raise a high titer of functional anti-Mtb polysaccharide antibodies, and is similar or compares favorably with the antibody level induced by conventional conjugate vaccine. Moreover, there is no restriction to specific immunogenic polysaccharide used in the TB-MAPS construct, which is typically a Mtb capsular polysaccharide or other bacterial capsular or noncapsular polysaccharide, or the various Mtb antigen peptide or polypeptides used in TB-MAPS conjugate to generate a robust anti-polysaccharide antibody response. Additionally, the strong antibody response, as well as Th17 and/or Th1 response and/or a Th22 response are specific to multiple Mtb protein antigens presented via the TB-MAPS composition. This is important in that the TB-MAPS immunogenic composition presents a major advantage by eliciting two forms of immunity—that is, a conventional immune response to an immunogenic polysaccharide and Mtb-antigens, as well as a T-cell response and, more specifically, any one or more of Th17, Th1, Th2 or Th22 responses to a Mtb peptide or protein present in the TB-MAPS composition. Moreover, the TB-MAPS immunogenic composition as disclosed herein provides a potential to enhance specific B-cell or T-cell responses by modifying the protein/polysaccharide ratio, complex size, or by incorporating specific co-stimulatory factor, such as TLR2/4 ligands, etc., into the composition.

Accordingly, the TB-MAPS immunogenic composition as disclosed herein uses an affinity-pair method to complex the Mtb antigens to the immunogenic polysaccharide, therefore enabling a modular approach that is easy and highly flexible for the preparation of a *Mycobacterium tuberculosis* (Mtb) vaccine composition. The TB-MAPS immunogenic composition is highly specific and stable; it can remain in the cold for months and retain its potency. The assembly process is simple enough to ensure high reproducibility; there are only a few steps required, which reduces the risk of lot-to-lot variation, of great industrial advantage. The TB-MAPS immunogenic composition assembly is highly efficient (over 95%), even at low concentrations of protein and polysaccharide (such as 0.1 mg/ml); this is a major advantage, because inefficiencies in conjugate manufacture (typically efficiencies are in the <50% range) represent a major hurdle and reason for the high cost of vaccines. For formulation: it is easy to adjust the composition and physical properties of the final product. The protein:polysaccharide ratio in the complex is adjustable; with moderate biotinylation of polymer, protein:polysaccharide can be 10:1 (w/w) or more;

conversely, the ratio can be 1:10 or less if such is the interest based on immunological goals. Additionally, the size of the immunogenic TB-MAPS composition can be adjusted by the choice of immunogenic polysaccharide size. The methods of making the TB-MAPS provide for ease in combining Mtb protein antigens and immunogenic polysaccharide with little modification, and allows the generation of a multivalent TB-MAPS composition by loading multiple Mtb peptide or protein antigens onto single immunogenic construct. As such, the TB-MAPS immunogenic composition as disclosed herein can be used to decrease the number of vaccines required to immunize a subject against *Mycobacterium tuberculosis* (Mtb), in particular, different strains of *Mycobacterium tuberculosis* (Mtb).

In some embodiments, the TB-MAPS immunogenic compositions as disclosed herein can be used to protect or treat a human susceptible to *M. tuberculosis* (Mtb) infection, by means of administering the TB-MAPS immunogenic compositions via a systemic, dermal or mucosal route or be used to generate a polyclonal or monoclonal antibody preparation that could be used to confer passive immunity on another subject. These administrations can include injection via the intramuscular, intraperitoneal, intradermal or subcutaneous routes; or via mucosal administration to the oral/alimentary, respiratory or genitourinary tracts. In one embodiment, intranasal administration is used for the treatment or prevention of nasopharyngeal carriage of *M. tuberculosis* (Mtb), thus attenuating infection at its earliest stage. In some embodiments, the TB-MAPS immunogenic compositions as disclosed herein may also be used to generate antibodies that are functional as measured by the killing of bacteria in either an animal efficacy model of *M. tuberculosis* or via an opsonophagocytic killing assay.

In some embodiments, aspects of the invention disclosed herein relate to a TB-MAPS immunogenic composition comprising an immunogenic polysaccharide, at least one *Mycobacterium tuberculosis* (Mtb) peptide or polypeptide antigen, and at least one complementary affinity-molecule pair comprising: (a) a first affinity molecule associated with the immunogenic polysaccharide, and (b) a complementary affinity molecule associated with the at least one *Mycobacterium tuberculosis* (Mtb) peptide or polypeptide antigen, where the first affinity molecule associates with the complementary affinity molecule to link the Mtb peptide or polypeptide antigen and the immunogenic polysaccharide.

Accordingly, one aspect of the present invention relates to an immunogenic composition comprising a polymer, at least one protein or peptide antigen, and at least one complementary affinity-molecule pair, where the complementary affinity-molecule pair comprises a first affinity molecule that associates with the polymer and a complementary affinity molecule that associates with the protein or peptide antigen, so that when the first affinity molecule associates with the complementary affinity molecule, it indirectly links the antigen to the polymer.

Provided herein also is a method of vaccinating a subject, e.g., a mammal, e.g., a human with the immunogenic compositions as disclosed herein, the method comprising administering a vaccine composition comprising a TB-MAPS composition as disclosed herein to the subject.

DESCRIPTION OF THE DRAWINGS

FIGS. 1A-1C show exemplary TB-MAPS composition and its capacity to elicit antibody and T cell immune response. FIG. 1A is a Table of exemplary TB-MAPS compositions; TB-MAPS1 (MAPS1) and TB-MAPS2 (MAPS2). FIG. 1A shows formed complexes of the pneumococcal type 1 PS (BCPS1) with four different TB protein fusions as indicated: the fusion of ESAT6/CFP10, TB9.8/TB10.4, MPT64 and MPT83, all with rhizavidin at the N terminus. More specifically, TB-MAPS 1 has a biotinylated pneumococcal type 1 capsular polysaccharide (BCPS1), and 6 different TB protein or polypeptide antigens ESAT6, CFP10, TB9.8, TB10.4, MPT64 and MPT83, each individually or as a double fusion with a rhizavidin protein (Rhavi) (i.e., Rhavi-ESAT6/CFP10 and Rhavi-TB9.8/TB10.4 are double fusion proteins with a Rhizavidin protein as disclosed herein). TB-MAPS2 (also referred herein to Lipo-MAPS) differs from TB-MAPS1 in that is also comprises a lipidated Rhizavidin protein onto BCPS1 to evaluate whether the inclusion of this lipidated version (and consequently, TLR2 activation) would enhance immunogenicity and/or protection in mice. FIGS. 1B and 1C show antibody and T cell responses to TB-MAPS constructs. C57BL/6 mice (10 per group) were immunized with either control (aluminum hydroxide, alum), TB-MAPS1 with alum or TB-MAPS2 three times at 2 week interval. Two weeks following the last immunization, mice were bled, their sera evaluated for antibody responses (IgG) to the included proteins, and their whole blood stimulated with Mtb lysate for cytokine elicitation (IFN-gamma and IL-17A). FIG. 1B shows antibody responses to each of the Mtb antigens, with TB-MAPS1 or TB-MAPS2-immunized mice made significantly greater antibody responses to the proteins than control mice ($p<0.0001$ for both MAPS groups compared to control group); furthermore, the addition of the lipidated rhizavidin on TB-MAPS2 also significantly augmented this response in at least two of the included proteins ($p=0.0002$ for MPT64, and $p=0.02$ for MPT83). FIG. 1C shows induction of IFNγ and IL-17A cytokines and thus T cell responses where mice that were immunized with TB-MAPS1 and TB-MAPS2 made significantly greater IFNγ or IL-17A than control mice ($p<0.0001$ for both MAPS groups compared to control group), and TB-MAPS2 generated significantly greater responses than TB-MAPS alone ($p=0.0029$ for IL17A and $p=0.0068$ for IFN-gamma).

FIGS. 2A-2D show exemplary TB-MAPS compositions and its administration in combination with BCG. FIG. 2A is a Table of two additional formulations of TB-MAPS: TB-MAPS3 and TB-MAPS4. TB-MAPS3 comprises three Mtb antigens on the pneumococcal type 1 PS (BCPS1); TB9.8, TB10.4 and MPT83, which exist as a triple fusion protein to a rhizavidin protein as disclosed herein, as well as a lipidated rhizavidin protein. TB-MAPS4 comprises seven Mtb antigens on the pneumococcal type 1 PS (BCPS1); MPT51, TB9.8 and TB10.4 and MPT83 (which exist as a triple fusion protein with Rhavi), ESAT6 and CFP10 and MPT64 (which exist as a triple fusion protein with Rhavi), and a lipidated Rhizavidin protein. The inventors performed a comparison of these TB-MAPS compositions administered following a BCG vaccination to administration of BCG alone, which is the standard immunization received by children in most developing countries. Both TB-MAPS3 and TB-MAPS4 vaccine formulations contained lipidated rhizavidin. FIG. 2B shows the immunization scheme used; mice were immunized three times as indicated in the table, at two week intervals. The groups were as follows: Control (saline followed by 2 alum injections; BCG (BCG followed by two alum injections); BCG/MAPS3 (BCG followed by 2 administrations of the TB-MAPS3 composition); BCG/MAPS4 (BCG followed by 2 administrations of the TB-MAPS4 composition). FIG. 2C shows that both TB-MAPS vaccine-containing strategies were immunogenic with respect to T cell responses (e.g., IFN-γ release by Th1 cells or IL-17A by Th17 cells) in response to stimulation with either Mtb lysate or a mixture of the proteins. Importantly, in all evaluated cases, BCG followed by MAPS4 was significantly more immunogenic than control ($p<0.0001$), BCG alone ($p<0.0001$) or BCG followed by administration of TB-MAPS3 ($P<0.01$). With respect to IL-17A responses, BCG followed by TB-MAPS3 was more immunogenic than BCG regardless of the stimulus ($p=0.04$ for Mtb lysate stimulation, $p=0.0015$ for protein stimulation). FIG. 2D shows that BCG followed by TB-MAPS3 or TB-MAPS4 compositions conferred significant protection against pulmonary infection (left panel, $p<0.0001$) or dissemination to the spleen (right panel, $p<0.0001$). Importantly, in the case of BCG followed by TB-MAPS4, protection against pulmonary infection was significantly enhanced compared to BCG alone ($p=0.0002$), which is not observed with the TB-MAPS3 construct, which demonstrates the superiority of the MAPS4 vs. MAPS3. A non-significant, but highly suggestive trend, toward superiority of the BCG-MAPS strategy (with either TB-MAPS3 or TB-MAPS4) towards protection against splenic dissemination ($P=0.069$). An unexpected result from this experiment was that BCG reduces Th17 (IL-17A) responses. Indeed, when BCG was given prior to TB-MAPS3, the IL-17A response was lower than when TB-MAPS2 was given alone (see FIG. 1C), TB-MAPS2 response averages 1024 pg/ml; whereas in FIG. 20, the response to BCG/TB-MAPS3 is 128 pg/ml. No such trend is observed with IFN-γ responses, indicating that BCG reduces Th17 while maintaining IFN-γ responses. Given the importance of IL-17A in protection against Mtb, this inhibitory effect may be deleterious to the subject. Co-administration of BCG and TB-MAPS followed by TB-MAPS is used prevent this inhibition of MAPS-induced Th17 responses.

FIGS. 3A-3D show a large mouse experiment to evaluate whether co-administration (at different sites) of BCG and different TB-MAPS formulations followed by additional doses of TB-MAPS is superior to the control arm, BCG alone, or TB-MAPS alone. FIG. 3A shows the TB-MAPS compositions used in the study described herein. The difference between TB-MAPS4 and TB-MAPS5 is the addition of two antigens PPE41 and PE25, which are fused together to Rhavi, with the intent to evaluate whether the inclusion of these two antigens would improve efficacy and/or immunogenicity of TB-MAPS. As previously described, the controls used are saline+alum and BCG+alum. FIG. 3B show the schematic of the vaccination schedule used in this study, where the first dose is saline, BCG alone, a TB-MAPS composition alone, or a BCG vaccine administered in combination with a TB-MAPS composition (strategies 2 and 3), but administered at separate sites. The second and third dose can be alum or the TB-MAPS composition alone. FIG. 3C shows IFN-gamma (left) and IL-17A production, indicating Th1 and Th17 T-cell responses in response to stimulation with either Mtb lysate or a mixture of the proteins, and demonstrates that all TB-MAPS (strategies 1-3 or TB-MAPS4 or TB-MAPS5 alone) were superior to either BCG ($P<0.05$ for Mtb lysate stimulation, $p<0.0001$ for protein stimulation) or control ($p<0.0001$ regardless of stimulant) in eliciting IFNγ responses. Additionally, BCG administered substantially simultaneously at different sites with TB-MAPS, results in less inhibition of Th17 responses compared to when BCG was administered alone or followed by TB-MAPS (see BCG/TB-MAPS4 Strategy 1 vs. BCG/MAPS4 Strategy 2 for IL-17A responses, $p=0.0027$ for Mtb lysate stimulation and $p=0.0032$ for protein stimulation). Thus, BCG+ TB-MAPS administration concurrently, but administered at separate or different sites would be preferable to preserve Th17 responses. TB-MAPS4 and TB-MAPS5 alone are both able to generate robust IFNγ responses. FIG. 3D shows colony forming units (CFU) in the lung (left) and the spleen (right) for each treatment group and shows that BCG co-administered at different sites with TB-MAPS4 (Strategy 3) provides 2 log reduction in pulmonary colony forming units (CFU) counts in the lung as compared to the control arm, and is significantly more protective than BCG alone. The left panel shows that BCG/TB-MAPS4 Strategy 2 or 3 is significantly more protective against pulmonary infection than BCG alone ($P<0.05$ and $P<0.01$, respectively), whereas BCG followed by 2 doses of TB-MAPS (Strategy 1) is less protective (only showing a trend towards superiority compared to BCG, $P=0.09$). TB-MAPS4 or TB-MAPS5 showed similar protection compared with BCG. For splenic dissemination, protection was similar across all groups with the notable exception of BCG/TB-MAPS4 Strategy 2, which provided the most protection compared to BCG alone ($p=0.0008$).

FIG. 5A shows IL-17A release after mice are administered BCG alone, or BCG administered at the same time as administration of TB-MAPS3 or TB-MAPS4 at separate sites. FIG. 5B shows IFNγ release after mice are administered BCG alone, or BCG administered at the same time as administration of TB-MAPS3 or TB-MAPS4 at separate sites. Mice immunized with TB-MAPS3 and TB-MAPS4 significantly increased IL-17A and IFNγ levels when compared to control or BCG vaccinated mice.

FIG. 6A shows CFU in the lung after mice are administered BCG alone, or BCG administered at the same time as administration of TB-MAPS3 or TB-MAPS4 at separate sites. FIG. 6B shows CFU in the spleen after mice are administered BCG alone, or BCG administered at the same time as administration of TB-MAPS3 or TB-MAPS4 at separate sites. Mice immunized with TB-MAPS3 and TB-MAPS4 significantly reduced colony forming units (CFU) in the lung and spleen when compared to control or BCG vaccinated mice.

DETAILED DESCRIPTION OF THE INVENTION

Figures 2A, 2B, 2C:
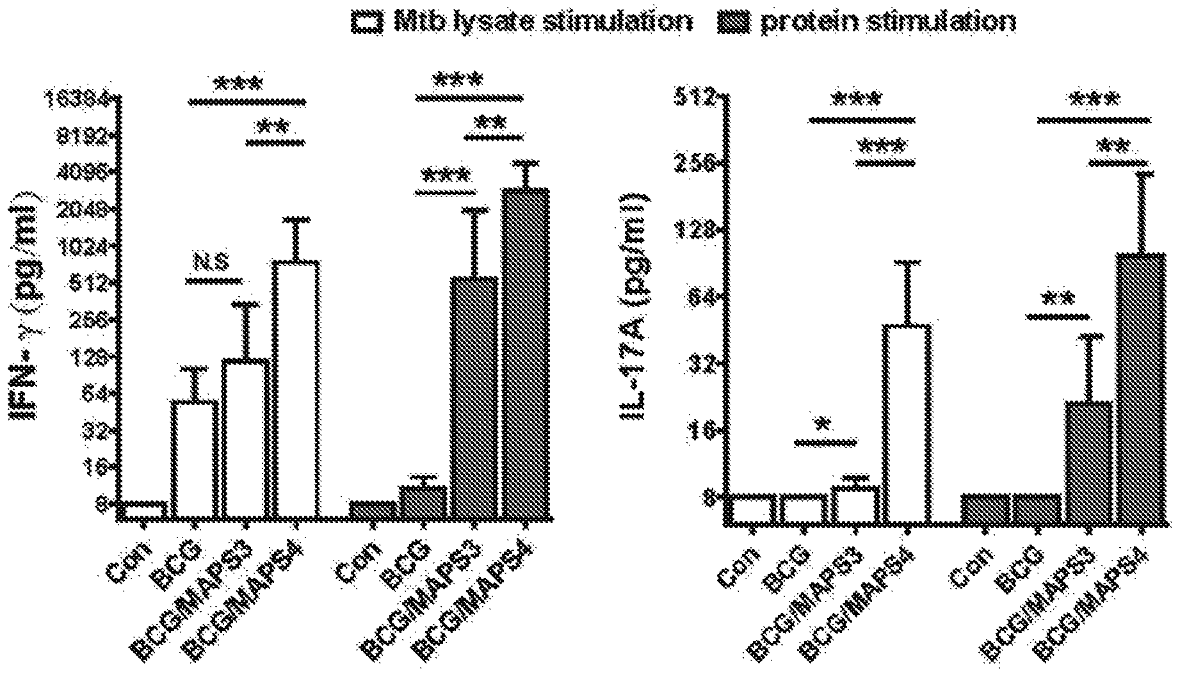
Figure 3C:
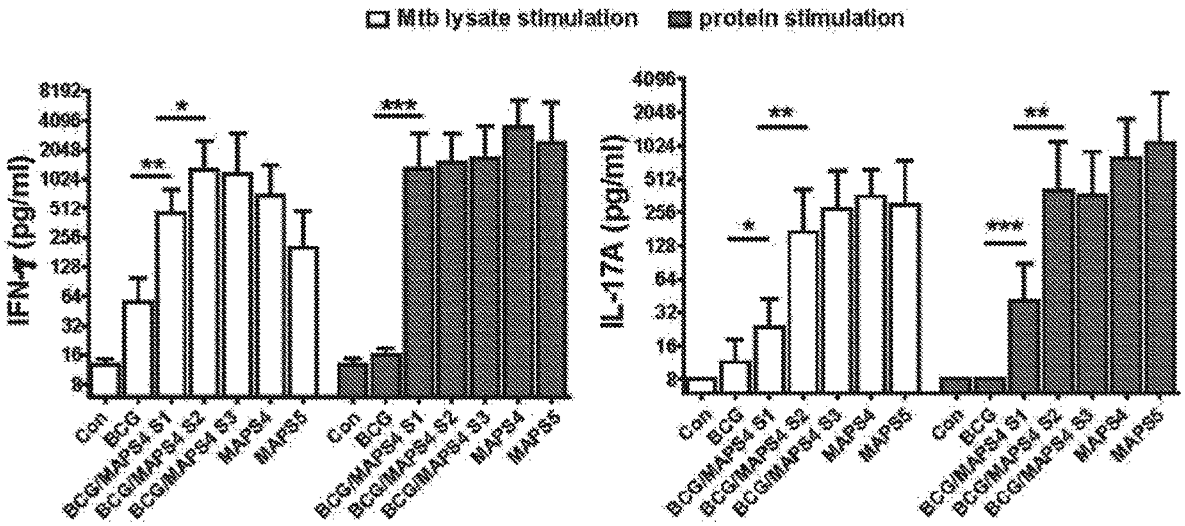
Figure 3D:
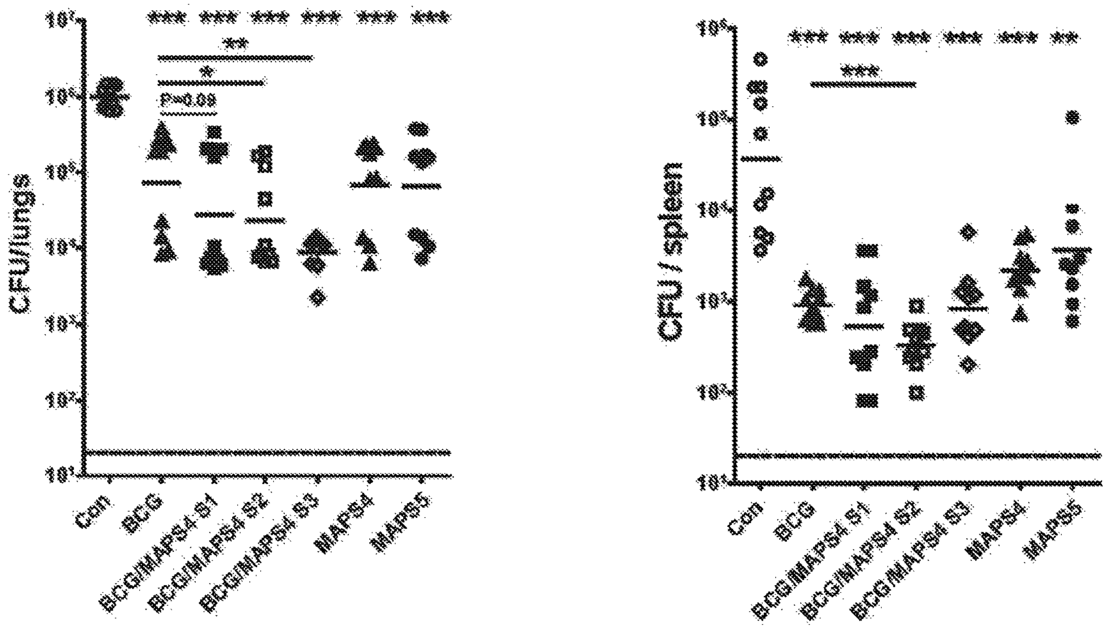
Figure 4:
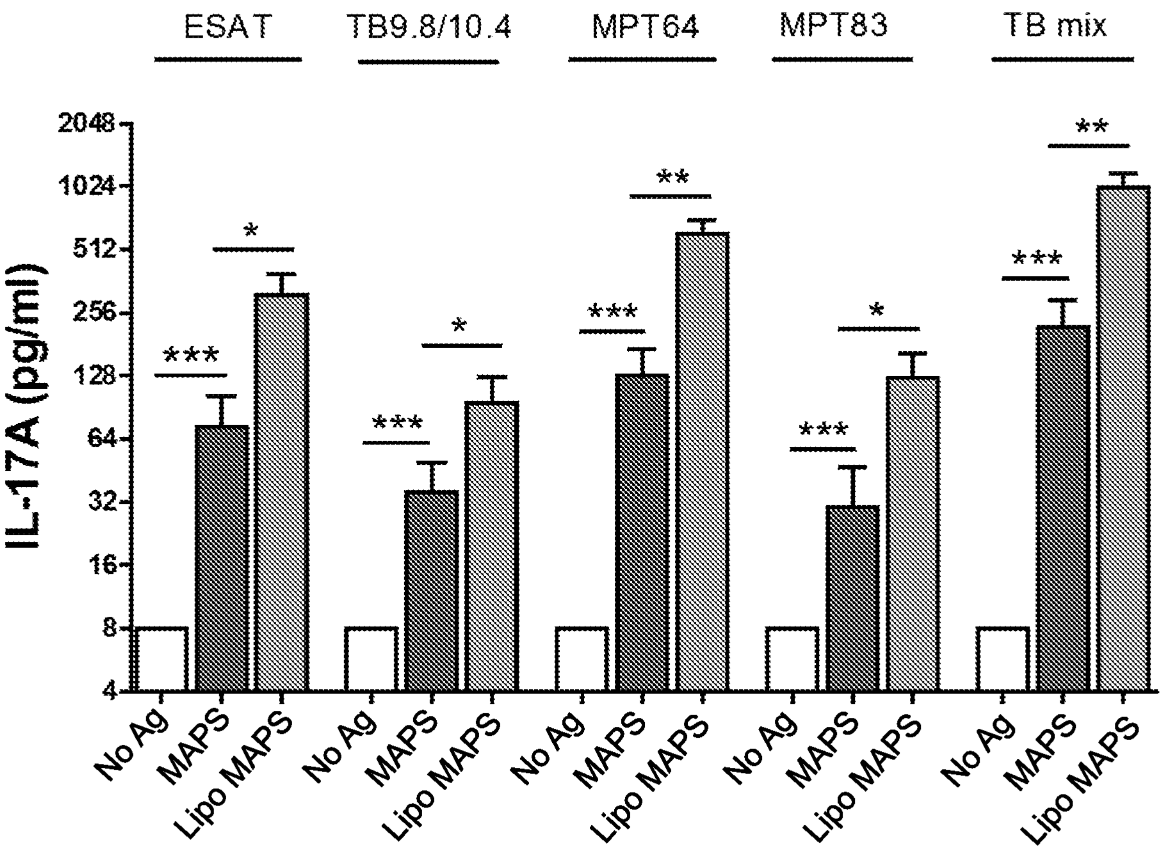
FIG. 4 shows that the addition of Lipo MAPS increasing the T-cell immune response. IL-17 released on exposure to each Mtb antigen is measured as a measure of Th17 T-cell responses after mice are immunized with TB-MAPS4 and TB-MAPS2/Lipo MAPS, and shows that IL-17A levels as significantly increased as compared to control mice, and Lipo MAPS generated significantly greater responses than TB-MAPS alone. This work is prior art, Zhang, F., et al. 110, PNAS, 33 (2013).
Figure 5A:
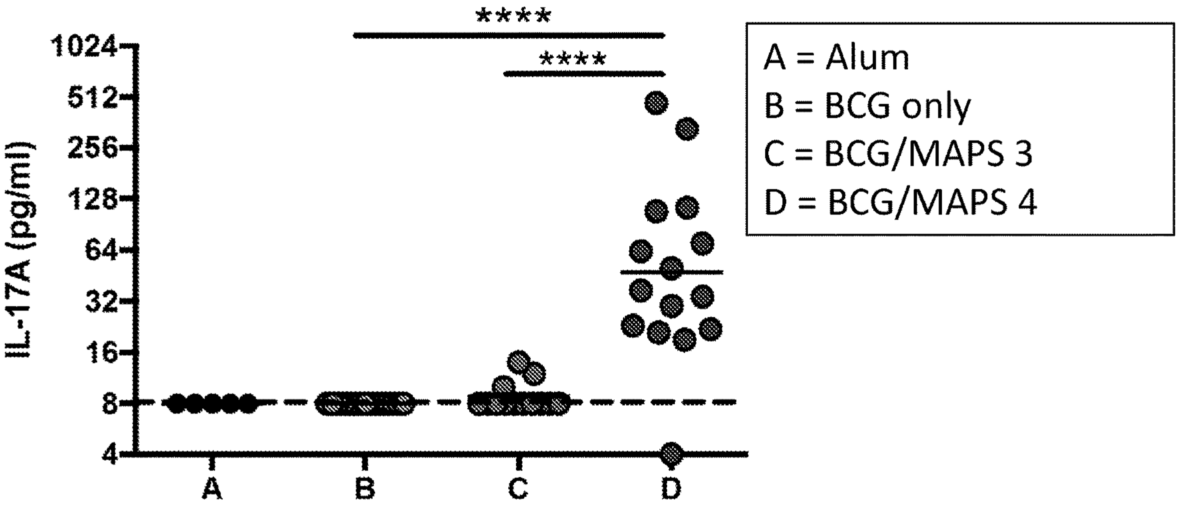
FIGS. 5A-5B show the T-cell response following administration of exemplary TB-MAPS.
Figure 5B:
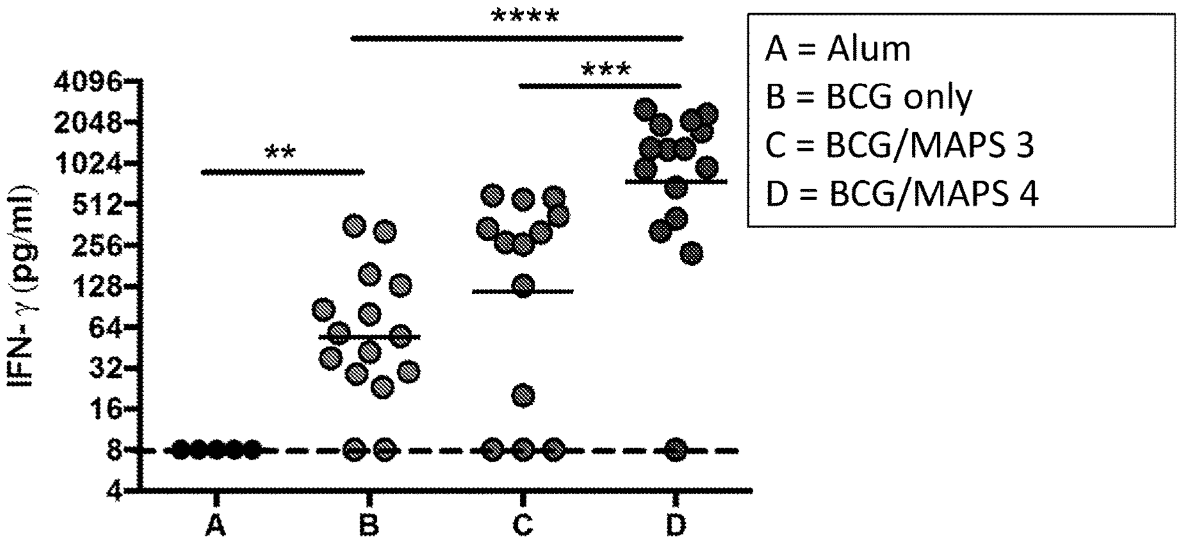
Figure 6A:
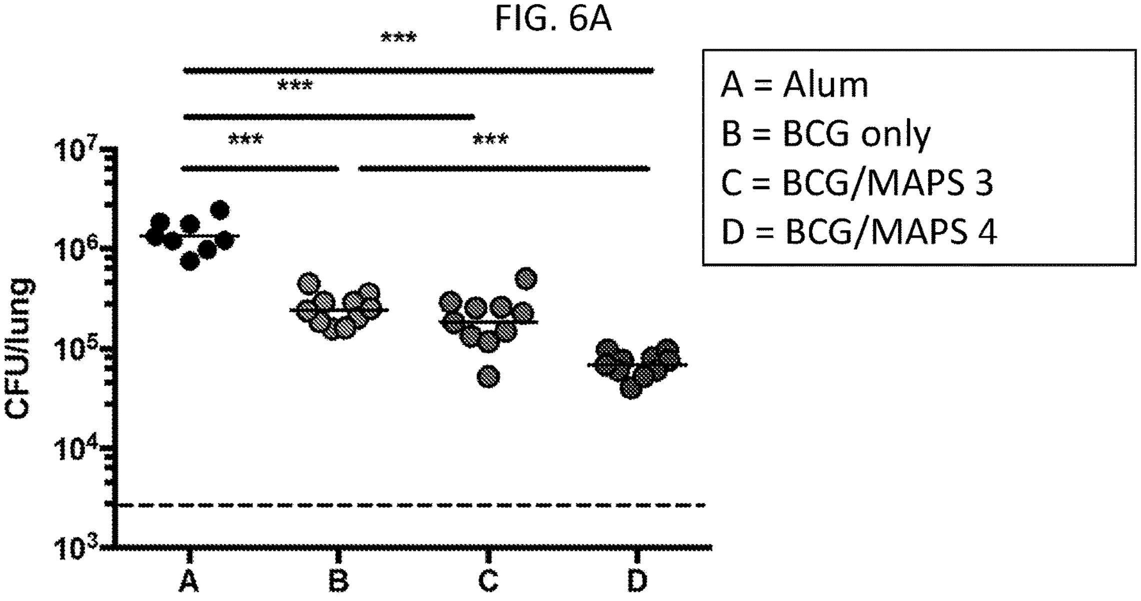
FIGS. 6A-6B show the effect of TB-MAPS administration on colony formation in the lung and spleen.
Figure 6B:
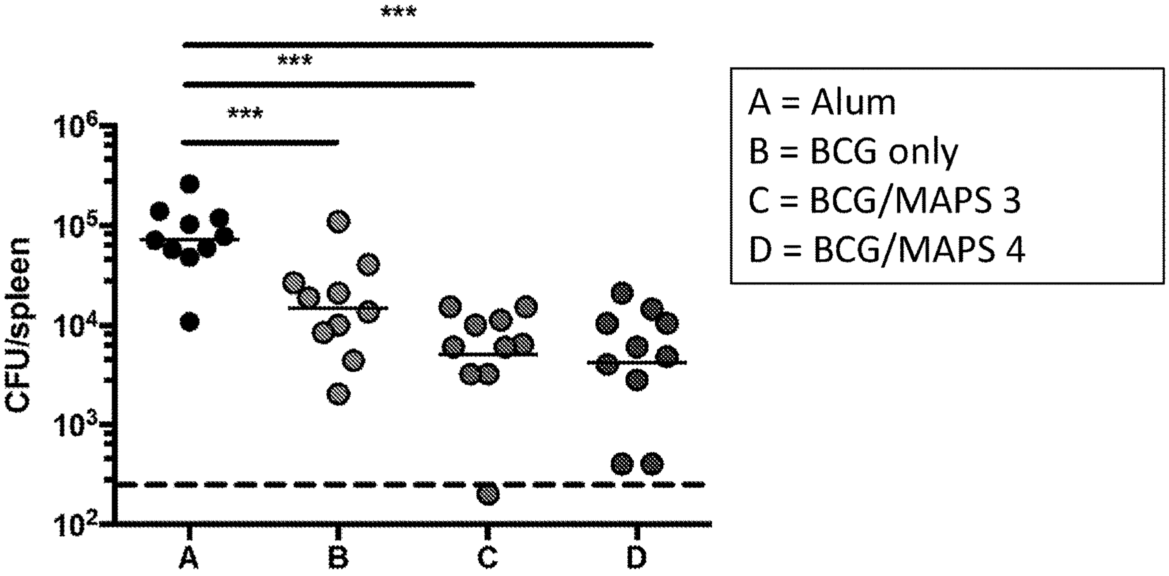
Figure 7:
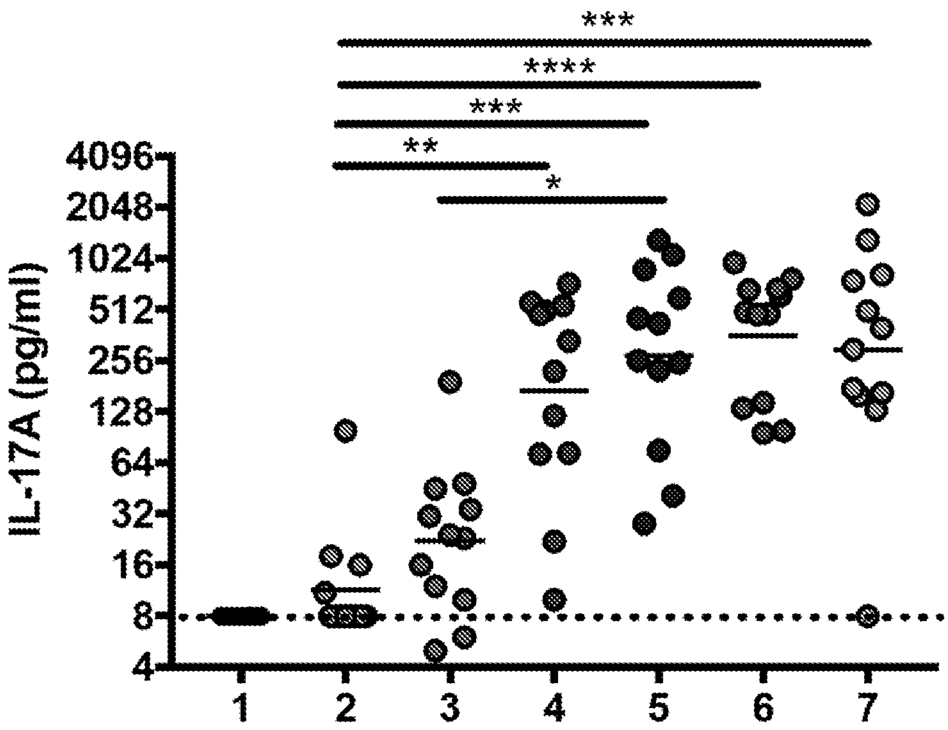
FIG. 7 shows that co-administration of BCG and TB-MAPS or TB-MAPS alone increases IL-17a levels. Mice were administered BCG alone, TB-MAPS4 alone, TB-MAPS5 alone, or BCG in combination with TB-MAPS4 at a separate site, followed by booster administration of TB-MAPS compositions as shown in the inset as described. "≥" indicates the vaccination was followed by another administration of the TB-MAPS composition (e.g., a booster administration of the immune composition). T-cell response was measured by IL-17a levels. Co-administration of BCG and TB-MAPS, or TB-MAPS significantly increased IL-17A when compared to control or BCG vaccinated mice.
Figure 8:
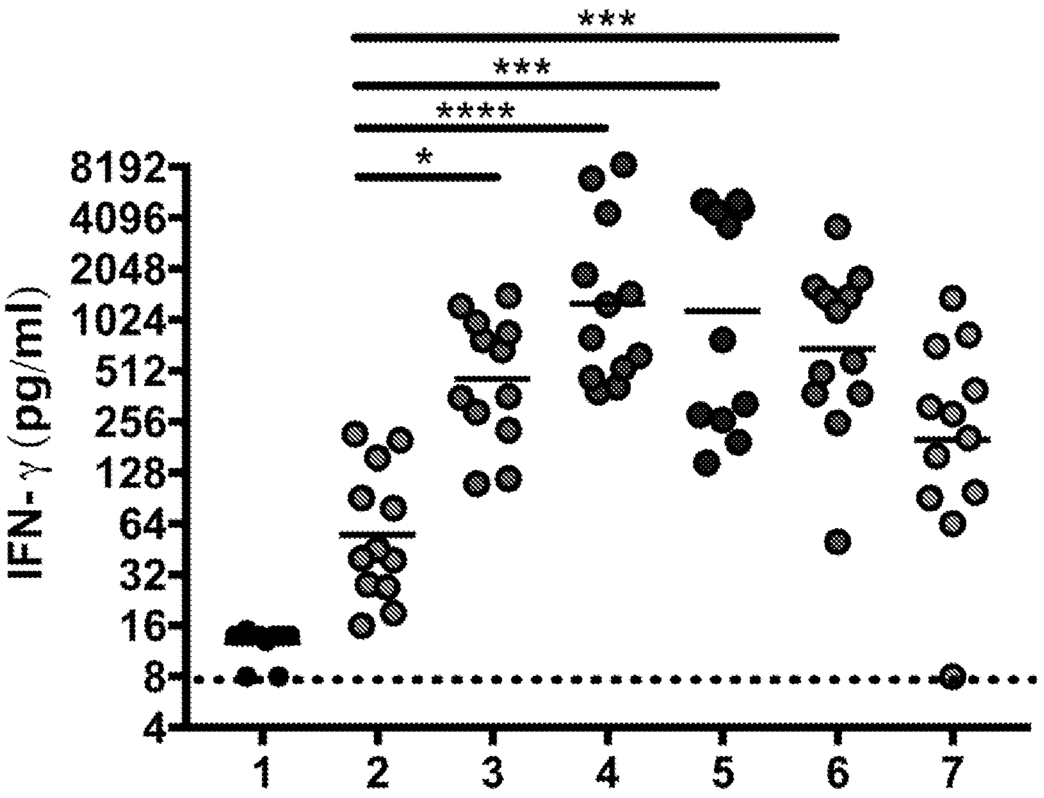
FIG. 8 shows that co-administration of a BCG composition and a TB-MAPS immune composition, at separate sites, or TB-MAPS alone increases IFNγ levels. Mice were administered BCG alone, TB-MAPS4 alone, TB-MAPS5 alone, or BCG in combination with TB-MAPS4 at a separate site, followed by booster administration of TB-MAPS compositions as shown in the inset as described. "≥" indicates the vaccination was followed by another administration of the TB-MAPS composition (e.g., a booster administration of the immune composition). T-cell response was measured by IFNγ levels. Co-administration of BCG and TB-MAPS, or TB-MAPS significantly increased IFNγ when compared to control or BCG vaccinated mice.
Figure 9:
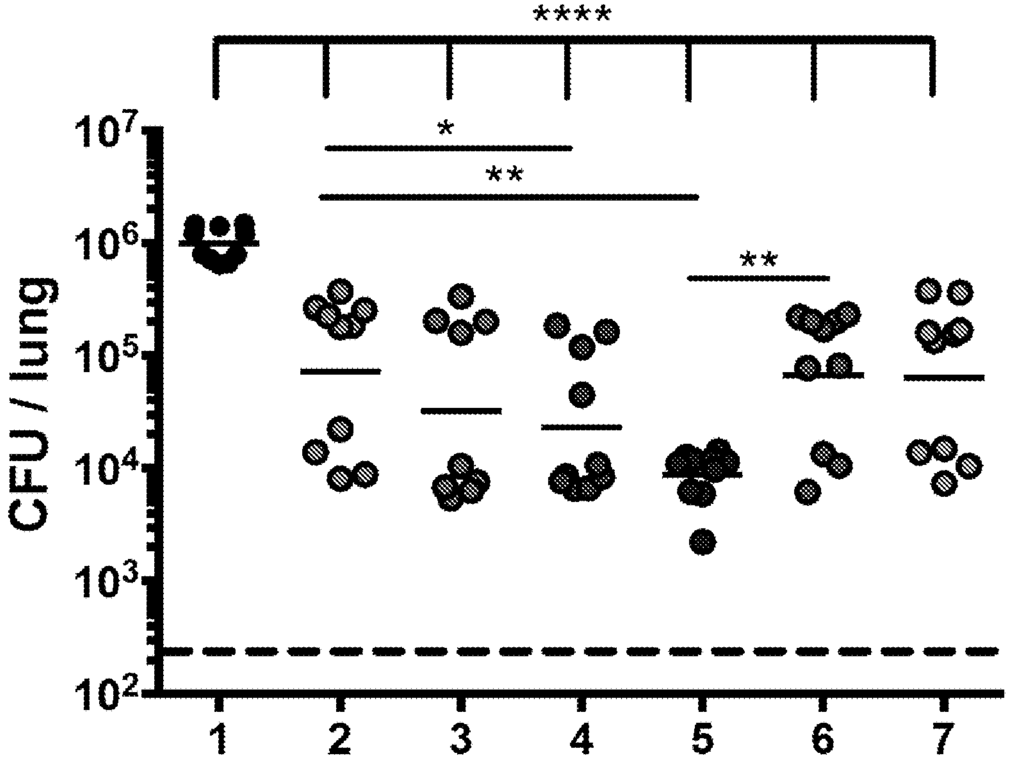
FIG. 9 shows that co-administration of a BCG composition and a TB-MAPS immune composition, at separate sites, or TB-MAPS composition alone reduces TB infection in the lung. Mice were administered BCG alone, TB-MAPS4 alone, TB-MAPS5 alone, or BCG in combination with TB-MAPS4 at a separate site, followed by booster administration of TB-MAPS compositions as shown in the inset as described. "≥" indicates the vaccination was followed by another administration of the TB-MAPS composition (e.g., a booster administration of the immune composition). Colony forming units (CFU) were measured in the lungs. Co-administration of BCG and TB-MAPS (at separate sites), or administration of a TB-MAPS immune composition significantly reduced CFU as compared to control or BCG vaccinated mice.
Figure 10:
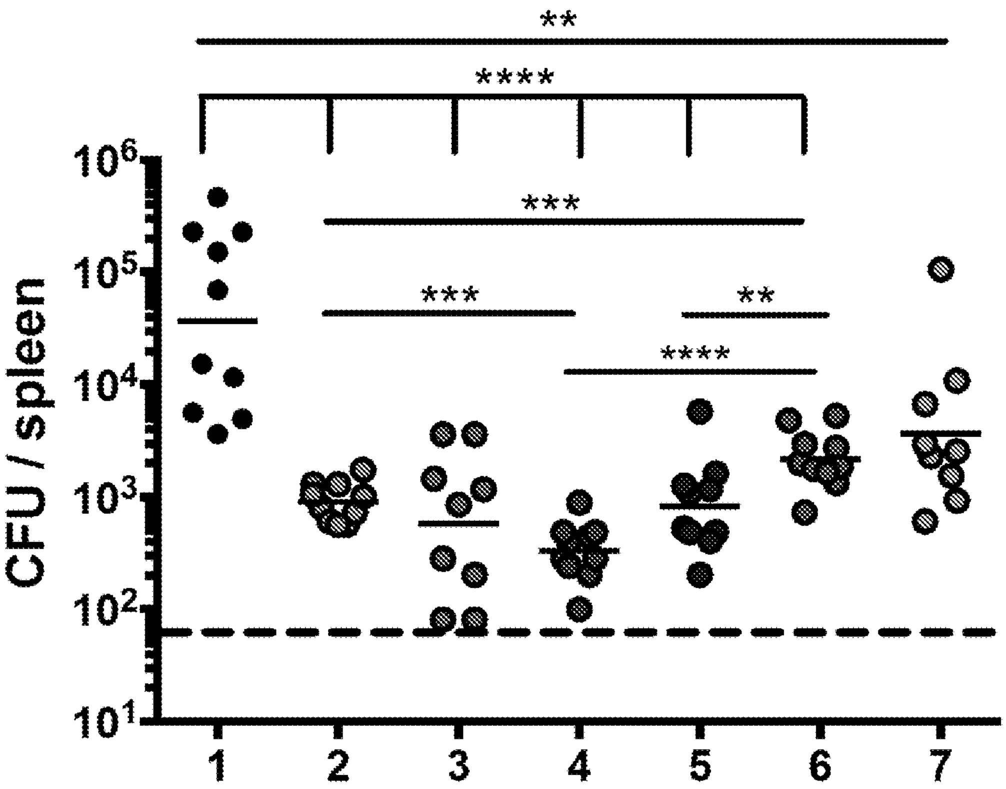
FIG. 10 shows that co-administration of a BCG composition and a TB-MAPS immune composition, at separate sites, or TB-MAPS composition alone reduces splenic dissemination of TB. Mice were administration of the TB-MAPS composition (e.g., a booster administration of the immune composition) as described. "≥" indicates the vaccination was followed by another administration of the TB-MAPS composition (e.g., a booster administration of the immune composition). Co-administration of BCG and TB-MAPS4 (at separate sites) followed by at least one (group 4) or two booster TB-MAPS4 doses (e.g., group 5) significantly reduced CFU in the spleen as compared to the other vaccinated mice.

The present invention relates immunogenic compositions and compositions comprising an immunogenic complex that comprises at least one *Mycobacterium tuberculosis* antigen, or multiple *Mycobacterium tuberculosis* antigens, attached to an immunogenic polysaccharide scaffold for use in eliciting an immune response (both a cellular and humoral immune response) to each of the Mtb antigens attached to the immunogenic polysaccharide and to the immunogenic polysaccharide, when administered to a subject.

More specifically, disclosed herein is an immunogenic Multiple Antigen Presenting System (MAPS) comprising an immunogenic polysaccharide, and attached to the immunogenic polysaccharide via an affinity binding pair, at least one *Mycobacterium tuberculosis* (TB) antigen. Such a *Mycobacterium tuberculosis*-MAPS (TB-MAPS) composition as disclosed herein is useful for the production of immunogenic compositions, such as those useful in vaccines, as well as for treatment. The TB-MAPS immunogenic composition as disclosed herein stimulates a humoral and cellular immune response: it can generate anti-polysaccharide antibody and the B-cell and T-cell, e.g., Th1/Th17 responses to multiple *Mycobacterium tuberculosis* (TB) antigen using single TB-MAPS immunogenic construct. A combination of B- and T-cell immunity to *Mycobacterium tuberculosis* will be a useful vaccine strategy against *Mycobacterium tuberculosis* invasive disease.

The inventors previously developed a vaccine platform referred to the Multiple-Antigen-Presenting-System (MAPS), as disclosed in US patent Application 2014/0154287, which is incorporated herein in its entirety by reference, which enables the induction of broad adaptive immune responses. Herein, the inventors have developed and optimized the system for the treatment and prevention of infection from *Mycobacterium tuberculosis*. In particular, the inventors have developed a system for the administration of a TB-MAPS immunogenic composition to be administered at a separate site, but at substantially the same time, or as a booster administration to the classical BCG vaccine.

In particular, the inventors have generated a TB-MAPS immunogenic composition comprising an immunogenic polysaccharide (such as, for example, a *S. aureus* (SA) CP5, CP8 or *S. pneumoniae* CP1, a TB polysaccharide or other PS or variants or combinations thereof), at least one *Mycobacterium tuberculosis* (TB) protein or peptide antigen; and at least one complementary affinity-molecule pair comprising (i) a first affinity molecule that associates with the immunogenic polysaccharide, and (ii) a complementary affinity molecule that associates with the *Mycobacterium tuberculosis* (TB) protein or peptide antigen, such that the first and complementary affinity molecules serve as an indirect link between the immunogenic polysaccharide and TB protein or peptide antigens. Such a system allows for a modular immunogenic composition, where one or more TB protein or peptide antigens can be attached to the immunogenic polysaccharide in a modular fashion, allowing for flexibility in the number and type of Mtb antigens attached to immunogenic polysaccharide. Accordingly, the immunogenic polysaccharide can attach at least 1, or at least 2, or a plurality of the same or different TB protein or peptide antigens. In some embodiments, the immunogenic polysaccharide is antigenic can be a pneumococcal capsular polysaccharide, e.g., Type 1 (CP1) capsular polysaccharide from *S. pneumoniae*.

Herein, the inventors have used an exemplary TB-specific MAPS immunogenic composition referred to as TB-MAPS4, which comprises 9 different TB peptide antigens to demonstrate that B- and T-cell mediated immune mechanisms contribute differentially to host defense against TB in models lung colonization and splenic dissemination.

In some embodiments, the TB-MAPS immune composition comprises at least one or more Mtb antigens, where the Mtb antigen is an antigenic protein or polypeptide selected from any of the group of: Early secreted antigen target-6 (ESAT6), Culture filtrate protein-10 (CFP10), MPT51, MPT64, MPT83, TB9.8, TB10.4, Proline Proline Glutamic acid-41 (PPE41), and Proline Glutamic acid-25 (PE25). In some embodiments, the TB-MAPS immunogenic composition as disclosed herein comprises one or more peptide or polypeptide fragments of these proteins, as long as the fragment is antigenic, and/or comprises one or more epitopes to induce an immune response. Exemplary fragments can comprise, for example, but are not limited to CFP10 (1-40), CFP10 (45-80), MPT64 (25-228), MPT83 (58-220), and MPT51 (33-299). In some embodiments, a TB-MAPS immunogenic composition as disclosed herein comprises at least 2, or at least 3, or at least 4, or at least 5, or all 6 peptide or polypeptide TB-antigens selected from any of: ESAT6, TB9.8, TB10.4, CFP10 (1-40), CFP10 (45-80), MPT64 (25-228), MPT83 (58-220), and MPT51 (33-299), or proteins or peptides of at least 85% sequence identity thereto. In some embodiments, any of the above listed Mtb antigens can be substituted for a different TB peptide or polypeptide antigen known to one of ordinary skill in the art. Exemplary Mtb antigens can be any peptide or polypeptide comprising at least part of the TbH9 (also known as Mtb 39A), DPV (also known as Mtb8.4), 381, Mtb41, Mtb40, Mtb32A, MPT64, MPT83, Mtb9.9A, Mtb16, Mtb72f, Mtb59f, Mtb88f, Mtb7lf, Mtb46f and Mtb31f, wherein 'T' indicates that it is a fusion or two or more proteins, provided that the any peptide or polypeptide is immunogenic, or is antigenic. Other Mtb antigens can be used, and are disclosed herein.

Accordingly, the embodiments herein provide for an immunogenic composition and methods useful for raising an immune response to *Mycobacterium tuberculosis* in a subject, which can be used on its own or in conjunction with or, in some embodiments in an admixture with essentially any existing vaccine approaches. In some embodiments, the immunogenic composition as disclosed herein is administered to the subject at substantially the same time (e.g., within about 0-10 mins, or about 10-20 mins, or about 20-30 mins, or about 30-60 mins) as the administration of another TB vaccine, such as, for example, a BCG vaccine.

The widely used and accepted vaccine against TB is Bacille Calmette-Guerin (BCG), which is administered in a single dose at infancy according to the methods as disclosed in U.S. patent Ser. No. 10/524,586 which is incorporated herein in its entirety by reference. As disclosed herein, administration of BCG at infancy offers little to no protection against adult pulmonary TB. Its main efficacy lies in the prevention of severe disseminated disease, and to a lesser extent, pulmonary disease in infancy. BCG is only partially effective: it provides some protection against severe forms of pediatric TB, but is not completely protective against disease in infants and is unreliable against adult pulmonary TB. BCG cannot be administered to those infected with HIV. Disease in latently infected adults and adolescents accounts for most of the disease burden, and transmission, worldwide. There is therefore an urgent need for new, safe and effective vaccines that prevent against all forms of TB, including drug-resistant strains, in all age groups, including those with HIV.

BCG, like most vaccines, stimulates antibodies and creates a resistance without damaging the organism. The BCG vaccine recruits both CD4 and/or CD8 T cells as a response to protective mycobacterial antigens. After recruiting these cells, the new cells are exposed to the macrophage product interleukin 12 which calls for T cells to secrete interferon-γ. When *Mycobacterium tuberculosis* enters the cell, interferon-γ reduces the pH in the phagosomal membrane and produces superoxide and nitric oxide, which can destroy *Mycobacterium tuberculosis*.

BCG is dervied from *Mycobacterium bovis*. The *Mycobacterium bovis* strain of the BCG vaccine is similar to *Mycobacterium tuberculosis*, but there are some structural and functional differences between the two strains. Recent genetic sequencing has shown that the BCG vaccine and *Mycobacterium tuberculosis* have three distinct genomic regions (2). The first genomic difference, named RD 3, is a 9.3-kb genomic segment that is absent in BCG compared to virulent *Mycobacterium bovis* and *Mycobacterium tuberculosis* (2). However, researchers concluded that the absence of RD3 occurred during the derivation of BCG and that RD3 did not make *Mycobacterium tuberculosis* virulent. A similar conclusion was made for the genomic segment RD2, which also disappeared from the BCG strain after it had already been used as a vaccine. However, researchers discovered through two-dimensional gel electrophoresis that RD1, a 9.5-kb DNA segment absent in BCG, could have significant implications as to why BCG is not virulent for humans. RD1 was found to repress at least ten proteins involved the in the regulation of multiple genetic loci which suggests that it is likely that a regulatory mutation is responsible for the lack of virulence in BCG (2).

Administration of the Immunogenic TB-MAPS Composition

In some embodiments, the immunogenic TB-MAPS composition, described herein below, is used in conjunction with the BCG vaccine to increase protection again *Mycobacterium tuberculosis* by eliciting a stronger immune response to *Mycobacterium tuberculosis* antigens. In some embodiments, the immunogenic TB-MAPS composition is administered to a subject to elicit an immune response to *Mycobacterium tuberculosis*. In some embodiments, antibodies are generated upon administration of TB-MAPS immunogenic composition as disclosed herein to a subject. At a first time point, a first dose of TB-MAPS is administered to a subject substantially simultaneously with a composition comprising a BCG vaccine, or within 24 hours thereof, and the administration is done at different sites (i.e., a first site (site one) and a second site (site two)). The immune response generated by TB-MAPS is enhanced by the administration of one or more additional TB-MAPS immunogenic compositions, also referred to herein as TB-MAPS boosters. For example, a second dose of a TB-MAPS immune composition as disclosed herein can be administered at a second time point, for example, between about 2-4 weeks, or between about 4-6 weeks, or between about 6-8 weeks, or between about 1-2 months, or between about 2-3 months, or between about 3-6 months, or between about 6-12 months, or between about 1-2 years after the first administration of the TB-MAPS composition.

In some embodiments, a third dose of a TB-MAPS composition as disclosed herein can be administered at a third time point, e.g., between about 2-4 weeks, or between about 4-6 weeks, or between about 6-8 weeks, or between about 1-2 months, or between about 2-3 months, or between about 3-6 months, or between about 6-12 months, or between about 1-2 years after the second dose of the TB-MAPS composition. It is envisioned that the administration of the TB-MAPS composition as disclosed herein at the second and third time point (e.g., dose 2 and dose 3) can be administered at the first site (e.g., site one), at the second site (e.g., site two), or both, or at a different site.

In some embodiments, the immunogenic TB-MAPS composition is administered to a subject by itself (without the subject being administered at the same time a BCG vaccine, or at a time after the subject has previously been administered a BCG vaccine) to increase protection again *Mycobacterium tuberculosis*. For example, at a first time point, a first dose of TB-MAPS immune composition as disclosed herein is administered to a subject. Then, in some embodiments, the subject is administered at a second time point, a second dose (i.e., a booster) of a TB-MAPS composition as disclosed herein, where the second time point is administered, for example, between about 2-4 weeks, or between about 4-6 weeks, or between about 6-8 weeks, or between about 1-2 months, or between about 2-3 months, or between about 3-6 months, or between about 6-12 months, or between about 1-2 years after the first time point. In some embodiments, the subject can be administered at a third time point, a third dose of the TB-MAPS immune composition as disclosed herein (i.e., a second booster), where the third time point is administered between about 2-4 weeks, or between about 4-6 weeks, or between about 6-8 weeks, or between about 1-2 months, or between about 2-3 months, or between about 3-6 months, or between about 6-12 months, or between about 1-2 years after the second time point. In some embodiments, the administration of the TB-MAPS compositions can be administered at the same or different sites. In some embodiments, administration of the immunogenic TB-MAPS composition is used to vaccinate a subject against or prevent Tuberculosis.

The inventors demonstrate that the protection against *Mycobacterium tuberculosis* was significantly increased in mice that were administered a TB-MAPS composition as disclosed herein at a first time point in conjunction with a BCG vaccine, where the TB-MAPS composition and the BCG vaccine were administered at separate sites, as compared to unvaccinated mice, control mice or BCG vaccinated mice. Protection against *Mycobacterium tuberculosis* was further increased when the first dose of immunogenic TB-MAPS was followed by a second and third administration of TB-MAPS composition, at a second time point and a third time point, respectively. Three sequential administrations of the TB-MAPS composition at a first, second and third time point respectively (i.e., the initial TB-MAPS administration, followed by two booster TB-MAPS administrations), increased protection against *Mycobacterium tuberculosis* compared to unvaccinated, control, or BCG vaccinated subjects, although it was not greater than the administration of TB-MAPS in conjunction with BCG at separate sites. The inventors surprisingly demonstrate herein a 2 log reduction of pulmonary colony counts in the Tuberculosis mouse model when TB-MAPS was administered with the BCG vaccine followed by 2 additional administrations of TB-MAPS. In contrast, the BCG vaccine alone only resulted in a 1 log reduction in pulmonary colony counts in the Tuberculosis mouse model, demonstrating that the administration of a TB-MAPS composition with the administration of the BCG vaccine, at separate sites, has a greater efficacy in inducing the immune response than BCG alone.

An important role of Th17 cells (which produce the cytokine IL-17A) has been previously demonstrated, particularly for BCG vaccine-induced protection. The precise mechanism is unclear, though it appears that Th17 cells facilitate the early formation of protective immunity in the lung. TB-MAPS elicits a significant Th17 response in the vaccinated subjects. Surprisingly, the inventors discovered that the BCG vaccination reduced the Th17 response when the TB-MAPS composition was administered one month after administration of the BCG vaccine, whereas, surprisingly administering a TB-MAPS composition in conjunction with administration of a BCG vaccine at separate sites (e.g., a first site, and a second site) abolished this decrease in Th17 response.

*Mycobacterium tuberculosis* Multiple-Antigen Presenting System (TB-MAPS)

While it is envisioned that the TB-MAPS immunogenic composition as disclosed herein comprises immunogenic polysaccharides from *Mycobacterium tuberculosis*, the TB-MAPS can use immunogenic polysaccharides from a variety of different bacterial cells. In some embodiments, a polysaccharide from *M. Tuberculosis* is selected from, alpha glucan, lipoarabinomannan, arabinomannan (arabi), or a Mtb polysaccharide comprising either arabinomannan and/or glucan. In some embodiments, the immunogenic polysaccharide is for example, but not limited to, Glucan or Arabi nomannan from *Mycobacterium tuberculosis*, Type 5 (CP5) or Type 8 (CP8), or a combination of Type 5 or Type 8 capsular polysaccharide from *Staphylococcus aureus*, or can be a pneumococcal capsular polysaccharide, e.g., Type 1 (CP1) capsular polysaccharide from *S. pneumoniae*, or other capsular or noncapsular PS. In some embodiments, the polysaccharide is a capsular polysaccharide. In some embodiments, the polysaccharide is not a capsular polysaccharide (i.e., a noncapsular PS). With the different combinations of immunogenic polysaccharides and different combinations of TB peptide or polypeptide antigens, the TB-MAPS composition is a flexible and versatile composition that can be designed and manufactured to elicit a particular, broad spectrum immune response to *Mycobacterium tuberculosis*. Table 1 provides a simple example guide for envisioning the flexibility of TB-MAPS embodiments.

Table 1 shows the versatility of the TB-MAPS platform: a TB-MAPS immune composition can comprise an antigenic polysaccharide backbone and at least one TB-antigen, and optionally one or more non-Mtb antigens. The antigenic or immunogenic polysaccharide backbone can be a synthetic or antigenic polysaccharide from *Mycobacterium tuberculosis* or alternatively a different a pathogen (exemplary antigenic polysaccharides are listed in the last column). A TB-MAPS composition can comprise at least one TB-antigen (exemplary Mtb antigens are listed), and can optionally comprise non-Mtb antigens.

TABLE 1

| | | | | |
|---|---|---|---|---|
| TB-MAPS | Immunogenic polymer backbone: | Immunogenic polysaccharide | synthetic | Exemplary antigenic polysaccharides for synthetic<br>*Pneumococcal* capsular PS (e.g., CP1 from Type 1 serotypes) or other serotypes |
| | | | From pathogen | *Pneumococcal* cell wall PS<br>*Salmonella typhi* Vi |
| | | Other immunogenic polysaccharides from viruses etc. | | *Staphylococcus aureus* capsular PS (e.g., CP5, CP8 from Type 5 and Type 8 serotypes) |
| | Antigens: | TB-Antigens | e.g., MPT51, ESAT6, CFP10, MPT64, TB9.8, TB10.4, MPT83, | *Haemophilus influenzae* Type b (Hib) PS, other Haemophili<br>*Mycobacterium tuberculosis* PS (e.g., D-Glucan, or alpha-glucan, and lipoArabinomannan, |

TABLE 1-continued

| | | |
|---|---|---|
| | PPE41, PE25 | arabinomannan, or a Mtb polysaccharide comprising either arabinomannan and/or glucan) |
| | | *Streptococcus* PS (Group A or Group B) |
| | | Meningoccus PS |
| | | Anthrax PS |
| Non-Mtb antigens | Bacterial proteins/toxins | Enteric pathogens |
| | Viral proteins | pseudomonas |
| | Cancer antigens | Fungal pathogens (Cryptococcus, other) |
| | Plant toxins | Glycoproteins from viruses |

Polysaccharides

One component of the TB-MAP immunogenic composition as disclosed herein is a "backbone," typically an antigenic or immunogenic polysaccharide (PS), and can comprise additional elements that do not negatively impact the antigenic polysaccharide's function of (i) inducing an immune response to the polysaccharide and (ii) presenting the associated TB-antigen(s) to the immune system in immunogenic fashion. In some embodiments, the immunogenic polysaccharide is a synthetic polysaccharide.

It is envisioned that the polysaccharide used in the TB-MAPS composition is immunogenic, that is, it helps induce a specific immune response, and herein is referred to as an "immunogenic polysaccharide" or "antigenic polysaccharide". The specific immune response recognizes the particular immunogenic PS and provides a unique response to the immunogenic complex as opposed to a different immunogenic complex. As explained herein, the response includes both a humoral and cell-mediated response.

In some embodiments, the immunogenic polysaccharide is a naturally occurring polysaccharide, e.g., a polysaccharide derived or purified from bacterial cells, and can be, for example, a capsular or noncaspular PS. In some embodiments, the immunogenic polysaccharide is derived or purified from eukaryotic cells, e.g., fungi, insect or plant cells. In yet other embodiments, the immunogenic polysaccharide is derived from mammalian cells, such as virus-infected cells or cancer cells. In general, such immunogenic polysaccharides are well known in the art and are encompassed for use in the methods and compositions as disclosed herein.

Polysaccharides are of native size or alternatively may be sized, for instance by microfluidisation, ultrasonic irradiation or by chemical treatment. The invention also covers oligosaccharides derived from *Mycobacterium tuberculosis*.

In some embodiments, an immunogenic polysaccharide for use in the TB-MAPS complex as disclosed herein can comprise any of the polysaccharides or oligosaccharides or lipopolysaccharides from *Mycobacterium tuberculosis*. In some embodiments, the immunogenic polysaccharide is selected from any of, or a combination of: alpha glucan, lipoarabinomannan, arabinomannan, or a Mtb polysaccharide comprising either arabinomannan and/or glucan. Other Mtb polysaccharides are envisioned for use in the TB-MAPS immunogenic composition as disclosed herein, such as those disclosed in Biochem J (1994) 297; 351-357, which is incorporated herein in its entirety by reference.

In some embodiments, an immunogenic polysaccharide for use in the TB-MAPS complex as disclosed herein can comprise more than one type of polysaccharide. For example, an immunogenic polysaccharide for use in the TB-MAPS complex as disclosed herein can comprise a portion of polysaccharide A (e.g., D-Glucan from Mtb), and the remaining portion of polysaccharide B (e.g., LipoArabinomannan from Mtb). The antigenic polysaccharide does not need to be from the same organism, e.g., for example an immunogenic polysaccharide for use in the TB-MAPS complex as disclosed herein can comprise a portion of polysaccharide A (e.g., D-Glucan from Mtb), and the remaining portion of polysaccharide B (e.g., a pneumococcus polysaccharide or other bacterial capsular PS or noncapsular PS). There is no limit to the amount of different types of immunogenic polysaccharides which can be used in a single MAPS backbone entity. In some embodiments, where the immunogenic polysaccharide for use in the TB-MAPS complex as disclosed herein is a branched polymer, the chain polysaccharide can be polysaccharide A, and the branches can be at least 1 or at least 2 or at least 3 or more different antigenic polysaccharides.

In some embodiments, the immunogenic polysaccharide for use in the TB-MAPS complex as disclosed herein is a branched polymer. In some embodiments, an immunogenic polysaccharide for use in the TB-MAPS complex as disclosed herein is a single chain polymer.

In some embodiments, the immunogenic polysaccharide for use in the TB-MAPS complex as disclosed herein comprises at least 10 carbohydrate repeating units, or at least 20, or at least 50, or at least 75, or at least 100, or at least 150, or at least 200, or at least 250, or at least 300, or at least 350, or at least 400, or at least 450, or at least 500, or more than 500 repeating units, inclusive.

In one aspect of the invention, the immunogenic polysaccharide (PS) for use in the TB-MAPS complex as disclosed herein can have a molecular mass of <500 kDa or >500 kDa. In another aspect of the invention, the PS has a molecular mass of <70 kDa. In some embodiments, an immunogenic polysaccharide for use in the TB-MAPS complex as disclosed herein is a large molecular weight polymer, e.g., a polymer can be of an average molecular weight of between about 425-500 kDa, inclusive, for example, at least 300 kDa, or at least 350 kDa, or at least 400 kDa, or at least 425 kDa, or at least 450 kDa, or at least 500 kDa or greater than 500 kDa, inclusive, but typically less than 500 kDa. In some embodiments, an immunogenic polysaccharide for use in the TB-MAPS complex as disclosed herein can be a small molecular weight polymer, e.g., a polymer can be of an average molecular weight of between about 60kDA to about 90 kDa, for example, at least 50 kDa, or at least 60 kDa, or at least 70 kDa, or at least 80 kDa, or at least 90 kDa, or at least 100 kDa, or greater than 100 kDa, inclusive, but generally less than about 120 kDa.

In some embodiments, the immunogenic polysaccharide for use in the TB-MAPS complex as disclosed herein is harvested and purified from a natural source; and in other embodiments, the polysaccharide is synthetic. Methods to produce synthetic polymers, including synthetic polysaccharides, are known to persons of ordinary skill and are encompassed in the compositions and methods as disclosed herein.

In some embodiments, the immunogenic polysaccharide or oligosaccharide included in a TB-MAPS immunogenic composition as disclosed herein has a molecular weight of between 20 kDa and 1000 kDa. In some embodiments, the immunogenic polysaccharide or oligosaccharide of a TB-MAPS immunogenic compositions as disclosed herein has a molecular weight of between 200 kDa and 5000 kDa, or a molecular weight range of between 70 kDa and 300 kDa, or a molecular weight range of between 500 kDa and 2500 kDa.

High molecular weight capsular polysaccharides are able to induce certain antibody immune responses due to a higher valence of the epitopes present on the antigenic surface. The isolation of "high molecular weight immunogenic capsular polysaccharides" is contemplated for use in the compositions and methods of the present invention. In some embodiments, high molecular weight immunogenic polysaccharide can be isolated and purified ranging from 20 kDa to 1000 kDa in molecular weight. In one embodiment, high molecular weight immunogenic polysaccharides can be isolated and purified ranging from 50 kDa to 700 kDa in molecular weight, or ranging from 50 kDa to 300 kDa in molecular weight, or ranging from 70 kDa to 300 kDa, or ranging from 90 kDa to 250 kDa, or ranging from 90 kDa to 150 kDa in molecular weight, or ranging from 90 kDa to 120 kDa in molecular weight, or ranging from 80 kDa to 120 kDa in molecular weight. In some embodiments, a immunogenic polysaccharides or oligosaccharides included in a TB-MAPS immunogenic compositions as disclosed herein has a high molecular weight of any of 70 kDa to 100 kDa in molecular weight; 70 kDa to 110 kDa in molecular weight; 70 kDa to 120 kDa in molecular weight; 70 kDa to 130 kDa in molecular weight; 70 kDa to 140 kDa in molecular weight; 70 kDa to 150 kDa in molecular weight; 70 kDa to 160 kDa in molecular weight; 80 kDa to 110 kDa in molecular weight; 80 kDa to 120 kDa in molecular weight; 80 kDa to 130 kDa in molecular weight; 80 kDa to 140 kDa in molecular weight; 80 kDa to 150 kDa in molecular weight; 80 kDa to 160 kDa in molecular weight; 90 kDa to 110 kDa in molecular weight; 90 kDa to 120 kDa in molecular weight; 90 kDa to 130 kDa in molecular weight; 90 kDa to 140 kDa in molecular weight; 90 kDa to 150 kDa in molecular weight; 90 kDa to 160 kDa in molecular weight; 100 kDa to 120 kDa in molecular weight; 100 kDa to 130 kDa in molecular weight; 100 kDa to 140 kDa in molecular weight; 100 kDa to 150 kDa in molecular weight; 100 kDa to 160 kDa in molecular weight; and similar desired molecular weight ranges. Any whole number integer within any of the above ranges is contemplated as an embodiment of the invention.

In one embodiment, the conjugate has a molecular weight of between about 50 kDa and about 5000 kDa in molecular weight. In one embodiment, the conjugate has a molecular weight of between about 200 kDa and about 5000 kDa in molecular weight. In one embodiment, the immunogenic conjugate has a molecular weight of between about 500 kDa and about 2500 kDa. In one embodiment, the immunogenic conjugate has a molecular weight of between about 500 kDa and about 2500 kDa. In one embodiment, the immunogenic conjugate has a molecular weight of between about 600 kDa and about 2800 kDa. In one embodiment, the immunogenic conjugate has a molecular weight of between about 700 kDa and about 2700 kDa. In one embodiment, the immunogenic conjugate has a molecular weight of between about 1000 kDa and about 2000 kDa; between about 1800 kDa and about 2500 kDa; between about 1100 kDa and about 2200 kDa; between about 1900 kDa and about 2700 kDa; between about 1200 kDa and about 2400 kDa; between about 1700 kDa and about 2600 kDa; between about 1300 kDa and about 2600 kDa; between about 1600 kDa and about 3000 kDa. Any whole number integer within any of the above ranges is contemplated as an embodiment of the TB-MAPS immunogenic composition as disclosed herein.

In one embodiment, the immunogenic polysaccharide has a degree of O-acetylation between 10-100%. In one embodiment, the degree of 0-acetylation is between 50-100%. In one embodiment, the degree of 0-acetylation is between 75-100%. In one embodiment, the immunogenic conjugate generates an antibody that is functional as measured by killing bacteria in either an animal efficacy model or via an opsonophagocytic killing assay.

In some embodiments, an immunogenic polysaccharide or oligosaccharide included in a TB-MAPS immunogenic composition as disclosed herein can be O-acetylated. In an embodiment, the degree of O-acetylation of capsular polysaccharide or oligosaccharide is 10-100%, 20-100%, 30-100%, 40-100%, 50-100%. 60-100%, 70-100%, 80-100%, 90-100%, 50-90%, 60-90%, 70-90% or 80-90%.

The degree of 0-acetylation of the polysaccharide or oligosaccharide can be determined by any method known in the art, for example, by proton NMR (Lemercinier and Jones 1996, Carbohydrate Research 296; 83-96, Jones and Lemercinier 2002, J Pharmaceutical and Biomedical analysis 30; 1233-1247, WO 05/033148 or WO 00/56357). A further commonly used method is that described by Hestrin (1949) J. Biol. Chem. 180; 249-261.

O-acetyl groups can be removed by hydrolysis, for example by treatment with a base such as anhydrous hydrazine (Konadu et al 1994; Infect. Immun. 62; 5048-5054) or treatment with 0.1N NaOH for 1-8 hours. In order to maintain high levels of O-acetylation on type 5 and/or 8 polysaccharide or oligosaccharide, treatments which would lead to hydrolysis of the O-acetyl groups are minimized. For example, treatment at extremes of pH are minimized.

In some embodiments, the immunogenic polysaccharides of the TB-MAPS immunogenic composition as disclosed herein are used to generate antibodies that are functional as measured by the killing of bacteria in an animal efficacy model or an opsonophagocytic killing assay that demonstrates that the antibodies kill the bacteria. Such functionality may not be observed using an assay that monitors the generation of antibodies alone, which is not indicative of the importance of 0-acetylation in efficacy.

Other Immunogenic Polysaccharides

In some embodiments, an immunogenic polysaccharide for use in the TB-MAPS complex as disclosed herein a polysaccharide or oligosaccharide that is not a *M. tuberculosis* polysaccharide. For example, in some embodiments an immunogenic polysaccharide for use in the TB-MAPS complex as disclosed herein can be a pneumococcal polysaccharide, e.g., a capsular polysaccharide from *Streptococcus pneumoniae* from any of the over 93 serotypes of pneumococcus that have been identified to date, for example, including but not limited to serotypes 1, 2, 3, 4, 5, 6A, 6B, 6C, 6D, 7F, 8, 9N, 9V, 10A, 11A, 12F, 14, 15B, 17F, 18C, 19A, 19F, 20, 22F, 23F, and 33F. Additional pneumococcal serotypes may be identified and included in the present TB-MAPS immunogenic composition as described herein. More than one pneumococcal polysaccharide can be included as the polymer backbone of the present immunogenic compositions or in a vaccine comprising the present TB-MAPS composition. In some embodiments, an immunogenic polysaccharide for use in the TB-MAPS complex as disclosed herein is Type 1 capsular polysaccharide (CP1) from *Streptococcus pneumoniae.*

In some embodiments, an immunogenic polysaccharide for use in the TB-MAPS complex as disclosed herein can comprises *N. meningitides* capsular polysaccharides from at least one, two, three or four of the serogroups A, C, W, W135, or Y. In some embodiments, an immunogenic polysaccharide for use in the TB-MAPS complex as disclosed herein is selected from the group consisting of: *Salmonella typhi* Vi capsular polysaccharide, pneumococcal capsular polysaccharides, pneumococcal cell wall polysaccharide, *Haemophilus influenzae* Type b (Hib) capsular polysaccharide, Haemophili polysaccharide, Meningococcal polysaccharide, polysaccharides or oligosaccharides from Gram-positive bacteria (e.g., *Staphylococcus aureus* capsular polysaccharide, *Bacillus anthracis* polysaccharide), *Streptococcus* polysaccharides (e.g., Gp A and Gp B), *Pseudomonas* polysaccharide, fungal polysaccharides (e.g., cryptococcys polysaccharides), viral polysaccharides (e.g., glycoprotein) and other bacterial capsular or cell wall polysaccharides. In some embodiments, an immunogenic polysaccharide is selected from any of the following, dextran, Vi polysaccharide of *Salmonella typhi*, pneumococcal capsular polysaccharide, pneumococcal cell wall polysaccharide (CWPS), meningococcal polysaccharide, *Haemophilus influenzae* type b polysaccharide, or any another polysaccharide of viral, prokaryotic, or eukaryotic origin.

In some embodiments, an immunogenic polysaccharide for use in the TB-MAPS complex as disclosed herein is selected from the group consisting of: *Salmonella typhi* Vi capsular polysaccharides, pneumococcal capsular polysaccharides, pneumococcal cell wall polysaccharides, *Haemophilus influenzae* Type b (Hib) polysaccharides, Haemophili polysaccharides, Meningococcal polysaccharides, polysaccharides or oligosaccharides or lipopolysaccharides from Gram-positive bacteria (e.g., *Staphylococcus aureus* capsular polysaccharides, *Bacillus anthracis* polysaccharides), *Streptococcus* polysaccharides (e.g., Gp A and Gp B), *Pseudomonas* polysaccharides, polysaccharides or oligosaccharides or lipopolysaccharides from Gram-negative bacteria, other bacterial capsular or cell wall polysaccharides, fungal polysaccharides (e.g., *cryptococcus* polysaccharides), viral polysaccharides (e.g., glycoprotein), or polysaccharides derived from cancer cells.

In some embodiments, an immunogenic polysaccharide for use in the TB-MAPS complex as disclosed herein consists of or comprises an antigenic sugar moiety. For example, in some embodiments, a polysaccharide for use in the methods and immunogenic compositions as disclosed herein is a Vi polysaccharide of *Salmonella typhi.* The Vi capsular polysaccharide has been developed against bacterial enteric infections, such as typhoid fever. Robbins et al., 150 J. Infect. Dis. 436 (1984); Levine et al., 7 Baillieres Clin. Gastroenterol. 501 (1993). Vi is a polymer of $\alpha$-1→4-galacturonic acid with an N acetyl at position C-2 and variable 0-acetylation at C-3. The virulence of *S. typhi* correlates with the expression of this molecule. Sharma et al., 101 PNAS 17492 (2004). The Vi polysaccharide vaccine of *S. typhi* has several advantages: Side effects are infrequent and mild, a single dose yields consistent immunogenicity and efficacy. Vi polysaccharide may be reliably standardized by physicochemical methods verified for other polysaccharide vaccines, Vi is stable at room temperature and it may be administered simultaneously with other vaccines without affecting immunogenicity and tolerability. Azze et al., 21 Vaccine 2758 (2003).

Thus, the Vi polysaccharide of *S. typhi* may be cross-linked to a first affinity molecule as disclosed herein, for attaching at least one antigen to the polysaccharide. In some embodiments, the antigen can be from the same or from another organism, such that the resulting immunogenic composition confers at least some level of immunity against one pathogen, or two different pathogens: if the antigen confers protection against Mtb, an immunogenic composition where the polymer scaffold is a Vi polysaccharide can raise an immunogenic response against both *S. typhi* and Mtb. Other examples include combining sugars from encapsulated bacteria (such as meningococcus, *S. aureus*, pneumococcus, Hib, etc.) and tuberculosis antigens, to provide an immunogenic composition that raises an immune response against two different pathogens.

In some embodiments, a polysaccharide for use in the TB-MAPS complex as disclosed herein is a capsular polysaccharide (CP) or oligosaccharide. In some embodiments, a polysaccharide for use in the TB-MAPS complex as disclosed herein is a noncapsular polysaccharide or oligosaccharide.

Other immunogenic polysaccharide (PS) for use in the TB-MAPS complex as disclosed herein can include bacterial cell wall polysaccharides (CWPS), or carbohydrate antigens of cancers.

In some embodiments, an immunogenic polysaccharide for use in the TB-MAPS complex as disclosed herein that can serve as a backbone for one or more TB-antigens or non-TB antigen types are exemplified in Table 2:

TABLE 2

Example immunogenic polysaccharides for the TB-MAPS backbone and associated example antigens

| Polysaccharide | | Protein Antigens: Typical Number of antigens attached to the PS | Protein Antigens: Exemplary Antigen origins |
|---|---|---|---|
| Dextran | D90 (60-90 KD) | Two | *Mycobacterium tuberculosis* |
| | D150 (150 KD) | Three | *Mycobacterium tuberculosis* |
| | D270 (270 KD) | Three | *Mycobacterium tuberculosis* |
| | D500 (425-575 KD) | two; three; six | *Mycobacterium tuberculosis* |

TABLE 2-continued

Example immunogenic polysaccharides for the TB-MAPS backbone and associated example antigens

| Polysaccharide | | Protein Antigens: Typical Number of antigens attached to the PS | Protein Antigens: Exemplary Antigen origins |
|---|---|---|---|
| Pneumococcal capsular polysaccharide | Serotype 1 | one, two, three, five | *pneumococcus, Mycobacterium tuberculosis, Staphylococcus aureus* |
| | Serotype 3 | Five | *pneumococcus, Mycobacterium tuberculosis, Staphylococcus aureus* |
| | Serotype 5 | one; two; three; five | *pneumococcus, Mycobacterium tuberculosis, Staphylococcus aureus* |
| | Serotype 6B | Two | *Pneumococcus, Staphylococcus aureus* |
| | Serotype 7 | Three | *Pneumococcus, Staphylococcus aureus* |
| | Serotype 14 | one; two; three; five | *pneumococcus, Mycobacterium tuberculosis* |
| | Serotype 19 | Three | *Pneumococcus, Staphylococcus aureus* |
| *Mycobacterium tuberculosis* | D-Glucan | one; two; three; four, five, six | *Mycobacterium tuberculosis* |
| | LipoArabinomannan | one; two; three; four, five, six | *Mycobacterium tuberculosis* |
| *Staphylococcus aureus* Pneumococcal cell wall polysaccharide | | one; two; three; four, five, six, | *Pneumococcus, Mycobacterium tuberculosis, Staphylococcus aureus* |
| *S. typhi* Vi polysaccharide | | one; two; three; four, five, six | *Pneumococcus, Mycobacterium tuberculosis, Staphylococcus aureus* |

In some embodiments, an immunogenic polysaccharide for use in the TB-MAPS complex as disclosed herein can comprise additional polymers, for example, polyethylene glycol-based polymers, poly(ortho ester) polymers, polyacryl carriers, PLGA, polyethylenimine (PEI), polyamidoamine (PAMAM) dendrimers, β-amino ester polymers, polyphosphoester (PPE), liposomes, polymerosomes, nucleic acids, phosphorothioated oligonucleotides, chitosan, silk, polymeric micelles, protein polymers, virus particles, virus-like-particles (VLPs) or other micro-particles. See, e.g., El-Sayed et al., *Smart Polymer Carriers for Enhanced Intracellular Delivery of Therapeutic Molecules,* 5 Exp. Op. Biol. Therapy, 23 (2005). Biocompatible polymers developed for nucleic acid delivery may be adapted for use as a backbone herein. See, e.g., Biocompatible Pol. Nucl. Acid. Deliv. (Domb et al., eds., John Wiley & Sons, Inc. Hoboken, NJ, 2011).

For example, VLPs resemble viruses, but are non-infectious because they do not contain any viral genetic material. The expression, including recombinant expression, of viral structural proteins, such as envelope or capsid components, can result in the self-assembly of VLPs. VLPs have been produced from components of a wide variety of virus families including Parvoviridae (e.g., adeno-associated virus), Retroviridae (e.g., HIV), and Flaviviridae (e.g., Hepatitis B or C viruses). VLPs can be produced in a variety of cell culture systems including mammalian cell lines, insect cell lines, yeast, and plant cells. Recombinant VLPs are particularly advantageous because the viral component can be fused to recombinant antigens as described herein.

*M. tuberculosis* Antigens

It is well recognized that any single animal model of *Mycobacterium tuberculosis* infection is unlikely to adequately represent the pathophysiology of disease in humans; therefore, evaluation of any potential candidate in several models would appear prudent. At the same time, the large number of virulence factors (including polysaccharides, surface proteins, and secreted toxins produced by *M. tuberculosis* (Mtb), may provide credence to the idea that multiple, genetically conserved antigens should be included in a candidate vaccine. Finally, a closer examination of mechanisms of immunity to *M. tuberculosis* (Mtb) in humans may also provide clues for an effective vaccine strategy. A growing body of literature now suggests that T-cell immunity, the other arm of acquired host defense, plays a critical role in TB defense. Indeed, individuals previously infected with *M. tuberculosis* (Mtb), or with suppressed or impaired cellular immunity, are at very high risk for *M. tuberculosis* (Mtb) infection. Therefore, the inventors have developed a TB-MAPS immunogenic composition as disclosed herein that induces both B- and T-cell acquired immune responses in the organism may provide optimal protection against this organism.

Herein, the inventors have generated a TB-MAPS immunogenic composition comprising containing several conserved Mtb antigens to elicit a broad range of immune responses. More specifically, the inventors demonstrate a vaccine platform, referred herein as the *Mycobacterium tuberculosis* Multiple-Antigen-Presenting-System (TB-MAPS), which comprises an immunogenic polysaccharide with affinity-coupled complexes of Mtb antigens that can induce broad B- and T-cell responses. The immune response generated with the TB-MAPS vaccine was compared to a multi-component TB subunit vaccine using a conventional approach (i.e., immunization with purified proteins alone, and not attached to an immunogenic polysaccharide). In addition, the immune response after administration of a TB-MAPS composition was compared to the response elicited by BCG vaccination, and in comparison with administration of the TB-MAPS composition at substantially the same time or at a later time point as administration of a BCG vaccine, where they were administered at a different site. The inventors demonstrated the immunogenicity of these vaccines (i.e., the Mtb antigens alone, or Mtb antigens as part of the TB-MAPS complex) and different strategies (TB-MAPS alone, BCG alone, or TB-MAPS with BCG, administered at the same time or at a later time point) in mice, compared their efficacy to elicit a T-Cell response, and determined their capacity to provide protection against pulmonary TB.

An immunogenic Mtb antigen for use in the immunogenic compositions and methods described herein can be any Mtb antigen, including, but not limited to pathogenic peptides, toxins, toxoids, subunits thereof, or combinations thereof. In some embodiments, a Mtb antigen, which in some embodiments, is fused to the complementary affinity molecule, e.g., a biotin-binding protein such as rhizavidin as disclosed herein, can be any Mtb antigen, peptide, polypeptide, or polysaccharide, expressed by *Mycobacterium tuberculosis* bacterium.

In some embodiments, the TB-MAPS comprises at least one or more Mtb antigens, where the Mtb antigen is an antigenic protein or polypeptide, and can be selected from any of the group of: Early secreted antigen target-6 (ESAT6), Culture filtrate protein-10 (CFP10), MPT51, MPT64, MPT83, TB9.8, TB10.4, Proline Proline Glutamic acid-41 (PPE41), and Proline Glutamic acid-25 (PE25), or a an antigenic fragment or portion thereof. In some embodiments, the TB-MAPS immunogenic composition as disclosed herein comprises one or more peptide or polypeptide fragments of these proteins, as long as the protein fragment is antigenic, and/or comprises one or more epitopes to induce an immune response.

Exemplary Mtb antigens for use in the TB-MAPS composition as disclosed herein can be selected from any of, for example, but are not limited to: Early secreted antigen target-6 (ESAT6), Culture filtrate protein-10 (CFP10), MPT51, MPT64, MPT83, TB9.8, TB10.4, Proline Proline Glutamic acid-41 (PPE41), and Proline Glutamic acid-25 (PE25).

In some embodiments, a TB-MAPS immunogenic composition as disclosed herein comprises at least 2, or at least 3, or at least 4, or at least 5, or at least 6, or at least 7, or at least 8, or all 9 peptide or polypeptide Mtb-antigens of ESAT6, CFP10 (1-40), CFP10 (45-80), MPT64 (25-228), MPT83 (58-220), and MPT51 (33-299), TB9.8, TB10.4, PPE41, and PE25, or proteins or peptides of at least 85% sequence identity thereto. It is envisioned that any of the above listed Mtb antigens can be substituted for a different TB peptide or polypeptide antigen known to one of ordinary skill in the art. Exemplary Mtb antigens can be any peptide or polypeptide comprising at least part of TbH9 (also known as Mtb 39A), DPV (also known as Mtb8.4), 381, Mtb41, Mtb40, Mtb32A, MPT64, MPT83, Mtb9.9A, Mtb16, Mtb72f, Mtb59f, Mtb88f, Mtb71f, Mtb46f and Mtb31f, wherein "f" indicates that it is a fusion or two or more proteins, provided that the any peptide or polypeptide is immunogenic, or is antigenic. Other Mtb antigens can be used, and are disclosed herein.

MPT51

MPT51 (also known as Rv 3803c) is a *M. tuberculosis* protein found in the genome of mycobacteria and binds to the fibronectin of the extracellular matrix, which may have a role in host tissue attachment and virulence. The MPT51 antigen is specific to *M. tuberculosis.*

MPT51 Sequence: In some embodiments, the MPT51 antigen for use in the TB-MAPS immunogenic composition as disclosed herein comprises a polypeptide or peptide comprising at least part of SEQ ID NO: 4, which corresponds to the full length MPT51 mature protein from *M. tuberculosis.*

```
                                          (SEQ ID NO: 4)
MKGRSALLRALWIAALSFGLGGVAVAAEPTAKAAPYENLMVPSPSMGRDI

PVAFLAGGPHAVYLLDAFNAGPDVSNWVTAGNAMNTLAGKGISVVAPAGG

AYSMYNMWEQDGSKQWDTFLSAELPDWLAANRGLAPGGHAAVGAAQGGYG

AMALAAFHPDRFGFAGSMSGFLYPSNTTTNGAIAAGMQQFGGVDTNGMWG

APQLGRWKWHDPWVHASLLAQNNTRVWVWSPTNPGASDPAAMIGQAAEAM

GNSRMFYNQYRSVGGHNGHFDFPASGDNGWGSWAPQLGAMSGDIVGAIR
```

In some embodiments, the MPT51 antigen for use in the TB-MAPS immunogenic composition as disclosed herein is MPT51 (33-299) (SEQ ID NO: 3), or a fragment or protein of at least 85% amino acid sequence identity thereto. SEQ ID NO: 3 has the following amino acid sequence:

```
                                          (SEQ ID NO: 3)
AAPYENLMVPSPSMGRDIPVAFLAGGPHAVYLLDAFNAGPDVSNWVTAGN

AMNTLAGKGISVVAPAGGAYSMYTNWEQDGSKQWDTFLSAELPDWLAANR

GLAPGGHAAVGAAQGGYGAMALAAFHPDRFGFAGSMSGFLYPSNTTTNGA

IAAGMQQFGGVDTNGMWGAPQLGRWKWHDPWVHASLLAQNNTRVWVWSPT

NPGASDPAAMIGQAAEAMGNSRMFYNQYRSVGGHNGHFDFPASGDNGWGS

WAPQLGAMSGDIVGAIR
```

In one embodiment, a TB-MAPS composition may include a polypeptide, peptide, or protein that is or is at least 70%, 75%, 80%, 85%, 90%, 95%, 96%, 97%, 98%, or 99% identical or similar to a MPT51 of SEQ ID NO: 3 or SEQ ID NO: 4. In certain aspects a MPT51 antigen peptide or polypeptide will have all, or part of the amino acid sequence of SEQ ID NO: 3 or SEQ ID NO: 4, e.g., will comprise at least 50, or at least 60, or at least 70, or at least 80, or at least 90, or at least 100, or at least 120, or at least 140, or at least 160, or at least 180, or at least 200, or at least 220 or at least 240, or at least 260, or at least 280, or at least 300 amino acids of SEQ ID NO: 3 or SEQ ID NO: 4. In one embodiment, a MPT51 antigen peptide or polypeptide present in the TB-MAPS immunogenic composition is a polypeptide, peptide, or protein that is or is at least 70%, 75%, 80%, 85%, 90%, 95%, 96%, 97%, 98%, or 99% identical or similar to SEQ ID NO: 3 or SEQ ID NO: 4.

The term "MPT51 protein" refers to a protein that includes isolated wild-type MPT51 polypeptides from *M. tuberculosis* and segments thereof, as well as variants that stimulate an immune response against *M. tuberculosis* bacteria MPT51 proteins.

Early Secreted Antigen Target-6 (ESAT6)

Early secretory antigenic target 6 (ESAT6) is a 6 kDa protein produced by *Mycobacterium tuberculosis*. ESAT6 is a secretory protein and potent T cell antigen. It is used in diagnosis TB by the whole blood interferon γ test QuantiFERON-TB Gold, in conjunction with CFP-10. ESAT-6 has been shown to directly bind to the TLR2 receptor, inhibiting downstream signal transduction.

Along with the ESX-1 secretion system, ESAT-6 and Culture filtrate protein-10 (CFP-10) have been implicated in several virulence mechanisms of mycobacteria. They modulate both innate and adaptive immune responses and inactivation of ESAT-6 results in dramatically reduced virulence of *M. tuberculosis*. ESAT-6 induces apoptosis of macrophages by activating caspase expression. ESAT-6, CFP-10 and the ESAT6:CFP-10 complex inhibit LPS-induced NF-kappaB dependent gene expression by suppressing production of reactive oxygen species. ESAT-6 alone or in complex with CFP-10 has also been shown to interact with host proteins like laminin on the basolateral surface of pneumocytes leading to lysis of these cells that aid in the dissemination of pulmonary *M. tuberculosis*.

ESAT6 Sequence: In some embodiments, the ESAT6 antigen for use in the TB-MAPS immunogenic composition as disclosed herein comprises a polypeptide or peptide comprising at least part of SEQ II NO: 5, which corresponds to the full length ESAT6 mature protein from *M. tuberculosis*.

(SEQ ID NO: 5)
MTEQQWNFAGIEAAASAIQGNVTSIHSLLDEGKQSLTKLAAAWGGSGSEA

YQGVQQKWDATATELNNALQNLARTISEAGQAMASTEGNVTGMFA

In one embodiment, a TB-MAPS composition may include a polypeptide, peptide, or protein that is or is at least 70%, 75%, 80%, 85%, 90%, 95%, 96%, 97%, 98%, or 99% identical or similar to a ESAT6 of SEQ ID NO: 5. In certain aspects a ESAT6 antigen peptide or polypeptide will have all, or part of the amino acid sequence of SEQ ID NO: 5, e.g., will comprise at least 50, or at least 60, or at least 70, or at least 80, or at least 90, or at least 100 amino acids of SEQ ID NO: 5. In one embodiment, a ESAT6 antigen peptide or polypeptide present in the TB-MAPS immunogenic composition is a polypeptide, peptide, or protein that is or is at least 70%, 75%, 80%, 85%, 90%, 95%, 96%, 97%, 98%, or 99% identical or similar to SEQ ID NO: 5.

The term "ESAT6 protein" refers to a protein that includes isolated wild-type ESAT6 polypeptides from *M. tuberculosis* bacteria and segments thereof, as well as variants that stimulate an immune response against *M. tuberculosis* bacteria ESAT6 proteins.

Culture Filtrate Protein-10 (CFP10)

10-kDa culture filtrate protein (CFP-10) is an antigen that contributes to the virulence *Mycobacterium tuberculosis*. CFP-10 forms a tight 1: heterodimeric complex with 6kDaA early secreted antigen target (ESAT-6). In the mycobacterial cell, these two proteins are interdependent on each other for stability. The ESAT-6/CFP-10 complex is secreted by the ESX-1 secretion system, also known as the RD1 region. *Mycobacterium tuberculosis* uses this ESX-1 secretion system to deliver virulence factors into host macrophage and monocyte white blood cells during infection. In *Mycobacterium tuberculosis*, the core components of the whole ESX-1 secretion system include Rv3877, and two AAA ATPases, including Rv3870 and Rv3871, a cytosolic protein. The ESAT-6/CFP-10 heterodimer complex is targeted for secretion by a C-terminal signal sequence on CFP-10 that is recognized by the cytosolic Rv3871 protein. Rv3871 then interacts with the CFP-10 C-terminal, and escorts the ESAT-6/CFP-10 complex to Rv3870 and Rv3877, a multi-transmembrane protein which makes up the pore that spans the cytosolic membrane of the virulent host cell. Once ESAT-6/CFP-10 is next to the membrane of the virulent host cell, the CFP-10 C-terminal attaches and binds itself to the cells surface. The ESAT6/CFP-10 complex's secretion and attachment to the virulent host cell shows its contribution to the pathogenicity of *Mycobacterium tuberculosis*.

The 10-kDa culture filtrate protein (CFP-10) and 6kDaA early secreted antigen target (ESAT6) complex is a 100 amino-acid sequence protein. ESAT6/CFP-10 has a hydrophobic nature as well as a high content of α-helical structures. Resonance structure analysis of the complex reveals two similar helix-turn-helix hairpin structures formed by the individual proteins, which lie anti-parallel to each other and forms a four-helix bundle. Its long flexible arm projecting off the four-helix bundle, formed by the seven amino-acid C-terminal of CFP-10, is essential for binding and attaching to the surface of host white blood cells; such as macrophages and monocytes. If this C-terminus is cleaved off, the complex shows greatly reduced attachment ability.

CFP10 Sequence: In some embodiments, the CFP10 antigen for use in the TB-MAPS immunogenic composition as disclosed herein comprises a polypeptide or peptide comprising at least part of SEQ ID NO: 8, which corresponds to the full length CFP-10 mature protein from *M. tuberculosis*.

(SEQ ID NO: 8)
MAEMKTDAATLAQEAGNFERISGDLKTQIDQVESTAGSLQGQWRGAAGTA

AQAAVVRFQEAANKQKQELDEISTNIRQAGVQYSRADEEQQQALSSQMGF

In some embodiments, the CFP10 antigen for use in the TB-MAPS immunogenic composition as disclosed herein is CFP10 (1-41) (SEQ ID NO: 6), or a fragment or protein of at least 85% amino acid sequence identity thereto. SEQ ID NO: 6 has the following amino acid sequence:

(SEQ ID NO: 6)
MAEMKTDAATLAQEAGNFERISGDLKTQIDQVESTAGSLQG

In some embodiments, the CFP10 antigen for use in the TB-MAPS immunogenic composition as disclosed herein is CFP10 (45-80) (SEQ ID NO: 7), or a fragment or protein of at least 85% amino acid sequence identity thereto. SEQ ID NO: 7 has the following amino acid sequence:

(SEQ ID NO: 7)
GAAGTAAQAAVVRFQEAANKQKQELDEISTNIRQAG

In one embodiment, a TB-MAPS composition may include a polypeptide, peptide, or protein that is or is at least 70%, 75%, 80%, 85%, 90%, 95%, 96%, 97%, 98%, or 99% identical or similar to a CFP10 of SEQ ID NO: 6, SEQ ID NO: 7, or SEQ ID NO: 8. In certain aspects a CFP10 antigen peptide or polypeptide will have all, or part of the amino acid sequence of SEQ ID NO: 6, SEQ ID NO: 7, or SEQ ID NO: 8, e.g., will comprise at least 50, or at least 60, or at least 70, or at least 80, or at least 90, or at least 100 amino acids of SEQ ID NO: 6, SEQ ID NO: 7, or SEQ ID NO: 8. In one embodiment, a CFP10 antigen peptide or polypeptide present in the TB-MAPS immunogenic composition is a polypeptide, peptide, or protein that is or is at least 70%, 75%, 80%, 85%, 90%, 95%, 96%, 97%, 98%, or 99% identical or similar to SEQ ID NO: 6, SEQ ID NO: 7, or SEQ ID NO: 8.

The term "CFP10 protein" refers to a protein that includes isolated wild-type CFP10 polypeptides from *M. tuberculosis* bacteria and segments thereof, as well as variants that stimulate an immune response against *M. tuberculosis* bacteria CFP10 proteins.

MPT64

MPT64 is one of the major culture filtrate protein (24 kDa) encoded by the RD2 region genes and has been shown to be a specific antigen that differentiates the *M. tuberculosis* complex from the mycobacteria other than tuberculosis (MOTT) species.

MPT64 Sequence: In some embodiments, the MPT64 antigen for use in the TB-MAPS immunogenic composition as disclosed herein comprises a polypeptide or peptide comprising at least part of SEQ ID NO: 10, which corresponds to the full length MPT64 mature protein from *M. tuberculosis*.

(SEQ ID NO: 10)
MRIKIFMLVTAVVLLCCSGVATAAPKTYCEELKGTDTGQACQIQMSDPAY
NINISLPSYYPDQKSLENYIAQTRDKFLSAATSSTPREAPYELNITSATY
QSAIPPRGTQAVVLKVYQNAGGTHPTTTYKAFDWDQAYRKPITYDTLWQA
DTDPLPVVFPIVQGELSKQTGQQVSIAPNAGLDPVNYQNFAVTNDGVIFF
FNPGELLPEAAGPTQVLVPRSAIDSMLA

In some embodiments, the MPT64 antigen for use in the TB-MAPS immunogenic composition as disclosed herein is MPT64 (25-228) (SEQ ID NO: 9), or a fragment or protein of at least 85% amino acid sequence identity thereto. SEQ ID NO: 9 has the following amino acid sequence:

(SEQ ID NO: 9)
PKTYCEELKGTDTGQACQIQMSDPAYNINISLPSYYPDQKSLENYIAQTR
DKFLSAATSSTPREAPYELNITSATYQSAIPPRGTQAVVLKVYQNAGGTH
PTTTYKAFDWDQAYRKPITYDTLWQADTDPLPVVFPIVQGELSKQTGQQV
SIAPNAGLDPVNYQNFAVTNDGVIFFFNPGELLPEAAGPTQVLVPRSAID
SMLA

In one embodiment, a TB-MAPS composition may include a polypeptide, peptide, or protein that is or is at least 70%, 75%, 80%, 85%, 90%, 95%, 96%, 97%, 98%, or 99% identical or similar to a MPT64 of SEQ ID NO: 9 or SEQ ID NO: 10. In certain aspects a MPT64 antigen peptide or polypeptide will have all, or part of the amino acid sequence of SEQ ID NO: 9, e.g., will comprise at least 50, or at least 60, or at least 70, or at least 80, or at least 90, or at least 100, or at least 120, or at least 140, or at least 160, or at least 180, or at least 200, or at least 220 or at least 240 amino acids of SEQ ID NO: 9 or SEQ ID NO. In one embodiment, a MPT64 antigen peptide or polypeptide present in the TB-MAPS immunogenic composition is a polypeptide, peptide, or protein that is or is at least 70%, 75%, 80%, 85%, 90%, 95%, 96%, 97%, 98%, or 99% identical or similar to SEQ ID NO: 9 or SEQ ID NO 10.

The term "MPT64 protein" refers to a protein that includes isolated wild-type MPT64 polypeptides from *M. tuberculosis* bacteria and segments thereof, as well as variants that stimulate an immune response against *M. tuberculosis* bacteria MPT64 proteins.

MPT83

MPT83 (Rv2873) is a cell wall-associated lipo-glycoprotein of *M. tuberculosis*, whose function is unknown, although it has been suggested to play a role in adhesion and dissemination based on sequence analysis. Its homologues in *M. bovis*, MPB83 and MBP70, are sero-dominant antigens during *M. bovis* infection in both cattle and badgers. DNA vaccination studies in cattle revealed that MPB83 is immunogenic, generating strong T cell and B cell responses. Interestingly, pre-treatment of animals with anti-MPB83 antibodies resulted in increased survival during *M. bovis* infection. The expression of MBP83 varies between different strains of BCG owing to a point mutation in the positive regulator, Sigma factor K (SigK). During in vitro culture *M. tuberculosis* expresses relatively small quantities of MPT83 and MPT70, but the expression level of MPT83 is increased during infection.

MPT83 Sequence: In some embodiments, the MPT83 antigen for use in the TB-MAPS immunogenic composition as disclosed herein comprises a polypeptide or peptide comprising at least part of SEQ ID NO: 12, which corresponds to the full length MPT83 mature protein from *M. tuberculosis*.

(SEQ ID NO: 12)
MINVQAKPAAAASLAAIAIAFLAGCSSTKPVSQDTSPKPATSPAAPVTTA
AMADPAADLIGRGCAQYAAQNPTGPGSVAGMAQDPVATAASNNPMLSTLT
SALSGKLNPDVNLVDTLNGGEYTVFAPTNAAFDKLPAATIDQLKTDAKLL
SSILTYHVIAGQASPSRIDGTHQTLQGADLTVIGARDDLMVNNAGLVCGG
VHTANATVYMIDTVLMPPAQ

In some embodiments, the MPT83 antigen for use in the TB-MAPS immunogenic composition as disclosed herein is MPT83 (58-220) (SEQ ID NO: 11), or a fragment or protein of at least 85% amino acid sequence identity thereto. SEQ ID NO: 11 has the following amino acid sequence:

(SEQ ID NO: 11)
DLIGRGCAQYAAQNPTGPGSVAGMAQDPVATAASNNPMLSTLTSALSGKL
NPDVNLVDTLNGGEYTVFAPTNAAFDKLPAATIDQLKTDAKLLSSILTYH
VIAGQASPSRIDGTHQTLQGADLTVIGARDDLMVNNAGLVCGGVHTANAT
VYMIDTVLMPPAQ

In one embodiment, a TB-MAPS composition may include a polypeptide, peptide, or protein that is or is at least 70%, 75%, 80%, 85%, 90%, 95%, 96%, 97%, 98%, or 99% identical or similar to a MPT83 of SEQ ID NO: 11 or SEQ ID NO: 12. In certain aspects a MPT83 antigen peptide or polypeptide will have all, or part of the amino acid sequence of SEQ ID NO: 11 or SEQ ID NO: 12, e.g., will comprise at least 50, or at least 60, or at least 70, or at least 80, or at least 90, or at least 100, or at least 120, or at least 140, or at least 160, or at least 180, or at least 200, or at least 220 amino acids of SEQ ID NO: 11 or SEQ ID NO: 12. In one embodiment, a MPT83 antigen peptide or polypeptide present in the TB-MAPS immunogenic composition is a polypeptide, peptide, or protein that is or is at least 70%, 75%, 80%, 85%, 90%, 95%, 96%, 97%, 98%, or 99% identical or similar to SEQ ID NO: 11 or SEQ ID NO: 12.

The term "MPT83 protein" refers to a protein that includes isolated wild-type MPT83 polypeptides from *M. tuberculosis* bacteria and segments thereof, as well as variants that stimulate an immune response against *M. tuberculosis* bacteria MPT83 proteins.

TB9.8

TB9.8 is a low-molecular-mass culture filtrate antigen of *M. tuberculosis*.

TB9.8 Sequence: In some embodiments, the TB9.8 antigen for use in the TB-MAPS immunogenic composition as disclosed herein comprises a polypeptide or peptide comprising at least part of SEQ ID NO: 13, which corresponds to the full length TB9.8 mature protein from *M. tuberculosis*.

(SEQ ID NO: 13)
MSLLDAHIPQLVASQSAFAAKAGLMRHTIGQAEQAAMSAQAFHQGESSAA

FQAAHARFVAAAAKVNTLLDVAQANLGEAAGTYVAADAAAASTYTGF

In one embodiment, a TB-MAPS composition may include a polypeptide, peptide, or protein that is or is at least 70%, 75%, 80%, 85%, 90%, 95%, 96%, 97%, 98%, or 99% identical or similar to a TB9.8 of SEQ ID NO: 13. In certain aspects a TB9.8 antigen peptide or polypeptide will have all, or part of the amino acid sequence of SEQ ID NO: 13, e.g., will comprise at least 50, or at least 60, or at least 70, or at least 80, or at least 90, or at least 100, amino acids of SEQ ID NO: 13. In one embodiment, a TB9.8 antigen peptide or polypeptide present in the TB-MAPS immunogenic composition is a polypeptide, peptide, or protein that is or is at least 70%, 75%, 80%, 85%, 90%, 95%, 96%, 97%, 98%, or 99% identical or similar to SEQ ID NO: 13.

The term "TB9.8 protein" refers to a protein that includes isolated wild-type TB9.8 polypeptides from *M. tuberculosis* bacteria and segments thereof, as well as variants that stimulate an immune response against *M. tuberculosis* bacteria TB9.8 proteins.

TB10.4

TB10.4 is a low-molecular-mass culture filtrate antigen of *M. tuberculosis*.

TB10.4 Sequence: In some embodiments, the TB10.4 antigen for use in the TB-MAPS immunogenic composition as disclosed herein comprises a polypeptide or peptide comprising at least part of SEQ ID NO: 14, which corresponds to the full length TB10.4 mature protein from *M. tuberculosis*.

(SEQ ID NO: 14)
MSQIMYNYPAMLGHAGDMAGYAGTLQSLGAEIAVEQAALQSAWQGDTGIT

YQAWQAQWNQAMEDLVRAYHAMSSTHEANTMAMMARDTAEAAKWGG

In one embodiment, a TB-MAPS composition may include a polypeptide, peptide, or protein that is or is at least 70%, 75%, 80%, 85%, 90%, 95%, 96%, 97%, 98%, or 99% identical or similar to a TB10.4 of SEQ ID NO: 14. In certain aspects a TB10.4 antigen peptide or polypeptide will have all, or part of the amino acid sequence of SEQ ID NO: 14, e.g., will comprise at least 50, or at least 60, or at least 70, or at least 80, or at least 90, or at least 100, amino acids of SEQ ID NO: 14. In one embodiment, a TB10.4 antigen peptide or polypeptide present in the TB-MAPS immunogenic composition is a polypeptide, peptide, or protein that is or is at least 70%, 75%, 80%, 85%, 90%, 95%, 96%, 97%, 98%, or 99% identical or similar to SEQ ID NO: 14.

The term "TB10.4 protein" refers to a protein that includes isolated wild-type TB10.4 polypeptides from *M. tuberculosis* bacteria and segments thereof, as well as variants that stimulate an immune response against *M. tuberculosis* bacteria TB10.4 proteins.

PPE41

In 1998, the Mtb genome highlighted, for the first time, the presence of genes grouped into two large families that were shown to comprise approximately 7% of the genome 44 size. This was a surprise to the field of mycobacteriology, and led to the speculation that this multitude of repetitive genes, found mostly in slow-growing pathogenic mycobacteria, likely influence the function and immuno-pathogenicity of Mtb. Based on the presence of conserved Pro-Glu (PE) and Pro-Pro-Glu (PPE) motifs at their N-terminus, the encoded genes were named PE and PPE respectively. The laboratory strain of Mtb H37Rv contains 99 pe genes, 61 being in the PE-PGRS (polymorphic GC-rich sequences), a subfamily earlier used for fingerprinting Mtb strains, and 69 ppe genes. The proteins belonging to the PE family share a highly conserved N-terminal domain about 90-110 amino acids in length. The PE family is further divided into the PE and PE PGRS subfamilies. PE-PGRS proteins are characterized by the presence of a polymorphic domain, rich in Gly-Gly-Ala/Gly-Gly-Asn amino acid repeats, which can vary in sequence and size. Pe-pgrs genes are found scattered throughout the genome and are mostly not co-transcribed with other genes. Conversely, many of the pe genes are adjacent to ppe genes and a number of studies have demonstrated that these pe/ppe couplets are co-expressed. At least some of the corresponding proteins are found as heterodimers that are present on the cell surface or secreted.

PPE41 Sequence: In some embodiments, the PPE41 antigen for use in the TB-MAPS immunogenic composition as disclosed herein comprises a polypeptide or peptide comprising at least part of SEQ ID NO: 15, which corresponds to the full length PPE41 mature protein from *M. tuberculosis*.

(SEQ ID NO: 15)
MHFEAYPPEVNSANIYAGPGPDSMLAAARAWRSLDVEMTAVQRSFNRTLL

SLMDAWAGPVVMQLMEAAKPFVRWLTDLCVQLSEVERQIHEIVRAYEWAH

HDMVPLAQIYNNRAERQILIDNNALGQFTAQIADLDQEYDDFWDEDGEVM

RDYRLRVSDALSKLTPWKAPPPIAHSTVLVAPVSPSTASSRTDT

In one embodiment, a TB-MAPS composition may include a polypeptide, peptide, or protein that is or is at least 70%, 75%, 80%, 85%, 90%, 95%, 96%, 97%, 98%, or 99% identical or similar to a PPE41 of SEQ ID NO: 15. In certain aspects a PPE41 antigen peptide or polypeptide will have all, or part of the amino acid sequence of SEQ ID NO: 15, e.g., will comprise at least 50, or at least 60, or at least 70, or at least 80, or at least 90, or at least 100, or at least 120, or at least 140, or at least 160, or at least 180, or at least 200 amino acids of SEQ ID NO: 15. In one embodiment, a PPE41 antigen peptide or polypeptide present in the TB-MAPS immunogenic composition is a polypeptide, peptide, or protein that is or is at least 70%, 75%, 80%, 85%, 90%, 95%, 96%, 97%, 98%, or 99% identical or similar to SEQ ID NO: 15.

The term "PPE41 protein" refers to a protein that includes isolated wild-type PPE41 polypeptides from *M. tuberculosis* bacteria and segments thereof, as well as variants that stimulate an immune response against *M. tuberculosis* bacteria PPE41 proteins.

PE25

In 1998, the Mtb genome highlighted, for the first time, the presence of genes grouped into two large families that were shown to comprise approximately 7% of the genome 44 size. This was a surprise to the field of mycobacteriology, and led to the speculation that this multitude of repetitive genes, found mostly in slow-growing pathogenic mycobacteria, likely influence the function and immuno-pathogenicity of Mtb. Based on the presence of conserved Pro-Glu (PE) and Pro-Pro-Glu (PPE) motifs at their N-terminus, the encoded genes were named PE and PPE respectively. The laboratory strain of Mtb H37Rv contains 99 pe genes, 61 being in the PE-PGRS (polymorphic GC-rich sequences) a subfamily earlier used for fingerprinting Mtbstrains) and 69 ppe genes. The proteins belonging to the PE family share a highly conserved N-terminal domain about 90-110 amino acids in length. The PE family is further divided into the PE and PE_PGRS subfamilies. PE-PGRS proteins are characterized by the presence of a polymorphic domain, rich in Gly-Gly-Ala/Gly-Gly-Asn amino acid repeats, which can vary in sequence and size. Pe-pgrs genes are found scattered throughout the genome and are mostly not co-transcribed with other genes. Conversely, many of the pe genes are adjacent to ppe genes and a number of studies have demonstrated that these pe/ppe couplets are co-expressed. At least some of the corresponding proteins are found as heterodimers that are present on the cell surface or secreted.

PE25 Sequence: In some embodiments, the PE25 antigen for use in the TB-MAPS immunogenic composition as disclosed herein comprises a polypeptide or peptide comprising at least part of SEQ ID NO: 16, which corresponds to the full length PE25 mature protein from *M. tuberculosis*.

```
                                   (SEQ ID NO: 16)
MSFVITNPEALTVAATEVRRIRDRAIQSDAQVAPMTTAVRPPAADLVSEK

AATFLVEYARKYRQTIAAAAVVLEEFAHALTTGADKYATAEADNIKTFS
```

In one embodiment, a TB-MAPS composition may include a polypeptide, peptide, or protein that is or is at least 70%, 75%, 80%, 85%, 90%, 95%, 96%, 97%, 98%, or 99% identical or similar to a PE25 of SEQ ID NO: 16. In certain aspects a PE25 antigen peptide or polypeptide will have all, or part of the amino acid sequence of SEQ ID NO: 16, e.g., will comprise at least 50, or at least 60, or at least 70, or at least 80, or at least 90, or at least 100, amino acids of SEQ ID NO: 16. In one embodiment, a PE25 antigen peptide or polypeptide present in the TB-MAPS immunogenic composition is a polypeptide, peptide, or protein that is or is at least 70%, 75%, 80%, 85%, 90%, 95%, 96%, 97%, 98%, or 99% identical or similar to SEQ ID NO: 16.

The term "PE25 protein" refers to a protein that includes isolated wild-type PE25 polypeptides from *M. tuberculosis* bacteria and segments thereof, as well as variants that stimulate an immune response against *M. tuberculosis* bacteria PE25 proteins.

Other Mtb Antigens

While exemplary Mtb antigens used in the TB-MAPS composition as disclosed herein can be one or more of, or all 9 of Early secreted antigen target-6 (ESAT6), Culture filtrate protein-10 (CFP10), MPT51, MPT64, MPT83, TB9.8, TB10.4, Proline Proline Glutamic acid-41 (PPE41), and Proline Glutamic acid-25 (PE25) or fragments thereof, e.g., CFP10 (1-40), CFP10 (45-80), MPT64 (25-228), MPT83 (58-220), and MPT51 (33-299) or proteins or peptides having at least 85% sequence identity thereto, it is envisioned that any of the above listed Mtb antigens can be substituted for a different TB peptide or polypeptide antigen known to one of ordinary skill in the art.

For example, in some embodiments, any one or more Mtb antigens useful in the TB-MAPS composition as disclosed herein include, but are not limited to, a peptide or polypeptide comprising at least part of the TbH9 (also known as Mtb 39A), DPV (also known as Mtb8.4), 381, Mtb41, Mtb40, Mtb32A, MPT64, MPT83, Mtb9.9A, Mtb16, Mtb72f, Mtb59f, Mtb88f, Mtb7lf, Mtb46f and Mtb31f, wherein "f" indicates that it is a fusion or two or more proteins, provided that the any peptide or polypeptide is immunogenic, or is antigenic. Other Mtb antigens can be used, and are disclosed herein.

Mtb-Antigen Fusion Proteins

In some embodiments, the Mtb antigen for use in the MAPS complex as disclosed herein is fused to a recombinant biotin-binding protein. In some embodiment, the recombinant biotin-binding protein is a rhizavidin protein. In some embodiments, the Rhizavidin (Rhavi) protein comprises SEQ ID NO: 1 or a protein or polypeptide of at least 85% amino acid sequence identity to SEQ ID NO: 1.

In some embodiments, the recombinant biotin-binding protein comprises an *E. coli* signal sequence fused to the N-terminus of an amino acid sequence comprising amino acids 45-179 of wild-type Rhizavidin (rhavi) which is as follows:

```
                                   (SEQ ID NO: 1)
FDASNFKDFSSIASASSSWQNQSGSTMIIQVDSFGNVSGQYVNRAQGTGC

QNSPYPLTGRVNGTFIAFSVGWNNSTENCNSATGWTGYAQVNGNNTEIVT

SWNLAYEGGSGPAIEQGQDTFQYVPTTENKSLLKD.
```

In some embodiments, the recombinant biotin-binding protein consists of, or consists essentially of, the amino acid sequence corresponding to amino acids 45-179 of the wild-type Rhizavidin. Amino acid sequence of the wild-type Rhizavidin is: MIITSLYATFGTIADGRRTSGGKTMIRTNAVAALVFAVATSALAFDASNFKDFSSIASASSSWQN QSGSTMIIQVDSFGNVSGQYVNRAQGTGCQNSPYPLTGRVNGTFIAFSVGWNNSTENCNSATG WTGYAQVNGNNTEIVTSWNLAYEGGSGPAIEQGQDTFQYVPTTENKSLLKD (SEQ ID NO: 2). In other words, the biotin-binding domain does not comprise (i.e., lacks) amino acids 1-44 (MIITSLYATFGTIADGRRTSGGKTMIRTNAVAALVFAVATSALA, SEQ ID NO: 18).

In some embodiments, the recombinant biotin-binding protein useful in a fusion protein with at least one TB-antigen as disclosed herein comprises an amino acid sequence having at least 50% identity, at least 55% identity, at least 60% identity, at least 65% identity, at least 70% identity, at least 75% identity, at least 80% identity, preferably at least 85% identity, at least 90% identity, at least 95% identity, at least 96% identity, at least 97% identity, at least 98% identity, or at least 99% identity, and more preferably at least 99.3% identity to SEQ ID NO: 1.

A TB-antigen for use in the TB-MAPS composition as disclosed herein can be genetically fused to rhizavidin (rhavi), which is a dimeric biotin-binding protein from *Rhizobium etli*, according to the methods as disclosed in U.S. Pat. No. 9,499,593 which is incorporated herein in its entirety by reference.

In some embodiments, a biotin-binding protein useful in the TB-MAPS composition as disclosed herein comprises a sequence $X^1$-$X^2$-$X^3$, or $X^1$-$X^2$-$X^3$-$X^4$ wherein $X^2$ is a peptide having the amino acid sequence corresponding to amino acids 45-179 of the wild-type Rhizavidin (i.e., SEQ ID NO: 1) and $X^1$ and $X^3$ and $X^4$ are independently absent, or a peptide of 1 to about 100 amino acids with the proviso that the N-terminus of $X^1$ does not comprise an amino acid sequence corresponding to N-terminus of amino acids 1-44 of the wild-type Rhizavidin.

In some embodiments, the biotin-binding proteins can comprise a signal peptide conjugated to the N-terminus of the biotin-binding protein, i.e. $X^1$ can comprise a signal peptide. The signal peptide is also called a leader peptide in the N-terminus, which may or may not be cleaved off after the translocation through the membrane. In some embodiments, the *E. coli* signal sequence is the Dsba signal sequence which comprises at least MKKIWLALAGLVLAFSASA (SEQ ID NO: 19) or MKKIWLALAGLVLAFSASAAQDP (SEQ ID NO: 24). In some embodiments, the signal sequence is MKKVAAFVALSLLMAGC (SEQ ID NO: 21). Secretion/signal peptides are described in more detail below. In some embodiments, the signal sequence is MKKIWLALAGLVLAFSASA (SEQ ID NO: 20), MAPFEPLASGILLLLWLIAPSRA (SEQ ID NO: 39), MKKVAAFVALSLLMAGC (SEQ ID NO: 21), or a derivative or functional portion thereof. The signal sequence can be fused with the sequence comprising amino acids 45-179 of wild-type rhavi by a flexible peptide linker.

In some embodiments, the biotin-binding protein is a fusion protein with one or more TB-antigens. For example, the C-terminal of SEQ ID NO: 1 (or a protein of at least 80% or 85% or more sequence identity thereto) is fused to at least 1, or at least 2 or at least 3, or at least 4 or more TB-antigens.

In some embodiments, a biotin-binding protein is a fusion protein comprising a C-terminal of SEQ ID NO: 1 (or a protein of at least 80% or 85% or more sequence identity thereto) is fused to any one or more of: Early secreted antigen target-6 (ESAT6), Culture filtrate protein-10 (CFP10), MPT51, MPT64, MPT83, TB9.8, TB10.4, Proline Proline Glutamic acid-41 (PPE41), and Proline Glutamic acid-25 (PE25), or fragments thereof. In some embodiments, a biotin-binding protein is a fusion protein comprising the C-terminal of SEQ ID NO: 1 (or a protein of at least 80% or 85% or more sequence identity thereto) fused to any one or more of: CFP10 (1-40), CFP10 (45-80), MPT64 (25-228), MPT83 (58-220), and MPT51 (33-299) or proteins or peptides having at least 85% sequence identity thereto.

Aspects of the present invention are directed to an isolated recombinant rhizavidin fusion protein comprising SEQ ID NO: 1 (or a protein of at least 80% or 85% or more sequence identity thereto) fused to MPT51 (Rhavi-MPT51). Aspects of the present invention are directed to an isolated recombinant rhizavidin fusion protein comprising SEQ ID NO: 1 (or a protein of at least 80% or 85% or more sequence identity thereto) fused to MPT51 (33-299) (Rhavi-MPT51 (33-299)). Aspects of the present invention are directed to an isolated recombinant rhizavidin fusion protein comprising SEQ ID NO: 1 (or a protein of at least 80% or 85% or more sequence identity thereto) fused to ESAT6 (Rhavi-ESAT6). Aspects of the present invention are directed to an isolated recombinant rhizavidin fusion protein comprising SEQ ID NO: 1 (or a protein of at least 80% or 85% or more sequence identity thereto) fused to CFP10 (1-41) (Rhavi-CFP10 (1-41)). Aspects of the present invention are directed to an isolated recombinant rhizavidin fusion protein comprising SEQ ID NO: 1 (or a protein of at least 80% or 85% or more sequence identity thereto) fused to CFP10 (45-80) (Rhavi-CFP10 (45-80)). Aspects of the present invention are directed to an isolated recombinant rhizavidin fusion protein comprising SEQ ID NO: 1 (or a protein of at least 80% or 85% or more sequence identity thereto) fused to CFP10 (1-41) and CPF10 (45-80) (Rhavi-CFP10 (1-41)-CPF10 (45-80)). Aspects of the present invention are directed to an isolated recombinant rhizavidin fusion protein comprising SEQ ID NO: 1 (or a protein of at least 80% or 85% or more sequence identity thereto) fused to CFP10 (Rhavi-CFP10). Aspects of the present invention are directed to an isolated recombinant rhizavidin fusion protein comprising SEQ ID NO: 1 (or a protein of at least 80% or 85% or more sequence identity thereto) fused to MPT64 (Rhavi-MPT64). Aspects of the present invention are directed to an isolated recombinant rhizavidin fusion protein comprising SEQ ID NO: 1 (or a protein of at least 80% or 85% or more sequence identity thereto) fused to MPT64 (25-228) (Rhavi-MPT64 (25-228)). Aspects of the present invention are directed to an isolated recombinant rhizavidin fusion protein comprising SEQ ID NO: 1 (or a protein of at least 80% or 85% or more sequence identity thereto) fused to MPT83 (Rhavi-MPT83). Aspects of the present invention are directed to an isolated recombinant rhizavidin fusion protein comprising SEQ ID NO: 1 (or a protein of at least 80% or 85% or more sequence identity thereto) fused to MPT83 (58-220) (Rhavi-MPT64 (58-220)). Aspects of the present invention are directed to an isolated recombinant rhizavidin fusion protein comprising SEQ ID NO: 1 (or a protein of at least 80% or 85% or more sequence identity thereto) fused to TB9.8 (Rhavi-TB9.8). Aspects of the present invention are directed to an isolated recombinant rhizavidin fusion protein comprising SEQ ID NO: 1 (or a protein of at least 80% or 85% or more sequence identity thereto) fused to TB10.4 (Rhavi-TB10.4). Aspects of the present invention are directed to an isolated recombinant rhizavidin fusion protein comprising SEQ ID NO: 1 (or a protein of at least 80% or 85% or more sequence identity thereto) fused to PPE41 (Rhavi-PPE41). Aspects of the present invention are directed to an isolated recombinant rhizavidin fusion protein comprising SEQ ID NO: 1 (or a protein of at least 80% or 85% or more sequence identity thereto) fused to PE25 (Rhavi-PE25).

In some embodiments, a biotin-binding protein is a fusion protein comprising a the C-terminal of SEQ ID NO: 1 (or a protein of at least 80% or 85% or more sequence identity thereto) fused to at least two antigens (e.g., referred to herein as a "double fusion protein") where the Mtb antigen is selected from any one of: MPT51, ESAT6, CFP10, MPT64, MPT83, TB9.8, TB10.4, PPE41, PE25, or fragments thereof, or proteins or peptides having at least 85% sequence identity thereto. In some embodiments, a biotin-binding protein is a fusion protein comprising a the C-terminal of SEQ ID NO: 1 (or a protein of at least 80% or 85% or more sequence identity thereto) fused to at least three antigens (e.g., referred to herein as a "triple fusion protein") where the Mtb antigen is selected from any one of: MPT51, ESAT6, CFP10, MPT64, MPT83, TB9.8, TB10.4, PPE41, PE25, or fragments thereof, or proteins or peptides having at least 85% sequence identity thereto. The Mtb-antigens may be the same antigens (e.g., SEQ ID NO: 1-A-A, or SEQ ID NO: 1-A-A-A), or alternatively different Mtb antigens (e.g., SEQ ID NO: 1-A-B, SEQ ID NO: 1-A-B-C), where A, B and C are different Mtb-antigens. Exemplary Rhizavidin fusion proteins comprising 2 (i.e., a double fusion protein) or 3 Mtb-antigens (i.e., a tripe-fusion protein) are shown in Tables 3A and 3B. Table 3C also provides exemplary Rhizavidin fusion proteins used the TB-MAPS compositions in the Examples.

Table 3A. Exemplary Rhizavidin fusion proteins comprising different combinations of 2 Mtb-antigens. It is noted that the order of the 2 antigens fused to the Rhizavidin protein of SEQ ID NO: 1 (referred to as "Rhavi") or a homologue of at least 80% identity thereto can be in any order, e.g., Rhavi-MPT64-ESAT6, or alternatively, Rhavi-ESAT6-MPT64, or MPT64-Rhavi-ESAT6 or ESAT6-Rhavi-MPT64, for example.

TABLE 3A

| Combinations of any 2 Mtb antigens; (i) Exemplary double fusion proteins fused to Rhavi (36 possible combinations) | | | | | |
|---|---|---|---|---|---|
| MPT51, ESAT6 | MPT51, PPE41 | ESAT6, MPT83 | CFP10, MPT83 | MPT64, PPE41 | TB10.4, MPT83 |
| MPT51, CFP10 | MPT51, PE25 | ESAT6, PPE41 | CFP10, PPE41 | MPT64, PE25 | TB10.4, PPE41 |
| MPT51, MPT64 | ESAT6, CFP10 | ESAT6, PE25 | CFP10, PE25 | TB9.8, TB10.4 | TB10.4, PE25 |
| MPT51, TB9.8 | ESAT6, MPT64 | CFP10, MPT64 | MPT64, TB9.8 | TB9.8, MPT83 | MPT83, PPE41 |
| MPT51, TB10.4 | ESAT6, TB9.8 | CFP10, TB 9.8 | MPT64, TB10.4 | TB9.8, PPE41 | MPT83, PE25 |
| MPT51, MPT83 | ES AT6, TB10.4 | CFP10, TB10.4 | MPT64, MPT83 | TB9.8, PE25 | PPE41, PE25 |

Table 3B. Exemplary Rhizavidin fusion proteins comprising different combinations of 3 TB-antigens. It is noted that the order of the 3 antigens fused to the Rhizavidin protein of SEQ ID NO: 1 (referred to as "Rhavi") or a homologue of at least 80% identity thereto can be in any order, e.g., Rhavi-MPT64-MPT83-TB9.8, or alternatively, Rhavi-MPT83-TB9.8-MPT64, or MPT64-Rhavi-TB9.8-MPT83, or MPT83-Rhavi-TB9.8-MPT64 for example.

TABLE 3B

| Combinations of any 3B Mtb antigens; (i) Exemplary triple fusion proteins with Rhavi, or (ii) TB-MAPS combo (84 possible combinations) | | | | | |
|---|---|---|---|---|---|
| MPT51, ESAT6, CFP10 | MPT51, MPT64, TB10.4 | ESAT6, CFP10, MPT64 | ESAT6, TB9.8, PE25 | CFP10, TB9.8, PPE41 | MPT64, TB10.4, PE25 |
| MPT51, ESAT6, MPT64 | MPT51, MPT64, MPT83 | ESAT6, CFP10, TB9.8 | ESAT6, TB10.4, MPT83 | CFP10, TB9.8, PE25 | MPT64, MPT83, PPE41 |
| MPT51, ESAT6, TB9.8 | MPT51, MPT64, PPE41 | ESAT6, CFP10, TB10.4 | ESAT6, TB10.4, PPE41 | CFP10, TB10.4, MPT83 | MPT64, MPT83, PE25 |
| MPT51, ESAT6, TB10.4 | MPT51, MPT64, PE25 | ESAT6, CFP10, MPT83 | ESAT6, TB10.4, PE25 | CFP10, TB10.4, PPE41 | MPT64, PPE41, PE25 |
| MPT51, ESAT6, MPT83 | MPT51, TB9.8, TB10.4 | ESAT6, CFP10, PPE41 | ESAT6, MPT83, PPE41 | CFP10, TB10.4, PE25 | TB9.8, TB10.4, MPT83 |
| MPT51, ESAT6, PPE41 | MPT51, TB9.8, MPT83 | ESAT6, CFP10, PE25 | ESAT6, MPT83, PE25 | CFP10, MPT83, PPE41 | TB9.8, TB10.4, PPE41 |
| MPT51, ESAT6, PE25 | MPT51, TB9.8, PPE41 | ESAT6, MPT64, TB9.8 | ES AT6, PPE41, PE25 | CFP10, MPT83, PE25 | TB9.8, TB10.4, PE25 |
| MPT51, CFP10, MPT64 | MPT51, TB9.8, PE25 | ESAT6, MPT64, TB10.4 | CFP10, MPT64, TB9.8 | CFP10, PPE41, PE25 | TB9.8, MPT83, PPE41 |
| MPT51, CFP10, TB9.8 | MPT51, TB10.4, MPT83 | ESAT6, MPT64, MPT83 | CFP10, MPT64, TB10.4 | MPT64, TB9.8, TB10.4 | TB9.8, MPT83, PE25 |
| MPT51, CFP10, TB10.4 | MPT51, TB10.4, PPE41 | ESAT6, MPT64, PPE41 | CFP10, MPT64, MPT83 | MPT64, TB9.8, MPT83 | TB9.8, PPE41, PE25 |
| MPT51, CFP10, MPT83 | MPT51, TB10.4, PE25 | ESAT6, MPT64, PE25 | CFP10, MPT64, PPE41 | MPT64, TB9.8, PPE41 | TB10.4, MPT83, PPE41 |
| MPT51, CFP10, PPE41 | MPT51, MPT83, PPE41 | ESAT6, TB9.8, TB10.4 | CFP10, MPT64, PE25 | MPT64, TB9.8, PE25 | TB10.4, MPT83, PE25 |
| MPT51, CFP10, PE25 | MPT51, MPT83, PE25 | ESAT6, TB9.8, MPT83 | CFP10, TB9.8, TB10.4 | MPT64, TB10.4, MPT83 | TB10.4, PPE41, PE25 |
| MPT51, MPT64, TB9.8 | MPT51, PPE41, PE25 | ES AT6, TB9.8, PPE41 | CFP10, TB9.8, MPT83 | MPT64, TB10.4, PPE41 | MPT83, PPE41, PE25 |

MPT51=MPT51 protein or a fragment thereof, e.g., MPT51(33-299), ESAT6=ESAT6 protein or a fragment thereof, CFP10=CFP10 protein or a fragment thereof, e.g., CFP10(1-41) or CFP10 (45-80), or both CFP10(1-41) and CFP10(45-80), MPT64=MPT64 protein or a fragment thereof, e.g., MPT64(25-228); MPT83=MPT83 protein or a fragment thereof, e.g., MPT83(58-220); TB9.8=TB9.8 protein or a fragment thereof, TB910.4=TB10.4 protein or a fragment thereof, PPE41=PPE41 protein or a fragment thereof, PE25=PE25 protein or a fragment thereof. It is envisioned that any of the Mtb antigens in the Rhavi-antigen-antigen fusion proteins shown in Tables 3A and 3B can be substituted or replaced with any other Mtb antigen as disclosed herein, or known to one of ordinary skill in the art.

Table 3C: Exemplary Rhizavidin double and triple fusion proteins for use in the TB-MAPS compositions.

TABLE 3C

| Exemplary double and triple fusion proteins. | | |
|---|---|---|
| | Proteins | Constructs |
| Mtb proteins | ESAT6/CFP10 | ESAT6-(KLGS)-CFP10(45-80)-(GS)-CFP10(1-41) |
| | TB9.8/TB10.4 | TB9.8-(KLGGS)-TB10.4 |
| | MPT64 | MPT64(25-228) |
| | MPT83 | MPT83(58-220) |
| | MPT51 | MPT51(33-299) |
| | PPE41/PE25 | PPE41-(AAA)-PE25 |

TABLE 3C-continued

| Exemplary double and triple fusion proteins. | | |
|---|---|---|
| | Proteins | Constructs |
| Rhavi-Mtb fusion proteins | Rhavi-ESAT6/CFP10 | Rhavi-(GGGGSSS)-ESAT6/CFP10 |
| | Rhavi-TB9.8/TB10.4 | Rhavi-(GGGGSSS)-TB9.8/TB 10.4 |
| | Rhavi-MPT64 | Rhavi-(GGGGSSS)-MPT64 |
| | Rhavi-MPT83 | Rhavi-(GGGGSSS)-MPT83 |
| | Rhavi-MPT51 | Rhavi-(GGGGSSS)-MPT51 |
| | Rhavi-ESAT6/CFP10-MPT64 | Rhavi-(TDPNSSS)-ESAT6/CFP10-(AAA)-MPT64 |
| | Rhavi-TB 9.8/TB 10.4-MPT83 | Rhavi-(TDPNSSS)-TB9.8/TB10.4-(AAA)-MPT83 |
| | Rhavi-PPE41/PE25 | Rhavi-(TDPNSSS)-PPE41/PE25 |

Table 3C shows exemplary double and triple fusion proteins. For example, Rhavi-TB9.8/TB10.4 is a double fusion protein, and Rhavi-ESAT6/CFP10 is a triple fusion protein comprising ESAT6, CFP10(45-80), and CFP10(1-41). Rhavi-ESAT6/CFP10-MPT64 is an example of a larger fusion protein, comprising ESAT6, CFP10(45-80), CFP10 (1-41), and MPT64.

In some embodiments, a rhizavidin fusion protein comprising at least one or more Mtb antigen can comprise a lipidation sequence at the N-terminus, e.g., MKKVAAF-VALSLLMAGC (SEQ ID NO: 29) or an amino acid 85% identity thereto. In some embodiments, the TB-MAPS composition can also comprise a rhizavidin protein comprising SEQ ID NO: 1 or a protein with 85% sequence identity thereto, that comprises a lipidation sequence at the N-terminus, e.g., MKKVAAFVALSLLMAGC (SEQ ID NO: 29) or an amino acid 85% identity thereto, but the rhizavidin protein is not fused to a Mtb antigen or other antigen (e.g., Rhavi is not part of a Rhavi-antigen fusion protein). Lipidated rhizavidin proteins and lapidated rhizavidin fusion proteins are disclosed in US application US2016/0090404, entitled "Modified biotin-binding protein, fusion proteins thereof and applications", which is incorporated herein in its entirety by reference.

As used herein, the term "lipidated biotin-binding protein" refers to a biotin-binding protein that is covalently linked with a lipid. The lipidated biotin-binding proteins are ligands or agonists of Toll like receptor 2. Accordingly, also provided herein are methods for inducing an immune response in subject. The method comprising administering to the subject a composition comprising a lipidated biotin-binding protein.

In some embodiments, a rhizavidin fusion protein comprising a Mtb antigen can comprise a signal peptide linked to the N-terminus of the biotin-binding domain either directly (e.g., via a bond) or indirectly (e.g., by a linker). In some embodiments, the signal peptide can be linked to the N-terminus of the biotin-binding domain by a peptide linker. The peptide linker sequence can be of any length. For example, the peptide linker sequence can be one, two, three, four, five, six, seven, eight, nine, ten, eleven, twelve, thirteen, fourteen, fifteen or more amino acids in length. In some embodiments, the peptide linker is four amino acids in length.

The peptide linker sequence can comprise any amino acid sequence. For example, the peptide linker can comprise an amino acid sequence which can be cleaved by a signal peptidase. In some embodiments, the peptide linker comprises the amino acid sequence AQDP (SEQ ID NO: 22) or VSDP (SEQ ID NO: 23).

In some embodiments, a rhizavidin fusion protein comprising a Mtb antigen can be conjugated at its C-terminus to a peptide of 1-100 amino acids. Such peptides at the C-terminus can be used for purification tags, linkers to other domains, and the like. In some embodiments, a rhizavidin fusion protein comprising a Mtb antigen comprises on its N- or C-terminus one or more (e.g., one, two, three, four, five, six, seven, eight, nine, ten or more) purification tags. Examples of purification tags include, but are not limited to a histidine tag, a c-my tag, a Halo tag, a Flag tag, and the like. In some embodiments, a rhizavidin fusion protein comprising a Mtb antigen for use in the TB-MAPS immunogenic composition as disclosed herein comprises a peptide of amino acid sequence GGGGSSSVDK-LAAALEHHHHHH (SEQ ID NO: 28). This peptide at the C-terminus provides a histidine tag for purification and a place for insertion of other domains, e.g. antigenic domains, in the biotin protein. Further, while Helppolainen et al. (Biochem J., 2007, 405: 397-405) describe expression of Rhizavidin in *E. coli*, there is no teaching or suggestion in Helppolainen et al. for conjugating an additional peptide to the C-terminus of the biotin-binding domain of Rhizavidin.

A purification tag can be conjugated to a rhizavidin fusion protein comprising a Mtb antigen as disclosed herein by a peptide linker to enhance the probability that the tag is exposed to the outside.

In some embodiments, a rhizavidin fusion protein described herein comprises at least one linker peptide, and the linker peptide can be located between the Rhizavidin protein and a Mtb antigen, and/or between one Mtb antigen and another Mtb antigen in the case of double and triple rhizavidin fusion proteins as described herein. In some embodiments the length of the linker can be at least one (e.g., one, two, three, four, five six, seven, eight, nine, ten, eleven, twelve, thirteen, fourteen, or fifteen) amino acids in length. The linker peptide can comprise any amino acid sequence without limitations. In some embodiments, the linker peptide comprises the amino acid sequence VDK-LAAALE (SEQ ID NO: 25) or GGGGSSSVDKLAAALE (SEQ ID NO: 26). In some embodiments, a rhizavidin fusion protein comprising a Mtb antigen as disclosed herein can comprise at its C-terminus the amino acid sequence VDK-LAAALEHHHHHH (SEQ ID NO: 27) or GGGGSSSVDK-LAAALEHHHHHH (SEQ ID NO: 28). In some embodiments, the linker protein is selected in any of: KLGS (SEQ ID NO: 51); GS (SEQ ID NO: 52), KLGGS (SEQ ID NO: 53), AAA (SEQ ID NO: 54), GGGGSSS (SEQ ID NO: 35) and TDPNSSS (SEQ ID NO: 36).

As discussed herein, a rhizavidin fusion protein comprising a Mtb antigen for use in the TB-MAPS immunogenic composition as disclosed herein consists of amino acids 45-179 of wild-type Rhizavidin.

In some embodiments, rhizavidin fusion protein comprising a Mtb antigen for use in the TB-MAPS immunogenic composition as disclosed herein can comprise an N-terminal signal sequence as disclosed herein. In some embodiments, the signal sequence is attached to the N-terminal of the complementary affinity molecule as disclosed herein.

In some embodiments, a rhizavidin fusion protein comprising a Mtb antigen for use in the TB-MAPS immunogenic composition as disclosed herein has a spacer peptide, e.g., a 14-residue spacer (GSPGISGGGGGILE) (SEQ ID NO: 17) separating the Mtb antigen from the rhizavidin protein. The coding sequence of such a short spacer can be constructed by annealing a complementary pair of primers. One of skill in the art can design and synthesize oligonucleotides that will code for the selected spacer. Spacer peptides should generally have non-polar amino acid residues, such as glycine and proline.

Lipidated Rhizavidin Fusion Protein or Biotin-Binding Protein

In another aspect provided herein is a lipidated biotin-binding protein, e.g., a lipidated rhizavidin fusion protein comprising a Mtb antigen for use in the TB-MAPS immunogenic composition as disclosed herein. As used herein, the term "lipidated biotin-binding protein" refers to a biotin-binding protein that is covalently conjugated with a lipid. The lipid moieties could be a diacyl or triacyl lipid.

In some embodiments, a rhizavidin fusion protein comprising a Mtb antigen for use in the TB-MAPS immunogenic composition as disclosed herein comprises a lipidation sequence. As used herein, the term "lipidation sequence" refers to an amino acid sequence that facilitates lipidation in bacteria, e.g., *E. coli*, of a polypeptide carrying the lipidating sequence. The lipidation sequence can be present at the N-terminus or the C-terminus of the protein. The lipidation sequence can be linked to the recombinant biotin-binding protein to form a fusion protein, which is in lipidated form when expressed in *E. coli* by conventional recombinant technology. In some embodiments, a lipidation sequence is located at the N-terminus of the biotin-binding protein.

Any lipidation sequence known to one of ordinary skill in the art can be used. In some embodiments, the lipidating sequence is MKKVAAFVALSLLMAGC (SEQ ID NO: 29) or a derivative or functional portion thereof. Other exemplary lipidating sequences include, but are not limited to, MNSKKLCCICVLFSLLAGCAS (SEQ ID NO: 31), MRYSKLTMLIPCALLLSAC (SEQ ID NO: 32), MFVTSKKMTAAVLAITLAMSLSAC (SEQ ID NO: 33), MIKRVLVVSMVGLSLVGC (SEQ ID NO: 34), and derivatives or functional portions thereof.

In some embodiments, the lipidation sequence can be fused to a rhizavidin fusion protein comprising a Mtb antigen via a peptide linker, wherein the peptide linker attaches the lipidating sequence to the biotin-binding protein. In some embodiment, the peptide linker comprises the amino acid sequence VSDP (SEQ ID NO: 23) or AQDP (SEQ ID NO: 22).

In some embodiments, a rhizavidin fusion protein comprising a Mtb antigen for use in the TB-MAPS immunogenic composition as disclosed herein that is a lipoprotein as described herein have enhanced immunogenicity. Without wishing to be bound by a theory, lipid moieties at the N-terminals of the lipoproteins or lipopeptides contribute to the adjuvant activity. Accordingly, additional embodiments provide immunogenic or vaccine compositions for inducing an immunological response, comprising the isolated biotin-binding lipoprotein, or a suitable vector for in vivo expression thereof, or both, and a suitable carrier, as well as to methods for eliciting an immunological or protective response comprising administering to a host the isolated recombinant biotin-binding lipoprotein, the vector expressing the recombinant biotin-binding lipoprotein, or a composition containing the recombinant lipoprotein or vector, in an amount sufficient to elicit the response.

A TB-MAPS immunogenic composition comprising a rhizavidin fusion protein comprising a Mtb antigen that is a lipoprotein elicits an immunological response-local or systemic. The response can, but need not, be protective.

Combinations of Mtb Antigens Present on the TB-MAPS Immunogenic Composition

In some embodiments, a TB-MAPS complex comprises at least 2 Mtb antigens, e.g., MPT51, such as but not limited to MPT51 as disclosed herein, and one or more Mtb antigens selected from a Early secreted antigen target-6 (ESAT6), Culture filtrate protein-10 (CFP10), MPT51, MPT64, MPT83, TB9.8, TB10.4, Proline Proline Glutamic acid-41 (PPE41), and Proline Glutamic acid-25 (PE25), or fragments thereof.

In some embodiments, a TB-MAPS immunogenic composition as disclosed herein can comprise all 9 Mtb antigens selected from: Early secreted antigen target-6 (ESAT6), Culture filtrate protein-10 (CFP10), MPT51, MPT64, MPT83, TB9.8, TB10.4, Proline Proline Glutamic acid-41 (PPE41), and Proline Glutamic acid-25 (PE25), or fragments thereof, for example, but not limited to: CFP10 (1-40), CFP10 (45-80), MPT64 (25-228), MPT83 (58-220), and MPT51 (33-299) or proteins or peptides having at least 85% sequence identity thereto. It is envisioned that any of the above listed Mtb antigens can be substituted for a different TB peptide or polypeptide antigen known to one of ordinary skill in the art.

In alternative embodiments, the TB-MAPS immunogenic compositions as disclosed herein can comprise any Mtb antigen that elicits an immune response in a subject. In some embodiments, the TB-MAPS composition comprises at least one, or at least 2 Mtb antigens. In some embodiments, the TB-MAPS immunogenic composition comprises at least 2, or at least 3, or at least 4, or between 2-4, or between 3-5, or between 6-8, or between 8-10 or between 10-12, or between 10-15, or between 15-20 or more than 20 TB protein or polypeptide antigens. In some embodiments, the antigens can be the same, e.g., all MPT51 antigens, or a combination of different antigens, e.g., ESAT6, MPT64, TB10.4, etc. In some embodiments, the TB-MAPS composition comprises at least a CFP10 antigen (e.g., CFP10(1-40)) and at least 1 more, or at least 2 more, or at least 3 more or at least 4 more, or at least 5 more Mtb antigens as disclosed herein.

Exemplary combinations of different Mtb antigen present on a TB-MAPS immunogenic composition as disclosed herein are shown in Tables 4A-4I.

In particular, Tables 4A-4I show exemplary combination of different Mtb antigens present on a TB-MAPS complex which are useful in the compositions and methods as disclosed herein. Tables 4A-4I have used an exemplary set of 9 Mtb antigens, and it is envisioned that any of the Mtb antigens can be substituted for a different Mtb peptide or polypeptide antigen known to one of ordinary skill in the art. In some embodiments, a TB-MAPS immunogenic composition comprises a combination of 2, 3, 4, 5, 6, 7, 8 or 9 of the exemplary Mtb antigens selected from Early secreted antigen target-6 (ESAT6), Culture filtrate protein-10 (CFP10), MPT51, MPT64, MPT83, TB9.8, TB10.4, Proline Proline Glutamic acid-41 (PPE41), and Proline Glutamic acid-25 (PE25), or fragments thereof, e.g., CFP10 (1-40), CFP10 (45-80), MPT64 (25-228), MPT83 (58-220), and MPT51 (33-299) or proteins or peptides having at least 85% sequence identity thereto.

In some embodiments where the Mtb antigens can be part of a double or triple fusion protein described herein. (e.g., MPT51, ESAT6, CFP10, where MPT51 is fused to TB9.8 and TB10.4 (MPT51-TB.98-TB10.4)). The antigens can be repeated in different fusion proteins comprising one TB-MAPS composition.

Table 4B-41 show exemplary combinations of 2, 3, 4, 5, 6, 7, 8 and 9 Mtb antigens present in the TB-MAPS complex. MPT51=MPT51, or MPT51(33-299), ESAT6=ESAT6, CFP10=CFP10 (1-41), CFP10 (45-80), or both, MPT64=MPT64 or MPT64 (25-228), MPT83=MPT83 or MPT83(58-220), TB9.8=TB9.8, TB10.4=TB10.4, PPE41=PPE41, PE25=PE25. Table 4A:

TABLE 4A

| TB-MAPS combination with one Mtb antigen (9 possible combinations) | | |
|---|---|---|
| MPT51 | ESAT6 | CFP10 |
| MPT64 | TB9.8 | TB10.4 |
| MPT83 | PPE41 | PE25 |

TABLE 4B

| TB-MAPS comprising a combination of 2 Mtb antigens (36 possible combinations) | | | | | |
|---|---|---|---|---|---|
| MPT51, ESAT6 | MPT51, PPE41 | ESAT6, MPT83 | CFP10, MPT83 | MPT64, PPE41 | TB10.4, MPT83 |
| MPT51, CFP10 | MPT51, PE25 | ESAT6, PPE41 | CFP10, PPE41 | MPT64, PE25 | TB10.4, PPE41 |
| MPT51, MPT64 | ESAT6, CFP10 | ESAT6, PE25 | CFP10, PE25 | TB9.8, TB10.4 | TB10.4, PE25 |
| MPT51, TB9.8 | ESAT6, MPT64 | CFP10, MPT64 | MPT64, TB9.8 | TB9.8, MPT83 | MPT83, PPE41 |
| MPT51, TB10.4 | ESAT6, TB9.8 | CFP10, TB9.8 | MPT64, TB10.4 | TB9.8, PPE41 | MPT83, PE25 |
| MPT51, MPT83 | ES AT6, TB10.4 | CFP10, TB10.4 | MPT64, MPT83 | TB9.8, PE25 | PPE41, PE25 |

TABLE 4C

| TB-MAPS comprising a combination of 3 MTBantigens (84 possible combinations) | | | | | |
|---|---|---|---|---|---|
| MPT51, ESAT6, CFP10 | MPT51, MPT64, TB10.4 | ESAT6, CFP10, MPT64 | ESAT6, TB9.8, PE25 | CFP10, TB9.8, PPE41 | MPT64, TB10.4, PE25 |
| MPT51, ESAT6, MPT64 | MPT51, MPT64, MPT83 | ESAT6, CFP10, TB9.8 | ESAT6, TB10.4, MPT83 | CFP10, TB9.8, PE25 | MPT64, MPT83, PPE41 |
| MPT51, ESAT6, TB9.8 | MPT51, MPT64, PPE41 | ESAT6, CFP10, TB10.4 | ESAT6, TB10.4, PPE41 | CFP10, TB10.4, MPT83 | MPT64, MPT83, PE25 |
| MPT51, ESAT6, TB10.4 | MPT51, MPT64, PE25 | ESAT6, CFP10, MPT83 | ESAT6, TB10.4, PE25 | CFP10, TB10.4, PPE41 | MPT64, PPE41, PE25 |
| MPT51, ESAT6, MPT83 | MPT51, TB9.8, TB10.4 | ESAT6, CFP10, PPE41 | ESAT6, MPT83, PPE41 | CFP10, TB10.4, PE25 | TB9.8, TB10.4, MPT83 |
| MPT51, ESAT6, PPE41 | MPT51, TB9.8, MPT83 | ESAT6, CFP10, PE25 | ESAT6, MPT83, PE25 | CFP10, MPT83, PPE41 | TB9.8, TB10.4, PPE41 |
| MPT51, ESAT6, PE25 | MPT51, TB9.8, PPE41 | ES AT6, MPT64, TB9.8 | ESAT6, PPE41, PE25 | CFP10, MPT83, PE25 | TB9.8, TB10.4, PE25 |
| MPT51, CFP10, MPT64 | MPT51, TB9.8, PE25 | ES AT6, MPT64, TB10.4 | CFP10, MPT64, TB9.8 | CFP10, PPE41, PE25 | TB9.8, MPT83, PPE41 |
| MPT51, CFP10, TB9.8 | MPT51, TB10.4, MPT83 | ES AT6, MPT64, MPT83 | CFP10, MPT64, TB10.4 | MPT64, TB9.8, TB10.4 | TB9.8, MPT83, PE25 |
| MPT51, CFP10, TB10.4 | MPT51, TB10.4, PPE41 | ES AT6, MPT64, PPE41 | CFP10, MPT64, MPT83 | MPT64, TB9.8, MPT83 | TB9.8, PPE41, PE25 |
| MPT51, CFP10, MPT83 | MPT51, TB10.4, PE25 | ES AT6, MPT64, PE25 | CFP10, MPT64, PPE41 | MPT64, TB9.8, PPE41 | TB10.4, MPT83, PPE41 |
| MPT51, CFP10, PPE41 | MPT51, MPT83, PPE41 | ES AT6, TB9.8, TB10.4 | CFP10, MPT64, PE25 | MPT64, TB9.8, PE25 | TB10.4, MPT83, PE25 |
| MPT51, CFP10, PE25 | MPT51, MPT83, PE25 | ES AT6, TB9.8, MPT83 | CFP10, TB9.8, TB10.4 | MPT64, TB10.4, MPT83 | TB10.4, PPE41, PE25 |
| MPT51, MPT64, TB9.8 | MPT51, PPE41, PE25 | ES AT6, TB9.8, PPE41 | CFP10, TB9.8, MPT83 | MPT64, TB10.4, PPE41 | MPT83, PPE41, PE25 |

TABLE 4D

| TB-MAPS comprising a combination of 4 MTBantigens (126 possible combinations) | | | | | |
|---|---|---|---|---|---|
| MPT51, ESAT6, CFP10, MPT64 | MPT51, CFP10, MPT64, TB9.8 | MPT51, MPT64, TB10.4, PE25 | ESAT6, CFP10, TB9.8, PPE41 | ESAT6, TB9.8, MPT83, PPE41 | CFP10, TB9.8, MPT83, PE25 |
| MPT51, ESAT6, CFP10, TB9.8 | MPT51, CFP10, MPT64, TB10.4 | MPT51, MPT64, MPT83, PPE41 | ESAT6, CFP10, TB9.8, PE25 | ESAT6, TB9.8, MPT83, PE25 | CFP10, TB9.8, PPE41, PE25 |
| MPT51, ESAT6, CFP10, TB10.4 | MPT51, CFP10, MPT64, MPT83 | MPT51, MPT64, MPT83, PE25 | ESAT6, CFP10, TB10.4, MPT83 | ESAT6, TB9.8, PPE41, PE25 | CFP10, TB10.4, MPT83, PPE41 |
| MPT51, ESAT6, CFP10, MPT83 | MPT51, CFP10, MPT64, PPE41 | MPT51, MPT64, PPE41, PE25 | ESAT6, CFP10, TB10.4, PPE41 | ESAT6, TB10.4, MPT83, PPE41 | CFP10, TB10.4, MPT83, PE25 |
| MPT51, ESAT6, CFP10, PPE41 | MPT51, CFP10, MPT64, PE25 | MPT51, TB9.8, TB10.4, MPT83 | ESAT6, CFP10, TB10.4, PE25 | ESAT6, TB10.4, MPT83, PE25 | CFP10, TB10.4, PPE41, PE25 |
| MPT51, ESAT6, | MPT51, CFP10, | MPT51, TB9.8, | ESAT6, CFP10, | ESAT6, TB10.4, | CFP10, MPT83, |

TABLE 4D-continued

| TB-MAPS comprising a combination of 4 MTBantigens (126 possible combinations) | | | | | |
|---|---|---|---|---|---|
| CFP10, PE25 | TB9.8, TB10.4 | TB10.4, PPE41 | MPT83, PPE41 | PPE41, PE25 | PPE41, PE25 |
| MPT51, ESAT6, MPT64, TB9.8 | MPT51, CFP10, TB9.8, MPT83 | MPT51, TB9.8, TB10.4, PE25 | ESAT6, CFP10, MPT83, PE25 | ESAT6, MPT83, PPE41, PE25 | MPT64, TB9.8, TB10.4, MPT83 |
| MPT51, ESAT6, MPT64, TB10.4 | MPT51, CFP10, TB9.8, PPE41 | MPT51, TB9.8, MPT83, PPE41 | ESAT6, CFP10, PPE41, PE25 | CFP10, MPT64, TB9.8, TB10.4 | MPT64, TB9.8, TB10.4, PPE41 |
| MPT51, ESAT6, MPT64, MPT83 | MPT51, CFP10, TB9.8, PE25 | MPT51, TB9.8, MPT83, PE25 | ESAT6, MPT64, TB9.8, TB10.4 | CFP10, MPT64, TB9.8, MPT83 | MPT64, TB9.8, TB10.4, PE25 |
| MPT51, ESAT6, MPT64, PPE41 | MPT51, CFP10, TB10.4, MPT83 | MPT51, TB9.8, PPE41, PE25 | ESAT6, MPT64, TB9.8, MPT83 | CFP10, MPT64, TB9.8, PPE41 | MPT64, TB9.8, MPT83, PPE41 |
| MPT51, ESAT6, MPT64, PE25 | MPT51, CFP10, TB10.4, PPE41 | MPT51, TB10.4, MPT83, PPE41 | ESAT6, MPT64, TB9.8, PPE41 | CFP10, MPT64, TB9.8, PE25 | MPT64, TB9.8, MPT83, PE25 |
| MPT51, ESAT6, TB9.8, TB10.4 | MPT51, CFP10, TB10.4, PE25 | MPT51, TB10.4, MPT83, PE25 | ESAT6, MPT64, TB9.8, PE25 | CFP10, MPT64, TB10.4, MPT83 | MPT64, TB9.8, PPE41, PE25 |
| MPT51, ESAT6, TB9.8, MPT83 | MPT51, CFP10, MPT83, PPE41 | MPT51, TB10.4, PPE41, PE25 | ESAT6, MPT64, TB10.4, MPT83 | CFP10, MPT64, TB10.4, PPE41 | MPT64, TB10.4, MPT83, PPE41 |
| MPT51, ESAT6, TB9.8, PPE41 | MPT51, CFP10, MPT83, PE25 | MPT51, MPT83, PPE41, PE25 | ESAT6, MPT64, TB10.4, PPE41 | CFP10, MPT64, TB10.4, PE25 | MPT64, TB10.4, MPT83, PE25 |
| MPT51, ESAT6, TB9.8, PE25 | MPT51, CFP10, PPE41, PE25 | ESAT6, CFP10, MPT64, TB9.8 | ESAT6, MPT64, TB10.4, PE25 | CFP10, MPT64, MPT83, PPE41 | MPT64, TB10.4, PPE41, PE25 |
| MPT51, ESAT6, TB10.4, MPT83 | MPT51, MPT64, TB9.8, TB10.4 | ESAT6, CFP10, MPT64, TB10.4 | ESAT6, MPT64, MPT83, PPE41 | CFP10, MPT64, MPT83, PE25 | MPT64, MPT83, PPE41, PE25 |
| MPT51, ESAT6, TB10.4, PPE41 | MPT51, MPT64, TB9.8, MPT83 | ESAT6, CFP10, MPT64, MPT83 | ESAT6, MPT64, MPT83, PE25 | CFP10, MPT64, PPE41, PE25 | TB9.8, TB10.4, MPT83, PPE41 |
| MPT51, ESAT6, TB10.4, PE25 | MPT51, MPT64, TB9.8, PPE41 | ESAT6, CFP10, MPT64, PPE41 | ESAT6, MPT64, PPE41, PE25 | CFP10, TB9.8, TB10.4, MPT83 | TB9.8, TB10.4, MPT83, PE25 |
| MPT51, ESAT6, MPT83, PPE41 | MPT51, MPT64, TB9.8, PE25 | ESAT6, CFP10, MPT64, PE25 | ESAT6, TB9.8, TB10.4, MPT83 | CFP10, TB9.8, TB10.4, PPE41 | TB9.8, TB10.4, PPE41, PE25 |
| MPT51, ESAT6, MPT83, PE25 | MPT51, MPT64, TB10.4, MPT83 | ESAT6, CFP10, TB9.8, TB10.4 | ESAT6, TB9.8, TB10.4, PPE41 | CFP10, TB9.8, TB10.4, PE25 | TB9.8, MPT83, PPE41, PE25 |
| MPT51, ESAT6, PPE41, PE25 | MPT51, MPT64, TB10.4, PPE41 | ESAT6, CFP10, TB9.8, MPT83 | ESAT6, TB9.8, TB10.4, PE25 | CFP10, TB9.8, MPT83, PPE41 | TB10.4, MPT83, PPE41, PE25 |

TABLE 4E

| TB-MAPS comprising a combination of 5 Mtb antigens (126 possible combinations) | | | | | |
|---|---|---|---|---|---|
| MPT51, ESAT6, CFP10, MPT64, TB9.8 | MPT51, ESAT6, MPT64, TB10.4, PE25 | MPT51, CFP10, MPT64, MPT83, PPE41 | MPT51, MPT64, TB10.4, PPE41, PE25 | ESAT6, CFP10, TB9.8, MPT83, PE25 | CFP10, MPT64, TB9.8, TB10.4, MPT83 |
| MPT51, ESAT6, CFP10, MPT64, TB10.4 | MPT51, ESAT6, MPT64, MPT83, PPE41 | MPT51, CFP10, MPT64, MPT83, PE25 | MPT51, MPT64, MPT83, PPE41, PE25 | ESAT6, CFP10, TB9.8, PPE41, PE25 | CFP10, MPT64, TB9.8, TB10.4, PPE41 |
| MPT51, ESAT6, CFP10, MPT64, MPT83 | MPT51, ESAT6, MPT64, MPT83, PE25 | MPT51, CFP10, MPT64, PPE41, PE25 | MPT51, TB9.8, TB10.4, MPT83, PPE41 | ESAT6, CFP10, TB10.4, MPT83, PPE41 | CFP10, MPT64, TB9.8, TB10.4, PE25 |
| MPT51, ESAT6, CFP10, MPT64, PPE41 | MPT51, ESAT6, MPT64, PPE41, PE25 | MPT51, CFP10, TB9.8, TB10.4, MPT83 | MPT51, TB9.8, TB10.4, MPT83, PE25 | ESAT6, CFP10, TB10.4, MPT83, PE25 | CFP10, MPT64, TB9.8, MPT83, PPE41 |
| MPT51, ESAT6, CFP10, MPT64, PE25 | MPT51, ESAT6, TB9.8, TB10.4, MPT83 | MPT51, CFP10, TB9.8, TB10.4, PPE41 | MPT51, TB9.8, TB10.4, PPE41, PE25 | ESAT6, CFP10, TB10.4, PPE41, PE25 | CFP10, MPT64, TB9.8, MPT83, PE25 |
| MPT51, ESAT6, CFP10, TB9.8, TB10.4 | MPT51, ESAT6, TB9.8, TB10.4, PPE41 | MPT51, CFP10, TB9.8, TB10.4, PE25 | MPT51, TB9.8, MPT83, PPE41, PE25 | ESAT6, CFP10, MPT83, PPE41, PE25 | CFP10, MPT64, TB9.8, PPE41, PE25 |
| MPT51, ESAT6, CFP10, TB9.8, MPT83 | MPT51, ESAT6, TB9.8, TB10.4, PE25 | MPT51, CFP10, TB9.8, MPT83, PPE41 | MPT51, TB10.4, MPT83, PPE41, PE25 | ESAT6, MPT64, TB9.8, TB10.4, MPT83 | CFP10, MPT64, TB10.4, MPT83, PPE41 |
| MPT51, ESAT6, CFP10, TB9.8, PPE41 | MPT51, ESAT6, TB9.8, MPT83, PPE41 | MPT51, CFP10, TB9.8, MPT83, PE25 | ESAT6, CFP10, MPT64, TB9.8, TB10.4 | ESAT6, MPT64, TB9.8, TB10.4, PPE41 | CFP10, MPT64, TB10.4, MPT83, PE25 |
| MPT51, ESAT6, CFP10, TB9.8, PE25 | MPT51, ESAT6, TB9.8, MPT83, PE25 | MPT51, CFP10, TB9.8, PPE41, PE25 | ESAT6, CFP10, MPT64, TB9.8, MPT83 | ESAT6, MPT64, TB9.8, TB10.4, PE25 | CFP10, MPT64, TB10.4, PPE41, PE25 |
| MPT51, ESAT6, CFP10, TB10.4, MPT83 | MPT51, ESAT6, TB9.8, PPE41, PE25 | MPT51, CFP10, TB10.4, MPT83, PPE41 | ESAT6, CFP10, MPT64, TB9.8, PPE41 | ESAT6, MPT64, TB9.8, MPT83, PPE41 | CFP10, MPT64, MPT83, PPE41, PE25 |
| MPT51, ESAT6, CFP10, TB10.4, PPE41 | MPT51, ESAT6, TB10.4, MPT83, PPE41 | MPT51, CFP10, TB10.4, MPT83, PE25 | ESAT6, CFP10, MPT64, TB9.8, PE25 | ESAT6, MPT64, TB9.8, MPT83, PE25 | CFP10, TB9.8, TB10.4, MPT83, PPE41 |
| MPT51, ESAT6, CFP10, TB10.4, PE25 | MPT51, ESAT6, TB10.4, MPT83, PE25 | MPT51, CFP10, TB10.4, PPE41, PE25 | ES AT6, CFP10, MPT64, TB10.4, MPT83 | ES AT6, MPT64, TB9.8, PPE41, PE25 | CFP10, TB9.8, TB10.4, MPT83, PE25 |
| MPT51, ESAT6, CFP10, MPT83, PPE41 | MPT51, ESAT6, TB10.4, PPE41, PE25 | MPT51, CFP10, MPT83, PPE41, PE25 | ESAT6, CFP10, MPT64, TB10.4, PPE41 | ESAT6, MPT64, TB10.4, MPT83, PPE41 | CFP10, TB9.8, TB10.4, PPE41, PE25 |

TABLE 4E-continued

| TB-MAPS comprising a combination of 5 Mtb antigens (126 possible combinations) | | | | | |
|---|---|---|---|---|---|
| MPT51, ESAT6, CFP10, MPT83, PE25 | MPT51, ESAT6, MPT83, PPE41, PE25 | MPT51, MPT64, TB9.8, TB10.4, MPT83 | ESAT6, CFP10, MPT64, TB10.4, PE25 | ESAT6, MPT64, TB10.4, MPT83, PE25 | CFP10, TB9.8, MPT83, PPE41, PE25 |
| MPT51, ESAT6, CFP10, PPE41, PE25 | MPT51, CFP10, MPT64, TB9.8, TB10.4 | MPT51, MPT64, TB9.8, TB10.4, PPE41 | ESAT6, CFP10, MPT64, MPT83, PPE41 | ESAT6, MPT64, TB10.4, PPE41, PE25 | CFP10, TB10.4, MPT83, PPE41, PE25 |
| MPT51, ESAT6, MPT64, TB9.8, TB10.4 | MPT51, CFP10, MPT64, TB9.8, MPT83 | MPT51, MPT64, TB9.8, TB10.4, PE25 | ESAT6, CFP10, MPT64, MPT83, PE25 | ESAT6, MPT64, MPT83, PPE41, PE25 | MPT64, TB9.8, TB10.4, MPT83, PPE41 |
| MPT51, ESAT6, MPT64, TB9.8, MPT83 | MPT51, CFP10, MPT64, TB9.8, PPE41 | MPT51, MPT64, TB9.8, MPT83, PPE41 | ESAT6, CFP10, MPT64, PPE41, PE25 | ESAT6, TB9.8, TB10.4, MPT83, PPE41 | MPT64, TB9.8, TB10.4, MPT83, PE25 |
| MPT51, ESAT6, MPT64, TB9.8, PPE41 | MPT51, CFP10, MPT64, TB9.8, PE25 | MPT51, MPT64, TB9.8, MPT83, PE25 | ESAT6, CFP10, TB9.8, TB10.4, MPT83 | ESAT6, TB9.8, TB10.4, MPT83, PE25 | MPT64, TB9.8, TB10.4, PPE41, PE25 |
| MPT51, ESAT6, MPT64, TB9.8, PE25 | MPT51, CFP10, MPT64, TB10.4, MPT83 | MPT51, MPT64, TB9.8, PPE41, PE25 | ESAT6, CFP10, TB9.8, TB10.4, PPE41 | ESAT6, TB9.8, TB10.4, PPE41, PE25 | MPT64, TB9.8, MPT83, PPE41, PE25 |
| MPT51, ESAT6, MPT64, TB10.4, MPT83 | MPT51, CFP10, MPT64, TB10.4, PPE41 | MPT51, MPT64, TB10.4, MPT83, PPE41 | ESAT6, CFP10, TB9.8, TB10.4, PE25 | ESAT6, TB9.8, MPT83, PPE41, PE25 | MPT64, TB10.4, MPT83, PPE41, PE25 |
| MPT51, ESAT6, MPT64, TB10.4, PPE41 | MPT51, CFP10, MPT64, TB10.4, PE25 | MPT51, MPT64, TB10.4, MPT83, PE25 | ESAT6, CFP10, TB9.8, MPT83, PPE41 | ESAT6, TB10.4, MPT83, PPE41, PE25 | TB9.8, TB10.4, MPT83, PPE41, PE25 |

TABLE 4F

| TB-MAPS comprising a combination of 6 MTBantigens (84 possible combinations) | | | | | |
|---|---|---|---|---|---|
| MPT51, ESAT6, CFP10, MPT64, TB9.8, TB10.4 | MPT51, ESAT6, CFP10, TB9.8, MPT83, PE25 | MPT51, ESAT6, MPT64, TB10.4, PPE41, PE25 | MPT51, CFP10, MPT64, TB10.4, MPT83, PE25 | ESAT6, CFP10, MPT64, TB9.8, TB10.4, MPT83 | ESAT6, CFP10, TB10.4, MPT83, PPE41, PE25 |
| MPT51, ESAT6, CFP10, MPT64, TB9.8, MPT83 | MPT51, ESAT6, CFP10, TB9.8, PPE41, PE25 | MPT51, ESAT6, MPT64, MPT83, PPE41, PE25 | MPT51, CFP10, MPT64, TB10.4, PPE41, PE25 | ESAT6, CFP10, MPT64, TB9.8, TB10.4, PPE41 | ESAT6, MPT64, TB9.8, TB10.4, MPT83, PPE41 |
| MPT51, ESAT6, CFP10, MPT64, TB9.8, PPE41 | MPT51, ESAT6, CFP10, TB10.4, MPT83, PPE41 | MPT51, ESAT6, TB9.8, TB10.4, MPT83, PPE41 | MPT51, CFP10, MPT64, MPT83, PPE41, PE25 | ESAT6, CFP10, MPT64, TB9.8, TB10.4, PE25 | ESAT6, MPT64, TB9.8, TB10.4, MPT83, PE25 |
| MPT51, ESAT6, CFP10, MPT64, TB9.8, PE25 | MPT51, ESAT6, CFP10, TB10.4, MPT83, PE25 | MPT51, ESAT6, TB9.8, TB10.4, MPT83, PE25 | MPT51, CFP10, TB9.8, TB10.4, MPT83, PPE41 | ESAT6, CFP10, MPT64, TB9.8, MPT83, PPE41 | ESAT6, MPT64, TB9.8, TB10.4, PPE41, PE25 |
| MPT51, ESAT6, CFP10, MPT64, TB10.4, MPT83 | MPT51, ESAT6, CFP10, TB10.4, PPE41, PE25 | MPT51, ESAT6, TB9.8, TB10.4, PPE41, PE25 | MPT51, CFP10, TB9.8, TB10.4, MPT83, PE25 | ESAT6, CFP10, MPT64, TB9.8, MPT83, PE25 | ESAT6, MPT64, TB9.8, MPT83, PPE41, PE25 |
| MPT51, ESAT6, CFP10, MPT64, TB10.4, PPE41 | MPT51, ESAT6, CFP10, MPT83, PPE41, PE25 | MPT51, ESAT6, TB9.8, MPT83, PPE41, PE25 | MPT51, CFP10, TB9.8, TB10.4, PPE41, PE25 | ESAT6, CFP10, MPT64, TB9.8, PPE41, PE25 | ESAT6, MPT64, TB10.4, MPT83, PPE41, PE25 |
| MPT51, ESAT6, CFP10, MPT64, TB10.4, PE25 | MPT51, ESAT6, MPT64, TB9.8, TB10.4, MPT83 | MPT51, ESAT6, TB10.4, MPT83, PPE41, PE25 | MPT51, CFP10, TB9.8, MPT83, PPE41, PE25 | ESAT6, CFP10, MPT64, TB10.4, MPT83, PPE41 | ESAT6, TB9.8, TB10.4, MPT83, PPE41, PE25 |
| MPT51, ESAT6, CFP10, MPT64, MPT83, PPE41 | MPT51, ESAT6, MPT64, TB9.8, TB10.4, PPE41 | MPT51, CFP10, MPT64, TB9.8, TB10.4, MPT83 | MPT51, CFP10, TB10.4, MPT83, PPE41, PE25 | ESAT6, CFP10, MPT64, TB10.4, MPT83, PE25 | CFP10, MPT64, TB9.8, TB10.4, MPT83, PPE41 |
| MPT51, ESAT6, CFP10, MPT64, MPT83, PE25 | MPT51, ESAT6, MPT64, TB9.8, TB10.4, PE25 | MPT51, CFP10, MPT64, TB9.8, TB10.4, PPE41 | MPT51, MPT64, TB9.8, TB10.4, MPT83, PPE41 | ESAT6, CFP10, MPT64, TB10.4, PPE41, PE25 | CFP10, MPT64, TB9.8, TB10.4, MPT83, PE25 |
| MPT51, ESAT6, CFP10, MPT64, PPE41, PE25 | MPT51, ESAT6, MPT64, TB9.8, MPT83, PPE41 | MPT51, CFP10, MPT64, TB9.8, TB10.4, PE25 | MPT51, MPT64, TB9.8, TB10.4, MPT83, PE25 | ESAT6, CFP10, MPT64, MPT83, PPE41, PE25 | CFP10, MPT64, TB9.8, TB10.4, PPE41, PE25 |
| MPT51, ESAT6, CFP10, TB9.8, TB10.4, MPT83 | MPT51, ESAT6, MPT64, TB9.8, MPT83, PE25 | MPT51, CFP10, MPT64, TB9.8, MPT83, PPE41 | MPT51, MPT64, TB9.8, TB10.4, PPE41, PE25 | ESAT6, CFP10, TB9.8, TB10.4, MPT83, PPE41 | CFP10, MPT64, TB9.8, MPT83, PPE41, PE25 |
| MPT51, ESAT6, CFP10, TB9.8, TB10.4, PPE41 | MPT51, ESAT6, MPT64, TB9.8, PPE41, PE25 | MPT51, CFP10, MPT64, TB9.8, MPT83, PE25 | MPT51, MPT64, TB9.8, MPT83, PPE41, PE25 | ESAT6, CFP10, TB9.8, TB10.4, MPT83, PE25 | CFP10, MPT64, TB10.4, MPT83, PPE41, PE25 |
| MPT51, ESAT6, CFP10, TB9.8, TB10.4, PE25 | MPT51, ESAT6, MPT64, TB10.4, MPT83, PPE41 | MPT51, CFP10, MPT64, TB9.8, PPE41, PE25 | MPT51, MPT64, TB10.4, MPT83, PPE41, PE25 | ESAT6, CFP10, TB9.8, TB10.4, PPE41, PE25 | CFP10, TB9.8, TB10.4, MPT83, PPE41, PE25 |
| MPT51, ESAT6, CFP10, TB9.8, MPT83, PPE41 | MPT51, ESAT6, MPT64, TB10.4, MPT83, PE25 | MPT51, CFP10, MPT64, TB10.4, MPT83, PPE41 | MPT51, TB9.8, TB10.4, MPT83, PPE41, PE25 | ESAT6, CFP10, TB9.8, MPT83, PPE41, PE25 | MPT64, TB9.8, TB10.4, MPT83, PPE41, PE25 |

TABLE 4G

| TB-MAPS comprising a combination of 7 MTBantigens (36 possible combinations) | | | | | |
|---|---|---|---|---|---|
| MPT51, ESAT6, CFP10, MPT64, TB9.8, TB10.4, MPT83 | MPT51, ESAT6, CFP10, MPT64, TB10.4, MPT83, PPE41 | MPT51, ESAT6, CFP10, TB9.8, TB10.4, PPE41, PE25 | MPT51, ESAT6, MPT64, TB9.8, MPT83, PPE41, PE25 | MPT51, CFP10, MPT64, TB9.8, MPT83, PPE41, PE25 | ESAT6, CFP10, MPT64, TB9.8, TB10.4, PPE41, PE25 |
| MPT51, ESAT6, CFP10, MPT64, TB9.8, TB10.4, PPE41 | MPT51, ESAT6, CFP10, MPT64, TB10.4, MPT83, PE25 | MPT51, ESAT6, CFP10, TB9.8, MPT83, PPE41, PE25 | MPT51, ESAT6, MPT64, TB10.4, MPT83, PPE41, PE25 | MPT51, CFP10, MPT64, TB10.4, MPT83, PPE41, PE25 | ESAT6, CFP10, MPT64, TB9.8, MPT83, PPE41, PE25 |
| MPT51, ESAT6, CFP10, MPT64, TB9.8, TB10.4, PE25 | MPT51, ESAT6, CFP10, MPT64, TB10.4, PPE41, PE25 | MPT51, ESAT6, CFP10, TB10.4, MPT83, PPE41, PE25 | MPT51, ESAT6, TB9.8, TB10.4, MPT83, PPE41, PE25 | MPT51, CFP10, TB9.8, TB10.4, MPT83, PPE41, PE25 | ESAT6, CFP10, MPT64, TB10.4, MPT83, PPE41, PE25 |
| MPT51, ESAT6, CFP10, MPT64, TB9.8, MPT83, PPE41 | MPT51, ESAT6, CFP10, MPT64, MPT83, PPE41, PE25 | MPT51, ESAT6, MPT64, TB9.8, TB10.4, MPT83, PPE41 | MPT51, CFP10, MPT64, TB9.8, TB10.4, MPT83, PPE41 | MPT51, MPT64, TB9.8, TB10.4, MPT83, PPE41, PE25 | ESAT6, CFP10, TB9.8, TB10.4, MPT83, PPE41, PE25 |
| MPT51, ESAT6, CFP10, MPT64, TB9.8, MPT83, PE25 | MPT51, ESAT6, CFP10, TB9.8, TB10.4, MPT83, PPE41 | MPT51, ESAT6, MPT64, TB9.8, TB10.4, MPT83, PE25 | MPT51, CFP10, MPT64, TB9.8, TB10.4, MPT83, PE25 | ESAT6, CFP10, MPT64, TB9.8, TB10.4, MPT83, PPE41 | ESAT6, MPT64, TB9.8, TB10.4, MPT83, PPE41, PE25 |
| MPT51, ESAT6, CFP10, MPT64, TB9.8, PPE41, PE25 | MPT51, ESAT6, CFP10, TB9.8, TB10.4, MPT83, PE25 | MPT51, ESAT6, MPT64, TB9.8, TB10.4, PPE41, PE25 | MPT51, CFP10, MPT64, TB9.8, TB10.4, PPE41, PE25 | ESAT6, CFP10, MPT64, TB9.8, TB10.4, MPT83, PE25 | CFP10, MPT64, TB9.8, TB10.4, MPT83, PPE41, PE25 |

TABLE 4H

| TB-MAPS comprising a combination of 8 Mtb antigens (9 possible combinations) | | |
|---|---|---|
| MPT51, ESAT6, CFP10, MPT64, TB9.8, TB10.4, MPT83, PPE41 | MPT51, ESAT6, CFP10, MPT64, TB9.8, MPT83, PPE41, PE25 | MPT51, ESAT6, MPT64, TB9.8, TB10.4, MPT83, PPE41, PE25 |
| MPT51, ESAT6, CFP10, MPT64, TB9.8, TB10.4, MPT83, PE25 | MPT51, ESAT6, CFP10, MPT64, TB10.4, MPT83, PPE41, PE25 | MPT51, CFP10, MPT64, TB9.8, TB10.4, MPT83, PPE41, PE25 |
| MPT51, ESAT6, CFP10, MPT64, TB9.8, TB10.4, PPE41, PE25 | MPT51, ESAT6, CFP10, TB9.8, TB10.4, MPT83, PPE41, PE25 | ESAT6, CFP10, MPT64, TB9.8, TB10.4, MPT83, PPE41, PE25 |

TABLE 41

| TB-MAPS comprising a combination of all Mtb antigens |
|---|
| MPT51, ESAT6, CFP10, MPT64, TB9.8, TB10.4, MPT83, PPE41, PE25 |

In Tables 4A-4I, MPT51=MPT51 protein or a fragment thereof, e.g., MPT51(33-299), ESAT6=ESAT6 protein or a fragment thereof, CFP10=CFP10 protein or a fragment thereof, e.g., CFP10(1-41) or CFP10 (45-80), or both CFP10 (1-41) and CFP10(45-80), MPT64=MPT64 protein or a fragment thereof, e.g., MPT64(25-228); MPT83=MPT83 protein or a fragment thereof, e.g., MPT83(58-220); TB9.8=TB9.8 protein or a fragment thereof, TB10.4=TB10.4 protein or a fragment thereof, PPE41=PPE41 protein or a fragment thereof, PE25=PE25 protein or a fragment thereof. It is envisioned that any of the Mtb antigens in the Rhavi-antigen-antigen fusion proteins shown in Tables 4A-4I can be substituted or replaced with any other Mtb antigen as disclosed herein, or known to one of ordinary skill in the art.

It is envisioned that any of the above-identified antigens in Tables 3A-3G can be switched out for a different Mtb antigen, including a different peptides or polypeptides of ESAT6, CFP10, MPT51, MPT64, MPT83, TB9.8, TB10.4, PPE41, and PE25, or peptides or polypeptides at least 85% sequence identity thereto, or completely different Mtb antigens. In some embodiments, a Mtb antigen identified in tables 4A-4I can be substituted or switched out with a non-Mtb antigen, as disclosed herein.

Accordingly, in some embodiments, an ordinary skilled artisan can substitute any of the antigens listed in 4A-4I with any other Mtb antigen not listed herein and known to an ordinary skilled artisan, or even substitute a Mtb antigen listed in Tables 4A-4I with a non-Mtb antigen.

In addition to one or more *M. tuberculosis* antigens present in the MAPS complex, the MAPS complex may comprise non-*M. tuberculosis* (non-TB) immunogenic antigens, including but not limited to pathogenic peptides, toxins, toxoids, subunits thereof, or combinations thereof (e.g., cholera toxin, tetanus toxoid).

In some embodiments, an antigen is derived (e.g., obtained) from a pathogenic organism. In some embodiments, the antigen is a cancer or tumor antigen, e.g., an antigen derived from a tumor or cancer cell.

In some embodiments, an antigen derived from a pathogenic organism is an antigen associated with an infectious disease; it can be derived from any of a variety of infectious agents, including virus, bacterium, fungus or parasite.

In some embodiments, a target antigen is any antigen associated with a pathology, for example an infectious disease or pathogen, or cancer or an immune disease such as an autoimmune disease. In some embodiments, an antigen can be expressed by any of a variety of infectious agents, including virus, bacterium, fungus or parasite. A target antigen for use in the methods and compositions as disclosed herein can also include, for example, pathogenic peptides, toxins, toxoids, subunits thereof, or combinations thereof (e.g., cholera toxin, tetanus toxoid).

Non-limiting examples of infectious viruses include: Retroviridae; Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bungaviridae (for example, Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and HSV-2, varicella zoster virus, cytomegalovirus (CMV), Marek's disease virus, herpes viruses); Poxviridae (variola viruses, vaccinia viruses, pox viruses); and Iridoviridae (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses). The compositions and methods described herein are contemplated for use in treating infections with these viral agents.

Examples of fungal infections that may be addressed by inclusion of antigens in the present embodiments include aspergillosis; thrush (caused by *Candida albicans*); cryptococcosis (caused by *Cryptococcus*); and histoplasmosis. Thus, examples of infectious fungi include, but are not limited to, *Cryptococcus neoformans, Histoplasma capsulatum, Coccidioides immitis, Blastomyces dermatitidis, Chlamydia trachomatis, Candida albicans*. Components of these organisms can be included as antigens in the MAPS described herein.

In one aspect of the invention, an non-Mtb antigen to be used in combination with one or more Mtb antigens on the MAPS complex is derived from an infectious microbe such as *Bordetella pertussis, Brucella*, Enterococci sp., *Neisseria meningitidis, Neisseria gonorrheae, Moraxella*, typeable or nontypeable *Haemophilus, Pseudomonas, Salmonella, Shigella, Enterobacter, Citrobacter, Klebsiella, E. coli, Helicobacter pylori*, Clostridia, *Bacteroides*, Chlamydiaceae, *Vibrio cholera, Mycoplasma*, Treponemes, Borelia *burgdorferi, Legionella* pneumophilia, Mycobacteria sps (such as *M. tuberculosis, M. avium, M. intracellulare*, M. kansaii, *M. gordonae, M. leprae*), *Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Leptospira* sps., Pasturella *multocida, Bacteroides* sp., *Fusobacterium nucleatum, Streptobacillus moniliformis, Treponema pallidium, Treponema pertenue*, and *Actinomyces* israelli.

In some embodiments, a non-Mtb antigen useful in a TB-MAPS complex as disclosed herein is an antigen from an enteric bacterium, or a non-enteric gram-negative bacterium. In some embodiments, a non-Mtb antigen useful in a TB-MAPS complex as disclosed herein can be selected from any of, or a combination of: a pneumococcal antigen, tuberculosis antigen, HIV antigen, seasonal or epidemic influenza antigen, pertussis antigen, meningococcal antigen, *haemophilus* antigen, HPV antigen, *E. coli* antigens, *salmonella* antigens, *enterobacter* antigens, *acinetobacter* pathogen antigens, pseudomona antigens, *klebsiella* antigens, *citrobacter* antigens, *serratia* antigens, *Clostridium difficile* antigens from an enteric bacteria, antigens from non-enteric gram-negative bacteria, toxoids, toxins or toxin portions thereof.

In some embodiments, a non-Mtb antigen useful in a TB-MAPS complex as disclosed herein is a pneumococcal antigen, a tuberculosis antigen, an anthrax antigen, a HIV antigens, a seasonal or epidemic influenza antigen, a HPV antigen, an *Acinetobacter* antigens, a-*Clostridium difficile* antigen, an enteric Gram-negative bacterial antigen or non-enteric Gram-negative bacterial antigen, a Gram-positive bacterial antigens, a toxoid, toxin or toxin portion, a fungal antigen, a viral antigen, a cancer antigen or any combinations thereof.

In some embodiments, a non-Mtb antigen useful in a TB-MAPS complex as disclosed herein is an enteric Gram-negative bacterial antigen, selected from the group of: *E. coli* antigens, *Salmonella* antigens, *Enterobacter* antigens, *Klebsiella* antigens, *Citrobacter* antigens and *Serratia* antigens, or combinations thereof. In some embodiments, a non-Mtb antigen useful in a TB-MAPS complex as disclosed herein is a nonenteric Gram-negative bacterial antigens are selected from the group of: Pertussis antigens, Meningococcal antigens, *Haemophilus* antigens, and *Pseudomonas* antigens or combinations thereof.

Additional parasite pathogens from which antigens can be derived include, for example: *Entamoeba histolytica, Plasmodium falciparum, Leishmania* sp., *Toxoplasma gondii, Rickettsia*, and the Helminths.

In some embodiments, a non-Mtb antigen useful in a TB-MAPS complex as disclosed herein is a truncated pneumococcal PsaA protein, pneumolysin toxoid pneumococcal serine/threonine protein kinase (StkP), pneumococcal serine/threonine protein kinase repeating unit (StkPR), pneumococcal PcsB protein, staphylococcal alpha hemolysin, *Chlamydia* CT144, CT242 or CT812 polypeptides or fragments of these, *Chlamydia* DNA gyrase subunit B, *Chlamydia* sulfite synthesis/biphosphate phosphatase, *Chlamydia* cell division protein FtsY, *Chlamydia* methionyl-tRNA synthetase, *Chlamydia* DNA helicase (uvrD), *Chlamydia* ATP synthase subunit I (atpI), or *Chlamydia* metal dependent hydrolase.

In some embodiments, a non-Mtb antigen useful in a TB-MAPS complex as disclosed herein can be derived from a *Chlamydia* species for use in the immunogenic compositions of the present invention. Chlamydiaceae (consisting of Chlamydiae and *Chlamydophila*), are obligate intracellular gram-negative bacteria. *Chlamydia trachomatis* infections are among the most prevalent bacterial sexually transmitted infections, and perhaps 89 million new cases of genital chlamydial infection occur each year. The *Chlamydia* of the present invention include, for example, *C. trachomatis, Chlamydophila pneumoniae, C. muridarum, C. suis, Chlamydophila abortus, Chlamydophila psittaci, Chlamydophila caviae, Chlamydophila fells, Chlamydophila pecorum*, and *C. pneumoniae*. Animal models of chlamydial infection have established that T-cells play a critical role both in the clearance of the initial infection and in protection from re-infection of susceptible hosts. Hence, the immunogenic compositions as disclosed herein can be used to provide particular value by eliciting cellular immune responses against chlamydial infection.

More specifically, Chlamydial antigens useful as a non-Mtb antigen in a TB-MAPS complex as disclosed herein include DNA gyrase subunit B, sulfite synthesis/biphosphate phosphatase, cell division protein FtsY, methionyl-tRNA synthetase, DNA helicase (uvrD); ATP synthase subunit I (atpI) or a metal-dependent hydrolase (U.S. Patent Application Pub. No. 20090028891). Additional *Chlamydia trachomatis* antigens include CT144 polypeptide, a peptide having amino acid residues 67-86 of CT144, a peptide having amino acid residues 77-96 of CT144, CT242 protein, a peptide having amino acids 109-117 of CT242, a peptide having amino acids 112-120 of CT242 polypeptide, CT812 protein (from the pmpD gene), a peptide having amino acid residues 103-111 of the CT812 protein; and several other antigenic peptides from *C. trachomatis*, which are disclosed in US Patent Application: 2014/0154287 and WO 2009/020553. Additionally, *Chlamydia pneumoniae* antigens including homologues of the foregoing polypeptides (see U.S. Pat. No. 6,919,187), can be used an antigens in the immunogenic compositions and methods as disclosed herein.

In some embodiments, an TB or non-Mtb antigen for use in the TB-MAPS composition can be an intact (i.e., an entire or whole) antigen, or a functional portion of an antigen that comprises more than one epitope. In some embodiments, an antigen is a peptide functional portion of an antigen. By “intact” in this context is meant that the antigen is the full length antigen as that antigen polypeptide occurs in nature. This is in direct contrast to delivery of only a small portion or peptide of the antigen. Delivering an intact antigen to a cell enables or facilitates eliciting an immune response to a full range of epitopes of the intact antigen, rather than just a single or selected few peptide epitopes. Accordingly, the methods and immunogenic compositions described herein encompass intact antigens associated with the polymer for a more sensitive and have higher specificity of immune response as compared to use of a single epitope peptide-based antigen.

Alternatively, in some embodiments, an intact Mtb antigen can be divided into many parts, depending on the size of the initial antigen. Typically, where a whole antigen is a multimer polypeptide, the whole protein can be divided into sub-units and/or domains where each individual sub unit or domain of the antigen can be associated with the polymer according to the methods as disclosed herein. Alternatively, in some embodiments, an intact Mtb antigen can be divided into functional fragments, or parts, of the whole antigen, for example, at least two, or at least 3, or at least 4, or at least 5, or at least 6, or at least 7, or at least 8, or at least 9, or at least 10, or at least 11, or at least 12, or at least 13, or at least 15, or at least 20, or at least 25, or more than 25 portions (e.g., pieces or fragments), inclusive, and where each individual functional fragment of the antigen can be associated with the polymer according to the methods as disclosed herein.

The fragmentation or division of a full length Mtb antigen polypeptide can be an equal division of the full length antigen polypeptide, or alternatively, in some embodiments, the fragmentation is asymmetrical or unequal. As a non-limiting example, where an antigen is divided into two overlapping fragments, an antigen can be divided into fragments of approximately the same (equal) size, or alternatively one fragment can be about 45% of the whole antigen and the other fragment can be about 65%. As further non-limiting examples, a whole antigen can be divided into a combination of differently sized fragments, for example, where an antigen is divided into two fragments, fragments can be divided into about 40% and about 70%, or about 45% and about 65%; or about 35% and about 75%; or about 25% and about 85%, inclusive, of the whole antigen. Any combination of overlapping fragments of a full length whole antigen is encompassed for use in the generation of a panel of overlapping polypeptides of an antigen. As an illustrative example only, where an antigen is divided into 5 portions, the portions can divided equally (i.e., each overlapping fragment is about 21% to 25% of the entire full length if the antigen) or unequally (i.e., an antigen can be divided into the following five overlapping fragments; fragment 1 is about 25%, fragment 2 is about 5%, fragment 3 is about 35%, fragment 4 is about 10% and fragment 5 is about 25% of the size of the full length antigen, provided each fragment overlaps with at least one other fragment).

Typically, a panel of antigen portions can substantially cover the entire length of the whole (or intact) antigen polypeptide. Accordingly, in some embodiments, an immunogenic composition comprises a polymer with many different, and/or overlapping fragments of the same intact antigen. Overlapping protein fragments of an antigen can be produced much quicker and cheaper, and with increased stability as compared to the use of peptide antigens alone. Further in some embodiments, antigens which are polypeptides larger than simple peptides are preferred as conformation is important for epitope recognition, and the larger antigen polypeptides or fragments will provide a benefit over peptide fragments.

One of ordinary skill in the art can divide a whole antigen into overlapping proteins of an antigen to create a panel of polypeptides of the antigen. By way of an illustrative example only, a Mtb antigen MPT51 can be divided into, for example at least 10 portions to generate a panel of 10 different polypeptides, each comprising a different but overlapping MPT51-specific antigens fragments.

A target antigen for use in the methods and compositions described herein can be expressed by recombinant means, and can optionally include an affinity or epitope tag to facilitate purification, which methods are well-known in the art. Chemical synthesis of an oligopeptide, either free or conjugated to carrier proteins, can be used to obtain antigen of the invention. Oligopeptides are considered a type of polypeptide. An antigen can be expressed as a fusion with a complementary affinity molecule, e.g., but not limited to rhizavidin or a derivative or functional fragment thereof. Alternatively, it is also possible to prepare target antigen and then conjugate it to a complementary affinity molecule, e.g., but not limited to rhizavidin or a derivative or functional fragment thereof.

Polypeptides can also by synthesized as branched structures such as those disclosed in U.S. Pat. Nos. 5,229,490 and 5,390,111. Antigenic polypeptides include, for example, synthetic or recombinant B-cell and T-cell epitopes, universal T-cell epitopes, and mixed T-cell epitopes from one organism or disease and B-cell epitopes from another.

An antigen can be obtained through recombinant means or chemical polypeptide synthesis, as well as antigen obtained from natural sources or extracts, can be purified by means of the antigen’s physical and chemical characteristics, such as by fractionation or chromatography. These techniques are well-known in the art.

In some embodiments, an antigen can be solubilized in water, a solvent such as methanol, or a buffer. Suitable buffers include, but are not limited to, phosphate buffered saline $Ca^{2+}/Mg^{2+}$ free (PBS), normal saline (150 mM NaCl in water), and Tris buffer. Antigen not soluble in neutral buffer can be solubilized in 10 mM acetic acid and then diluted to the desired volume with a neutral buffer such as PBS. In the case of antigen soluble only at acid pH, acetate-PBS at acid pH can be used as a diluent after solubilization in dilute acetic acid. Glycerol can be a suitable non-aqueous solvent for use the compositions, methods and kits described herein.

Typically, when designing a protein vaccine against a pathogen, an extracellular protein or one exposed to the environment on a virus is often the ideal candidate as the antigen component in the vaccine. Antibodies generated against that extracellular protein become the first line of defense against the pathogen during infection. The antibodies bind to the protein on the pathogen to facilitate antibody opsonization and mark the pathogen for ingestion and destruction by a phagocyte such as a macrophage. Antibody opsonization can also kill the pathogen by antibody-dependent cellular cytotoxicity. The antibody triggers a release of lysis products from cells such as monocytes, neutrophils, eosinophils, and natural killer cells.

In one embodiment of the invention described herein, antigens for use in the compositions as disclosed herein all wild type proteins, as in the amino acid residues have the sequences found in naturally occurring viruses and have not been altered by selective growth conditions or molecular biological methods.

In one embodiment, the immunogenic compositions described as herein can comprise antigens which are glycosylated proteins. In other words, an antigen of interest can each be a glycosylated protein. In one embodiment of the immunogenic compositions as described herein, antigens, or antigen-fusion polypeptides are O-linked glycosylated. In another embodiment of the immunogenic compositions as described herein, antigens, or antigen-fusion polypeptides are N-linked glycosylated. In yet another embodiment of the immunogenic compositions as described herein, antigens, or antigen-fusion are both O-linked and N-linked glycosylated. In other embodiments, other types of glycosylations are possible, e.g., C-mannosylation. Glycosylation of proteins occurs predominantly in eukaryotic cells. N-glycosylation is important for the folding of some eukaryotic proteins, providing a co-translational and post-translational modification mechanism that modulates the structure and function of membrane and secreted proteins. Glycosylation is the enzymatic process that links saccharides to produce glycans, and attaches them to proteins and lipids. In N-glycosylation, glycans are attached to the amide nitrogen of asparagine side chain during protein translation. The three major saccharides forming glycans are glucose, mannose, and N-acetylglucosamine molecules. The N-glycosylation consensus is Asn-Xaa-Ser/Thr, where Xaa can be any of the known amino acids. O-linked glycosylation occurs at a later stage during protein processing, probably in the Golgi apparatus. In O-linked glycosylation, N-acetyl-galactosamine, O-fucose, O-glucose, and/or N-acetylglucosamine is added to serine or threonine residues. One skilled in the art can use bioinformatics software such as NetNGlyc 1.0 and NetOGlyc Prediction softwares from the Technical University of Denmark to find the N- and O-glycosylation sites in a polypeptide in the present invention. The NetNglyc server predicts N-Glycosylation sites in proteins using artificial neural networks that examine the sequence context of Asn-Xaa-Ser/Thr sequons. The NetNGlyc 1.0 and NetOGlyc 3.1 Prediction software can be accessed at the EXPASY website. In one embodiment, N-glycosylation occurs in the target antigen polypeptide of the fusion polypeptide described herein.

Affinity Molecule Pairs

As disclosed herein, a key aspect of the TB-MAPS composition is the attachment of the Mtb antigens to the immunogenic polysaccharide. As discussed herein, a Mtb antigen is connected to an immunogenic polysaccharide via a complementary affinity pair. This connecting of the Mtb antigen to the immunogenic polysaccharide is mediated by the immunogenic polysaccharide being connected to a first affinity molecule, which associates a second (e.g., complementary) affinity molecule, which is attached to the Mtb antigen. An example complementary affinity pair is biotin and a biotin-binding protein, e.g. biotin and rhizavidin protein or fragment thereof.

Exemplary examples of the affinity complementary affinity pairs for use in the TB-MAPS immunogenic composition include, but without limitation, biotin binding proteins or avidin-like proteins that bind to biotin. For example, where the first affinity binding molecule is biotin (which associates with the polymer), the complementary affinity molecule can be a biotin binding protein or an avidin-like protein or a derivative thereof, e.g., but not limited to, avidin, rhizavidin, or streptavidin or variants, derivatives or functional portions thereof.

In some embodiments, the first affinity binding molecule is biotin, a biotin derivative, or a biotin mimic, for example, but not limited to, amine-PEG3-biotin (((+)-biotinylation-3-6,9-trixaundecanediamine) or a derivative or functional fragment thereof. A specific biotin mimetic has a specific peptide motif containing sequence of $DX_aAX_bPX_c$ (SEQ ID NO: 37), or $CDX_aAX_bPX_cCG$ (SEQ ID NO: 38), where $X_a$ is R or L, $X_b$ is S or T, and $X_c$ is Y or W. These motifs can bind avidin and Neutravidin, but streptavidin. See, e.g., Gaj et al., 56 Prot. Express. Purif. 54 (2006). In some embodiments the first affinity binding molecule is lipoic acid or a derivative thereof, or HABA (hydroxyazobenzene-benzoic acid, or dimethyl-HABA).

The linkage of the first affinity molecule to the immunogenic polysaccharide, and the complementary affinity molecule to the Mtb antigen can be a non-covalent linkage, or a chemical mechanism, for instance covalent binding, affinity binding, intercalation, coordinate binding and complexation. Covalent binding provides for very stable binding, and is particularly well-suited for the present embodiments. Covalent binding can be achieved either by direct condensation of existing side chains or by the incorporation of external bridging molecules.

For example, in some embodiments, a Mtb antigen can be non-covalently bonded to one of the pairs in a complementary affixing pair. In alternative embodiments, an antigen can be covalently bonded or fused to one of the pairs in a complementary affixing pair. Methods for generation of fusion proteins are well known in the art, and are discussed herein.

In other embodiments, a first affinity binding molecule is linked to the immunogenic polysaccharide by a non-covalent bond, or by a covalent bond. In some embodiments, a cross-linking reagent is used to covalently bond the first affinity binding molecule to the immunogenic polysaccharide as disclosed herein.

In some embodiments, the first affinity binding molecule associates with the complementary affinity molecule by non-covalent bond association as known in the art, including, but not limited to, electrostatic interaction, hydrogen bound, hydrophobic interaction (i.e., van der Waals forces), hydrophilic interactions, and other non-covalent interactions. Other higher order interactions with intermediate moieties are also contemplated.

In some embodiments, the complementary affinity molecule is an avidin-related polypeptide. In specific embodiments, the complementary affinity molecule is rhizavidin, such as recombinant rhizavidin of SEQ ID NO: 1 or a protein having an amino acid that has at least 85% sequence identity to SEQ ID NO: 1. In particular, the recombinant rhizavidin is a modified rhizavidin that can be expressed in *E. coli* with a high yield. The typical yield is >30 mg per liter of *E. coli* culture. Rhizavidin has a lower sequence homology to egg avidin (22.4% sequence identity and 35.0% similarity) compared with other avidin-like proteins. Use of the modified rhizavidin reduces the risk of the MAPS inducing an egg-related allergic reaction in a subject. Moreover, antibody to recombinant modified rhizavidin has no apparent cross-reactivity to egg avidin (and vice versa).

Additional affinity pairs that may be useful in the methods and compositions described herein include antigen-antibody, metal/ion-metal/ion-binding protein, lipid/lipid binding protein, saccharide/saccharide binding protein, amino acid/peptide/amino acid or peptide binding protein, enzyme-substrate or enzyme-inhibitor, ligand-agonist/receptor, or biotin mimetic. When using alternative affinity pairs, alternative means of attaching the respective polymer and antigen may also be employed, such as in vitro enzymatic reactions rather than genetic fusion. More specifically, antigen-antibody affinity pair provides for a very strong and specific interaction. The antigen can be any epitope including protein, peptide, nucleic acid, lipid, poly/oligosaccharide, ion, etc. The antibody can be any type of immunoglobulin, or the Ag-binding portion of an immunoglobulin, such as a Fab fragment. Regarding metal/ion-metal/ion binding protein, examples include Ni NTA vs. histidine-tagged protein, or Zn vs. Zn binding protein. Regarding lipid/lipid binding protein, examples include cholesterol vs. cholesterol binding protein. Regarding saccharide/saccharide binding protein, examples include maltose vs. maltose binding protein, mannose/glucose/oligosaccharide vs. lectin. Enzyme-substrate/inhibitors include substrates from a wide range of substances, including protein, peptide, amino acid, lipid, sugar, or ions. The inhibitor can be the analog of the real substrate which can generally bind to the enzymes more tightly and even irreversibly. For example, trypsin vs. soy trypsin inhibitor. The inhibitor can be natural or synthetic molecule. Regarding other ligand/agonist-receptor, ligand can be from a wide range of substance, including protein, peptide, amino acid, lipid, sugar, ion, agonist can be the analog of the real ligand. Examples include the LPS vs. TLR4 interaction.

Cross-Linking Reagents

Many bivalent or polyvalent linking agents are useful in coupling at least one or more affinity molecules to the immunogenic polysaccharide of the TB-MAPS immunogenic composition as disclosed herein. For example, representative coupling agents can include organic compounds such as thioesters, carbodiimides, succinimide esters, disocyanates, glutaraldehydes, diazobenzenes and hexamethylene diamines. This listing is not intended to be exhaustive of the various classes of coupling agents known in the art but, rather, is exemplary of the more common coupling agents. See Killen & Lindstrom, 133 J. Immunol. 1335 (1984); Jansen et al., 62 Imm. Rev. 185 (1982); Vitetta et al.

In some embodiments, cross-linking reagents agents described in the literature are encompassed for use in the methods, immunogenic compositions and kits as disclosed herein. See, e.g., Ramakrishnan, et al., 44 Cancer Res. 201 (1984) (describing the use of MBS (M-maleimidobenzoyl-N-hydroxysuccinimide ester)); Umemoto et al., U.S. Pat. No. 5,030,719 (describing the use of a halogenated acetyl hydrazide derivative coupled to an antibody by way of an oligopeptide linker). Particular linkers include: (a) EDC (1-ethyl-3-(3-dimethylamino-propyl) carbodiimide hydrochloride; (b) SMPT (4-succinimidyloxycarbonyl-alpha-methyl-alpha-(2-pyridyl-dithio)-toluene (Pierce Chem. Co., Cat. (21558G); (c) SPDP (succinimidyl-6 [3-(2-pyridyldithio) propionamido] hexanoate (Pierce Chem. Co., Cat #21651 G); (d) Sulfo-LC-SPDP (sulfosuccinimidyl 6 [3-(2-pyridyldithio)-propianamide]hexanoate (Pierce Chem. Co. Cat. #2165-G); and (f) sulfo-NHS (N-hydroxysulfo-succinimide: Pierce Chem. Co., Cat. #24510) conjugated to EDC.

The linkages or linking agents described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage can be cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

Additional cross linkers for —SH (thiolated CP) to —$NH_2$ linkages include but are not limited to: sulfa-LC-SMPT; sulfo-LC-SMPT (4-sulfosuccinimidyl-6-methyl-a-(2-pyridyldithio)toluamido]hexanoate)); sulfo-KMUS (N-[k-maleimidoundecanoyloxy]sulfosuccinimide ester); sulfo-LC-SPDP (sulfosuccinimidyl 6-(3'-[2-pyridyldithio]-propionamido)hexanoate) which cleaves by thiols; sulfo-SMPB (sulfosuccinimidyl 4-[p-maleimidophenyl]butyrate); sulfo-SIAB (N-sulfosuccinimidyl[4-iodoacetyl]aminobenzoate); sulfa-EMCS ([N-e-maleimidocaproyloxy]sulfosuccinimide ester); EMCA (N-e-maleimidocaproic acid); sulfo-SMCC (sulfosuccinimidyl 4-[N-maleimidomethyl] cyclohexane-1-carboxylate); sulfo-MBS (m-maleimidobenzoyl-N-hydroxysulfosuccinimide ester); sulfo-GMBS (N-[g-maleimidobutyryloxy]sulfosuccinimide ester); BMPA (N-.beta.-maleimidopropionic acid); 2-immunothiolane hydrochloride; 3-(2-pyridyldithio)propionic acid N-succinimidyl ester; 3-malemidopropionic acid N-succinimidyl ester; 4-maleimidobutyric acid N-succinimidyl ester; SMPT (4-succinimidyloxycarbonyl-methyl-a-[2-pyridyldithio]toluene); LC-SMCC (succinimidyl-4-[N-maleimidomethyl]cyclohexane-1-carboxy-[6-amidocaproate-]); KMUA (N-k-maleimidoundecanoic acid); LC-SPDP (succinimidyl 6-(3-[2-pyridyldithio]-propionamido)hexanoate); SMPH (succinimidyl-6-[.beta.-maleimidopropionamido]hexanoate); SMPB (succinimidyl 4-[p-maleimidophenyl]butyrate); SIAB (N-succinimidyl[4-iodoacetyl]aminobenzoate); EMCS ([N-e-Maleimidocaproyloxy]succinimide ester); SMCC (succinimidyl4-[N-maleimidomethyl]cyclohexane-1-carboxylate); MBS (m-Maleimidobenzoyl-N-hydroxysuccinimide ester); SBAP (succinimidyl 3-[bromoacetamido] propionate); BMPS (N-[.beta.-maleimidopropyloxylsuccinimide ester); AMAS N-(a- maleimidoacetoxy)succinimide ester); SIA (N-succinimidyl iodoacetate); and N-succinimidyl (4-iodoacetyl)-aminobenzoate.

The agents can also be crosslinked using crosslinkers for —SH to —OH groups. Such cross linkers include but are not limited to PMPI (N-[p-maleimidophenyl]isocyanate).

Exemplary cross-linking molecules for use in the methods and immunogenic compositions as disclosed herein include, but are not limited to those listed in Tables 5 and 6.

TABLE 5

Exemplary homobifunctional crosslinkers*

| Crosslinking Target | Crosslinker Reactive Groups, Features | Example Products |
|---|---|---|
| Amine-to-Amine | NHS esters | DSG; DSS; BS3; TSAT (trifunctional); Bioconjugate Toolkit Reagent Pairs |
| | NHS esters, PEG spacer | BS(PEG)5; BS(PEG)9 |
| | NHS esters, thiol-cleavable | DSP; DTSSP |
| | NHS esters, misc-cleavable | DST; BSOCOES; EGS; Sulfo-EGS |
| | Imidoesters | DMA; DMP; DMS |
| | Imidoesters, thiol-cleavable | DTBP |
| | Other | DFDNB; THPP (trifunctional); Aldehyde-Activated Dextran Kit |
| Sulfhydryl-to-Sulfhydryl | Maleimides | BMOE; BMB; BMH; TMEA (trifunctional) |
| | Maleimides, PEG spacer | BM(PEG)2; BM(PEG)3 |
| | Maleimides, cleavable | BMDB; DTME |
| | Pyridyldithiols (cleavable) | DPDPB |
| | Other | HBVS (vinylsulfone) |
| Nonselective | Aryl azides | BASED (thiol-cleavable) |

*crosslinking reagents that have the same type of reactive group at either end. Reagents are classified by what chemical groups they cross link (left column) and their chemical composition (middle column). Products are listed in order of increasing length within each cell.

TABLE 6

Exemplary heterobifunctional crosslinkers*

| Crosslinking Targets | Crosslinker Reactive Groups, Features | Example Products |
|---|---|---|
| Amine-to-Sulfhydryl | NHS ester/Maleimide | AMAS; BMPS; GMBS and Sulfo-GMBS; MBS and Sulfo-MBS; SMCC and Sulfo-SMCC; EMCS and Sulfo-EMCS; SMPB and Sulfo-SMPB; SMPH; LC-SMCC; Sulfo-KMUS |
| | NHS ester/Maleimide, PEG spacer | SM(PEG)2; SM(PEG)4; SM(PEG)6; SM(PEG)8; SM(PEG)12; SM(PEG)24 |
| | Pyridyldithiol, cleavable | SPDP; LC-SPDP and Sulfo-LC-SPDP; SMPT; Sulfo-LC-SMPT |
| | NHS esters/Haloacetyl | SIA; SBAP; STAB; Sulfo-STAB |
| Amine-to-Nonselective | NHS ester/Aryl Azide | NHS-ASA<br>ANB-NOS<br>Sulfo-HSAB<br>Sulfo-NHS-LC-ASA<br>SANPAH and Sulfo-SANPAH |
| | NHS ester/Aryl Azide, cleavable | Sulfo-SFAD; Sulfo-SAND; Sulfo-SAED |
| | NHS ester/Diazirine | SDA and Sulfo-SDA; LC-SDA and Sulfo-LC-SDA |
| | NHS ester/Diazirine, cleavable | SDAD and Sulfo-SDAD |
| Amine-to-Carboxyl | Carbodiimide | DCC; EDC |
| Sulfhydryl-to-Nonselective | Pyridyldithiol/Aryl Azide | APDP |
| Sulfhydryl-to-Carbohydrate | Maleimide/Hydrazide | BMPH; EMCH; MPBH; KMUH |
| | Pyridyldithiol/Hydrazide | BMPH; EMCH; MPBH; KMUH |
| Carbohydrate-to-Nonselective | Hydrazide/Aryl Azide | ABH |
| Hydroxyl-to-Sulfhydryl | Isocyanate/Maleimide | PMPI |
| Amine-to-DNA | NHS ester/Psoralen | SPB |

*crosslinking reagents that have the different reactive groups at either end. Reagents are classified by what chemical groups they cross link (left column) and their chemical composition (middle column). Products are listed in order of increasing length within each cell.

Co-Stimulatory Factor

In some embodiments, an immunogenic composition comprising the TB-MAPS as disclosed herein comprises at least one co-stimulatory molecule. In some embodiments, the co-stimulatory factor is cross-linked to the immunogenic polysaccharide. In some embodiments, the co-stimulatory factor is associated to the immunogenic polysaccharide by a complementary affinity pair similar to how the Mtb antigen is associated with the immunogenic polysaccharide. In some embodiments, where the complementary affinity pair which links the co-stimulatory factor to the immunogenic polysaccharide is the same, or a different complementary affinity pair which links the Mtb antigen to the immunogenic polysaccharide.

In some embodiments, at least one, or at least 2, or at least 3, or at least 5, or at least 10, or at least 15, or at least 20, or at least 50, or at least 100, or more than about 100, inclusive, co-stimulatory factors can be associated with the immunogenic polysaccharide as disclosed herein. In some embodiments, the co-stimulatory factors can be the same co-stimulator factor, or they can be a variety of different co-stimulatory factors associated with the immunogenic polysaccharide.

In some embodiments, the co-stimulator factor is a ligand/agonist of Toll like receptors, e.g., but not limited to TLR1, TLR2, TLR3, TLR4, TLR5, TLR6, TLR7, TLR8, TLR9, TLR10, TLR11, etc. In some embodiments, a co-stimulator factor is a NOD ligand/agonist, or an activator/agonist of the inflammasome. Without wishing to be bound by theory, the inflammasome is a multiprotein oligomer consisting of caspase 1, PYCARD, NALP and sometimes caspase 5 or caspase 11 and promotes the maturation of inflammatory cytokines interleukin 1-β and interleukin 18.

In some embodiments, a co-stimulator factor is a cytokine. In some embodiments, a cytokine is selected from the group consisting of: GM-CSF; IL-1α; IL-1β; IL-2; IL-3; IL-4; IL-5; IL-6; IL-7; IL-8; IL-10; IL-12; IL-23; IFN-α; IFN-β; IFN-γ; MIP-1α; MIP-1β; TGF-β; TNFα, and TNFβ. In some embodiments, the co-stimulatory factor is an adjuvant, which may be associated with the polymer, as just discussed, or may be added to the MAPS composition prior to or concurrent with administration to a subject. Adjuvants are further described elsewhere herein.

Production of Mtb Antigens and Mtb Antigens Fused to the Complementary Affinity Molecule Recombinant proteins may be conveniently expressed and purified by a person skilled in the art, or by using commercially available kits, for example ProBond™ Purification System (Invitrogen Corp., Carlsbad, CA). In some embodiments, recombinant antigens can be synthesized and purified by protein purification methods using bacterial expression systems, yeast expression systems, baculovirus/insect cell expression system, mammalian cell expression systems, or transgenic plant or animal systems as known to persons of ordinary skill in the art.

The fusion polypeptides as described herein, e.g., a rhizavidin protein of SEQ ID NO: 1 fused to at least one, or at least two, or at least 3 Mtb antigens (e.g., the fusion proteins described herein in Tables 3A, 3B, 3C, or, for example, Rhavi-ESAT6, Rhavi-TB9.8, Rhavi-TB10.4, Rhavi-CFP10 (1-40), Rhavi-CFP10 (45-80), Rhavi-MPT64 (25-228), Rhavi-MPT83 (58-220), Rhavi-MPT51 (33-299), Rhavi-PPE41, and Rhavi-PE25) can all be synthesized and purified by protein and molecular methods that are well known to one skilled in the art. Molecular biology methods and recombinant heterologous protein expression systems are used. For example, recombinant protein can be expressed in bacteria, mammalian, insect, yeast, or plant cells; or in transgenic plant or animal hosts.

In one embodiment, provided herein is an isolated polynucleotide encoding a fusion polypeptide or a non-fusion polypeptide described herein. Conventional polymerase chain reaction (PCR) cloning techniques can be used to construct a chimeric or fusion coding sequence encoding a fusion polypeptide as described herein. A coding sequence can be cloned into a general purpose cloning vector such as pUC19, pBR322, pBLUESCRIPT® vectors (Stratagene, Inc.) or PCR TOPO® (Invitrogen). The resultant recombinant vector carrying the nucleic acid encoding a polypeptide as described herein can then be used for further molecular biological manipulations such as site-directed mutagenesis to create a variant fusion polypeptide as described herein or can be subcloned into protein expression vectors or viral vectors for protein synthesis in a variety of protein expression systems using host cells selected from the group consisting of mammalian cell lines, insect cell lines, yeast, bacteria, and plant cells.

Each PCR primer should have at least 15 nucleotides overlapping with its corresponding templates at the region to be amplified. The polymerase used in the PCR amplification should have high fidelity such as PfuULTRA® polymerase (Stratagene) for reducing sequence mistakes during the PCR amplification process. For ease of ligating several separate PCR fragments together, for example in the construction of a fusion polypeptide, and subsequently inserting into a cloning vector, the PCR primers should also have distinct and unique restriction digestion sites on their flanking ends that do not anneal to the DNA template during PCR amplification. The choice of the restriction digestion sites for each pair of specific primers should be such that the fusion polypeptide coding DNA sequence is in-frame and will encode the fusion polypeptide from beginning to end with no stop codons. At the same time the chosen restriction digestion sites should not be found within the coding DNA sequence for the fusion polypeptide. The coding DNA sequence for the intended polypeptide can be ligated into cloning vector pBR322 or one of its derivatives, for amplification, verification of fidelity and authenticity of the chimeric coding sequence, substitutions/or specific site-directed mutagenesis for specific amino acid mutations and substitutions in the polypeptide.

Alternatively the coding DNA sequence for the polypeptide can be PCR cloned into a vector using for example, the TOPO® cloning method comprising topoisomerase-assisted TA vectors such as pCR®-TOPO, pCR®-Blunt II-TOPO, pENTR/D-TOPO®, and pENTR/SD/D-TOPO® (Invitrogen, Inc., Carlsbad, CA). Both pENTR/D-TOPO®, and pENTR/SD/D-TOPO® are directional TOPO entry vectors which allow the cloning of the DNA sequence in the 5'→3' orientation into a GATEWAY® expression vector. Directional cloning in the 5'→3' orientation facilitates the unidirectional insertion of the DNA sequence into a protein expression vector such that the promoter is upstream of the 5' ATG start codon of the fusion polypeptide coding DNA sequence, enabling promoter driven protein expression. The recombinant vector carrying the coding DNA sequence for the fusion polypeptide can be transfected into and propagated in general cloning *E. coli* such as XL1Blue, SURE® (STRATAGENE®) and TOP-10 cells (Invitrogen).

One skilled in the art would be able to clone and ligate the coding region of the antigen of interest with the coding region of the complementary affinity molecule to construct a chimeric coding sequence for a fusion polypeptide comprising the antigen or a fragment thereof and the complementary affinity molecule of a derivative thereof using specially designed oligonucleotide probes and polymerase chain reaction (PCR) methodologies that are well known in the art. One skilled in the art would also be able to clone and ligate the chimeric coding sequence for a fusion protein into a selected vector, e.g., bacterial expression vector, an insect expression vector or baculovirus expression vector. The coding sequences of antigen and the target antigen polypeptide or fragment thereof should be ligated in-frame and the chimeric coding sequence should be ligated downstream of the promoter, and between the promoter and the transcription terminator. Subsequent to that, the recombinant vector is transfected into regular cloning *E. coli*, such as XL1Blue. Recombinant *E. coli* harboring the transfer vector DNA is then selected by antibiotic resistance to remove any *E. coli* harboring non-recombinant plasmid DNA. The selected transformant *E. coli* are grown and the recombinant vector DNA can be subsequently purified for transfection into *S. frugiperda* cells.

In some embodiments, the Mtb antigens as disclosed herein can comprise a signal peptide for translocation into periplasmic space of bacteria. The signal peptide is also called a leader peptide in the N-terminus, which may or may not be cleaved off after the translocation through the membrane. One example of a signal peptide is MKKIWLALAGLVLAFSASA (SEQ ID NO: 20) as disclosed herein. Another signal sequence is MAPFEPLASGILLLLWLIAPSRA (SEQ ID NO: 39). Other examples of signal peptides can be found at SPdb, a Signal Peptide Database, which is found at the world wide web site of "proline.bic-.nus.edu.sg/spdb/".

In some embodiments, where the antigen is fused to a complementary affinity protein, the signal sequence can be located at the N-terminal of the complementary affinity protein. For example, if an antigen is fused to an avidin-like protein, the signal sequence can be located at the N-terminal of the complementary affinity protein. In some embodiments, the signal sequence is cleaved off from the complementary affinity protein before the complementary affinity protein associates with the first affinity molecule.

In some embodiments, a Mtb antigen and/or complementary affinity protein as described herein lacks a signal sequence.

The polypeptides described herein can be expressed in a variety of expression host cells e.g., bacteria, yeasts, mammalian cells, insect cells, plant cells, algal cells such as *Chlamydomonas*, or in cell-free expression systems. In some embodiments the nucleic acid can be subcloned from the cloning vector into a recombinant expression vector that is appropriate for the expression of fusion polypeptide in bacteria, mammalian, insect, yeast, or plant cells or a cell-free expression system such as a rabbit reticulocyte expression system. Some vectors are designed to transfer coding nucleic acid for expression in mammalian cells, insect cells and year in one single recombination reaction. For example, some of the GATEWAY® (Invitrogen) destination vectors are designed for the construction of baculovirus, adenovirus, adeno-associated virus (AAV), retrovirus, and lentiviruses, which upon infecting their respective host cells, permit heterologous expression of fusion polypeptides in the appropriate host cells. Transferring a gene into a destination vector is accomplished in just two steps according to manufacturer's instructions. There are GATEWAY® expression vectors for protein expression in insect cells, mammalian cells, and yeast. Following transformation and selection in *E. coli*, the expression vector is ready to be used for expression in the appropriate host.

Examples of other expression vectors and host cells are the strong CMV promoter-based pcDNA3.1 (Invitrogen) and pCINEO vectors (Promega) for expression in mammalian cell lines such as CHO, COS, HEK-293, Jurkat, and MCF-7; replication incompetent adenoviral vector vectors pADENO-X™, pAd5F35, pLP-ADENO™-X-CMV (CLONTECH®), pAd/CMV/V5-DEST, pAd-DEST vector (Invitrogen) for adenovirus-mediated gene transfer and expression in mammalian cells; pLNCX2, pLXSN, and pLAPSN retrovirus vectors for use with the RETRO-X™ system from Clontech for retroviral-mediated gene transfer and expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells; adenovirus-associated virus expression vectors such as pAAV-MCS, pAAV-IRES-hrGFP, and pAAV-RC vector (Stratagene) for adeno-associated virus-mediated gene transfer and expression in mammalian cells; BACpak6 baculovirus (Clontech) and pFASTBAC™ HT (Invitrogen) for the expression in *S. frugiperda* 9 (Sf9), Sf11, Tn-368 and BTI-TN-5B4-1 insect cell lines; pMT/BiP/V5-His (Invitrogen) for the expression in *Drosophila* schneider S2 cells; *Pichia* expression vectors pPICZα, pPICZ, pFLDα and pFLD (Invitrogen) for expression in *P. pastoris* and vectors pMETα and pMET for expression in *P. methanolica*; pYES2/GS and pYD1 (Invitrogen) vectors for expression in yeast *S. cerevisiae*.

Recent advances in the large scale expression heterologous proteins in *Chlamydomonas reinhardtii* are described. Griesbeck, 34 Mol. Biotechnol. 213 (2006); Fuhrmann, 94 Methods Mol Med. 191 (2006). Foreign heterologous coding sequences are inserted into the genome of the nucleus, chloroplast and mitochondria by homologous recombination. The chloroplast expression vector p64 carrying the most versatile chloroplast selectable marker aminoglycoside adenyl transferase (aadA), which confers resistance to spectinomycin or streptomycin, can be used to express foreign protein in the chloroplast. The biolistic gene gun method can be used to introduce the vector in the algae. Upon its entry into chloroplasts, the foreign DNA is released from the gene gun particles and integrates into the chloroplast genome through homologous recombination.

Also included in the invention are complementary affinity molecule fused to an antigen. In some embodiments, the fusion construct can also optionally comprise purification tags, and/or secretion signal peptides. These fusion proteins may be produced by any standard method. For example, for production of a stable cell line expressing an antigen-complementary affinity molecule fusion protein, PCR-amplified antigen nucleic acids may be cloned into the restriction site of a derivative of a mammalian expression vector. For example, KA, which is a derivative of pcDNA3 (Invitrogen) contains a DNA fragment encoding an influenza virus hemagglutinin tag (HA). Alternatively, vector derivatives encoding other tags, such as c-myc or poly Histidine tags, can be used. The antigen-complementary affinity molecule fusion expression construct may be co-transfected, with a marker plasmid, into an appropriate mammalian cell line (e.g., COS, HEK293T, or NIH 3T3 cells) using, for example, LIPOFECTAMINE™ (Gibco-BRL, Gaithersburg, MD) according to the manufacturer's instructions, or any other suitable transfection technique known in the art. Suitable transfection markers include, for example, β-galactosidase or green fluorescent protein (GFP) expression plasmids or any plasmid that does not contain the same detectable marker as the antigen-complementary affinity molecule fusion protein. The fusion protein expressing cells can be sorted and further cultured, or the tagged antigen-complementary affinity molecule fusion protein can be purified. In some embodiments, an antigen-complementary affinity molecule fusion protein is amplified with a signal peptide. In alternative embodiments, a cDNA encoding an antigen-complementary affinity molecule fusion protein can be amplified without the signal peptide and subcloned into a vector (pSecTagHis) having a strong secretion signal peptide. In another example, antigen-complementary affinity molecule fusion protein can have an alkaline phosphatase (AP) tag, or a histadine (His) tag for purification. Any method known to persons of ordinary skill in the art for protein purification of the antigen and/or antigen-complementary affinity molecule fusion protein is encompassed for use in the methods of the invention.

In some embodiments, any of the polypeptides described herein is produced by expression from a recombinant baculovirus vector. In another embodiment, any of the polypeptides described herein is expressed by an insect cell. In yet another embodiment, any of the polypeptides described herein is isolated from an insect cell. There are several benefits of protein expression with baculovirus in insect cells, including high expression levels, ease of scale-up, production of proteins with posttranslational modifications, and simplified cell growth. Insect cells do not require $CO_2$ for growth and can be readily adapted to high-density suspension culture for large-scale expression. Many of the post-translational modification pathways present in mammalian systems are also utilized in insect cells, allowing the production of recombinant protein that is antigenically, immunogenically, and functionally similar to the native mammalian protein.

Baculoviruses are DNA viruses in the family Baculoviridae. These viruses are known to have a narrow host-range that is limited primarily to Lepidopteran species of insects (butterflies and moths). The baculovirus *Autographa californica* Nuclear Polyhedrosis Virus (AcNPV), which has become the prototype baculovirus, replicates efficiently in susceptible cultured insect cells. AcNPV has a double-stranded closed circular DNA genome of about 130,000 base-pairs and is well characterized with regard to host range, molecular biology, and genetics. The Baculovirus Expression Vector System (BEVS) is a safe and rapid method for the abundant production of recombinant proteins in insect cells and insects. Baculovirus expression systems are powerful and versatile systems for high-level, recombinant protein expression in insect cells. Expression levels up to 500 mg/l have been reported using the baculovirus expression system, making it an ideal system for high-level expression. Recombinant baculoviruses that express foreign genes are constructed by way of homologous recombination between baculovirus DNA and chimeric plasmids containing the gene sequence of interest. Recombinant viruses can be detected by virtue of their distinct plaque morphology and plaque-purified to homogeneity.

Recombinant fusion proteins described herein can be produced in insect cells including, but not limited to, cells derived from the Lepidopteran species *S. frugiperda*. Other insect cells that can be infected by baculovirus, such as those from the species *Bombyx mori, Galleria* mellanoma, Trichplusia *ni*, or Lamanthria *dispar*, can also be used as a suitable substrate to produce recombinant proteins described herein. Baculovirus expression of recombinant proteins is well known in the art. See U.S. Pat. Nos. 4,745,051; 4,879,236; 5,179,007; 5,516,657; 5,571,709; 5,759,809. It will be understood by those skilled in the art that the expression system is not limited to a baculovirus expression system. What is important is that the expression system directs the N-glycosylation of expressed recombinant proteins. The recombinant proteins described herein can also be expressed in other expression systems such as Entomopox viruses (the poxviruses of insects), cytoplasmic polyhedrosis viruses (CPV), and transformation of insect cells with the recombinant gene or genes constitutive expression. A good number of baculovirus transfer vectors and the corresponding appropriately modified host cells are commercially available, for example, pAcGP67, pAcSECG2TA, pVL1392, pVL1393, pAcGHLT, and pAcAB4 from BD Biosciences; pBAC-3, pBAC-6, pBACgus-6, and pBAC-surf-1 from NOVAGEN®, and pPolh-FLAG and pPolh-MAT from SIGMA ALDRICH®.

The region between the promoter and the transcriptional terminator can have multiple restriction enzyme digestion sites for facilitating cloning of the foreign coding sequence, in this instance, the coding DNA sequence for an antigen polypeptide, and a complementary affinity molecule. Additional sequences can be included, e.g., signal peptides and/or tag coding sequences, such as His-tag, MAT-Tag, FLAG tag, recognition sequence for enterokinase, honeybee melittin secretion signal, beta-galactosidase, glutathione S-transferase (GST) tag upstream of the MCS for facilitating the secretion, identification, proper insertion, positive selection of recombinant virus, and/or purification of the recombinant protein.

Standard techniques known to those of skill in the art can be used to introduce mutations (to create amino acid substitutions in an antigen polypeptide sequence of the fusion polypeptide described herein, e. g., in the antigen in the nucleotide sequence encoding the fusion polypeptide described herein, including, for example, site-directed mutagenesis and PCR-mediated mutagenesis. Preferably, the variant fusion polypeptide has less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions, inclusive, relative to the fusion polypeptides described herein.

Certain silent or neutral missense mutations can also be made in the DNA coding sequence that do not change the encoded amino acid sequence or the capability to promote transmembrane delivery. These types of mutations are useful to optimize codon usage, or to improve recombinant protein expression and production.

Specific site-directed mutagenesis of a coding sequence for the fusion polypeptide in a vector can be used to create specific amino acid mutations and substitutions. Site-directed mutagenesis can be carried out using, e. g., the QUICKCHANGE® site-directed mutagenesis kit from Stratagene according to the manufacturer's instructions.

In one embodiment, described herein are expression vectors comprising the coding DNA sequence for the polypeptides described herein for the expression and purification of the recombinant polypeptide produced from a protein expression system using host cells selected from, e.g., bacteria, mammalian, insect, yeast, or plant cells. The expression vector should have the necessary 5' upstream and 3' downstream regulatory elements such as promoter sequences, ribosome recognition and TATA box, and 3' UTR AAUAAA transcription termination sequence for efficient gene transcription and translation in its respective host cell. The expression vector is, preferably, a vector having the transcription promoter selected from a group consisting of CMV (cytomegalovirus) promoter, RSV (Rous sarcoma virus) promoter, 3-actin promoter, SV40 (simian virus 40) promoter and muscle creatine kinase promoter, and the transcription terminator selected from a group consisting of SV40 poly(A) and BGH terminator; more preferably, an expression vector having the early promoter/enhancer sequence of cytomegalovirus and the adenovirus tripartite leader/intron sequence and containing the replication origin and poly(A) sequence of SV40. The expression vector can have additional coding regions, such as those encoding, for example, 6×-histidine (SEQ ID NO: 30), V5, thioredoxin, glutathione-S-transferase, c-Myc, VSV-G, HSV, FLAG, maltose binding peptide, metal-binding peptide, HA and "secretion" signals (Honeybee melittin, α-factor, PHO, Bip), which can be incorporated into the expressed fusion polypeptide. In addition, there can be enzyme digestion sites incorporated after these coding regions to facilitate their enzymatic removal if they are not needed. These additional nucleic acids are useful for the detection of fusion polypeptide expression, for protein purification by affinity chromatography, enhanced solubility of the recombinant protein in the host cytoplasm, and/or for secreting the expressed fusion polypeptide out into the culture media or the spheroplast of the yeast cells. The expression of the fusion polypeptide can be constitutive in the host cells or it can be induced, e.g., with copper sulfate, sugars such as galactose, methanol, methylamine, thiamine, tetracycline, infection with baculovirus, and (isopropyl-beta-D-thiogalactopyranoside) IPTG, a stable synthetic analog of lactose.

In another embodiment, the expression vector comprising a polynucleotide described herein is a viral vector, such as adenovirus, adeno-associated virus (AAV), retrovirus, and lentivirus vectors, among others. Recombinant viruses provide a versatile system for gene expression studies and therapeutic applications.

In some embodiments, the fusion polypeptides described herein are expressed from viral infection of mammalian cells. The viral vectors can be, for example, adenovirus, adeno-associated virus (AAV), retrovirus, and lentivirus. A simplified system for generating recombinant adenoviruses is presented by He et al., 95 PNAS 2509 (1998). The gene of interest is first cloned into a shuttle vector, e.g., pAdTrack-CMV. The resultant plasmid is linearized by digesting with restriction endonuclease PmeI, and subsequently cotransformed into *E. coli*. BJ5183 cells with an adenoviral backbone plasmid, e.g. pADEASY-1 of Stratagene's ADEASY™ Adenoviral Vector System. Recombinant adenovirus vectors are selected for kanamycin resistance, and recombination confirmed by restriction endonuclease analyses. Finally, the linearized recombinant plasmid is transfected into adenovirus packaging cell lines, for example HEK 293 cells (E1-transformed human embryonic kidney cells) or 911 (E1-transformed human embryonic retinal cells). Fallaux, et al. 7 Human Gene Ther. 215 (1996). Recombinant adenovirus is generated within the HEK 293 cells.

Recombinant lentivirus has the advantage of delivery and expression of fusion polypeptides in dividing and non-dividing mammalian cells. The HIV-1 based lentivirus can effectively transduce a broader host range than the Moloney Leukemia Virus (MoMLV)-based retroviral systems. Preparation of the recombinant lentivirus can be achieved using, for example, the pLenti4/V5-DEST™, pLenti6/V5-DEST™ or pLenti vectors together with VIRAPOWER™ Lentiviral Expression systems from Invitrogen, Inc.

Recombinant adeno-associated virus (rAAV) vectors are applicable to a wide range of host cells including many different human and non-human cell lines or tissues. rAAVs are capable of transducing a broad range of cell types and transduction is not dependent on active host cell division. High titers, $>10^8$ viral particle/ml, are easily obtained in the supernatant and $10^{11}$-$10^{12}$ viral particle/ml with further concentration. The transgene is integrated into the host genome so expression is long term and stable.

Large scale preparation of AAV vectors is made by a three-plasmid cotransfection of a packaging cell line: AAV vector carrying the coding nucleic acid, AAV RC vector containing AAV rep and cap genes, and adenovirus helper plasmid pDF6, into 50×150 mm plates of subconfluent 293 cells. Cells are harvested three days after transfection, and viruses are released by three freeze-thaw cycles or by sonication.

AAV vectors can be purified by two different methods depending on the serotype of the vector. AAV2 vector is purified by the single-step gravity-flow column purification method based on its affinity for heparin. Auricchio et. al., 12 Human Gene Ther. 71 (2001); Summerford & Samulski, 72 J. Virol. 1438 (1998); Summerford & Samulski, 5 Nat. Med. 587 (1999). AAV2/1 and AAV2/5 vectors are currently purified by three sequential CsCl gradients.

Without wishing to be bound to theory, when proteins are expressed by a cell, including a bacterial cell, the proteins are targeted to a particular part in the cell or secreted from the cell. Thus, protein targeting or protein sorting is the mechanism by which a cell transports proteins to the appropriate positions in the cell or outside of it. Sorting targets can be the inner space of an organelle, any of several interior membranes, the cell's outer membrane, or its exterior via secretion. This delivery process is carried out based on information contained in the protein itself. Correct sorting is crucial for the cell; errors can lead to diseases.

With some exceptions, bacteria lack membrane-bound organelles as found in eukaryotes, but they may assemble proteins onto various types of inclusions such as gas vesicles and storage granules. Also, depending on the species of bacteria, bacteria may have a single plasma membrane (Gram-positive bacteria), or both an inner (plasma) membrane and an outer cell wall membrane, with an aqueous space between the two called the periplasm (Gram-negative bacteria). Proteins can be secreted into the environment, according to whether or not there is an outer membrane. The basic mechanism at the plasma membrane is similar to the eukaryotic one. In addition, bacteria may target proteins into or across the outer membrane. Systems for secreting proteins across the bacterial outer membrane may be quite complex and play key roles in pathogenesis. These systems may be described as type 1 secretion, type II secretion, etc.

In most Gram-positive bacteria, certain proteins are targeted for export across the plasma membrane and subsequent covalent attachment to the bacterial cell wall. A specialized enzyme, sortase, cleaves the target protein at a characteristic recognition site near the protein C-terminus, such as an LPXTG motif (SEQ ID NO: 40) (where X can be any amino acid), then transfers the protein onto the cell wall. A system analogous to sortase/LPXTG (SEQ ID NO: 40), having the motif PEP-CTERM (SEQ ID NO: 41), termed exosortase/PEP-CTERM (SEQ ID NO: 41), is proposed to exist in a broad range of Gram-negative bacteria.

Proteins with appropriate N-terminal targeting signals are synthesized in the cytoplasm and then directed to a specific protein transport pathway. During, or shortly after its translocation across the cytoplasmic membrane, the protein is processed and folded into its active form. Then the translocated protein is either retained at the periplasmic side of the cell or released into the environment. Since the signal peptides that target proteins to the membrane are key determinants for transport pathway specificity, these signal peptides are classified according to the transport pathway to which they direct proteins. Signal peptide classification is based on the type of signal peptidase (SPase) that is responsible for the removal of the signal peptide. The majority of exported proteins are exported from the cytoplasm via the general "Secretory (Sec) pathway". Most well known virulence factors (e.g. exotoxins of *Staphylococcus aureus*, protective antigen of *Bacillus* anthraces, lysteriolysin 0 of *Listeria monocytogenes*) that are secreted by Gram-positive pathogens have a typical N-terminal signal peptide that would lead them to the Sec-pathway. Proteins that are secreted via this pathway are translocated across the cytoplasmic membrane in an unfolded state. Subsequent processing and folding of these proteins takes place in the cell wall environment on the trans-side of the membrane. In addition to the Sec system, some Gram-positive bacteria also contain the Tat-system that is able to translocate folded proteins across the membrane. Pathogenic bacteria may contain certain special purpose export systems that are specifically involved in the transport of only a few proteins. For example, several gene clusters have been identified in mycobacteria that encode proteins that are secreted into the environment via specific pathways (ESAT-6) and are important for mycobacterial pathogenesis. Specific ATP-binding cassette (ABC) transporters direct the export and processing of small antibacterial peptides called bacteriocins. Genes for endolysins that are responsible for the onset of bacterial lysis are often located near genes that encode for holin-like proteins, suggesting that these holins are responsible for endolysin export to the cell wall. Wooldridge, Bact. Secreted Prots: Secretory Mechs. & Role in Pathogen. (Caister Academic Press, 2009)

In some embodiments, the signal sequence useful in the present invention is OmpA Signal sequence, however any signal sequence commonly known by persons of ordinary skill in the art which allows the transport and secretion of antimicrobial agents outside the bacteriophage infected cell are encompassed for use in the present invention.

Signal sequence that direct secretion of proteins from bacterial cells are well known in the art, for example as disclosed in International application WO 2005/071088. For example, one can use some of the non-limited examples of signal peptide shown in Table 7, which can be attached to the amino-terminus or carboxyl terminus of the antimicrobial peptide (Amp) or antimicrobial polypeptide to be expressed by the antimicrobial-agent engineered bacteriophage, e.g., AMP-engineered bacteriophage. Attachment can be via fusion or chimera composition with selected antigen or antigen-complementary affinity molecule fusion protein resulting in the secretion from the bacterium infected with the antimicrobial-agent engineered bacteriophage, e.g. AMP-engineered bacteriophage.

TABLE 7

Example signal peptides to direct secretion of a protein or peptide antigen or antigen-complementary affinity molecule fusion protein of a bacterial cell.

| Secretion Pathway | Signal Peptide Amino Acid sequence ($NH_2$—$CO_2$) | Gene | Genus/ Species |
|---|---|---|---|
| secA1 | MKKIMLVITLILVSPIAQQ TEAKD (SEQ ID NO: 42) | Hly (LLO) | *Listeria monocytogenes* |
| | MKKKIISAILMSTVILSAA APLSGVYADT (SEQ ID NO: 43) | Usp45 | *Lactococcus lactis* |
| | MKKRKVLIPLMALSTILVS LSTGNEVIQAEV (SEQ ID NO: 44) | Pag (protective antigen) | *Bacillus anthracis* |
| secA2 | MNMKKATIAATAGIAVTAF AAPTIASAST (SEQ ID NO: 45) | lap (invasion-associated protein p60) | *Listeria monocytogenes* |
| | MQKTRKERILEALQEEKKN KKSKKFKTGATIAGVTAIA TSITVPGIEVIVSADE (SEQ ID NO: 46) | NamA Imo2691 (autolysin) | *Listeria monocytogenes* |
| | MKKLKMASCALVAGLMFSG LTPNAFAED (SEQ ID NO: 47) | *BA_0281 (NLP/P60 family) | *Bacillus anthracis* |
| | MAKKFNYKLPSMVALTLVG SAVTAHQVQAAE (SEQ ID NO: 48) | *atl (autolysin) | *Staphylococcus aureus* |

TABLE 7-continued

Example signal peptides to direct secretion of a protein or peptide antigen or antigen-complementary affinity molecule fusion protein of a bacterial cell.

| Secretion Pathway | Signal Peptide Amino Acid sequence ($NH_2$—$CO_2$) | Gene | Genus/ Species |
|---|---|---|---|
| Tat | MTDKKSENQTEKTETKENK GMTRREMLKLSAVAGTGIA VGATGLGTILNVVDQVDKA LT (SEQ ID NO: 49) | Imo0367 | *Listeria monocytogenes* |
| | MAYDSRFDEWVQKLKEESF QNNTFDRRKFIQGAGKIAG LGLGLTIAQSVGAFG (SEQ ID NO: 50) | PhoD (alkaline phosphatase) | *Bacillus subtillis* |

The polypeptides as described herein, e.g., antigens or antigen-complementary affinity molecule fusion protein can be expressed and purified by a variety methods known to one skilled in the art, for example, the fusion polypeptides described herein can be purified from any suitable expression system. Fusion polypeptides can be purified to substantial purity by standard techniques, including selective precipitation with such substances as ammonium sulfate; column chromatography, immunopurification methods, and others; which are well-known in the art. See, e.g., Scopes, Protein Purification: Principles & Practice (1982); U.S. Pat. No. 4,673,641.

A number of procedures can be employed when recombinant proteins are purified. For example, proteins having established molecular adhesion properties can be reversibly fused to the protein of choice. With the appropriate ligand, the protein can be selectively adsorbed to a purification column and then freed from the column in a relatively pure form. The fused protein is then removed by enzymatic activity. Finally, the protein of choice can be purified using affinity or immunoaffinity columns.

After the protein is expressed in the host cells, the host cells can be lysed to liberate the expressed protein for purification. Methods of lysing the various host cells are featured in "Sample Preparation-Tools for Protein Research" EMD Bioscience and in the Current Protocols in Protein Sciences (CPPS). An example purification method is affinity chromatography such as metal-ion affinity chromatograph using nickel, cobalt, or zinc affinity resins for histidine-tagged fusion polypeptides. Methods of purifying histidine-tagged recombinant proteins are described by Clontech using their TALON® cobalt resin and by NOVAGEN® in their pET system manual, 10th edition. Another preferred purification strategy is immuno-affinity chromatography, for example, anti-myc antibody conjugated resin can be used to affinity purify myc-tagged fusion polypeptides. When appropriate protease recognition sequences are present, fusion polypeptides can be cleaved from the histidine or myc tag, releasing the fusion polypeptide from the affinity resin while the histidine-tags and myc-tags are left attached to the affinity resin.

Standard protein separation techniques for purifying recombinant and naturally occurring proteins are well known in the art, e.g., solubility fractionation, size exclusion gel filtration, and various column chromatography.

Solubility fractionation: Often as an initial step, particularly if the protein mixture is complex, an initial salt fractionation can separate many of the unwanted host cell proteins (or proteins derived from the cell culture media) from the protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size exclusion filtration: The molecular weight of the protein of choice can be used to isolate it from proteins of greater and lesser size using ultrafiltration through membranes of different pore size (for example, AMICON® or MILLIPORE® membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column chromatography: The protein of choice can also be separated from other proteins on the basis of its size, net surface charge, hydrophobicity, and affinity for ligands. In addition, antibodies raised against recombinant or naturally occurring proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech). For example, an antigen polypeptide can be purified using a PA63 heptamer affinity column. Singh et al., 269, J. Biol. Chem. 29039 (1994).

In some embodiments, a combination of purification steps comprising, for example: (a) ion exchange chromatography, (b) hydroxyapatite chromatography, (c) hydrophobic interaction chromatography, and (d) size exclusion chromatography can be used to purify the fusion polypeptides described herein.

Cell-free expression systems are also contemplated. Cell-free expression systems offer several advantages over traditional cell-based expression methods, including the easy modification of reaction conditions to favor protein folding, decreased sensitivity to product toxicity and suitability for high-throughput strategies such as rapid expression screening or large amount protein production because of reduced reaction volumes and process time. The cell-free expression system can use plasmid or linear DNA. Moreover, improvements in translation efficiency have resulted in yields that exceed a milligram of protein per milliliter of reaction mix. Commercially available cell-free expression systems include the TNT coupled reticulocyte lysate Systems (Promega) which uses rabbit reticulocyte-based in vitro system.

Determining the Efficacy of a TB-MAPS Immunogenic Composition

The effectiveness of a TB-MAPS immunogenic composition as disclosed herein can be measured using the methods disclosed in the Examples, as well as by proliferation assays, by chromium release assays to measure the ability of a T-cell to lyse its specific target cell, or by measuring the levels of B-cell activity by measuring the levels of circulating antibodies specific for the antigen in serum. An immune response may also be detected by measuring the serum levels of antigen specific antibody, as described herein. For example, the immune response is assessed by measuring the T-Cell response. In some embodiments, blood from an immunized animal was incubated with individual or a combination of recombinated antigens. The supernatant of this mixture is collected and assessed for INFγ and IL-17A via ELISA technology. The level of protection of the immune response may be measured by challenging the immunized host with the antigen that has been administered. For example, if the antigen to which an immune response is desired is a bacterium, the level of protection induced by the immunogenic amount of the antigen is measured by detecting the number of bacterial colonies present in the lungs or spleen. In one embodiment, the amount of protection may be measured colonization of *Mycobacterium tuberculosis* in the lungs associated with pulmonary Tuberculosis. In one embodiment, the amount of protection may be measured by colonization of *Mycobacterium tuberculosis* in the spleen associated with splenic dissemination of Tuberculosis. The amount of each of the antigens in the multi-antigen or multi-component vaccine or immunogenic compositions will vary with respect to each of the other components and can be determined by methods known to the skilled artisan. Such methods would include procedures for measuring immunogenicity and/or in vivo efficacy. In certain embodiments, the term "about" leans within 20%, preferably within 10%, and more preferably within 5%.

In some embodiments, the invention further provides antibodies and antibody compositions which bind specifically and selectively to the TB-MAPS immunogenic composition as disclosed herein. In some embodiments, antibodies are generated upon administration of a TB-MAPS immunogenic composition as disclosed herein to a subject.

Antibodies or antibody compositions of the invention may be used in a method of treating or preventing a Tuberculosis infection, disease or condition associated with a *M. tuberculosis* pathogen in a subject, the method comprising generating a polyclonal or monoclonal antibody preparation, and using said antibody or antibody composition to confer passive immunity to the subject. Antibodies of the invention may also be useful for diagnostic methods, e.g., detecting the presence of or quantifying the levels of MPT51, MPT64 or a conjugate thereof.

Several known animal models may be used to assess the efficacy of any one of the TB-MAPS immunogenic composition as disclosed herein. For example, such models are described below:

HDA model: 8- to 10-week-old female BALB/c mice were infected with a freshly grown culture of *M. tuberculosis*. Bacteria were grown in 7H9 medium (Difco Inc., Lawrence, KS) supplemented with 10% oleic acid-albumin-dextrose-catalase and Tween 80 and propagated to late log phase with an optical density at 600 nm ($OD_{600}$) of 0.8 to 1.0. Ten milliliters of the freshly grown *M. tuberculosis* culture was placed in the Glas-Col nebulizer with settings of 13 to 17 SCFH compressed air and 80 SCFH main (negative air). The procedures included a 15-min preheat cycle, a nebulizing cycle of 30 to 40 min, a cloud decay cycle of 15 to 30 min, with decontamination for 15 min (Glas-Col, Inc.). Active Immunization and Challenge Model: In this model, mice are actively immunized subcutaneously (s.c.) with a TB-MAPS immunogenic composition as disclosed herein at 0, 3 and 6 weeks (or a similar schedule known to those skilled in the art) and challenged with *M. tuberculosis* at week 8 (or other similar schedule known to those skilled in the art) by the intravenous or intraperitoneal route. The bacterial challenge dose is calibrated to achieve approximately 20% survival in the control group over a 14 day period. Statistical evaluation of survival studies can be carried out by Kaplan-Meier analysis.

I.V. infection model: 8- to 12-week-old mice were injected with *M. tuberculosis* Erdman with 6 to 7 $\log_{10}$ CFU delivered in 0.1 ml of sterile phosphate-buffered saline via injection of the lateral tail vein. Bacteria were suspended repetitively through a SurGuard safety hypodermic needle (26 gauge; VWR, Wilmington, DE) in order to obtain a single-cell bacterial suspension. Enumeration of the *M. tuberculosis* inoculum from all infection routes was determined by CFU counts on 7H11 agar plates (as described below). The actual bacterial load delivered to the animals was determined from three mice per group the day after the infection in the lungs from all aerogenically challenged animals and in lungs and spleens from five mice in the i.v.-infected group. At the start of treatment (defined by convention as day zero), the bacterial load was determined in lungs and spleens. The timing of the drug treatment varied depending on the infection model being evaluated and was based on published and unpublished data. Treatment regimens ranged from 1 to 6 months with 5 to 8 mice per treatment group for each sacrifice point during treatment and 10 to 22 mice per group for assessment of relapse of infection. To assess relapse, animals were observed without drug intervention for 3 months. Passive Infectious Endocarditis Model: The infectious endocarditis model has also been adapted for active immunization studies.

TB fluorescence imaging model: Six- to 12-week-old CB-17 SCID mice or SCID Hairless Outbred (SHO) mice (Charles River, Germany) were anaesthetized with a ketamine (125 mg/kg, WDT, Garbsen, Germany) and Rompun (2.5 mg/kg, active ingredient xylazine; Bayer, Leverkusen, Germany) solution by intraperitoneal injection, and infected with parental Mtb H37Rv or its fluorescent derivatives in 20 mL of PBS via the intranasal route, with inocula as indicated in the figure legends. The input inocula were confirmed by plating 10-fold dilutions onto 7H11 agar plates containing 10% OADC supplement and 0.5% glycerol, and incubating for 6 weeks at 378C.

Formulations of an Immune Composition and Methods of Use

Specific embodiments of the present invention provide for use of the TB-MAPS immunogenic compositions as disclosed herein to elicit an immune response to *M. tuberculosis* in an animal. More specifically, the compositions elicit both humoral and cellular immunity. Embodiments of the present invention provide at least partial protection from or partial improvement after infection by, in particular, *M. tuberculosis.*

In one embodiment, provided herein is a method of vaccinating a mammal comprising administering the TB-MAPS immunogenic composition comprising at least one, or multiple Mtb antigens attached to an immunogenic polysaccharide for use in eliciting an immune response to the one or more antigens attached to the polymer when administered to a subject. In some embodiments, the immune response is a humoral and/or cellular immune response.

Accordingly, one aspect of the present invention relates to methods to elicit an immune response in a subject, comprising administering to the subject a TB-MAPS immunogenic composition comprising at least one type of immunogenic polysaccharide (e.g., CP5, CP8, a CP5-CP8 conjugate, pneumococcal PS1(CP 1) etc., at least one Mtb antigen, and at least one complementary affinity-molecule pair comprising (i) a first affinity molecule which associates with the immunogenic polysaccharide, and (ii) a complementary affinity molecule which associates with the Mtb antigen, to attach the Mtb antigen to the immunogenic polysaccharide, (e.g., the first affinity molecule associates with the complementary affinity molecule to link the Mtb antigen to the immunogenic polysaccharide).

Accordingly, one aspect of the present invention relates to methods to elicit a humoral and/or cellular immunity to multiple Mtb antigens at the same time, e.g., where the immunogenic composition administered to the subject comprises an immunogenic polysaccharide comprising at least 1, or at least 2, or a more, e.g., a plurality of the same or different Mtb antigens.

One aspect of the present invention relates to a method of immunization or vaccinating a subject, e.g., a bird or a mammal, e.g., a human against *M. tuberculosis* comprising administering a TB-MAPS immune composition as disclosed herein comprising at least one Mtb antigen derived from one or more pathogens. In some embodiments, a subject can be immunized against at least 1, or at least 2, or at least 2, or at least 3, or at least 5, or at least 10, or at least 15, or at least about 20, or at least 50, or at least about 100, or more than 100 different Mtb antigens at the same time, where the immunogenic polysaccharide of the TB-MAPS immunogenic composition has different Mtb antigens attached.

In some embodiments, a subject can be administered several different TB-MAPS immunogenic compositions as disclosed herein, for example, a subject can be administered a TB-MAPS composition comprising an immunogenic polysaccharide with a Mtb antigen, or a plurality of Mtb antigens, e.g., antigens A, B, C, and D etc., and also administered a TB-MAPS composition comprising an immunogenic polysaccharide comprising a different Mtb antigen, or a different set of Mtb antigens, e.g., antigens W, X, Y, and Z etc. Alternatively, a subject can be administered a TB-MAPS composition comprising a immunogenic polysaccharide A (e.g., CP5) with an Mtb antigen, or a plurality of Mtb antigens, e.g., antigens A, B, C, and D, etc., and also administered a TB-MAPS composition comprising a immunogenic polysaccharide B (e.g. CP8) comprising the same e.g., antigens A, B, C, and D etc., or a different set of antigens. It is envisioned that the present invention provides a methods for the immunization of a subject with as many Mtb antigens as desired, e.g., with a variety of different immunogenic complexes as described herein, to enable immunization with as many as 100 or more antigens.

In one embodiment, the TB-MAPS immunogenic compositions as described herein comprise a pharmaceutically acceptable carrier. In another embodiment, the TB-MAPS immunogenic composition described herein is formulated for administering to a bird, mammal, or human, as or in a vaccine. Suitable formulations can be found in, for example, Remington's Pharmaceutical Sciences (2006), or Introduction to Pharmaceutical Dosage Forms (4th ed., Lea & Febiger, Philadelphia, 1985).

In one embodiment, the TB-MAPS immunogenic compositions as described herein comprise pharmaceutically acceptable carriers that are inherently nontoxic and nontherapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. For all administrations, conventional depot forms are suitably used. Such forms include, for example, microcapsules, nano-capsules, liposomes, plasters, inhalation forms, nose sprays, sublingual tablets, and sustained release preparations. For examples of sustained release compositions, see U.S. Pat. Nos. 3,773,919, 3,887,699, EP 58,481A, EP 158,277A, Canadian Patent No. 1176565; Sidman et al., 22 Biopolymers 547 (1983); Langer et al., 12 Chem. Tech. 98 (1982). The proteins will usually be formulated at a concentration of about 0.1 mg/ml to 100 mg/ml per application per patient.

In one embodiment, other ingredients can be added to vaccine formulations, including antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

In some embodiments, the TB-MAPS immunogen composition as disclosed herein is administered with at least one adjuvant or an immune modulator, or both. Adjuvants are a heterogeneous group of substances that enhance the immunological response against an antigen that is administered simultaneously. In some instances, adjuvants improve the immune response so that less vaccine is needed. Adjuvants serve to bring the antigen—the substance that stimulates the specific protective immune response—into contact with the immune system and influence the type of immunity produced, as well as the quality of the immune response (magnitude or duration). Adjuvants can also decrease the toxicity of certain antigens; and provide solubility to some vaccine components. Almost all adjuvants used today for enhancement of the immune response against antigens are particles or form particles together with the antigen. In the book VACCINE DESIGN-SUBUNIT & ADJUVANT APPROACH (Powell & Newman, Eds., Plenum Press, 1995), many known adjuvants are described both regarding their immunological activity and regarding their chemical characteristics. The type of adjuvants that do not form particles are a group of substances that act as immunological signal substances and that under normal conditions consist of the substances that are formed by the immune system as a consequence of the immunological activation after administration of particulate adjuvant systems.

Adjuvants for immunogenic compositions and vaccines are well known in the art. Examples include, but not limited to, monoglycerides and fatty acids (e. g. a mixture of mono-olein, oleic acid, and soybean oil); mineral salts, e.g., aluminium hydroxide and aluminium or calcium phosphate gels; oil emulsions and surfactant based formulations, e.g., MF59 (microfluidised detergent stabilized oil-in-water emulsion), QS21 (purified saponin), AS02 [SBAS2] (oil-in-water emulsion+MPL+QS-21), MPL-SE, Montanide ISA-51 and ISA-720 (stabilised water-in-oil emulsion); particulate adjuvants, e.g., virosomes (unilamellar liposomal vehicles incorporating influenza haemagglutinin), ASO4 ([SBAS4] Al salt with MPL), ISCOMS (structured complex of saponins and lipids), polylactide co-glycolide (PLG); microbial derivatives (natural and synthetic), e.g., monophosphoryl lipid A (MPL), Detox (MPL+M. *Phlei* cell wall skeleton), AGP [RC-529] (synthetic acylated monosaccharide), Detox-PC, DC_Chol (lipoidal immunostimulators able to self-organize into liposomes), OM-174 (lipid A derivative), CpG motifs (synthetic oligonucleotides containing immunostimulatory CpG motifs), or other DNA structures, modified LT and CT (genetically modified bacterial toxins to provide non-toxic adjuvant effects); endogenous human immunomodulators, e.g., hGM-CSF or hIL-12 (cytokines that can be administered either as protein or plasmid encoded), Immudaptin (C3d tandem array), MoGM-CSF, TiterMax-G, CRL-1005, GERBU, TERamide, PSC97B, Adjumer, PG-026, GSK-I, GcMAF, B-alethine, MPC-026, Adjuvax, CpG ODN, Betafectin, Alum, and MF59 and inert vehicles, such as gold particles. Additional adjuvants are known in the art, see, e.g., U.S. Pat. No. 6,890,540; U. S. Patent Pub. No. 2005/0244420; PCT/S E97/01003.

Additional suitable adjuvants used to enhance an immune response of the TB-MAPS composition as disclosed herein further include, without limitation, MPL™ (3-O-deacylated monophosphoryi lipid A, Corixa; Hamilton, Mont.), which is described in U.S. Pat. No. 4,912,094. Also suitable for use as adjuvants are synthetic lipid A analogs or aminoalkyl glucosamine phosphate compounds (AGP), or derivatives or analogs thereof, which are available from Corixa, and those that are described in U.S. Pat. No. 6,113,918. One such AGP is 2-[(R)-3-Tetradecanoyloxytetradecanoylamino]ethyl 2-Deoxy-4-O-phosphono-3-O— [(R)-3-tetradecanoyoxytetradecanoyl]-2-[(R1-3-t-etradecanoyloxytetradecanoyl-amino]-b-D-glucopyranoside, which is also known as 529 (formerly known as RC529). This 529 adjuvant is formulated as an aqueous form (AF) or as a stable emulsion (SE). Still other adjuvants include muramyl peptides, such as N-acetyl-muramyl-L-threonyl-D-isoglutamine (thr-MDP), N-acetyl-normuramyl-L-alanine-2-(1'-2' dipalmitoyl-sn-glycero-hydroxyphosphoryloxy)-ethylamine (MTP-PE); oil-in-water emulsions, such as MF59 (U.S. Pat. No. 6,299, 884) (containing 5% Squalene, 0.5% polysorbate 80, and 0.5% Span 85 (optionally containing various amounts of MTP-PE) formulated into submicron particles using a microfluidizer such as Model 110Y microfluidizer (Microlluidics, Newton, Mass.)), and SAF (containing 10% Squalene, 0.4% polysorbate 80, 5% pluronic-blocked polymer L121, and thr-MDP, either microfluidized into a submicron emulsion or vortexed to generate a larger particle size emulsion); incomplete Freund's adjuvant (IFA); aluminum salts (alum), such as aluminum hydroxide, aluminum phosphate, aluminum sulfate; Amphigen; Avridine; L121/squalene; D-lactide-polylactide/glycoside; pluronic polyols; killed *Bordetella*; saponins, such as Stimulon™ QS-21 (Antigenics, Framingham, Mass.), described in U.S. Pat. No. 5,057,540, Iscomatrix® (CSL Limited, Parkville, Australia), described in U.S. Pat. No. 5,254,339, and immunostimulating complexes (ISCOMS); *Mycobacterium tuberculosis*; bacterial lipopolysaccharides; synthetic polynucleotides such as oligonucleotides containing a CpG motif (e.g., U.S. Pat. No. 6,207,646); IC-31 (Intercell AG, Vienna, Austria), described in EP Patent Nos. 1,296,713 and 1,326,634; a pertussis toxin (PT) or mutant thereof a cholera toxin or mutant thereof (e.g., U.S. Pat. Nos. 7,285,281, 7,332,174, 7,361,355 and 7,384,640); or an *E. coli* heat-labile toxin (LT) or mutant thereof, particularly LT-K63, LT-R72 (e.g., U.S. Pat. Nos. 6,149,919, 7,115,730 and 7,291,588).

In some embodiments, the TB-MAPS immunogen composition as disclosed herein is administered with at least one immune modulator. An "immunomodulator" or "immune modulator" is an agent that perturb or alter the immune system, such that either up-regulation or down-regulation of humoral and/or cell-mediated immunity is observed. In one embodiment, up-regulation of the humoral and/or cell-mediated arms of the immune system is provided. Examples of certain immunomodulators include, e.g., an adjuvant or cytokine, or Iscomatrix™ (CSL Limited; Parkville, Australia), described in U.S. Pat. No. 5,254,339 among others. Non-limiting examples of adjuvants that can be used in the immunogenic composition of the present invention include the RIBI adjuvant system (Ribi Inc.; Hamilton, Mont.), alum, mineral gels such as aluminum hydroxide gel, oil-in-water emulsions, water-in-oil emulsions such as, e.g., Freund's complete and incomplete adjuvants, Block copolymer (CytRx; Atlanta, Ga.), QS-21 (Cambridge Biotech Inc.; Cambridge, Mass.), SAF-M (Chixon; Emeryville, Calif.), Amphigen™ adjuvant, saponin, Quil A or other saponin fraction, monophosphoryl lipid A, and Avridine lipid-amine adjuvant. Non-limiting examples of oil-in-water emulsions useful in the immunogenic composition of the invention include modified SEAM62 and SEAM 1/2 formulations. Modified SEAM62 is oil-in-water emulsion containing 5% (v/v) squalene (Sigma), 1% (v/v) Span® 85 Detergent (ICI Surfactants), 0.7% (v/v) polysorbate 80 detergent (ICI Surfactants), 2.5% (v/v) ethanol, 200 mcg/ml Quil A, 100 mcg/ml cholesterol, and 0.5% (v/v) lecithin. Modified SEAM 1/2 is an oil-in-water emulsion comprising 5% (v/v) squalene, 1% (v/v) Span® 85 Detergent, 0.7% v/v) polysorbate 80 detergent, 2.5% (v/v) ethanol, 100 mcg/ml Quil A, and 50 mcg/ml cholesterol. Other "immunomodulators" that can be included in the immunogenic composition include, e.g., one or more interleukins, interferons, or other known cytokines or chemokines. In one embodiment, the adjuvant may be a cyclodextrin derivative or a polyanionic polymer, such as those described in U.S. Pat. Nos. 6,165,995 and 6,610,310, respectively. It is to be understood that the immunomodulator and/or adjuvant to be used will depend on the subject to which the immunogenic composition will be administered, the route of injection and the number of injections to be given.

In some embodiments, the TB-MAPS immunogen composition as disclosed herein is administered with at least one immune modulator. A number of cytokines or lymphokines have been shown to have immune modulating activity, and thus may be useful in a manner the same or similar to adjuvants, including, but not limited to, the interleukins 1-alpha., 1-beta., 2, 4, 5, 6, 7, 8, 10, 12 (see, e.g., U.S. Pat. No. 5,723,127), 13, 14, 15, 16, 17 and 18 (and its mutant forms); the interferons-α, β and γ; granulocyte-macrophage colony stimulating factor (GM-CSF) (see, e.g., U.S. Pat. No. 5,078,996 and ATCC Accession Number 39900); macrophage colony stimulating factor (M-CSF); granulocyte colony stimulating factor (G-CSF); and the tumor necrosis factors α and β. Still other adjuvants that are useful with the immunogenic compositions described herein include chemokines, including without limitation, MCP-1, MfP-1.alpha., MIP-1.beta., and RANTES; adhesion molecules, such as a selectin, e.g., L-selectin, P-selectin and E-selectin; mucin-like molecules, e.g., CD34, GlyCAM-1 and MadCAM-1; a member of the integrin family such as LFA-1, VLA-1, Mac-1 and p150.95; a member of the immunoglobulin superfamily such as PECAM, ICAMs, e.g., ICAM-1, ICAM-2 and ICAM-3, CD2 and LFA-3; co-stimulatory molecules such as B7-1, B7-2, CD40 and CD40L; growth factors including vascular growth factor, nerve growth factor, fibroblast growth factor, epidermal growth factor, PDGF, BL-1, and vascular endothelial growth factor; receptor molecules including Fas, TNF receptor, Flt, Apo-1, p55, WSL-1, DR3, TRAMP, Apo-3, AIR, LARD, NGRF, DR4, DR5, KILLER, TRAIL-R2, TRICK2, and DR6; and Caspases, including ICE.

In some embodiments an adjuvant is a particulate and can have a characteristic of being slowly biodegradable. Care must be taken to ensure that that the adjuvant do not form toxic metabolites. Preferably, in some embodiments, such adjuvants can be matrices used are mainly substances originating from a body. These include lactic acid polymers, poly-amino acids (proteins), carbohydrates, lipids and biocompatible polymers with low toxicity. Combinations of these groups of substances originating from a body or combinations of substances originating from a body and biocompatible polymers can also be used. Lipids are the preferred substances since they display structures that make them biodegradable as well as the fact that they are a critical element in all biological membranes.

In one embodiment, the immunogenic compositions as described herein for administration must be sterile for administration to a subject. Sterility is readily accomplished by filtration through sterile filtration membranes (e.g., 0.2 micron membranes), or by gamma irradiation.

In some embodiments, the immunogenic compositions described herein further comprise pharmaceutical excipients including, but not limited to biocompatible oils, physiological saline solutions, preservatives, carbohydrate, protein, amino acids, osmotic pressure controlling agents, carrier gases, pH-controlling agents, organic solvents, hydrophobic agents, enzyme inhibitors, water absorbing polymers, surfactants, absorption promoters and anti-oxidative agents. Representative examples of carbohydrates include soluble sugars such as hydropropyl cellulose, carboxymethyl cellulose, sodium carboxyl cellulose, hyaluronic acid, chitosan, alginate, glucose, xylose, galactose, fructose, maltose, saccharose, dextran, chondroitin sulfate, etc. Representative examples of proteins include albumin, gelatin, etc. Representative examples of amino acids include glycine, alanine, glutamic acid, arginine, lysine, and their salts. Such pharmaceutical excipients are well-known in the art.

In some embodiments, the immunogenic MAPS composition is administered in combination with other therapeutic ingredients including, e.g., y-interferon, cytokines, chemotherapeutic agents, or anti-inflammatory, or anti-viral agents. In some embodiments, the immunogenic composition as disclosed herein can be administered with one or more co-stimulatory molecules and/or adjuvants as disclosed herein.

In some embodiments, the immunogenic composition is administered in a pure or substantially pure form, but may be administered as a pharmaceutical composition, formulation or preparation. Such formulation comprises MAPS described herein together with one or more pharmaceutically acceptable carriers and optionally other therapeutic ingredients. Other therapeutic ingredients include compounds that enhance antigen presentation, e.g., gamma interferon, cytokines, chemotherapeutic agents, or anti-inflammatory agents. The formulations can conveniently be presented in unit dosage form and may be prepared by methods well known in the pharmaceutical art. For example, Plotkin and Mortimer, in Vaccines (2nd ed., W.B. Saunders Co., 1994) describes vaccination of animals or humans to induce an immune response specific for particular pathogens, as well as methods of preparing antigen, determining a suitable dose of antigen, and assaying for induction of an immune response.

Formulations of the TB-MAPS compositions as disclosed herein suitable for intravenous, intramuscular, intranasal, oral, sublingual, vaginal, rectal, subcutaneous, or intraperitoneal administration conveniently comprise sterile aqueous solutions of the active ingredient with solutions which are preferably isotonic with the blood of the recipient. Such formulations may be conveniently prepared by dissolving solid active ingredient in water containing physiologically compatible substances such as sodium chloride (e.g., 0.1M-2.0 M), glycine, and the like, and having a buffered pH compatible with physiological conditions to produce an aqueous solution, and rendering the solution sterile. These may be present in unit or multi-dose containers, for example, sealed ampoules or vials.

Liposomal suspensions can also be used as pharmaceutically acceptable carriers. These can be prepared according to methods known to those skilled in the art, for example, as described in U.S. Pat. No. 4,522,811.

Formulations for an intranasal delivery are described in U.S. Pat. Nos. 5,427,782; 5,843,451; 6,398,774.

The formulations of the TB-MAPS compositions as disclosed herein can incorporate a stabilizer. Illustrative stabilizers are polyethylene glycol, proteins, saccharide, amino acids, inorganic acids, and organic acids which may be used either on their own or as admixtures. Two or more stabilizers may be used in aqueous solutions at the appropriate concentration and/or pH. The specific osmotic pressure in such aqueous solution is generally in the range of 0.1-3.0 osmoses, preferably in the range of 0.80-1.2. The pH of the aqueous solution is adjusted to be within the range of pH 5.0-9.0, preferably within the range of pH 6-8.

In certain embodiments, a formulation of the invention which is compatible with parenteral administration comprises one or more non-ionic surfactants, including but not limited to polyoxyethylene sorbitan fatty acid esters, Polysorbate-80 (Tween 80), Polysorbate-60 (Tween 60), Polysorbate-40 (Tween 40) and Polysorbate-20 (Tween 20), polyoxyethylene alkyl ethers, including but not limited to Brij 58, Brij 35, as well as others such as Triton X-100; Triton X-114, NP40, Span 85 and the Pluronic series of non-ionic surfactants (e. g., Plutonic 121), with preferred components Polysorbate-80 at a concentration from about 0.001% to about 2% (with up to about 0.25% being preferred) or Polysorbate-40 at a concentration from about 0.001% to 1% (with up to about 0.5% being preferred).

In certain embodiments, a formulation of the TB-MAPS compositions as disclosed herein comprises one or more additional stabilizing agents suitable for parenteral administration, e.g., a reducing agent comprising at least one thiol (—SH) group (e.g., cysteine, N-acetyl cysteine, reduced glutathione, sodium thioglycolate, thiosulfate, monothioglycerol, or mixtures thereof). Alternatively or optionally, preservative-containing immunogenic composition formulations of the invention may be further stabilized by removing oxygen from storage containers, protecting the formulation from light (e.g., by using amber glass containers).

Preservative-containing immunogenic composition formulations of the TB-MAPS composition may comprise one or more pharmaceutically acceptable carriers or excipients, which includes any excipient that does not itself induce an immune response. Suitable excipients include but are not limited to macromolecules such as proteins, saccharides, polylactic acids, polyglycolic acids, polymeric amino acids, amino acid copolymers, sucrose (Paoletti et al, 2001, Vaccine, 19:2118), trehalose, lactose and lipid aggregates (such as oil droplets or liposomes). Such carriers are well known to the skilled artisan. Pharmaceutically acceptable excipients are discussed, e.g., in Gennaro, 2000, Remington: The Science and Practice of Pharmacy, 20.sup.th edition, ISBN: 0683306472.

In some embodiments, TB-MAPS compositions as disclosed herein may be lyophilized or in aqueous form, i.e. solutions or suspensions. Liquid formulations may advantageously be administered directly from their packaged form and are thus ideal for injection without the need for reconstitution in aqueous medium as otherwise required for lyophilized compositions of the invention.

When oral preparations are desired, the immunogenic compositions can be combined with typical carriers, such as lactose, sucrose, starch, talc magnesium stearate, crystalline cellulose, methyl cellulose, carboxymethyl cellulose, glycerin, sodium alginate or gum arabic among others.

In some embodiments, the TB-MAPS immunogenic compositions as described herein can be administered intravenously, intranasally, intramuscularly, subcutaneously, intraperitoneally, sublingually, vaginal, rectal or orally. In some embodiments, the route of administration is oral, intranasal, subcutaneous, or intramuscular. In some embodiments, the route of administration is intranasal administration.

Vaccination can be conducted by conventional methods. For example, a TB-MAPS immunogenic composition as disclosed herein can be used in a suitable diluent such as saline or water, or complete or incomplete adjuvants. The immunogenic composition can be administered by any route appropriate for eliciting an immune response. The TB-MAPS immunogenic composition can be administered once or at periodic intervals until an immune response is elicited. Immune responses can be detected by a variety of methods known to those skilled in the art, including but not limited to, antibody production, cytotoxicity assay, proliferation assay and cytokine release assays. For example, samples of blood can be drawn from the immunized mammal, and analyzed for the presence of antibodies against the antigens of the immunogenic composition by ELISA (see de Boer et. al., 115 Arch Virol. 147 (1990) and the titer of these antibodies can be determined by methods known in the art.

The precise dose of the TB-MAPS to be employed in the formulation will also depend on the route of administration and should be decided according to the judgment of the practitioner and each patient's circumstances. For example, a range of 25 μg-900 μg total protein can be administered monthly for three months.

Packaging and Dosage Forms

In some embodiments, the TB-MAPS immunogenic compositions as disclosed herein may be packaged in unit dose or multi-dose form (e.g. 2 doses, 4 doses, or more). For multi-dose forms, vials are typically but not necessarily preferred over pre-filled syringes. Suitable multi-dose formats include but are not limited to: 2 to 10 doses per container at 0.1 to 2 mL per dose. In certain embodiments, the dose is a 0.5 mL dose. See, e.g., International Patent Application WO2007/127668, which is incorporated by reference herein.

In some embodiments, the TB-MAPS immunogenic compositions as disclosed herein can be presented in vials or other suitable storage containers, or may be presented in pre-filled delivery devices, e.g., single or multiple component syringes, which may be supplied with or without needles. A syringe typically but need not necessarily contains a single dose of the preservative-containing immunogenic composition of the invention, although multi-dose, pre-filled syringes are also envisioned. Likewise, a vial may include a single dose but may alternatively include multiple doses.

Effective dosage volumes can be routinely established, but a typical dose of the composition for injection has a volume of 0.5 mL. In certain embodiments, the dose is formulated for administration to a human subject. In certain embodiments, the dose is formulated for administration to an adult, teen, adolescent, toddler or infant (i.e., no more than one year old) human subject and may in preferred embodiments be administered by injection.

Ultimately, the attending physician will decide the amount of the TB-MAPS immunogenic composition or vaccine composition to administer to particular individuals. As with all immunogenic compositions or vaccines, the immunologically effective amounts of the immunogens (e.g., the immunogenic polysaccharide and the Mtb antigens) must be determined empirically. Factors to be considered include the immunogenicity of the composition as a whole (e.g., it is important to note that the Mtb antigens induce a greater immune response when present in a TB-MAPS complex as compared to the mixture of the Mtb antigens alone (not complexed), the presence of an adjuvant or co-stimulant as disclosed herein, routes of administrations and the number of immunizing dosages to be administered. Such factors are known in the vaccine art and it is well within the skill of immunologists to make such determinations without undue experimentation.

Liquid immunogenic compositions of the TB-MAPS immunogenic compositions as disclosed herein are also suitable for reconstituting other immunogenic compositions which are presented in lyophilized form. Where an immunogenic composition is to be used for such extemporaneous reconstitution, in some embodiment, the present invention provides a kit with two or more vials, two or more ready-filled syringes, or one or more of each, with the contents of the syringe being used to reconstitute the contents of the vial prior to injection, or vice versa.

Alternatively, in some embodiments, the TB-MAPS immunogenic compositions as disclosed herein may be lyophilized and reconstituted, e.g., using one of a multitude of methods for freeze drying well known in the art to form dry, regular shaped (e.g., spherical) particles, such as micropellets or microspheres, having particle characteristics such as mean diameter sizes that may be selected and controlled by varying the exact methods used to prepare them. In some embodiments, the TB-MAPS immunogenic compositions as disclosed herein may further comprise an adjuvant which may optionally be prepared with or contained in separate dry, regular shaped (e.g., spherical) particles such as micropellets or microspheres. In some embodiments, the TB-MAPS immunogenic compositions as disclosed herein are present in a kit comprising a first component that includes a stabilized, dry TB-MAPS immunogenic composition as disclosed herein, optionally further comprising one or more preservatives, and a second component comprising a sterile, aqueous solution for reconstitution of the first component. In certain embodiments, the aqueous solution comprises one or more preservatives, and may optionally comprise at least one adjuvant (see, e.g., WO2009/109550 (incorporated herein by reference).

In yet another embodiment, a container of the multi-dose format is selected from one or more of the group consisting of, but not limited to, general laboratory glassware, flasks, beakers, graduated cylinders, fermentors, bioreactors, tubings, pipes, bags, jars, vials, vial closures (e.g., a rubber stopper, a screw on cap), ampoules, syringes, dual or multi-chamber syringes, syringe stoppers, syringe plungers, rubber closures, plastic closures, glass closures, cartridges and disposable pens and the like. The container of the present invention is not limited by material of manufacture, and includes materials such as glass, metals (e.g., steel, stainless steel, aluminum, etc.) and polymers (e.g., thermoplastics, elastomers, thermoplastic-elastomers). In a particular embodiment, the container of the format is a 5 mL Schott Type I glass vial with a butyl stopper. The skilled artisan will appreciate that the format set forth above is by no means an exhaustive list, but merely serve as guidance to the artisan with respect to the variety of formats available for the present invention. Additional formats contemplated for use in the present invention may be found in published catalogues from laboratory equipment vendors and manufacturers such as United States Plastic Corp. (Lima, Ohio), VWR.

Kits

The present invention also provides for kits for producing a TB-MAPS immunogenic composition as disclosed herein which is useful for an investigator to tailor an immunogenic composition with their preferred Mtb antigens, e.g., for research purposes to assess the effect of a Mtb antigen, or a combination of Mtb antigens on immune response. Such kits can be prepared from readily available materials and reagents. For example, such kits can comprise any one or more of the following materials: a container comprising an immunogenic polysaccharide, cross-linked with a plurality of first affinity molecules; and a container comprising a complementary affinity molecule which associates with the first affinity molecule, wherein the complementary affinity molecule associates with a Mtb antigen.

In another embodiment, the kit can comprise a container comprising an immunogenic polysaccharide, a container comprising a plurality of first affinity molecules, and a container comprising a cross-linking reagent for cross-linking the first affinity molecules to the immunogenic polysaccharide.

In some embodiments, the kit further comprises a means to attach the complementary affinity molecule to the antigen, where the means can be by a cross-linking reagent or by some intermediary fusion protein. In some embodiments, the kit can comprise at least one co-stimulation factor which can be added to the polymer. In some embodiments, the kit comprises a cross-linking reagent, for example, but not limited to, CDAP (1-cyano-4-dimethylaminopyridinium tetrafluoroborate), EDC (1-Ethyl-3-[3-dimethylaminopropyl] carbodiimide hydrochloride), sodium cyanoborohydride; cyanogen bromide; ammonium bicarbonate/iodoacetic acid for linking the co-factor to the polymer.

A variety of kits and components can be prepared for use in the methods described herein, depending upon the intended use of the kit, the particular target antigen and the needs of the user.

In some embodiments, the kit can comprise (a) a container comprising an immunogenic polysaccharide cross-linked with a plurality of first affinity molecules; and (b) a container comprising a complementary affinity molecule which associates with the first affinity molecule, wherein the complementary affinity molecule associates with at least one *Mycobacterium tuberculosis* antigen. In some embodiments, the kit can further comprise a means to attach the complementary affinity molecule to the antigen, e.g., a cross-linking agent as described herein. In some embodiments, the kit further comprises at least one co-stimulation factor. In some embodiments, the kit can also optionally comprise a container comprising an expression vector for expressing an antigen-affinity molecule fusion protein, for example, an expression vector comprising a sequence for a linker peptide, wherein the expression vector can express an antigen-affinity molecule fusion protein comprising a linker peptide between the antigen and the affinity molecule.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

As used herein and in the claims, the singular forms include the plural reference and vice versa unless the context clearly indicates otherwise. The term "or" is inclusive unless modified, for example, by "either." Other than in the operating examples, or where otherwise indicated, all numbers expressing quantities of ingredients or reaction conditions used herein should be understood as modified in all instances by the term "about." It is further to be understood that all base sizes or amino acid sizes, and all molecular weight or molecular mass values, given for nucleic acids or polypeptides are approximate, and are provided for description.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

The term "immunogenic" as used herein means an ability of an antigen (or an epitope of the antigen), such as a bacterial capsular polysaccharide or a conjugate immunogenic composition comprising the bacterial capsular polysaccharide and a polypeptide or peptide antigen, to elicit an immune response in a host such as a mammal, either humorally or cellularly mediated, or both.

The term "immunogenic composition" used herein is defined as a composition capable of eliciting an immune response, such as an antibody or cellular immune response, or both, when administered to a subject. The immunogenic compositions as disclosed herein may or may not be immunoprotective or therapeutic. When the immunogenic compositions as disclosed herein prevent, ameliorate, palliate or eliminate disease from the subject, then the immunogenic composition may optionally be referred to as a vaccine. As used herein, however, the term immunogenic composition is not intended to be limited to vaccines.

Accordingly, an “immunogenic composition” as used herein means any immunogenic polysaccharide conjugated to one or more first affinity molecules, where the first affinity molecule is bound to a complementary affinity molecule that is fused to, or otherwise attached to at least one *M. tuberculosis* peptide or polypeptide antigen, whereby both the immunogenic polysaccharide and the *M. tuberculosis* peptide or polypeptide antigen, each, serve as antigens or antigenic determinant (i.e., epitopes) of the immunogenic composition to elicit an immune response. That is, the immunogenic composition induces a more robust immune response than each of the components alone (i.e., the immunogenic polysaccharide alone, or one or more of the *M. tuberculosis* peptide or polypeptide antigens alone (i.e., a mixture of one or more of the *M. tuberculosis* peptide or polypeptide antigens that are not in a complex or conjugated to the polysaccharide). The immunogenic composition may serve to sensitize the host by the presentation of one or more of the *M. tuberculosis* peptide or polypeptide antigens in association with MHC molecules at a cell surface. In addition, antigen-specific T-cells or antibodies can be generated to allow for the future protection of an immunized host. Immunogenic composition thus can protect the host from one or more symptoms associated with infection by the *M. tuberculosis*, or may protect the host from death due to the infection with *M. tuberculosis*. In some embodiments, the TB-MAPS immunogenic compositions as disclosed herein can also be used to generate polyclonal or monoclonal antibodies, which may be used to confer passive immunity to a subject. In some embodiments, the TB-MAPS immunogenic compositions as disclosed herein can also be used to generate antibodies that are functional as measured by the killing of bacteria in either an animal efficacy model or via an opsonophagocytic killing assay.

The term “antigen” generally refers to a biological molecule, usually a protein or polypeptide, peptide, polysaccharide or conjugate in an immunogenic composition, or immunogenic substance that can stimulate the production of antibodies or T-cell responses, or both, in an animal, including compositions that are injected or absorbed into an animal. The immune response may be generated to the whole molecule (i.e., such as the TB-MAPS immunogenic composition, or to the whole immunogenic polysaccharide, or the whole peptide or polypeptide antigen), or to a various portions of the molecule (e.g., an epitope or hapten within a part of the TB-MAPS immunogenic composition, or to the whole immunogenic polysaccharide, or the whole peptide or polypeptide antigen). The term may be used to refer to an individual molecule or to a homogeneous or heterogeneous population of antigenic molecules. An antigen is recognized by antibodies, T-cell receptors or other elements of specific humoral and/or cellular immunity. The term “antigen” also includes all related antigenic epitopes. Epitopes of a given antigen can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by, e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) Proc. Natl. Acad. Sci. USA 81:3998-4002; Geysen et al. (1986) Molec. Immunol. 23:709-715; each of which is incorporated herein by reference as if set forth in its entirety. Similarly, conformational epitopes may be identified by determining spatial conformation of amino acids such as by, e.g., x-ray crystallography and 2-dimensional nuclear magnetic resonance. See, e.g., Epitope Mapping Protocols, supra. Furthermore, for purposes of the present invention, “antigen” also can be used to refer to a protein that includes modifications, such as deletions, additions and substitutions (generally conservative in nature, but they may be non-conservative), to the native sequence, so long as the protein maintains the ability to elicit an immunological response. These modifications may be deliberate, as through site-directed mutagenesis, or through particular synthetic procedures, or through a genetic engineering approach, or may be accidental, such as through mutations of hosts, which produce the antigens. Furthermore, the antigen can be derived, obtained, or isolated from a microbe, e.g., a bacterium, or can be a whole organism. Similarly, an oligonucleotide polynucleotide, which expresses an antigen, such as in nucleic acid immunization applications, is also included in the definition. Synthetic antigens are also included, e.g., polyepitopes, flanking epitopes, and other recombinant or synthetically derived antigens (Bergmann et al. (1993) Eur. J. Immunol. 23:2777 2781; Bergmann et al. (1996) J. Immunol. 157:3242 3249; Suhrbier (1997) Immunol. Cell Biol. 75:402 408; Gardner et al. (1998) 12th World AIDS Conference, Geneva, Switzerland, Jun. 28 to Jul. 3, 1998). In some embodiments, an antigen is a peptide or a polypeptide, e.g., a *M. tuberculosis* peptide or a polypeptide, or immunogenic polysaccharide and in other embodiments, it can be any chemical or moiety, e.g., a carbohydrate that elicits an immune response directed against the substance.

An “immune response” to an antigen or immunogenic composition is the development in a subject of a humoral and/or a cell-mediated immune response to molecules present in the antigen or vaccine composition of interest. For purposes of the present invention, a “humoral immune response” is an antibody-mediated immune response and involves the induction and generation of antibodies that recognize and bind with some affinity for the antigen in the immunogenic composition of the invention, while a “cell-mediated immune response” is one mediated by T-cells and/or other white blood cells. A “cell-mediated immune response” is elicited by the presentation of antigenic epitopes in association with Class I or Class II molecules of the major histocompatibility complex (MHC), CD1 or other non-classical MHC-like molecules. This activates antigen-specific CD4+ T helper cells or CD8+ cytotoxic lymphocyte cells (“CTLs”). CTLs have specificity for peptide antigens that are presented in association with proteins encoded by classical or non-classical MHCs and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide or other antigens in association with classical or non-classical MHC molecules on their surface. A “cell-mediated immune response” also refers to the production of cytokines, chemokines and other such molecules produced by activated T-cells and/or other white blood cells, including those derived from CD4+ and CD8+ T-cells. The ability of a particular antigen or composition to stimulate a cell-mediated immunological response may be determined by a number of assays, such as by lymphoproliferation (lymphocyte activation) assays, CTL cytotoxic cell assays, by assaying for T-lymphocytes specific for the antigen in a sensitized subject, or by measurement of cytokine production by T cells in response to re-stimulation with antigen. Such assays are well known in the art. See, e.g., Erickson et al. (1993) J. Immunol. 151:4189-4199; and Doe et al. (1994) Eur. J. Immunol. 24:2369-2376.

The term "treatment" (including variations thereof, e.g., "treat" or "treated") as used herein means any one or more of the following: (i) the prevention of infection or re-infection, as in a traditional vaccine, (ii) the reduction in the severity of, or, in the elimination of symptoms, and (iii) the substantial or complete elimination of the pathogen or disorder in question. Hence, treatment may be effected prophylactically (prior to infection) or therapeutically (following infection). In the present invention, prophylactic treatment is the preferred mode. According to a particular embodiment of the present invention, compositions and methods are provided that treat, including prophylactically and/or therapeutically immunize, a host animal against a microbial infection (e.g., a bacterium such as *Mycobacterium*). The methods of the present invention are useful for conferring prophylactic and/or therapeutic immunity to a subject. The methods of the present invention can also be practiced on subjects for biomedical research applications.

The term "site" refers to the location in which the TB-MAPS and/or BCG vaccine are administered via subcutaneous injection. Examples of potential sites include right deltoid, left deltoid, right vastus lateralis, right subcutaneous tissue on thigh, left vastus lateralis, left subcutaneous tissue on thigh.

The term "dose" refers to a single delivery of TB-MAPS immunogenic composition to a subject.

The term "mammal" as used herein means a human or non-human animal. More particularly, mammal refers to any animal classified as a mammal, including humans, domestic and farm animals, and zoo, sports and pet companion animals such as a household pet and other domesticated animal including, but not limited to, cattle, sheep, ferrets, swine, horses, rabbits, goats, dogs, cats, and the like. In some embodiments, a companion animal is a dog or cat. Preferably, the mammal is human.

The term an "immunogenic amount," and "immunologically effective amount," both of which are used interchangeably herein, refers to the amount of the antigen or immunogenic composition sufficient to elicit an immune response, either a cellular (T-cell) or humoral (B-cell or antibody) response, or both, as measured by standard assays known to one skilled in the art. The "immunogenic amount" of a particular immunogenic composition is generally dosed based on total immunogenic polysaccharide and attached or associated TB peptide or polypeptide antigens. For example, a TB-MAPS immunogenic composition as disclosed herein will have at least about 80% or more of, e.g., a polysaccharide with attached TB-antigens via the affinity binding pair. Accordingly, in some embodiments, a TB-MAPS immunogenic composition as disclosed herein can have 20%, or less, free immunogenic polysaccharide, and as such, a 100 mcg dose can have about 80 mcg of immunogenic polysaccharide-antigen TB-MAPS complex and about 20 mcg, or less, of a non-conjugated immunogenic polysaccharide. In some embodiments, the dose of the TB-antigens associated with the immunogenic polysaccharide is important and considered when calculating the dose of a TB-MAPS composition to administer to a subject. The amount of TB-MAPS complex can vary depending upon the number and types of the attached Mtb antigens, the immunogenic polysaccharide as well as any associated co-stimulants as disclosed herein, as well as route of administration, subject and disease to be treated. Generally, each TB-MAPS dose will comprise 0.1 to 100 mcg of an immunogenic polysaccharide and attached Mtb antigens, particularly 0.1 to 10 mcg, and more particularly 1 to 10 mcg.

The amount of a TB-MAPS immunogenic composition as disclosed herein can vary depending upon the *Mycobacterium*. Generally, each dose will comprise 0.1 to 100 mcg of immunogenic polysaccharide, particularly 0.1 to 10 mcg, and more particularly 1 to 10 mcg. The "immunogenic amount" of the different polysaccharide components in the immunogenic composition, may diverge and each may comprise 1 mcg, 2 mcg, 3 mcg, 4 mcg, 6 mcg, 6 mcg, 7 mcg, 8 mcg, 9 mcg, 10 mcg, 15 mcg, 20 mcg, 30 mcg, 40 mcg, 50 mcg, 60 mcg, 70 mcg, 80 mcg, 90 mcg, or about 100 mcg of any particular polysaccharide antigen.

*M. tuberculosis* "invasive disease" is the isolation of bacteria from a normally sterile site, where there is associated clinical signs/symptoms of disease. Normally sterile body sites include blood, CSF, pleural fluid, pericardial fluid, peritoneal fluid, joint/synovial fluid, bone, internal body site (lymph node, brain, heart, liver, spleen, vitreous fluid, kidney, pancreas, and ovary) or other normally sterile sites. Clinical conditions characterizing invasive diseases include bacteremia, pneumonia, cellulitis, osteomyelitis, endocarditis, septic shock and more.

The term "associates" as used herein refers to the linkage of two or more molecules by non-covalent or covalent bonds. In some embodiments, where linking of two or more molecules occurs by a covalent bond, the two or more molecules can be fused together, or cross-linked together. In some embodiments, where linking of two or more molecules occurs by a non-covalent bond, the two or more molecules can form a complex.

The term "complex" as used herein refers to a collection of two or more molecules, connected spatially by means other than a covalent interaction; for example, they can be connected by electrostatic interactions, hydrogen bound or by hydrophobic interactions (i.e., van der Waals forces).

The term "cross-linked" as used herein refers to a covalent bond formed between a polymer chain and a second molecule. The term "cross-linking reagent" refers to an entity or agent which is an intermediate molecule to catalyze the covalent linkage of a polymer with an entity, e.g., first affinity molecule or co-stimulatory factor.

As used herein, the term "fused" means that at least one protein or peptide is physically associated with a second protein or peptide. In some embodiments, fusion is typically a covalent linkage, however, other types of linkages are encompassed in the term "fused" include, for example, linkage via an electrostatic interaction, or a hydrophobic interaction and the like. Covalent linkage can encompass linkage as a fusion protein or chemically coupled linkage, for example via a disulfide bound formed between two cysteine residues.

As used herein, the term "fusion polypeptide" or "fusion protein" means a protein created by joining two or more polypeptide sequences together. The fusion polypeptides encompassed in this invention include translation products of a chimeric gene construct that joins the DNA sequences encoding one or more antigens, or fragments or mutants thereof, with the DNA sequence encoding a second polypeptide to form a single open-reading frame. In other words, a "fusion polypeptide" or "fusion protein" is a recombinant protein of two or more proteins which are joined by a peptide bond or via several peptides. In some embodiments, the second protein to which the antigens are fused to is a complementary affinity molecule which is capable of interacting with a first affinity molecule of the complementary affinity pair.

The terms "polypeptide" and "protein" may be used interchangeably to refer to a polymer of amino acid residues linked by peptide bonds, and for the purposes of the claimed invention, have a typical minimum length of at least 25 amino acids. The term "polypeptide" and "protein" can encompass a multimeric protein, e.g., a protein containing more than one domain or subunit. The term "peptide" as used herein refers to a sequence of peptide bond-linked amino acids containing less than 25 amino acids, e.g., between about 4 amino acids and 25 amino acids in length. Proteins and peptides can be composed of linearly arranged amino acids linked by peptide bonds, whether produced biologically, recombinantly, or synthetically and whether composed of naturally occurring or non-naturally occurring amino acids, are included within this definition. Both full-length proteins and fragments thereof greater than 25 amino acids are encompassed by the definition of protein. The terms also include polypeptides that have co-translational (e.g., signal peptide cleavage) and post-translational modifications of the polypeptide, such as, for example, disulfide-bond formation, glycosylation, acetylation, phosphorylation, lipidation, proteolytic cleavage (e.g., cleavage by metalloproteases), and the like. Furthermore, as used herein, a "polypeptide" refers to a protein that includes modifications, such as deletions, additions, and substitutions (generally conservative in nature as would be known to a person in the art) to the native sequence, as long as the protein maintains the desired activity. These modifications can be deliberate, as through site-directed mutagenesis, or can be accidental, such as through mutations of hosts that produce the proteins, or errors due to PCR amplification or other recombinant DNA methods.

By "signal sequence" is meant a peptide sequence which, when operably linked to a protein or peptide molecule, facilitates secretion of the product (e.g., protein or peptide). In some embodiments, the signal sequence is preferably located N-terminal of the protein. In some embodiments, the signal sequence is encoded by a nucleic acid sequence located at the 5' of the nucleic acid molecule encoding the protein or peptide to be secreted.

As used herein, the term "N-glycosylated" or "N-glycosylation" refers to the covalent attachment of a sugar moiety to asparagine residues in a polypeptide. Sugar moieties can include but are not limited to glucose, mannose, and N-acetylglucosamine. Modifications of the glycans are also included, e.g., siaylation.

An "antigen presenting cell" or "APC" is a cell that expresses the Major Histocompatibility complex (MHC) molecules and can display foreign antigen complexed with MHC on its surface. Examples of antigen presenting cells are dendritic cells, macrophages, B-cells, fibroblasts (skin), thymic epithelial cells, thyroid epithelial cells, glial cells (brain), pancreatic beta cells, and vascular endothelial cells.

The term "functional portion" or "functional fragment" as used in the context of a "functional portion of an antigen" refers to a portion of the antigen or antigen polypeptide that mediates the same effect as the full antigen moiety, e.g., elicits an immune response in a subject, or mediates an association with other molecule, e.g., comprises at least on epitope.

A "portion" of a target antigen as that term is used herein will be at least 3 amino acids in length, and can be, for example, at least 6, at least 8, at least 10, at least 14, at least 16, at least 17, at least 18, at least 19, at least 20 or at least 25 amino acids or greater, inclusive.

The terms "Cytotoxic T Lymphocyte" or "CTL" refers to lymphocytes which induce death via apoptosis or other mechanisms in targeted cells. CTLs form antigen-specific conjugates with target cells via interaction of TCRs with processed antigen (Ag) on target cell surfaces, resulting in apoptosis of the targeted cell. Apoptotic bodies are eliminated by macrophages. The term "CTL response" is used to refer to the primary immune response mediated by CTL cells.

The term "cell mediated immunity" or "CMI" as used herein refers to an immune response that does not involve antibodies or complement but rather involves the activation of, for example, macrophages, natural killer cells (NK), antigen-specific cytotoxic T-lymphocytes (T-cells), T-helper cells, neutrophils, and the release of various cytokines in response to a target antigen. Stated another way, CMI refers to immune cells (such as T cells and other lymphocytes) which bind to the surface of other cells that display a target antigen (such as antigen presenting cells (APC)) and trigger a response. The response may involve either other lymphocytes and/or any of the other white blood cells (leukocytes) and the release of cytokines. Cellular immunity protects the body by: (i) activating antigen-specific cytotoxic T-lymphocytes (CTLs) that are able to destroy body cells displaying epitopes of foreign antigen on their surface, such as virus-infected cells and cells with intracellular bacteria; (2) activating macrophages and NK cells, enabling them to destroy intracellular pathogens; and (3) stimulating cells to secrete a variety of cytokines or chemokines that influence the function of other cells such as T cells, macrophages or neutrophils involved in adaptive immune responses and innate immune responses.

The term "immune cell" as used herein refers to any cell which can release a cytokine, chemokine or antibody in response to a direct or indirect antigenic stimulation. Included in the term "immune cells" herein are lymphocytes, including natural killer (NK) cells, T-cells (CD4+ and/or CD8+ cells), B-cells, macrophages; leukocytes; dendritic cells; mast cells; monocytes; and any other cell which is capable of producing a cytokine or chemokine molecule in response to direct or indirect antigen stimulation. Typically, an immune cell is a lymphocyte, for example a T-cell lymphocyte.

A "protective" immune response refers to the ability of an immunogenic composition as disclosed herein to elicit an immune response, either humoral or cell mediated, or both, which serves to protect a subject from an infection. The protection provided need not be absolute, i.e., the infection need not be totally prevented or eradicated, if there is a statistically significant improvement compared with a control population of subjects, e.g. infected animals not administered the vaccine or immunogenic composition. Protection may be limited to mitigating the severity or rapidity of onset of symptoms of the infection. In general, a "protective immune response" would include the induction of an increase in antibody levels specific for a particular antigen in at least 50% of subjects, including some level of measurable functional antibody responses to each antigen. In particular situations, a "protective immune response" could include the induction of a two-fold increase in antibody levels or a fourfold increase in antibody levels specific for a particular antigen in at least 50% of subjects, including some level of measurable functional antibody responses to each antigen. In certain embodiments, opsonising antibodies correlate with a protective immune response. Thus, protective immune response may be assayed by measuring the percent decrease in the bacterial count in an opsonophagocytosis assay, for instance those described below. Preferably, there is a decrease in bacterial count of at least 10%, 25%, 50%, 65%, 75%, 80%, 85%, 90%, 95% or more.

The term "cytokine" as used herein refers to a molecule released from an immune cell in response to stimulation with an antigen. Examples of such cytokines include, but are not limited to: GM-CSF; IL-1α; IL-1β; IL-2; IL-3; IL-4; IL-5; IL-6; IL-7; IL-8; IL-10; IL-12; IL-17A, IL-17F, or other members of the IL-17 family, IL-22, IL-23, IFN-α; IFN-β; IFN-γ; MIP-1α; MIP-1β; TGF-β; TNFα, or TNFβ. The term "cytokine" does not include antibodies.

The term "subject" as used herein refers to any animal in which it is useful to elicit an immune response. The subject can be a wild, domestic, commercial or companion animal such as a bird or mammal. The subject can be a human. Although in one embodiment of the invention it is contemplated that the immunogenic compositions as disclosed herein can also be suitable for the therapeutic or preventative treatment in humans, it is also applicable to warm-blooded vertebrates, e.g., mammals, such as non-human primates, (particularly higher primates), sheep, dog, rodent (e.g., mouse or rat), guinea pig, goat, pig, cat, rabbits, cows, and non-mammals such as chickens, ducks, or turkeys. In another embodiment, the subject is a wild animal, for example a bird such as for the diagnosis of avian flu. In some embodiments, the subject is an experimental animal or animal substitute as a disease model. The subject may be a subject in need of veterinary treatment, where eliciting an immune response to an antigen is useful to prevent a disease and/or to control the spread of a disease, for example SIV, STL1, SFV, or in the case of live-stock, hoof and mouth disease, or in the case of birds Marek's disease or avian influenza, and other such diseases.

As used herein, the term "pathogen" refers to an organism or molecule that causes a disease or disorder in a subject. For example, pathogens include but are not limited to viruses, fungi, bacteria, parasites, and other infectious organisms or molecules therefrom, as well as taxonomically related macroscopic organisms within the categories algae, fungi, yeast, protozoa, or the like.

The term "wild type" refers to the naturally-occurring, normal polynucleotide sequence encoding a protein, or a portion thereof, or protein sequence, or portion thereof, respectively, as it normally exists in vivo.

The term "mutant" refers to an organism or cell with any change in its genetic material, in particular a change (i.e., deletion, substitution, addition, or alteration) relative to a wild-type polynucleotide sequence or any change relative to a wild-type protein sequence. The term "variant" may be used interchangeably with "mutant". Although it is often assumed that a change in the genetic material results in a change of the function of the protein, the terms "mutant" and "variant" refer to a change in the sequence of a wild-type protein regardless of whether that change alters the function of the protein (e.g., increases, decreases, imparts a new function), or whether that change has no effect on the function of the protein (e.g., the mutation or variation is silent).

The term "pharmaceutically acceptable" refers to compounds and compositions which may be administered to mammals without undue toxicity. The term "pharmaceutically acceptable carriers" excludes tissue culture medium. Exemplary pharmaceutically acceptable salts include but are not limited to mineral acid salts such as hydrochlorides, hydrobromides, phosphates, sulfates, and the like, and the salts of organic acids such as acetates, propionates, malonates, benzoates, and the like. Pharmaceutically acceptable carriers are well-known in the art.

It will be appreciated that proteins or polypeptides often contain amino acids other than the 20 amino acids commonly referred to as the 20 naturally occurring amino acids, and that many amino acids, including the terminal amino acids, can be modified in a given polypeptide, either by natural processes such as glycosylation and other post-translational modifications, or by chemical modification techniques which are well known in the art. Known modifications which can be present in polypeptides of the present invention include, but are not limited to, acetylation, acylation, ADP-ribosylation, amidation, covalent attachment of flavin, covalent attachment of a heme moiety, covalent attachment of a polynucleotide or polynucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formulation, gamma-carboxylation, glycation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

As used herein, the terms "homologous" or "homologues" are used interchangeably, and when used to describe a polynucleotide or polypeptide, indicate that two polynucleotides or polypeptides, or designated sequences thereof, when optimally aligned and compared, for example using BLAST, version 2.2.14 with default parameters for an alignment are identical, with appropriate nucleotide insertions or deletions or amino-acid insertions or deletions, typically in at least 70% of the nucleotides of the nucleotides for high homology. For a polypeptide, there should be at least 30% of amino acid identity in the polypeptide, or at least 50% for higher homology. The term "homolog" or "homologous" as used herein also refers to homology with respect to structure. Determination of homologs of genes or polypeptides can be easily ascertained by the skilled artisan. When in the context with a defined percentage, the defined percentage homology means at least that percentage of amino acid similarity. For example, 85% homology refers to at least 85% of amino acid similarity.

As used herein, the term "heterologous" reference to nucleic acid sequences, proteins or polypeptides mean that these molecules are not naturally occurring in that cell. For example, the nucleic acid sequence coding for a fusion antigen polypeptide described herein that is inserted into a cell, e.g. in the context of a protein expression vector, is a heterologous nucleic acid sequence.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Where necessary or desired, optimal alignment of sequences for comparison can be conducted by any variety of approaches, as these are well-known in the art.

The term "variant" as used herein may refer to a polypeptide or nucleic acid that differs from the naturally occurring polypeptide or nucleic acid by one or more amino acid or nucleic acid deletions, additions, substitutions or side-chain modifications, yet retains one or more specific functions or biological activities of the naturally occurring molecule. Amino acid substitutions include alterations in which an amino acid is replaced with a different naturally-occurring or a non-conventional amino acid residue. Such substitutions may be classified as "conservative," in which case an amino acid residue contained in a polypeptide is replaced with another naturally occurring amino acid of similar character either in relation to polarity, side chain functionality or size. Substitutions encompassed by variants as described herein may also be "non conservative," in which an amino acid residue which is present in a peptide is substituted with an amino acid having different properties (e.g., substituting a charged or hydrophobic amino acid with alanine), or alternatively, in which a naturally-occurring amino acid is substituted with a non-conventional amino acid. Also encompassed within the term "variant," when used with reference to a polynucleotide or polypeptide, are variations in primary, secondary, or tertiary structure, as compared to a reference polynucleotide or polypeptide, respectively (e.g., as compared to a wild-type polynucleotide or polypeptide).

The term "substantially similar," when used in reference to a variant of an antigen or a functional derivative of an antigen as compared to the original antigen means that a particular subject sequence varies from the sequence of the antigen polypeptide by one or more substitutions, deletions, or additions, but retains at least 50%, or higher, e.g., at least 60%, 70%, 80%, 90% or more, inclusive, of the function of the antigen to elicit an immune response in a subject. In determining polynucleotide sequences, all subject polynucleotide sequences capable of encoding substantially similar amino acid sequences are considered to be substantially similar to a reference polynucleotide sequence, regardless of differences in codon sequence. A nucleotide sequence is "substantially similar" to a given antigen nucleic acid sequence if: (a) the nucleotide sequence hybridizes to the coding regions of the native antigen sequence, or (b) the nucleotide sequence is capable of hybridization to nucleotide sequence of the native antigen under moderately stringent conditions and has biological activity similar to the native antigen protein; or (c) the nucleotide sequences are degenerate as a result of the genetic code relative to the nucleotide sequences defined in (a) or (b). Substantially similar proteins will typically be greater than about 80% similar to the corresponding sequence of the native protein.

Variants can include conservative or non-conservative amino acid changes, as described below. Polynucleotide changes can result in amino acid substitutions, additions, deletions, fusions and truncations in the polypeptide encoded by the reference sequence. Variants can also include insertions, deletions or substitutions of amino acids, including insertions and substitutions of amino acids and other molecules) that do not normally occur in the peptide sequence that is the basis of the variant, for example but not limited to insertion of ornithine which do not normally occur in human proteins. "Conservative amino acid substitutions" result from replacing one amino acid with another that has similar structural and/or chemical properties. Conservative substitution tables providing functionally similar amino acids are well known in the art. For example, the following six groups each contain amino acids that are conservative substitutions for one another: (1) Alanine (A), Serine (S), Threonine (T); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); and (6) Phenylalanine (F), Tyrosine (Y), Tryptophan (W). See, e.g., Creighton, PROTEINS (W.H. Freeman & Co., 1984).

The choice of conservative amino acids may be selected based on the location of the amino acid to be substituted in the peptide, for example if the amino acid is on the exterior of the peptide and exposed to solvents, or on the interior and not exposed to solvents. Selection of such conservative amino acid substitutions is within the skill of one of ordinary skill in the art. Accordingly, one can select conservative amino acid substitutions suitable for amino acids on the exterior of a protein or peptide (i.e. amino acids exposed to a solvent). These substitutions include, but are not limited to the following: substitution of Y with F, T with S or K, P with A, E with D or Q, N with D or G, R with K, G with N or A, T with S or K, D with N or E, I with L or V, F with Y, S with T or A, R with K, G with N or A, K with R, A with S, K or P.

Alternatively, one can also select conservative amino acid substitutions suitable for amino acids on the interior of a protein or peptide (i.e., the amino acids are not exposed to a solvent). For example, one can use the following conservative substitutions: where Y is substituted with F, T with A or S, I with L or V, W with Y, M with L, N with D, G with A, T with A or S, D with N, I with L or V, F with Y or L, S with A or T and A with S, G, T or V. In some embodiments, LF polypeptides including non-conservative amino acid substitutions are also encompassed within the term "variants." As used herein, the term "non-conservative" substitution refers to substituting an amino acid residue for a different amino acid residue that has different chemical properties. Non-limiting examples of non-conservative substitutions include aspartic acid (D) being replaced with glycine (G); asparagine (N) being replaced with lysine (K); and alanine (A) being replaced with arginine (R).

The term "derivative" as used herein refers to proteins or peptides which have been chemically modified, for example by ubiquitination, labeling, pegylation (derivatization with polyethylene glycol) or addition of other molecules. A molecule is also a "derivative" of another molecule when it contains additional chemical moieties not normally a part of the molecule. Such moieties can improve the molecule's solubility, absorption, biological half-life, etc. The moieties can alternatively decrease the toxicity of the molecule, or eliminate or attenuate an undesirable side effect of the molecule, etc. Moieties capable of mediating such effects are disclosed in REMINGTON'S PHARMACEUTICAL SCIENCES (21st ed., Tory, ed., Lippincott Williams & Wilkins, Baltimore, M D, 2006).

The term "functional" when used in conjunction with "derivative" or "variant" refers to a protein molecule which possesses a biological activity that is substantially similar to a biological activity of the entity or molecule of which it is a derivative or variant. "Substantially similar" in this context means that the biological activity, e.g., antigenicity of a polypeptide, is at least 50% as active as a reference, e.g., a corresponding wild-type polypeptide, e.g., at least 60% as active, 70% as active, 80% as active, 90% as active, 95% as active, 100% as active or even higher (i.e., the variant or derivative has greater activity than the wild-type), e.g., 110% as active, 120% as active, or more, inclusive.

The term "recombinant" when used to describe a nucleic acid molecule, means a polynucleotide of genomic, cDNA, viral, semisynthetic, and/or synthetic origin, which, by virtue of its origin or manipulation, is not associated with all or a portion of the polynucleotide sequences with which it is associated in nature. The term recombinant as used with respect to a peptide, polypeptide, protein, or recombinant fusion protein, means a polypeptide produced by expression from a recombinant polynucleotide. The term recombinant as used with respect to a host cell means a host cell into which a recombinant polynucleotide has been introduced. Recombinant is also used herein to refer to, with reference to material (e.g., a cell, a nucleic acid, a protein, or a vector) that the material has been modified by the introduction of a heterologous material (e.g., a cell, a nucleic acid, a protein, or a vector).

The term "vectors" refers to a nucleic acid molecule capable of transporting or mediating expression of a heterologous nucleic acid to which it has been linked to a host cell; a plasmid is a species of the genus encompassed by the term "vector." The term "vector" typically refers to a nucleic acid sequence containing an origin of replication and other entities necessary for replication and/or maintenance in a host cell. Vectors capable of directing the expression of genes and/or nucleic acid sequence to which they are operatively linked are referred to herein as "expression vectors". In general, expression vectors of utility are often in the form of "plasmids" which refer to circular double stranded DNA molecules which, in their vector form are not bound to the chromosome, and typically comprise entities for stable or transient expression or the encoded DNA. Other expression vectors that can be used in the methods as disclosed herein include, but are not limited to plasmids, episomes, bacterial artificial chromosomes, yeast artificial chromosomes, bacteriophages or viral vectors, and such vectors can integrate into the host's genome or replicate autonomously in the particular cell. A vector can be a DNA or RNA vector. Other forms of expression vectors known by those skilled in the art which serve the equivalent functions can also be used, for example self replicating extrachromosomal vectors or vectors which integrates into a host genome. Preferred vectors are those capable of autonomous replication and/or expression of nucleic acids to which they are linked.

The term "reduced" or "reduce" or "decrease" as used herein generally means a decrease by a statistically significant amount relative to a reference. For avoidance of doubt, "reduced" means statistically significant decrease of at least 10% as compared to a reference level, for example a decrease by at least 20%, at least 30%, at least 40%, at least t 50%, or least 60%, or least 70%, or least 80%, at least 90% or more, up to and including a 100% decrease (i.e., absent level as compared to a reference sample), or any decrease between 10-100% as compared to a reference level, as that term is defined herein.

The term "low" as used herein generally means lower by a statically significant amount; for the avoidance of doubt, "low" means a statistically significant value at least 10% lower than a reference level, for example a value at least 20% lower than a reference level, at least 30% lower than a reference level, at least 40% lower than a reference level, at least 50% lower than a reference level, at least 60% lower than a reference level, at least 70% lower than a reference level, at least 80% lower than a reference level, at least 90% lower than a reference level, up to and including 100% lower than a reference level (i.e., absent level as compared to a reference sample).

The terms "increased" or "increase" as used herein generally mean an increase by a statically significant amount; such as a statistically significant increase of at least 10% as compared to a reference level, including an increase of at least 20%, at least 30%, at least 40%, at least 50%, at least 60%, at least 70%, at least 80%, at least 90%, at least 100% or more, inclusive, including, for example at least 2-fold, at least 3-fold, at least 4-fold, at least 5-fold, at least 10-fold increase or greater as compared to a reference level, as that term is defined herein.

The term "high" as used herein generally means a higher by a statically significant amount relative to a reference; such as a statistically significant value at least 10% higher than a reference level, for example at least 20% higher, at least 30% higher, at least 40% higher, at least 50% higher, at least 60% higher, at least 70% higher, at least 80% higher, at least 90% higher, at least 100% higher, inclusive, such as at least 2-fold higher, at least 3-fold higher, at least 4-fold higher, at least 5-fold higher, at least 10-fold higher or more, as compared to a reference level.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment of the invention.

Although the foregoing invention has been described in some detail by way of illustration and example for purposes of clarity of understanding it will be readily apparent to one of ordinary skill in the art in light of the teachings of this invention that certain changes and modifications may be made thereto without departing from the spirit or scope of the appended claims. The following is meant to be illustrative of the present invention; however, the practice of the invention is not limited or restricted in any way by the examples.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Some embodiments of the technology described herein can be defined according to any of the following numbered paragraphs:

1) An immunogenic composition comprising an immunogenic polysaccharide, at least two *M. tuberculosis* (Mtb) peptide or polypeptide antigens, and at least one complementary affinity-molecule pair comprising:
   i. at least a first affinity molecule associated with the immunogenic polysaccharide, and
   ii. at least one or more complementary affinity molecules associated with the at least two Mtb peptide or polypeptide antigens,
   iii. wherein the first affinity molecule associates with the complementary affinity molecule to link the Mtb peptide or polypeptide antigens and the immunogenic polysaccharide.
2) The immunogenic composition of paragraph 1, wherein the at least two Mtb peptide or polypeptide antigens are together, or separately, part of a fusion protein with the complementary affinity molecule.
3) The immunogenic composition of paragraph 1, wherein the at least two Mtb peptide or polypeptide antigens are selected from any of the group comprising: MPT51, ESAT6, CFP10, MPT64, MPT83, TB9.8, TB10.4, PPE41, and PE25.
4) The immunogenic composition of paragraph 1, wherein the immunogenic composition comprises at least a MPT51 antigen and at least one additional *M. tuberculosis* (Mtb) peptide or polypeptide antigen selected from any of the group comprising: ESAT6, CFP10, MPT64, MPT83, TB9.8, TB10.4, PPE41, and PE25.
5) The immunogenic composition of paragraph 1, wherein the immunogenic composition comprises a MPT51 antigen and at least two or more additional *M. tuberculosis* (Mtb) peptide or polypeptide antigens selected from any of the group comprising: ESAT6, CFP10, MPT64, MPT83, TB9.8, TB10.4, PPE41, and PE25.
6) The immunogenic composition of paragraph 4, wherein the immunogenic composition comprises a MPT51 antigen, and an ESAT6 antigen, a CFP10 antigen, a MPT64 antigen, a MPT83, a TB9.8 antigen and a TB10.4 antigen.
7) The immunogenic composition of paragraph 6, wherein the immunogenic composition further comprises PEE41 or PE25, or both.
8) The immunogenic composition of paragraph 2, wherein the fusion protein comprises the at least two *M. tuberculosis* protein or peptide antigens, fused to the complementary affinity molecule
9) The immunogenic composition of paragraph 8, wherein a fusion protein comprising the at least two *M. tuberculosis* antigens comprises any of:
   i. an MPT51 antigen, fused to one or more *M. Tuberculosis* antigens selected from any of: ESAT6, CFP10, MPT64, MPT83, TB9.8, TB10.4, PPE41 and PE25;
   ii. an ESAT6 antigen, fused to one or more *M. Tuberculosis* antigens selected from any of: CFP10, MPT51, M64, MPT83, TB9.8, TB10.4, PPE41 and PE25;
   iii. a CFP10 antigen, fused to one or more *M. Tuberculosis* antigens selected from any of: MPT51, MPT64, MPT83, TB9.8, TB10.4, PPE41 and PE25;
   iv. a MPT64 antigen, fused to one or more *M. Tuberculosis* antigens selected from any of: MPT51, ESAT6, CFP10, MPT64, MPT83, TB9.8, TB10.4, PPE41 and PE25
   v. an MPT84 antigen, fused to one or more *M. Tuberculosis* antigens selected from any of: ESAT6, CFP10, MPT51, MPT64, MPT83, TB9.8, TB10.4, PPE41 and PE25
   vi. a TB9.8 antigen, fused to one or more *M. Tuberculosis* antigens selected from any of: ESAT6, CFP10, MPT51, MPT64, MPT83, TB10.4, PPE41 and PE25;
   vii. a TB10.4 antigen, fused to one or more *M. Tuberculosis* antigens selected from any of: ESAT6, CFP10, MPT51, MPT64, MPT83, TB9.8, PPE41 and PE25;
   viii. a PEE41 antigen, fused to one or more *M. Tuberculosis* antigens selected from any of: ESAT6, CFP10, MPT51, MPT64, MPT83, TB9.8, TB10.4 and PE25; or
   ix. a PE25 antigen, fused to one or more *M. Tuberculosis* antigens selected from any of: ESAT6, CFP10, MPT51, MPT64, MPT83, TB9.8, TB10.4 and PEE41.
10) The immunogenic composition of any of paragraphs 2 to 9, wherein the fusion protein comprising at least two *M. tuberculosis* antigens comprises an ESAT6 antigen fused to at least one fragment of CFP10 antigen.
11) The immunogenic composition of any of paragraphs 2 to 9, wherein the fusion protein comprising at least two *M. tuberculosis* antigens comprises an ESAT6 antigen fused to two fragments of CFP10 antigens.
12) The immunogenic composition of any of paragraphs 2 to 9, wherein the fusion protein comprising at least two *M. tuberculosis* antigens comprises TB9.8 fused to TB10.4.
13) The immunogenic composition of any of paragraphs 2 to 9, wherein the fusion protein comprising at least two *M. tuberculosis* antigens comprises PPE41 fused to PE25.
14) The immunogenic composition of any of paragraphs 2 to 13, wherein the fusion protein comprises the at least three *M. tuberculosis* peptide or protein antigens, fused to the complementary affinity molecule.
15) The immunogenic composition of any of paragraphs 2 to 14, wherein a fusion protein comprising at least three *M. tuberculosis* antigens comprises at least three antigens selected from: ESAT6, CFP10 and MPT64.
16) The immunogenic composition of any of paragraphs 2 to 14, wherein a fusion protein comprising at least three *M. tuberculosis* antigens comprises a ESAT6 antigen, at least two CFP10 antigens and at least a MPT64 antigen.
17) The immunogenic composition of any of paragraphs 2 to 14, wherein a fusion protein comprising at least three *M. tuberculosis* antigens comprises TB9.8, TB10.4 and MPT83.
18) The immunogenic composition of any of paragraphs 2 to 14, wherein a fusion protein comprising at least two *M. tuberculosis* antigens can comprise at least one linker peptide between each antigen.
19) The immunogenic composition of paragraph 16, wherein the linker peptide is selected from the group consisting of: KLGS (SEQ ID NO: 51); GS (SEQ ID NO: 52), KLGGS (SEQ ID NO: 53), AAA (SEQ ID NO: 54), GGGGSSS (SEQ ID NO: 35) and TDPNSSS (SEQ ID NO: 36).

20) The immunogenic composition of any of paragraphs 3 to 19, wherein the *M. tuberculosis* antigens are selected from: MPT51 (33-299), ESAT6 (1-95), CFP10 (1-40), CFP10 (45-80), MPT64 (25-228), MPT83 (58-220), TB9.8 (1-97), TB10.4 (1-96), PPE41 (1-194) and PE25 (1-99).

21) The immunogenic composition of any of paragraphs 1 to 20, wherein the MPT51 antigen comprises at least SEQ ID NO: 3 (MPT51 (33-299)) or a polypeptide with at least 85% sequence identity to SEQ ID NO: 3.

22) The immunogenic composition of any of paragraphs 1 to 20, wherein the MPT51 antigen comprises a fragment of at least 30 amino acids of SEQ ID NO: 3 or a polypeptide of at least 30 amino acids that has at least 85% sequence identity to a portion of SEQ ID NO: 3.

23) The immunogenic composition of any of paragraphs 1 to 20, wherein the ESAT6 antigen comprises at least SEQ ID NO: 5 (ESAT6 (1-95)) or a polypeptide with at least 85% sequence identity to SEQ ID NO: 4.

24) The immunogenic composition of any of paragraphs 1 to 20, wherein the ESAT6 antigen comprises a fragment of at least 30 amino acids of SEQ ID NO: 5 or a polypeptide of at least 30 amino acids that has at least 85% sequence identity to a portion of SEQ ID NO: 5.

25) The immunogenic composition of any of paragraphs 1 to 20, wherein the CFP10 antigen comprises at least SEQ ID NO: 6 (CFP10 (1-40)) or SEQ ID NO: 7 (CFP10 (45-80)) or at least or a polypeptide with at least 85% sequence identity to SEQ ID NO: 6 or SEQ ID NO: 7.

26) The immunogenic composition of any of paragraphs 1 to 20, wherein the CFP10 antigen comprises a fragment of at least 30 amino acids of SEQ ID NO:6 or SEQ ID NO: 7 or a polypeptide of at least 30 amino acids that has at least 85% sequence identity to a portion of SEQ ID NO: 6 or SEQ ID NO: 7.

27) The immunogenic composition of any of paragraphs 1 to 20, wherein the MPT64 antigen comprises at least SEQ ID NO: 9 (MPT64 25-228) or a polypeptide with at least 85% sequence identity to SEQ ID NO: 9.

28) The immunogenic composition of any of paragraphs 1 to 20, wherein the MPT64 antigen comprises a fragment of at least 30 amino acids of SEQ ID NO:9 or a polypeptide of at least 30 amino acids that has at least 85% sequence identity to a portion of SEQ ID NO: 9.

29) The immunogenic composition of any of paragraphs 1 to 20, wherein the MPT83 antigen comprises at least SEQ ID NO: 11 (MPT 58-220) or a polypeptide with at least 85% sequence identity to SEQ ID NO: 11.

30) The immunogenic composition of any of paragraphs 1 to 20, wherein the MPT83 antigen comprises a fragment of at least 30 amino acids of SEQ ID NO:11 or a polypeptide of at least 30 amino acids that has at least 85% sequence identity to a portion of SEQ ID NO: 11.

31) The immunogenic composition of any of paragraphs 1 to 20, wherein the TB9.8 antigen comprises at least SEQ ID NO: 13 (TB9.8 (1-97)) or a polypeptide with at least 85% sequence identity to SEQ ID NO: 13.

32) The immunogenic composition of any of paragraphs 1 to 20, wherein the TB9.8 antigen comprises a fragment of at least 30 amino acids of SEQ ID NO:13 or a polypeptide of at least 30 amino acids that has at least 85% sequence identity to a portion of SEQ ID NO: 13.

33) The immunogenic composition of any of paragraphs 1 to 20, wherein the TB10.4 antigen comprises at least SEQ ID NO: 14 (TB10.4 (1-96)) or a polypeptide with at least 85% sequence identity to a portion of SEQ ID NO: 13.

34) The immunogenic composition of any of paragraphs 1 to 20, wherein the TB10.4 antigen comprises a fragment of at least 30 amino acids of SEQ ID NO:14 or a polypeptide of at least 30 amino acids that has at least 85% sequence identity to a portion of SEQ ID NO: 14.

35) The immunogenic composition of any of paragraphs 1 to 20, wherein the PPE41 antigen comprises at least SEQ ID NO: 15 (PPE41 (1-194) or a polypeptide with at least 85% sequence identity a portion of SEQ ID NO: 15.

36) The immunogenic composition of any of paragraphs 1 to 20, wherein the PPE41 antigen comprises a fragment of at least 30 amino acids of SEQ ID NO:15 or a polypeptide of at least 30 amino acids that has at least 85% sequence identity to a portion of SEQ ID NO: 15.

37) The immunogenic composition of any of paragraphs 1 to 20, wherein the PE25 antigen comprises at least SEQ ID NO: 16 (PE25 (1-99) or a polypeptide with at least 85% sequence identity a portion of SEQ ID NO: 15.

38) The immunogenic composition of any of paragraphs 1 to 20, wherein the PE25 antigen comprises a fragment of at least 30 amino acids of SEQ ID NO:16 or a polypeptide of at least 30 amino acids that has at least 85% sequence identity to a portion of SEQ ID NO: 16.

39) The immunogenic composition of any of paragraphs 1 to 38, wherein the first affinity molecule is biotin or a derivative or mimic molecule thereof.

40) The immunogenic composition of any of paragraphs 1 to 39, wherein the first affinity molecule is a biotin derivative, lipoic acid, HABA (hydroxyazobenzene-benzoic acid) or/and dimethyl-HABA or an amine-PEG3-biotin ((+)-biotinylation-3-6, 9-trixaundecanediamine).

41) The immunogenic composition of any of paragraphs 1 to 40, wherein the complementary affinity molecule is a biotin-binding protein, or an avidin-like protein.

42) The immunogenic composition of any of paragraphs 1 to 41, wherein the complementary affinity molecule is a lipidated biotin-binding protein, or a lipidated avidin-like protein.

43) The immunogenic composition of paragraph 40, wherein the avidin-like protein or lipidated avidin-like protein is selected from the group consisting of: rhizavidin, avidin, streptavidin, or a homologue or derivative thereof.

44) The immunogenic composition of paragraph 41, wherein the rhizavidin is amino acids of SEQ ID NO: 1, or 85% sequence identity to amino acids of SEQ ID NO: 1.

45) The immunogenic composition of any of paragraphs 1 to 44, wherein the complementary affinity molecule is a lipidated rhizavidin protein comprising amino acids of SEQ ID NO: 1, or a lipidated rhizavidin protein having 85% sequence identity to amino acids of SEQ ID NO: 1, where the wherein the lipidated rhizavidin protein comprises at the N-terminus of the rhizavidin protein, a lipidation sequence selected from any of: MKKVAAFVALSLLMAGC (SEQ ID NO: 29); MNSKKLCCICVLFSLLAGCAS (SEQ ID NO: 31), MRYSKLTMLIPCALLLSAC (SEQ ID NO: 32), MFVTSKKMTAAVLAITLAMSLSAC (SEQ ID NO: 33) and MIKRVLVVSMVGLSLVGC (SEQ ID NO: 34).

46) The immunogenic composition of any of paragraphs 1 to 45, further comprising at least one flexible linker peptide attached to the antigen, wherein the flexible linker peptide attaches the antigen to the complementary affinity molecule.

47) The immunogenic composition of paragraph 46, wherein the flexible linker peptide is selected from any of: KLGS (SEQ ID NO: 51); GS (SEQ ID NO: 52), KLGGS (SEQ ID NO: 53), AAA (SEQ ID NO: 54), GGGGSSS (SEQ ID NO: 35) and TDPNSSS (SEQ ID NO: 36).

48) The immunogenic composition of paragraph 1, wherein the first affinity molecule is cross-linked to the immunogenic polysaccharide.

49) The immunogenic composition of paragraph 1, wherein the first affinity molecule is cross-linked to the immunogenic polysaccharide using a cross-linking reagent selected from any in the group consisting of: CDAP (1-cyano-4-dimethylaminopyridinium tetrafluoroborate); EDC (1-Ethyl-3-[3-dimethylaminopropyl] carbodiimide hydrochloride); sodium cyanoborohydride; cyanogen bromide; and ammonium bicarbonate/iodoacetic acid.

50) The immunogenic composition of paragraph 1, wherein the first affinity molecule is cross-linked to carboxyl, hydroxyl, aldehyde, amino, phenoxyl, hemiacetal, and mecapto functional groups of the immunogenic polysaccharide.

51) The immunogenic composition of paragraph 1, wherein the first affinity molecule is covalently bonded to the immunogenic polysaccharide.

52) The immunogenic composition of paragraph 1, wherein the first affinity molecule and complementary affinity molecule pair can be selected from a group consisting of: biotin/biotin-binding protein, antibody/antigen, enzyme/substrate, receptor/ligand, metal/metal-binding protein, carbohydrate/carbohydrate binding protein, lipid/lipid-binding protein, His tag/His tag-binding substance.

53) The immunogenic composition of any of paragraphs 1 to 52, wherein the antigen is non-covalently attached, or covalently attached to the complementary affinity molecule.

54) The immunogenic composition of any of paragraphs 1 to 53, wherein a secretion signal peptide is located at the N-terminal of the avidin-like protein.

55) The immunogenic composition of any of paragraphs 1 to 54, wherein the secretion signal sequence comprises at least MKKIWLALAGLVLAFSASA (SEQ ID NO: 19) or MKKIWLALAGLVLAFSASAAQDP (SEQ ID NO: 24) or an amino acid sequence having at least 85% identity thereof.

56) The immunogenic composition of any of paragraph 1 to 55 wherein the immunogenic polysaccharide is purified from living organisms or is a synthetic immunogenic polysaccharide.

57) The immunogenic composition of any of paragraph 1 to 56, wherein the living organism is selected from the group consisting of: bacteria, archaea, eukaryotic cells, fungi, insects, plants, animals, or chimeras thereof.

58) The immunogenic composition of any of paragraphs 1 to 67, wherein the immunogenic polysaccharide is selected from a polysaccharide from the group consisting of: *M. tuberculosis* polysaccharides (e.g. alpha-glucan, lipoarabinomannan or arabinomannan), *S. aureus* polysaccharides, Vi polysaccharide, pneumococcal capsular polysaccharides, pneumococcal cell wall polysaccharide, *Haemophilus influenzae* Type b polysaccharide, Meningococcal polysaccharides, O-antigens from Gram-negative bacteria and other bacterial capsular or cell wall polysaccharides.

59) The immunogenic composition of any of paragraph 1 to 58 wherein the immunogenic polysaccharide is from *M. tuberculosis.*

60) The immunogenic composition of any of paragraph 1 to 58 wherein the immunogenic polysaccharide is a pneumococcal polysaccharide.

61) The immunogenic composition of any of paragraphs 1 to 68, wherein the immunogenic polysaccharide is selected from type 1 capsular polysaccharide of *Streptococcus pneumoniae*, type 5 capsular polysaccharide of *S. aureus* or type 8 capsular polysaccharide of *S. aureus.*

62) The immunogenic composition of any of paragraphs 1 to 61, further comprising at least one co-stimulation factor associated to the immunogenic polysaccharide.

63) The immunogenic composition of any of paragraphs 1 to 62, wherein the co-stimulation factor is selected from the group consisting of: Toll like receptor ligand or agonists, NOD ligand or agonists, or activator/agonists of the inflammasome.

64) The immunogenic composition of paragraph 62, wherein the co-stimulation factor is attached to immunogenic polysaccharide directly, or via a complementary affinity-molecule pair comprising: a first affinity molecule which associates with the immunogenic polysaccharide, and a complementary affinity molecule which associates with the co-stimulation factor, wherein the first affinity molecule associates with the complementary affinity molecule to link the co-stimulatory factor to the immunogenic polysaccharide.

65) The immunogenic composition of paragraphs 1 to 64, wherein composition is used to elicit an immune response to *M. tuberculosis* in a subject.

66) The immunogenic composition of paragraphs 1 to 64 for use in a diagnostic for exposure to a pathogen or immune threat.

67) The immunogenic composition of paragraphs 1 to 64 for use in preventing infection by *M. tuberculosis.*

68) The immunogenic composition of paragraphs 1 to 64 for use in preventing colonization of a subject by *M. tuberculosis.*

69) Use of a composition of any one of paragraphs 1 to 64 for the vaccination against or prevention of *M. tuberculosis.*

70) A method of inducing an immune response in a subject against *M. tuberculosis*, the method comprising administering at a first time point, a composition comprising a TB-MAPS immune composition at a first site and a composition comprising a Bacille Calmette-Guerin (BCG) vaccine at a second site, wherein the TB-MAPS immune composition is defined according to paragraphs 1 to 64.

71) A method for inducing an immune response in a subject against *M. tuberculosis*, the method comprising administering the composition of paragraphs 1 to 64.

72) The method of paragraph 70 or 71, further comprising administering at a second time point the composition comprising the TB-MAPS immune composition.

73) The method of paragraphs 70 or 71, further comprising administering at a third time point the composition comprising the TB-MAPS immune composition.

74) The method of paragraph 72, wherein the second time point is at least 2 weeks after the first time point.

75) The method of paragraph 72, wherein the second time point is between 2-4 weeks, or between 4-8 weeks, or between 1-3 months, or between 3-6 months, or between 6-12 months, or between 1-2 years, or between 2-3 years, after the first time point.

76) The method of paragraph 73, wherein the third time point is at least 2 weeks after the second time point.

77) The method of paragraph 73, wherein the third time point is between 2-4 weeks, or between 4-8 weeks, or between 1-3 months, or between 3-6 months, or between 6-12 months, or between 1-2 years, or between 2-3 years, after the second time point.

78) The method of paragraphs 73 or 74, wherein the administration of the TB-MAPS immune composition at the second or third time point is at the first site, or second site, or both.

79) The method of paragraph 70, wherein the composition comprising the TB-MAPS immune composition and the composition comprising the BCG vaccine are administered at the substantially the same time or within 24 hours.

80) The method of paragraphs 70 or 71, wherein the subject has previously been administered a composition comprising a BCG vaccine.

81) The method of any of paragraphs 70 to 80, wherein the subject is a human.

82) The method of any of paragraphs 70 to 80, wherein the subject is an agricultural or non-domestic animal.

83) The method of any of paragraphs 70 to 80, wherein the subject is a domestic animal.

84) The method of any of paragraphs 70 to 80, wherein the composition comprising a TB-MAPS immune composition or the composition comprising BCG vaccine, or both, is administered via subcutaneous, intranasal, intradermal, or intra muscular injection, or via transdermal skin patch.

85) The method of any of paragraphs 70 to 84, wherein the immune response is an antibody or B-cell response.

86) The method of any of paragraphs 70 to 84, wherein the immune response is an antibody or B-cell response and T-cell response.

87) The method of any of paragraphs 70 to 84, wherein the immune response is to at least one peptide or polypeptide *M. tuberculosis* antigen.

88) The method of any of paragraphs 70 to 84, wherein the immune response is a CD4+ T cell response, including Th1, Th2 or Th17 response, or a CD8+ T cell response, or CD4+ and CD8+ T cell response.

89) The method of any of paragraphs 70 to 84, wherein the immune response is an antibody or B cell response to at least one antigenic polysaccharide and a CD4+ T cell response, including Th1, Th2 or Th17 response, or a CD8+ T cell response, or CD4+/CD8+ T cell response to at least one peptide or polypeptide antigen.

90) The method of any of paragraphs 70 to 84, wherein the immune response is an antibody or B cell response to at least one antigenic polysaccharide, and an antibody or B cell response and a CD4+ T cell response, including Th1, Th2 or Th17 response, or a CD8+ T cell response, or CD4+/CD8+ T cell response to at least one peptide or polypeptide antigen.

91) The method of any of paragraphs 70 to 84, wherein the immune response results in activation of IL-17A and INF-γ producing cells, or IL-17A producing cells.

92) The method of any of paragraphs 70 to 84, wherein the immune response is an antibody or B-cell response against the *M. tuberculosis* antigen which associates with the immunogenic polysaccharide.

93) A fusion protein comprising a Rhizavidin protein and at least one *M. tuberculosis* antigen selected from a group consisting of: MPT51, ESAT6, CFP10, wherein CFP10 is CFP10 (1-40) or CFP10 (45-80), or CFP10 (1-40) and CFP10 (45-80), MPT64, TB9.8, TB10.4, MPT83, PPE41, and PE25.

94) The fusion protein of paragraph 93, wherein the *M. tuberculosis* antigen is MPT51.

95) The fusion protein of paragraph 93, wherein the fusion protein comprises a MPT51 antigen and at least one additional *M. tuberculosis* antigen selected from a group consisting of: ESAT6, CFP10, wherein CFP10 is CFP10 (1-40) or CFP10 (45-80), or CFP10 (1-40) and CFP10 (45-80), MPT64, TB9.8, TB10.4, MPT83, PPE41, PE25.

96) The fusion protein of paragraph 93, wherein the fusion protein comprises a MPT51 antigen and at least two additional *M. tuberculosis* antigens selected from a group consisting of: ESAT6, CFP10, wherein CFP10 is CFP10 (1-40) or CFP10 (45-80), or CFP10 (1-40) and CFP10 (45-80), MPT64, TB9.8, TB10.4, MPT83, PPE41, PE25.

97) The fusion protein of paragraph 93, wherein the fusion protein comprises a ESAT6 antigen and at least one additional *M. tuberculosis* antigen selected from a group consisting of: MPT51, CFP10, wherein CFP10 is CFP10 (1-40) or CFP10 (45-80), or CFP10 (1-40) and CFP10 (45-80), MPT64, TB9.8, TB10.4, MPT83, PPE41, and PE25.

98) The fusion protein of paragraph 93, wherein the fusion protein comprises a ESAT6 antigen and at least two additional a *M. tuberculosis* antigens selected from a group consisting of: MPT51, CFP10, wherein CFP10 is CFP10 (1-40) or CFP10 (45-80), or CFP10 (1-40) and CFP10 (45-80), MPT64, TB9.8, TB10.4, MPT83, PPE41, and PE25.

99) The fusion protein of paragraph 93, wherein the fusion protein comprises a CFP10 antigen and at least one additional *M. tuberculosis* antigen selected from a group consisting of: MPT51, ESAT6, MPT64, TB9.8, TB10.4, MPT83, PPE41, and PE25.

100) The fusion protein of paragraph 93, wherein the fusion protein comprises a CFP10 antigen and at least two additional *M. tuberculosis* antigens selected from a group consisting of: MPT51, ESAT6, CFP10, MPT64, TB9.8, TB10.4, MPT83, PPE41, and PE25.

101) The fusion protein of paragraph 93, wherein the fusion protein comprises a MPT64 antigen and at least one additional *M. tuberculosis* antigen selected from a group consisting of: MPT51, ESAT6, CFP10, wherein CFP10 is CFP10 (1-40) or CFP10 (45-80), or CFP10 (1-40) and CFP10 (45-80), TB9.8, TB10.4, MPT83, PPE41, and PE25.

102) The fusion protein of paragraph 93, wherein the fusion protein comprises a MPT64 antigen and at least two additional *M. tuberculosis* antigens selected from a group consisting of: MPT51, ESAT6, CFP10, wherein CFP10 is CFP10 (1-40) or CFP10 (45-80), or CFP10 (1-40) and CFP10 (45-80), TB9.8, TB10.4, MPT83, PPE41, and PE25.

103) The fusion protein of paragraph 93, wherein the fusion protein comprises a TB9.8 antigen and at least one additional *M. tuberculosis* antigen selected from a group consisting of: MPT51, ESAT6, CFP10, wherein CFP10 is CFP10 (1-40) or CFP10 (45-80), or CFP10 (1-40) and CFP10 (45-80), MPT64, TB10.4, MPT83, PPE41, and PE25.

104) The fusion protein of paragraph 93, wherein the fusion protein comprises a TB9.8 antigen and at least two additional *M. tuberculosis* antigens selected from a group consisting of: MPT51, ESAT6, CFP10, wherein CFP10 is CFP10 (1-40) or CFP10 (45-80), or CFP10 (1-40) and CFP10 (45-80), MPT64, TB10.4, MPT83, PPE41, and PE25.

105) The fusion protein of paragraph 1, wherein the fusion protein comprises a TB10.4 antigen and at least one additional *M. tuberculosis* antigen selected from a group consisting of: MPT51, ESAT6, CFP10, wherein CFP10 is CFP10 (1-40) or CFP10 (45-80), or CFP10 (1-40) and CFP10 (45-80), MPT64, TB9.8, MPT83, PPE41, and PE25.

106) The fusion protein of paragraph 93, wherein the fusion protein comprises a TB10.4 antigen and at least two additional *M. tuberculosis* antigens selected from a group consisting of: MPT51, ESAT6, CFP10, wherein CFP10 is CFP10 (1-40) or CFP10 (45-80), or CFP10 (1-40) and CFP10 (45-80), MPT64, TB9.8, MPT83, PPE41, and PE25.

107) The fusion protein of paragraph 93, wherein the fusion protein comprises a MPT83 antigen and at least one additional *M. tuberculosis* antigen selected from a group consisting of: MPT51, ESAT6, CFP10, wherein CFP10 is CFP10 (1-40) or CFP10 (45-80), or CFP10 (1-40) and CFP10 (45-80), MPT64, TB9.8, TB10.4, PPE41, and PE25.

108) The fusion protein of paragraph 93, wherein the fusion protein comprises a MPT83 antigen and at least two additional *M. tuberculosis* antigens selected from a group consisting of: MPT51, ESAT6, CFP10, wherein CFP10 is CFP10 (1-40) or CFP10 (45-80), or CFP10 (1-40) and CFP10 (45-80), MPT64, TB9.8, TB10.4, PPE41, and PE25.

109) The fusion protein of paragraph 93, wherein the fusion protein comprises a PPE41 antigen and at least one additional *M. tuberculosis* antigen selected from a group consisting of: MPT51, ESAT6, CFP10, wherein CFP10 is CFP10 (1-40) or CFP10 (45-80), or CFP10 (1-40) and CFP10 (45-80), MPT64, TB9.8, TB10.4, MPT83, and PE25.

110) The fusion protein of paragraph 93, wherein the fusion protein comprises a PPE41 antigen and at least two additional *M. tuberculosis* antigens selected from a group consisting of: MPT51, ESAT6, CFP10, wherein CFP10 is CFP10 (1-40) or CFP10 (45-80), or CFP10 (1-40) and CFP10 (45-80), MPT64, TB9.8, TB10.4, MPT83, and PE25.

111) The fusion protein of paragraph 93, wherein the fusion protein comprises a PE25 antigen and at least one additional *M. tuberculosis* antigen selected from a group consisting of: MPT51, ESAT6, CFP10, wherein CFP10 is CFP10 (1-40) or CFP10 (45-80), or CFP10 (1-40) and CFP10 (45-80), MPT64, TB9.8, TB10.4, MPT83, and PPE41.

112) The fusion protein of paragraph 93, wherein the fusion protein comprises a PE25 antigen and at least two additional *M. tuberculosis* antigens selected from a group consisting of: MPT51, ESAT6, CFP10, wherein CFP10 is CFP10 (1-40) or CFP10 (45-80), or CFP10 (1-40) and CFP10 (45-80), MPT64, TB9.8, TB10.4, MPT83, and PPE41.

113) The fusion protein of any of paragraphs 92 to 112, wherein the *M. tuberculosis* antigens are selected from a group consisting of: MPT51 (33-299), ESAT6 (1-95), CFP10 (1-40), CFP10 (45-80), MPT64 (25-228), MPT83 (58-220), TB9.8 (1-97), TB10.4 (1-96), PPE41 (1-194) and PE25 (1-99).

114) The fusion protein of any of paragraphs 92 to 112, wherein the MPT51 antigen comprises at least SEQ ID NO: 3 (MPT51 (33-299) or a polypeptide with at least 85% sequence identity to SEQ ID NO: 3.

115) The fusion protein of any of paragraphs 92 to 112, wherein the MPT51 antigen comprises a fragment of at least 30 amino acids of SEQ ID NO: 3 or a polypeptide of at least 30 amino acids that has at least 85% sequence identity to a portion of SEQ ID NO: 3.

116) The fusion protein of any of paragraphs 92 to 112, wherein the ESAT6 antigen comprises at least SEQ ID NO: 5 (ESAT6 (1-95)) or a polypeptide with at least 85% sequence identity to SEQ ID NO: 4.

117) The fusion protein of any of paragraphs 92 to 112, wherein the ESAT6 antigen comprises a fragment of at least 30 amino acids of SEQ ID NO: 5 or a polypeptide of at least 30 amino acids that has at least 85% sequence identity to a portion of SEQ ID NO: 5.

118) The fusion protein of any of paragraphs 92 to 112, wherein the CFP10 antigen comprises at least SEQ ID NO: 6 (CFP10 (1-40)) or SEQ ID NO: 7 (CFP10 (45-80)) or at least or a polypeptide with at least 85% sequence identity to SEQ ID NO: 6 or SEQ ID NO: 7.

119) The fusion protein of any of paragraphs 92 to 112, wherein the CFP10 antigen comprises a fragment of at least 30 amino acids of SEQ ID NO:6 or SEQ ID NO: 7 or a polypeptide of at least 30 amino acids that has at least 85% sequence identity to a portion of SEQ ID NO: 6 or SEQ ID NO: 7.

120) The fusion protein of any of paragraphs 92 to 112, wherein the MPT64 antigen comprises at least SEQ ID NO: 9 (MPT64 (25-228)) or a polypeptide with at least 85% sequence identity to SEQ ID NO: 9.

121) The fusion protein of any of paragraphs 92 to 112, wherein the MPT64 antigen comprises a fragment of at least 30 amino acids of SEQ ID NO:9 or a polypeptide of at least 30 amino acids that has at least 85% sequence identity to a portion of SEQ ID NO: 9.

122) The fusion protein of any of paragraphs 92 to 112, wherein the MPT83 antigen comprises at least SEQ ID NO: 11 (MPT 58-220) or a polypeptide with at least 85% sequence identity to SEQ ID NO: 11.

123) The fusion protein of any of paragraphs 92 to 112, wherein the MPT83 antigen comprises a fragment of at least 30 amino acids of SEQ ID NO:11 or a polypeptide of at least 30 amino acids that has at least 85% sequence identity to a portion of SEQ ID NO: 11.

124) The fusion protein of any of paragraphs 92 to 112, wherein the TB9.8 antigen comprises at least SEQ ID NO: 13 (TB9.8 (1-97)) or a polypeptide with at least 85% sequence identity to SEQ ID NO: 13.

125) The fusion protein of any of paragraphs 92 to 112, wherein the TB9.8 antigen comprises a fragment of at least 30 amino acids of SEQ ID NO: 13 or a polypeptide of at least 30 amino acids that has at least 85% sequence identity to a portion of SEQ ID NO: 13.

126) The fusion protein of any of paragraphs 92 to 112, wherein the TB10.4 antigen comprises at least SEQ ID NO: 14 (TB10.4 (1-96)) or a polypeptide with at least 85% sequence identity to SEQ ID NO: 13.

127) The fusion protein of any of paragraphs 92 to 112, wherein the TB10.4 antigen comprises a fragment of at least 30 amino acids of SEQ ID NO:14 or a polypeptide of at least 30 amino acids that has at least 85% sequence identity to a portion of SEQ ID NO: 14.

128) The fusion protein of any of paragraphs 92 to 112, wherein the PPE41 antigen comprises at least SEQ ID NO: 15 (PPE4l (1-194) or a polypeptide with at least 85% sequence identity to SEQ ID NO: 15.

129) The fusion protein of any of paragraphs 92 to 112, wherein the PPE41 antigen comprises a fragment of at least 30 amino acids of SEQ ID NO: 15 or a polypeptide of at least 30 amino acids that has at least 85% sequence identity to a portion of SEQ ID NO: 15.

130) The fusion protein of any of paragraphs 92 to 112, wherein the PE25 antigen comprises at least SEQ ID NO: 16 (PE25 (1-99) or a polypeptide with at least 85% sequence identity to SEQ ID NO: 15.

131) The fusion protein of any of paragraphs 92 to 112, wherein the PE25 antigen comprises a fragment of at least 30 amino acids of SEQ ID NO:16 or a polypeptide of at least 30 amino acids that has at least 85% sequence identity to a portion of SEQ ID NO: 16.

132) The fusion proteins of any of paragraph 1 to 131, wherein rhizavidin protein is lipidated rhizavidin protein.

133) The fusion protein of any of paragraphs 92 to 132, the rhizavidin protein comprises amino acids of SEQ ID NO: 1, or a peptide or protein having 85% sequence identity to amino acids of SEQ ID NO: 1.

134) The fusion protein of any of paragraph 92 to 133, wherein the rhizavidin protein is a lipidated rhizavidin protein comprising amino acids of SEQ ID NO: 1, or is a lipidated rhizavidin protein having 85% sequence identity to amino acids of SEQ ID NO: 1.

135) The fusion protein of paragraph 134, wherein the lipidated rhizavidin protein comprising amino acids of SEQ ID NO: 1, or the lipidated rhizavidin protein having 85% sequence identity to amino acids of SEQ ID NO: 1 comprises at the N-terminus of the rhizavidin protein a lipidation sequence selected from any of: MKKVAAFVALSLLMAGC (SEQ ID NO: 29); MNSKKLCCICVLFSLLAGCAS (SEQ ID NO: 31), MRYSKLTMLIPCALLLSAC (SEQ ID NO: 32), MFVTSKKMTAAVLAITLAMSLSAC (SEQ ID NO: 33) and MIKRVLVVSMVGLSLVGC (SEQ ID NO: 34).

136) A kit comprising:
   a. a container comprising an immunogenic polysaccharide cross-linked with a plurality of first affinity molecules; and
   b. a container comprising a complementary affinity molecule which associates with the first affinity molecule, wherein the complementary affinity molecule associates with at least one *Mycobacterium tuberculosis* antigen.

137) The kit of paragraph 135, further comprising a container comprising a BCG vaccine.

138) The kit of paragraph 135, further comprising a means to attach the complementary affinity molecule to the antigen.

139) The kit of paragraph 135, further comprising at least one co-stimulation factor.

140) The kit of paragraphs 135 to 138, further comprising a cross-linking reagent which can be selected from the group consisting of: CDAP (1-cyano-4-dimethylaminopyridinium tetrafluoroborate), EDC (1-Ethyl-3-[3-dimethylaminopropyl] carbodiimide hydrochloride), sodium cyanoborohydride, cyanogen bromide, or ammonium bicarbonate/iodoacetic acid for linking the co-factor to the polysaccharide.

141) The kit of paragraph 135, optionally comprising a container comprising an expression vector for expressing an antigen-affinity molecule fusion protein.

142) The kit of paragraph 140, wherein the expression vector can optionally comprise a sequence for a linker peptide, wherein the expression vector can express an antigen-affinity molecule fusion protein comprising a linker peptide between the antigen and the affinity molecule.

143) The kit of paragraph 135, wherein the antigen-affinity molecule fusion protein is any of those selected from paragraphs 1 to 64.

144) A kit comprising:
   a. a container comprising an immunogenic composition of any of paragraphs 1-6464; and polysaccharide cross-linked with a plurality of first affinity molecules; and
   b. a container comprising a BCG vaccine.

EXAMPLES

The main goal of the work presented herein is to optimize and test in a relevant animal model a combined multivalent vaccine against *Mycobacterium tuberculosis* (Mtb), a pathogen that is associated with significant morbidity and mortality, especially in developing world settings.

Materials and Methods

Bacterial strains and culturing conditions: Mtb strain H37Rv was used for all mouse related experiments. For the mouse aerosolized infection inoculum, cells were cultured in Middlebrook 7H9 containing 0.2% (v/v) glycerol, 15 mM NaCl, 0.05% (v/v) tween 80, and 10% (v/v) OADC supplement) (Fischer Scientific, Waltham, MA) and maintained at 37° C.; with shaking at 100 rpm until log-phase growth. Cells were sonicated and diluted in PBS to desired concentration. Mtb H37Rv lysate (NR-14822, BEI Resources; 10 mg/ml stock) was used in whole blood T cell response assays. *E. coli* strain DH5-α was used for Mtb antigen cloning, and *E. coli* BL21 (DE3) or T7 shuffle express strains were used for Mtb protein expression (NEB, Cambridge, MA).

Cloning and purification of Mtb antigens and lipidated rhizavidin. DNA sequences encoding ESAT6, CFP10 (fragment 1-41 and fragment 45-80), TB9.8, TB10.4, MPT64 (25-228), MPT83 (58-220), MPT51 (33-299), PPE41 and PE25 were amplified from Mtb genomic DNA (H37Rv) by conventional PCR methods. Fusion constructs of ESAT6/CFP10, TB9.8/TB10.4 and PPE41/PE25 were prepared as shown in Table 1. For rhizavidin (rhavi) fusion proteins, 8 constructs, each of which contained up to 3 Mtb proteins, were prepared by inserting Mtb DNA sequence(s) at the 3' end of the rhavi gene. Lipidated rhavi was constructed by adding a lipidation box at the 5' end of the rhavi gene as described previously (Zhang et al. PNAS 2012). All DNA constructs were cloned into a pET21b vector (NEB) and transformed into *E. coli* BL21 (DE3) cells (for all Mtb proteins and lipidated rhavi) or T7 shuffle express cells (for rhavi-Mtb fusion proteins) for IPTG-induced expression. After expression, bacteria were pelleted, resuspended in 20 mM Tris buffer, pH 8.0, 500 mM NaCl (containing proteinase inhibitor, DNAse and 10 mM $MgCl_2$), and lysed by sonication. For lipidated rhavi, 0.5% sodium deoxycholate was used in the lysis buffer. His-tagged recombinant proteins were then purified from the supernatant of bacterial lysate after centrifugation, using a combination of affinity and size-exclusion chromatography. Purified proteins were stored at −80° C. till ready for use.

Preparation of MAPS Complex. Type 1 pneumococcal capsular polysaccharide (CPS1) was purchased from ATCC. Biotinylation of CPS1 was achieved using 1-cyano-4-dimethylaminopyridinium tetrafluoroborate (CDAP) as the activation reagent. The MAPS complex was assembled by incubation of biotinylated CPS1 with lipidated rhavi or individual Mtb rhavi fusion antigen at room temperature overnight. The input ratio of protein to polysaccharide was 3:1 (w/w). The assembled complex was isolated by size-exclusion chromatography. The fractions containing the MAPS complex were pooled and concentrated by ultrafiltration. The protein concentration in each MAPS complex was measured using a bicinchoninic acid (BCA) protein assay kit (Pierce). The incorporation of target antigens onto CPS1 was examined on a reduced SDS-PAGE gel.

Mouse immunization and infection. Six week-old C57BL/6J female mice were purchased from Jackson Laboratories (Bar Harbour, ME) and housed at a Harvard Center for Comparative Medicine (HCCM) facility under specific pathogen free (SPF) ABSL2 conditions for immunizations, and in an ABSL3 facility for Mtb infections. All mouse experiments were performed under Harvard Medical Area (HMA) IACUC approved animal use and care protocol 03000. MAPS vaccines were prepared one day prior to immunization. MAPS complexes containing different Mtb antigens were mixed at equal weight ratio, diluted to the appropriate concentration in saline, and then mixed with aluminum hydroxide (Brenntag) (1.25 mg/ml final concentration) for incubation at 4° C. overnight with rotation. BCG TICE (Merck) was purchased from the Boston Children's Hospital pharmacy and diluted to $1\times10^5$ CFU in 200 μl with saline just before immunization. Mice received subcutaneous immunizations with 200 μl of saline, BCG, aluminum hydroxide control, or MAPS vaccine as indicated, two weeks apart. For co-immunization with BCG and MAPS at the same time, each vaccine was administered separately on opposite flank of mice. Animals were bled retro-orbitally two weeks after the last immunization for analysis of antibody and T-cell responses.

Twelve days after bled, mice were infected with aerosolized Mtb at a concentration of $1\times10^6$ CFU/ml to achieve an estimated infection dose of ~100 CFU/mouse. Five age-matched naïve C57BL/6J mice housed with the immunized mice were included in the same infection experiment to enumerate bacterial deposition in the lung 24 hours after infection. To enumerate CFU in lungs and spleens of animals, organs were harvested in PBS and homogenized using a stomacher homogenizer under BSL3 conditions. 10-fold serial dilutions of homogenates in PBS were plated on 7H10 plates supplemented with OADC and cyclohexamide, and incubated at 37° C.; for three weeks. On average, 75-80 CFU of Mtb were recovered from the lungs of naïve mice 24 hours after infection. One month after infection, immunized mice were sacrificed by isofluorane overdose, lungs and spleens were harvested, plated and CFU's were enumerated three weeks later.

Antibody and cytokine analysis. Antigen-specific IgG antibody was measured by ELISA. Immulon 2 HB 96-microwell plates (Thermo Scientific) were coated with 1 μg/ml of individual recombinant Mtb protein (without Rhavi protein) in PBS at room temperature overnight. The plates were washed with PBS containing 0.05% Tween 20 (PBS-T) and then blocked with 1% BSA in PBS for 1 hour. After blocking, 3-fold serial dilutions of mouse sera were added and incubated for 2 hours, followed by 1 hour incubation with HRP-conjugated secondary antibody against mouse IgG. The plates were then washed and developed with SureBlue TMB Microwell Peroxidase Substrate (KPL). 1 M HCl was used to terminate the reactions before the plate was analyzed at A450 using an ELISA reader. Antibody titers were analyzed using Softmax Pro, version 5.3 (Molecular Devices), and expressed in arbitrary units relative to a standard serum.

For analysis of T-cell responses, 25 μl of heparinized blood from immunized animals were added to 225 μl DMEM (BioWhittaker) containing 10% low-endotoxin defined FBS (Hyclone), 50 μM 2-mercaptoethanol (Sigma) and ciprofloxacin (10 μg/ml, Cellgro) in sterile 96-well round-bottomed tissue culture plates (Thermo Scientific). The cultures were incubated at 37° C. for 6 days in the presence of a mixture of recombinant Mtb antigens (equal weight ratio, without Rhavi protein), or a Mtb lysate at indicated concentration. Supernatants were collected following centrifugation, and IFN-γ and IL-17A concentrations were determined by ELISA as per instructions of mouse IL-17A or IFN-γ ELISA kits (R&D Systems). ELISA plates were read at A450 using a spectrophotometer, and analyzed using Softmax Pro, version 5.3 (Molecular Devices).

Statistical analysis. All statistical analyses were done using PRISM (version 5.01 for Windows, GraphPad Software, Inc). Antibody titer, cytokine production, CFU in lungs and in spleens were compared between groups using the Mann-Whitney U test.

The current vaccine against TB, Bacille Calmette-Guerin (BCG), has an excellent safety track record (given to over 4 billion individuals) but offers little protection against adult pulmonary TB. Its main efficacy lies in the prevention of severe disseminated disease in infancy, and to a lesser extent, pulmonary disease at that age. BCG-induced protection is short-lived; at the same time, studies do not support any role for revaccination in adolescence or adulthood. Importantly, the underlying immunological mechanisms whereby BCG protects infants are not well understood, a major limitation that affects the prospects for improving BCG-based vaccine strategies. Despite this, most countries in TB endemic areas have universal immunization programs that include BCG vaccination at birth. Therefore, its replacement with another vaccine may represent a difficult hurdle. And, indeed, of the 9 vaccine candidates that are currently undergoing clinical trials in non-HIV infected individuals, all are subunit vaccines based on the premise of vaccination with BCG.

The two most commonly proposed strategies are based either on boosting the response elicited by BCG vaccination (by re-exposure to antigens that are included in BCG, such as antigens 85A and B) or generating additional immunity to novel antigens (such as ESAT6 or TB10.4, not present in BCG). Since CD4+ T cells and associated cytokines (INFγ and IL-17A) represent major mechanisms of protection against TB, priming effective T cell responses is a goal of novel TB vaccines. Adjuvants that promote Th1 or Th17 responses to protein antigens are being actively studied, but raise the specter of unacceptable side effects, particularly in children. An alternative approach that is being considered is to design recombinant BCG candidates; but this strategy may not offer significant advantages over BCG in humans.

In many cases, the presence of antibodies in serum can be correlated with resistance to infection against a bacterial pathogen, as in the case of Hepatitis B, meningococcus, pneumococcus among others. In contrast, it has been very difficult to use serologic information to predict susceptibility or resistance to Mtb. Numerous attempts were made in the early $20^{th}$ century to use serum therapy to treat TB, with very inconsistent results. Following these studies, several investigations provided circumstantial evidence for a role of humoral immunity in the defense against tuberculosis. Monoclonal antibodies directed against saccharides (such as arabinomannan (AM), lipoarabinomannan (LAM) and alpha-glucan (AG)) improve long-term survival following intravenous injection of Mtb in mice; furthermore, an AM-containing saccharide:protein conjugate vaccine elicited antibodies and protection against infection. Administration of Mtb coated with monoclonal antibodies specific for Heparin-binding Hemagglutinin Adhesin (HBHA) to mice reduced dissemination. There are also epidemiologic, circumstantial clues to suggest a role of antibodies in protecting against TB, such as a peak of childhood disease coinciding with the nadir of passively transferred maternal antibody, a reduced B-cell count in individuals with pulmonary TB when compared to latently infected individuals or persons without evidence of TB exposure, and the association between a lack of antibodies against specific Mtb antigens and risk of TB dissemination in adults and children. New data has renewed interest in evaluating a possible role of B cells and antibodies in protection against TB. In one study, antibodies from individuals with latent TB disease were significantly more potent at inhibiting Mtb growth, promoting inflammasome activation, phagolysosomal fusion and killing by macrophages than sera from patients with active disease. These data do not imply causality and could certainly be confounded by immunological differences between latent carriers and diseased individuals. Without wishing to be bound by theory, it is proposed that any contribution of B-cells may be indirect, by enhancing T-cell mediated protection against TB. The role of B-cells and antibodies in mediating resistance or protection against TB remains to be more clearly defined, there is clearly renewed interest in evaluating whether the inclusion of Mtb antigen-specific antibody responses in a vaccine strategy may augment protection conferred by T-cell responses alone.

A combined TB vaccine using the Multiple Antigen Presenting System (MAPS) vaccine technology. The inventors have developed MAPS, a platform technology for the generation of "conjugate-like" vaccines that can also elicit multipronged B- and CD4+ T-cell (Th1 and Th17) responses to target antigens. The work describing this technology has been published and applied to many organisms. MAPS uses purified polysaccharides (PS) and proteins as components that are associated by affinity interactions. Distinct from other subunit approaches, in the MAPS system, the isolated antigen components are specifically reassembled into an integrated macromolecular complex, based on the findings that, by mimicking chemical and physical features of a whole-cell construct, such a complex leads to the activation of comprehensive B- and T-cell immune responses and thus provides multipronged protection that is characteristic of whole-cell vaccines and not observed with typical protein-based subunit vaccines or chemically-conjugated PS vaccines. MAPS are used to build vaccines to elicit not only strong antibody but also CD4+ T cell responses (Th1 and Th17) to many antigens at the same time, requiring only aluminum hydroxide as adjuvant. The MAPS technology enables the inclusion of multiple antigens, potentially targeting various pathogens. This can be done in a modular fashion, allowing for optimization of the vaccine, as the role of individual components can easily be evaluated by addition or subtraction.

As described herein, the inventors' work has demonstrated that a TB-MAPS vaccine administered to mice can provide significant protection against pulmonary TB challenge, equivalent to what can be observed with the BCG vaccine. When BCG and TB-MAPS are administered substantially simultaneously to mice at separate sites, followed by two more immunizations with TB-MAPS, there is additional, significant protection against pulmonary challenge compared to BCG vaccination or TB-MAPS alone.

In the work described herein, different TB MAPS formulations were evaluated for their capacity to elicit antibody and/or Th1 and Th17 responses to included TB proteins. The ability of TB-MAPS vs. the BCG vaccine alone to generate protective immunity against pulmonary TB and splenic dissemination were assessed. We observed that the addition of lipidated rhizavidin enhanced immunogenicity of the TB-MAPS constructs. The inventors noted that surprisingly, BCG drove away from Th17 responses that are generally observed with TB-MAPS and that this inhibitory effect could be abrogated by co-administration (at different sites) of the BCG vaccine and the first dose of TB-MAPS. Finally, a strategy of combining the BCG vaccine with TB-MAPS (with an initial co-administration at different sites followed by TB-MAPS alone) is significantly superior to the BCG vaccine or TB-MAPS alone in conferring protection against pulmonary TB and dissemination.

These results are striking in that the 2 log reduction of pulmonary colony counts in the mouse model of tuberculosis is generally considered excellent; most strategies (as evidenced by the BCG vaccine) are associated with a 1 log reduction. These findings lead to a very important translational implication: since most children in the developing world are already receiving the BCG vaccine at birth, any strategy that DOES NOT include the BCG vaccine would be difficult to implement and possibly even unethical, given the reported efficacy of the BCG vaccine at birth in preventing dissemination. Thus, the approach described herein of co-administering TB-MAPS and BCG may offer a very practical solution to this problem, by allowing for a straight forward evaluation of the strategy. A clinical trial comparing the BCG vaccine alone to the BCG vaccine in conjunction with TB-MAPS (at different sites) followed by TB-MAPS doses. It should also be noted that TB-MAPS4 or TB-MAPS5 provides significant protection alone, so that a strategy of TB-MAPS alone could also be entertained. In conclusion, the inventors show herein that the MAPS technology can be applied to TB, for the creation of highly immunogenic and protective vaccines, either alone or in combination with the BCG vaccine.

The references cited in the specification and Examples are incorporated herein in their entirety.

The invention claimed is:

1. An immunogenic composition comprising an immunogenic complex, the immunogenic complex comprising:
   at least two biotinylated polysaccharide antigens,
   a lipidated biotin-binding protein; and
   a first fusion protein comprising:
   (i) a biotin-binding moiety and
   (ii) at least a MPT51 peptide antigen
   wherein at least the one of the biotinylated polysaccharide is non-covalently associated with the lipidated biotin-binding protein and at least one of the biotinylated polysaccharides is non-covalently associated with the biotin-binding moiety of the fusion protein.

2. The immunogenic composition of claim 1, wherein the immunogenic complex can further comprise a second fusion protein, the second fusion protein comprising:
   (i) a biotin-binding moiety;
   (ii) at least a first *Mycobacterium tuberculosis* (Mtb) peptide antigen; and
   (iii) at least a second *Mycobacterium tuberculosis* (Mtb) peptide antigen
   wherein the at least first Mtb peptide antigen is selected from any of the group comprising: ESAT6, CFP10, MPT64, MPT83, TB9.8, TB10.4, PPE41, and PE25 and wherein the at least second Mtb peptide antigen is selected from any of the group comprising: ESAT6, CFP10, MPT64, MPT83, TB9.8, TB10.4, PPE41, and PE25.

3. The immunogenic composition of claim 2, wherein the second fusion protein comprising the at least two Mtb peptide antigens comprises any of:
   (i) an MPT51 antigen, fused to one or more Mtb peptide antigens selected from any of: ESAT6, CFP10, MPT64, MPT83, TB9.8, TB10.4, PPE41 and PE25;
   (ii) an ESAT6 antigen, fused to one or more Mtb peptide antigens selected from any of: CFP10, MPT51, M64, MPT83, TB9.8, TB10.4, PPE41 and PE25;
   (iii) a CFP10 antigen, fused to one or more Mtb peptide antigens selected from any of: MPT51, MPT64, MPT83, TB9.8, TB10.4, PPE41 and PE25;
   (iv) a MPT64 antigen, fused to one or more Mtb peptide antigens selected from any of: MPT51, ESAT6, CFP10, MPT64, MPT83, TB9.8, TB10.4, PPE41 and PE25
   (v) an MPT84 antigen, fused to one or more Mtb peptide antigens selected from any of: ESAT6, CFP10, MPT51, MPT64, MPT83, TB9.8, TB10.4, PPE41 and PE25
   (vi) a TB9.8 antigen, fused to one or more Mtb peptide antigens selected from any of: ESAT6, CFP10, MPT51, MPT64, MPT83, TB10.4, PPE41 and PE25;
   (vii) a TB10.4 antigen, fused to one or more Mtb peptide antigens selected from any of: ESAT6, CFP10, MPT51, MPT64, MPT83, TB9.8, PPE41 and PE25;
   (viii) a PEE41 antigen, fused to one or more Mtb peptide antigens selected from any of: ESAT6, CFP10, MPT51, MPT64, MPT83, TB9.8, TB10.4 and PE25; or
   (ix) a PE25 antigen, fused to one or more Mtb peptide antigens selected from any of: ESAT6, CFP10, MPT51, MPT64, MPT83, TB9.8, TB10.4 and PEE41.

4. The immunogenic composition of claim 3, wherein the second fusion protein comprises any one of the following:
(i) an ESAT6 antigen fused to at least one fragment of CFP10 antigen,
(ii) an ESAT6 antigen fused to two fragments of CFP10 antigens,
(iii) a TB9.8 antigen fused to a TB10.4 antigen,
(iv) a PPE41 antigen fused to PE25 antigen;
(v) MPT51 antigen, and an ESAT6 antigen, a CFP10 antigen, a MPT64 antigen, a MPT83, a TB9.8 antigen and a TB10.4 antigen
(vi) an ESAT6 antigen fused to at least one fragment of CFP10 antigen and a MPT64 antigen; and
(vii) a TB9.8 antigen fused to a TB10.4 antigen and a MPT86 antigen.

5. The immunogenic composition of claim 2, wherein the second fusion protein comprises at least three Mtb peptide antigens selected from:
(i) ESAT6, CFP10 and MPT64,
(ii) a ESAT6 antigen, at least two CFP10 antigens and at least a MPT64 antigen,
(iii) TB9.8, TB10.4 and MPT83.

6. The immunogenic composition of claim 2, wherein the second fusion protein comprising at least two Mtb peptide antigens can comprise at least one linker peptide between each antigen.

7. The immunogenic composition of claim 2, wherein the first or second Mtb peptide antigen is selected from any of:
(i) a MPT51 antigen comprises at least SEQ ID NO: 3 or a polypeptide with at least 85% sequence identity to SEQ ID NO: 3;
(ii) a MPT51 antigen that comprises a fragment of at least 30 amino acids of SEQ ID NO: 3 or a polypeptide of at least 30 amino acids that has at least 85% sequence identity to a portion of SEQ ID NO: 3;
(iii) an ESAT6 antigen that comprises at least SEQ ID NO: 5 or a polypeptide with at least 85% sequence identity to SEQ ID NO: 4
(iv) an ESAT6 antigen that comprises a fragment of at least 30 amino acids of SEQ ID NO: 5 or a polypeptide of at least 30 amino acids that has at least 85% sequence identity to a portion of SEQ ID NO:5;
(v) a CFP10 antigen that comprises at least SEQ ID NO: 6 or SEQ ID NO: 7 or at least or a polypeptide with at least 85% sequence identity to SEQ ID NO: 6 or SEQ ID NO: 7;
(vi) a CFP10 antigen that comprises a fragment of at least 30 amino acids of SEQ ID NO:6 or SEQ ID NO: 7 or a polypeptide of at least 30 amino acids that has at least 85% sequence identity to a portion of SEQ ID NO: 6 or SEQ ID NO: 7;
(vii) a MPT64 antigen that comprises at least SEQ ID NO: 9 or a polypeptide with at least 85% sequence identity to SEQ ID NO: 9;
(viii) a MPT64 antigen that comprises a fragment of at least 30 amino acids of SEQ ID NO:9 or a polypeptide of at least 30 amino acids that has at least 85% sequence identity to a portion of SEQ ID NO: 9;
(ix) a MPT83 antigen that comprises at least SEQ ID NO: 11 or a polypeptide with at least 85% sequence identity to SEQ ID NO: 11;
(x) a MPT83 antigen that comprises a fragment of at least 30 amino acids of SEQ ID NO: 11 or a polypeptide of at least 30 amino acids that has at least 85% sequence identity to a portion of SEQ ID NO: 11;
(xi) a TB9.8 antigen that comprises at least SEQ ID NO: 13 or a polypeptide with at least 85% sequence identity to SEQ ID NO: 13;
(xii) a TB9.8 antigen that comprises a fragment of at least 30 amino acids of SEQ ID NO: 13 or a polypeptide of at least 30 amino acids that has at least 85% sequence identity to a portion of SEQ ID NO: 13;
(xiii) a TB10.4 antigen that comprises at least SEQ ID NO: 14 or a polypeptide with at least 85% sequence identity to a portion of SEQ ID NO: 14;
(xiv) a TB10.4 antigen that comprises a fragment of at least 30 amino acids of SEQ ID NO: 14 or a polypeptide of at least 30 amino acids that has at least 85% sequence identity to a portion of SEQ ID NO: 14;
(xv) a PPE41 antigen that comprises at least SEQ ID NO: 15 or a polypeptide with at least 85% sequence identity a portion of SEQ ID NO: 15;
(xvi) a PPE41 antigen that comprises a fragment of at least 30 amino acids of SEQ ID NO: 15 or a polypeptide of at least 30 amino acids that has at least 85% sequence identity to a portion of SEQ ID NO: 15;
(xvii) a PE25 antigen that comprises at least SEQ ID NO: 16 or a polypeptide with at least 85% sequence identity a portion of SEQ ID NO: 15; or
(xviii) a PE25 antigen that comprises a fragment of at least 30 amino acids of SEQ ID NO: 16 or a polypeptide of at least 30 amino acids that has at least 85% sequence identity to a portion of SEQ ID NO: 16.

8. The immunogenic composition of claim 1, wherein the biotin-binding protein of the fusion protein is selected from: an avidin-like protein or lipidated biotin-binding protein, or a lipidated avidin-like protein.

9. The immunogenic composition of claim 8, wherein the avidin-like protein or lipidated avidin-like protein is selected from the group consisting of: rhizavidin, avidin, streptavidin, or a homologue or derivative thereof.

10. The immunogenic composition of claim 8, wherein the rhizavidin protein is selected from any of:
(i) a rhizavidin protein that comprises amino acids of SEQ ID NO: 1, or a peptide or protein having 85% sequence identity to amino acids of SEQ ID NO: 1 or,
(ii) a rhizavidin protein that is a lipidated rhizavidin protein comprising amino acids of SEQ ID NO: 1, or is a lipidated rhizavidin protein having 85% sequence identity to amino acids of SEQ ID NO: 1; or,
(iii) a lipidated rhizavidin protein comprising amino acids of SEQ ID NO: 1, or the lipidated rhizavidin protein having 85% sequence identity to amino acids of SEQ ID NO: 1 comprises at the N-terminus of the rhizavidin protein a lipidation sequence selected from any of: MKKVAAFVALSLLMAGC (SEQ ID NO: 29); MNSKKLCCICVLFSLLAGCAS (SEQ ID NO: 31), MRYSKLTMLIPCALLLSAC (SEQ ID NO: 32), MFVTSKKMTAAVLAITLAMSLSAC (SEQ ID NO: 33) and MIKRVLVVSMVGLSLVGC (SEQ ID NO: 34).

11. The immunogenic composition of claim 1, wherein the immunogenic polysaccharide is selected from any of:
(i) an immunogenic polysaccharide purified from a living organism selected from the group consisting of: bacteria, archaea, eukaryotic cells, fungi, insects, plants, animals, or chimeras thereof;
(ii) a synthetic immunogenic polysaccharide;
(iii) a *Mycobacterium tuberculosis* polysaccharide, a *Staphylococcus aureus* polysaccharide, a Vi polysaccharide, a pneumococcal capsular polysaccharide, a pneumococcal cell wall polysaccharide, a *Haemophilus*

*influenzae* Type b polysaccharide, a Meningococcal polysaccharides, an O-antigen from Gram-negative bacteria and other bacterial capsular or cell wall polysaccharide;

(iv) a *Mycobacterium tuberculosis* polysaccharide;

(v) a pneumococcal polysaccharide;

(vi) a type 1 capsular polysaccharide from *Streptococcus pneumoniae;*

(vii) a type 5 capsular polysaccharide from *S. aureus*; or (viii) a type 8 capsular polysaccharide from *S. aureus.*

12. The immunogenic composition of claim 1, further comprising at least one co-stimulation factor associated to the immunogenic polysaccharide, wherein the co-stimulation factor is selected from the group consisting of: Toll like receptor ligand or agonists, NOD ligand or agonists, or activator/agonists of the inflammasome.

13. A method of inducing an immune response in a subject against *Mycobacterium tuberculosis*, the method comprising administering a TB-MAPS immune composition to the subject, wherein the TB-MAPS immune composition is defined according to claim 1.

14. The method of claim 13, the method comprising administering at a first time point, the composition comprising a TB-MAPS immune composition to the subject at a first site and further comprising administering a composition comprising a Bacille Calmette-Guerin (BCG) vaccine at a second site.

15. The method of claim 13, further comprising administering at a second time point the composition comprising the TB-MAPS immune composition and optionally, further comprising administering at a third time point the composition comprising the TB-MAPS immune composition.

16. The method of claim 14, wherein the composition comprising the TB-MAPS immune composition and the composition comprising the BCG vaccine are administered at the substantially the same time or within 24 hours.

17. The method of claim 13, wherein the subject is a human or an agricultural or non-domestic animal.

18. The method of claim 13, wherein the immune response is selected from any one or more of:

(i) an antibody or B-cell response;

(ii) an antibody or B-cell response and T-cell response;

(iii) an immune response to at least one peptide or polypeptide *M. tuberculosis* antigen;

(iv) a CD4+ T cell response, including Th1, Th2 or Th17 response, or a CD8+ T cell response, or CD4+ and CD8+ T cell response;

(v) an antibody or B cell response to at least one antigenic polysaccharide and a CD4+ T cell response, including Th1, Th2 or Th17 response, or a CD8+ T cell response, or CD4+/CD8+ T cell response to at least one peptide or polypeptide antigen;

(vi) an antibody or B cell response to at least one antigenic polysaccharide, and an antibody or B cell response and a CD4+ T cell response, including Th1, Th2 or Th17 response, or a CD8+ T cell response, or CD4+/CD8+ T cell response to at least one peptide or polypeptide antigen;

(vii) an immune response that results in activation of IL-17A and INF-γ producing cells, or IL-17A producing cells;

(viii) an antibody or B-cell response against the *M. tuberculosis* antigen which associates with the immunogenic polysaccharide.

19. A fusion protein comprising a Rhizavidin protein and at least one *Mycobacterium tuberculosis* (Mtb) peptide antigen, wherein the Mtb antigen is MPT51, wherein MPT51 comprises the amino acid sequence of SEQ ID NO: 3, or a peptide that has at least 85% sequence identity to SEO ID NO: 3.

20. The fusion protein of claim 19 selected from any of:

(i) a fusion protein comprising a Rhizavidin protein, a MPT51 antigen and at least one additional *Mycobacterium tuberculosis* antigen, wherein the *Mycobacterium tuberculosis* antigen is selected from a group consisting of: ESAT6, CFP10 (1-40), CFP10 (45-80), CFP10 (1-40) and CFP10 (45-80), MPT64, TB9.8, TB10.4, MPT83, PPE41 and PE25;

(ii) a fusion protein comprising a Rhizavidin protein, a MPT51 antigen and at least two additional *Mycobacterium tuberculosis* antigens, wherein the *Mycobacterium tuberculosis* antigens are selected from a group consisting of: ESAT6, CFP10 (1-40), CFP10 (45-80), MPT64, TB9.8, TB10.4, MPT83, PPE41 and PE25.

21. The fusion protein of claim 19, wherein the fusion protein comprises any one or more of *Mycobacterium tuberculosis* antigens selected from:

(i) a MPT51 antigen that comprises at least SEQ ID NO: 3 or a polypeptide with at least 85% sequence identity to SEQ ID NO: 3;

(ii) a MPT51 antigen that comprises a fragment of at least 30 amino acids of SEQ ID NO: 3 or a polypeptide of at least 30 amino acids that has at least 85% sequence identity to a portion of SEQ ID NO: 3;

(iii) a MPT51 antigen that comprises a fragment of at least 30 amino acids of SEQ ID NO: 3 or a polypeptide of at least 30 amino acids that has at least 85% sequence identity to a portion of SEQ ID NO: 3;

(iv) an ESAT6 antigen that comprises at least SEQ ID NO: 5 or a polypeptide with at least 85% sequence identity to SEQ ID NO: 4

(v) an ESAT6 antigen that comprises a fragment of at least 30 amino acids of SEQ ID NO: 5 or a polypeptide of at least 30 amino acids that has at least 85% sequence identity to a portion of SEQ ID NO:5;

(vi) a CFP10 antigen that comprises at least SEQ ID NO: 6 or SEQ ID NO: 7 or at least or a polypeptide with at least 85% sequence identity to SEQ ID NO: 6 or SEQ ID NO: 7;

(vii) a CFP10 antigen that comprises a fragment of at least 30 amino acids of SEQ ID NO:6 or SEQ ID NO: 7 or a polypeptide of at least 30 amino acids that has at least 85% sequence identity to a portion of SEQ ID NO: 6 or SEQ ID NO: 7;

(viii) a MPT64 antigen that comprises at least SEQ ID NO: 9 or a polypeptide with at least 85% sequence identity to SEQ ID NO: 9;

(ix) a MPT64 antigen that comprises a fragment of at least 30 amino acids of SEQ ID NO:9 or a polypeptide of at least 30 amino acids that has at least 85% sequence identity to a portion of SEQ ID NO: 9;

(x) a MPT83 antigen that comprises at least SEQ ID NO: 11 or a polypeptide with at least 85% sequence identity to SEQ ID NO: 11;

(xi) a MPT83 antigen that comprises a fragment of at least 30 amino acids of SEQ ID NO: 11 or a polypeptide of at least 30 amino acids that has at least 85% sequence identity to a portion of SEQ ID NO: 11;

(xii) a TB9.8 antigen that comprises at least SEQ ID NO: 13 or a polypeptide with at least 85% sequence identity to SEQ ID NO: 13;

(xiii) a TB9.8 antigen that comprises a fragment of at least 30 amino acids of SEQ ID NO: 13 or a polypeptide of at least 30 amino acids that has at least 85% sequence identity to a portion of SEQ ID NO: 13;

(xiv) a TB10.4 antigen that comprises at least SEQ ID NO: 14 or a polypeptide with at least 85% sequence identity to a portion of SEQ ID NO: 14;

(xv) a TB10.4 antigen that comprises a fragment of at least 30 amino acids of SEQ ID NO: 14 or a polypeptide of at least 30 amino acids that has at least 85% sequence identity to a portion of SEQ ID NO: 14;

(xvi) a PPE41 antigen that comprises at least SEQ ID NO: 15 or a polypeptide with at least 85% sequence identity a portion of SEQ ID NO: 15;

(xvii) a PPE41 antigen that comprises a fragment of at least 30 amino acids of SEQ ID NO: 15 or a polypeptide of at least 30 amino acids that has at least 85% sequence identity to a portion of SEQ ID NO: 15;

(xviii) a PE25 antigen that comprises at least SEQ ID NO: 16 or a polypeptide with at least 85% sequence identity a portion of SEQ ID NO: 15; or (xix) a PE25 antigen that comprises a fragment of at least 30 amino acids of SEQ ID NO: 16 or a polypeptide of at least 30 amino acids that has at least 85% sequence identity to a portion of SEQ ID NO: 16.

22. The fusion protein of claim 20, wherein the rhizavidin protein is selected from any of:

(i) a rhizavidin protein that comprises amino acids of SEQ ID NO: 1, or a peptide or protein having 85% sequence identity to amino acids of SEQ ID NO: 1, (ii) a rhizavidin protein that is a lipidated rhizavidin protein comprising amino acids of SEQ ID NO: 1, or is a lipidated rhizavidin protein having 85% sequence identity to amino acids of SEQ ID NO: 1; or, (iii) a lipidated rhizavidin protein comprising amino acids of SEQ ID NO: 1, or the lipidated rhizavidin protein having 85% sequence identity to amino acids of SEQ ID NO: 1 comprises at the N-terminus of the rhizavidin protein a lipidation sequence selected from any of: MKKVAAFVALSLLMAGC (SEQ ID NO: 29); MNSKKLCCICVLFSLLAGCAS (SEQ ID NO: 31), MRYSKLTMLIPCALLLSAC (SEQ ID NO: 32), MFVTSKKMTAAVLAITLAMSLSAC (SEQ ID NO: 33) and MIKRVLVVSMVGLSLVGC (SEQ ID NO: 34).

23. The immunogenic composition of claim 11, wherein the *Mycobacterium tuberculosis* polysaccharide is an alpha-glucan, a lipoarabinomannan or an 24 arabinomannan.

24. The immunogenic composition of claim 1, wherein the lipidated biotin-binding protein is a lipidated Rhizavadin protein (Lipo-Rhavi).

25. The immunogenic composition of claim 24, wherein the lipidated Rhizavadin protein (Lipo-Rhavi) comprises amino acids of SEQ ID NO: 1, or is a lipidated rhizavidin protein having 85% sequence identity to amino acids of SEQ ID NO: 1.

26. The immunogenic composition of claim 25, wherein the lipidated Rhizavadin protein (Lipo-Rhavi) comprises amino acids of SEQ ID NO: 29, or a lipidation sequence having 85% sequence identity to amino acids of SEQ ID NO: 29.

27. The immunogenic composition of claim 1, wherein the lipidated biotin-binding moiety is not part of a fusion protein with a peptide or polypeptide antigen.

28. The immunogenic composition of claim 1, wherein the immunogenic complex comprises:

(a) a biotinylated type 1 capsular polysaccharide (CPS) from *Streptococcus pneumoniae;*

(b) a lipidated Rhizavidin protein (Lipo-Rhavi);

(c) a first fusion protein comprising rhizavidin and a MPT51 peptide or fragment thereof, and (d) at least one or more additional fusion protein selected from:

a fusion protein comprising rhizavidin, and at least two antigens selected from: ESAT6, CFP10 and MPT64, or a fusion protein comprising rhizavidin, and at least two antigens selected from: TB9.8, TB10.4 and MPT83.

29. The immunogenic composition of claim 28, wherein the immunogenic complex comprises three fusion proteins selected from:

a fusion protein comprising rhizavidin, and at least two antigens selected from: ESAT6, CFP10 and MPT64, a fusion protein comprising rhizavidin, and at least two antigens selected from: TB9.8, TB10.4 and MPT83, and a fusion protein comprising rhizavidin, and MPT51.

30. The immunogenic composition of claim 29, wherein the immunogenic complex comprises at least one, or both two fusion proteins selected from:

a fusion protein comprising rhizavidin, and a ESAT6 peptide, a CFP10 peptide and a MPT64, and a fusion protein comprising rhizavidin, and a TB9.8 peptide, a TB10.4 peptide and a MPT83 peptide.

* * * * *

SEQUENCE LISTING

<160> NUMBER OF SEQ ID NOS: 54

<210> SEQ ID NO 1
<211> LENGTH: 135
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

```
Phe Asp Ala Ser Asn Phe Lys Asp Phe Ser Ser Ile Ala Ser Ala Ser
1               5                   10                  15

Ser Ser Trp Gln Asn Gln Ser Gly Ser Thr Met Ile Ile Gln Val Asp
            20                  25                  30

Ser Phe Gly Asn Val Ser Gly Gln Tyr Val Asn Arg Ala Gln Gly Thr
        35                  40                  45

Gly Cys Gln Asn Ser Pro Tyr Pro Leu Thr Gly Arg Val Asn Gly Thr
    50                  55                  60

Phe Ile Ala Phe Ser Val Gly Trp Asn Asn Ser Thr Glu Asn Cys Asn
65                  70                  75                  80

Ser Ala Thr Gly Trp Thr Gly Tyr Ala Gln Val Asn Gly Asn Asn Thr
                85                  90                  95

Glu Ile Val Thr Ser Trp Asn Leu Ala Tyr Glu Gly Gly Ser Gly Pro
            100                 105                 110

Ala Ile Glu Gln Gly Gln Asp Thr Phe Gln Tyr Val Pro Thr Thr Glu
        115                 120                 125

Asn Lys Ser Leu Leu Lys Asp
    130                 135
```

<210> SEQ ID NO 2
<211> LENGTH: 179
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

```
Met Ile Ile Thr Ser Leu Tyr Ala Thr Phe Gly Thr Ile Ala Asp Gly
1               5                   10                  15

Arg Arg Thr Ser Gly Gly Lys Thr Met Ile Arg Thr Asn Ala Val Ala
            20                  25                  30

Ala Leu Val Phe Ala Val Ala Thr Ser Ala Leu Ala Phe Asp Ala Ser
        35                  40                  45

Asn Phe Lys Asp Phe Ser Ser Ile Ala Ser Ala Ser Ser Ser Trp Gln
    50                  55                  60

Asn Gln Ser Gly Ser Thr Met Ile Ile Gln Val Asp Ser Phe Gly Asn
65                  70                  75                  80

Val Ser Gly Gln Tyr Val Asn Arg Ala Gln Gly Thr Gly Cys Gln Asn
                85                  90                  95

Ser Pro Tyr Pro Leu Thr Gly Arg Val Asn Gly Thr Phe Ile Ala Phe
            100                 105                 110

Ser Val Gly Trp Asn Asn Ser Thr Glu Asn Cys Asn Ser Ala Thr Gly
        115                 120                 125

Trp Thr Gly Tyr Ala Gln Val Asn Gly Asn Asn Thr Glu Ile Val Thr
    130                 135                 140

Ser Trp Asn Leu Ala Tyr Glu Gly Gly Ser Gly Pro Ala Ile Glu Gln
```

145 150 155 160

Gly Gln Asp Thr Phe Gln Tyr Val Pro Thr Thr Glu Asn Lys Ser Leu
165 170 175

Leu Lys Asp

<210> SEQ ID NO 3
<211> LENGTH: 267
<212> TYPE: PRT
<213> ORGANISM: Mycobacterium tuberculosis

<400> SEQUENCE: 3

Ala Ala Pro Tyr Glu Asn Leu Met Val Pro Ser Pro Ser Met Gly Arg
1 5 10 15

Asp Ile Pro Val Ala Phe Leu Ala Gly Gly Pro His Ala Val Tyr Leu
20 25 30

Leu Asp Ala Phe Asn Ala Gly Pro Asp Val Ser Asn Trp Val Thr Ala
35 40 45

Gly Asn Ala Met Asn Thr Leu Ala Gly Lys Gly Ile Ser Val Val Ala
50 55 60

Pro Ala Gly Gly Ala Tyr Ser Met Tyr Thr Asn Trp Glu Gln Asp Gly
65 70 75 80

Ser Lys Gln Trp Asp Thr Phe Leu Ser Ala Glu Leu Pro Asp Trp Leu
85 90 95

Ala Ala Asn Arg Gly Leu Ala Pro Gly Gly His Ala Ala Val Gly Ala
100 105 110

Ala Gln Gly Gly Tyr Gly Ala Met Ala Leu Ala Ala Phe His Pro Asp
115 120 125

Arg Phe Gly Phe Ala Gly Ser Met Ser Gly Phe Leu Tyr Pro Ser Asn
130 135 140

Thr Thr Thr Asn Gly Ala Ile Ala Ala Gly Met Gln Gln Phe Gly Gly
145 150 155 160

Val Asp Thr Asn Gly Met Trp Gly Ala Pro Gln Leu Gly Arg Trp Lys
165 170 175

Trp His Asp Pro Trp Val His Ala Ser Leu Leu Ala Gln Asn Asn Thr
180 185 190

Arg Val Trp Val Trp Ser Pro Thr Asn Pro Gly Ala Ser Asp Pro Ala
195 200 205

Ala Met Ile Gly Gln Ala Ala Glu Ala Met Gly Asn Ser Arg Met Phe
210 215 220

Tyr Asn Gln Tyr Arg Ser Val Gly Gly His Asn Gly His Phe Asp Phe
225 230 235 240

Pro Ala Ser Gly Asp Asn Gly Trp Gly Ser Trp Ala Pro Gln Leu Gly
245 250 255

Ala Met Ser Gly Asp Ile Val Gly Ala Ile Arg
260 265

<210> SEQ ID NO 4
<211> LENGTH: 299
<212> TYPE: PRT
<213> ORGANISM: Mycobacterium tuberculosis

<400> SEQUENCE: 4

Met Lys Gly Arg Ser Ala Leu Leu Arg Ala Leu Trp Ile Ala Ala Leu
1 5 10 15

Ser Phe Gly Leu Gly Gly Val Ala Val Ala Ala Glu Pro Thr Ala Lys
20 25 30

```
Ala Ala Pro Tyr Glu Asn Leu Met Val Pro Ser Pro Ser Met Gly Arg
        35                  40                  45

Asp Ile Pro Val Ala Phe Leu Ala Gly Gly Pro His Ala Val Tyr Leu
    50                  55                  60

Leu Asp Ala Phe Asn Ala Gly Pro Asp Val Ser Asn Trp Val Thr Ala
65                  70                  75                  80

Gly Asn Ala Met Asn Thr Leu Ala Gly Lys Gly Ile Ser Val Val Ala
                85                  90                  95

Pro Ala Gly Gly Ala Tyr Ser Met Tyr Thr Asn Trp Glu Gln Asp Gly
            100                 105                 110

Ser Lys Gln Trp Asp Thr Phe Leu Ser Ala Glu Leu Pro Asp Trp Leu
        115                 120                 125

Ala Ala Asn Arg Gly Leu Ala Pro Gly Gly His Ala Ala Val Gly Ala
    130                 135                 140

Ala Gln Gly Gly Tyr Gly Ala Met Ala Leu Ala Ala Phe His Pro Asp
145                 150                 155                 160

Arg Phe Gly Phe Ala Gly Ser Met Ser Gly Phe Leu Tyr Pro Ser Asn
                165                 170                 175

Thr Thr Thr Asn Gly Ala Ile Ala Ala Gly Met Gln Gln Phe Gly Gly
            180                 185                 190

Val Asp Thr Asn Gly Met Trp Gly Ala Pro Gln Leu Gly Arg Trp Lys
        195                 200                 205

Trp His Asp Pro Trp Val His Ala Ser Leu Leu Ala Gln Asn Asn Thr
    210                 215                 220

Arg Val Trp Val Trp Ser Pro Thr Asn Pro Gly Ala Ser Asp Pro Ala
225                 230                 235                 240

Ala Met Ile Gly Gln Ala Ala Glu Ala Met Gly Asn Ser Arg Met Phe
                245                 250                 255

Tyr Asn Gln Tyr Arg Ser Val Gly Gly His Asn Gly His Phe Asp Phe
            260                 265                 270

Pro Ala Ser Gly Asp Asn Gly Trp Gly Ser Trp Ala Pro Gln Leu Gly
        275                 280                 285

Ala Met Ser Gly Asp Ile Val Gly Ala Ile Arg
    290                 295


<210> SEQ ID NO 5
<211> LENGTH: 95
<212> TYPE: PRT
<213> ORGANISM: Mycobacterium tuberculosis

<400> SEQUENCE: 5

Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr Gln Gly Val Gln Gln Lys Trp Asp Ala Thr Ala Thr Glu
    50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala
                85                  90                  95
```

<210> SEQ ID NO 6
<211> LENGTH: 41
<212> TYPE: PRT
<213> ORGANISM: Mycobacterium tuberculosis

<400> SEQUENCE: 6

```
Met Ala Glu Met Lys Thr Asp Ala Ala Thr Leu Ala Gln Glu Ala Gly
1               5                   10                  15

Asn Phe Glu Arg Ile Ser Gly Asp Leu Lys Thr Gln Ile Asp Gln Val
            20                  25                  30

Glu Ser Thr Ala Gly Ser Leu Gln Gly
        35                  40
```

<210> SEQ ID NO 7
<211> LENGTH: 36
<212> TYPE: PRT
<213> ORGANISM: Mycobacterium tuberculosis

<400> SEQUENCE: 7

```
Gly Ala Ala Gly Thr Ala Ala Gln Ala Ala Val Val Arg Phe Gln Glu
1               5                   10                  15

Ala Ala Asn Lys Gln Lys Gln Glu Leu Asp Glu Ile Ser Thr Asn Ile
            20                  25                  30

Arg Gln Ala Gly
        35
```

<210> SEQ ID NO 8
<211> LENGTH: 100
<212> TYPE: PRT
<213> ORGANISM: Mycobacterium tuberculosis

<400> SEQUENCE: 8

```
Met Ala Glu Met Lys Thr Asp Ala Ala Thr Leu Ala Gln Glu Ala Gly
1               5                   10                  15

Asn Phe Glu Arg Ile Ser Gly Asp Leu Lys Thr Gln Ile Asp Gln Val
            20                  25                  30

Glu Ser Thr Ala Gly Ser Leu Gln Gly Gln Trp Arg Gly Ala Ala Gly
        35                  40                  45

Thr Ala Ala Gln Ala Ala Val Val Arg Phe Gln Glu Ala Ala Asn Lys
    50                  55                  60

Gln Lys Gln Glu Leu Asp Glu Ile Ser Thr Asn Ile Arg Gln Ala Gly
65                  70                  75                  80

Val Gln Tyr Ser Arg Ala Asp Glu Glu Gln Gln Gln Ala Leu Ser Ser
                85                  90                  95

Gln Met Gly Phe
            100
```

<210> SEQ ID NO 9
<211> LENGTH: 204
<212> TYPE: PRT
<213> ORGANISM: Mycobacterium tuberculosis

<400> SEQUENCE: 9

```
Pro Lys Thr Tyr Cys Glu Glu Leu Lys Gly Thr Asp Thr Gly Gln Ala
1               5                   10                  15

Cys Gln Ile Gln Met Ser Asp Pro Ala Tyr Asn Ile Asn Ile Ser Leu
            20                  25                  30

Pro Ser Tyr Tyr Pro Asp Gln Lys Ser Leu Glu Asn Tyr Ile Ala Gln
        35                  40                  45
```

-continued

```
Thr Arg Asp Lys Phe Leu Ser Ala Ala Thr Ser Ser Thr Pro Arg Glu
    50                  55                  60

Ala Pro Tyr Glu Leu Asn Ile Thr Ser Ala Thr Tyr Gln Ser Ala Ile
65                  70                  75                  80

Pro Pro Arg Gly Thr Gln Ala Val Val Leu Lys Val Tyr Gln Asn Ala
                85                  90                  95

Gly Gly Thr His Pro Thr Thr Thr Tyr Lys Ala Phe Asp Trp Asp Gln
            100                 105                 110

Ala Tyr Arg Lys Pro Ile Thr Tyr Asp Thr Leu Trp Gln Ala Asp Thr
        115                 120                 125

Asp Pro Leu Pro Val Val Phe Pro Ile Val Gln Gly Glu Leu Ser Lys
    130                 135                 140

Gln Thr Gly Gln Gln Val Ser Ile Ala Pro Asn Ala Gly Leu Asp Pro
145                 150                 155                 160

Val Asn Tyr Gln Asn Phe Ala Val Thr Asn Asp Gly Val Ile Phe Phe
                165                 170                 175

Phe Asn Pro Gly Glu Leu Leu Pro Glu Ala Ala Gly Pro Thr Gln Val
            180                 185                 190

Leu Val Pro Arg Ser Ala Ile Asp Ser Met Leu Ala
        195                 200


<210> SEQ ID NO 10
<211> LENGTH: 228
<212> TYPE: PRT
<213> ORGANISM: Mycobacterium tuberculosis

<400> SEQUENCE: 10

Met Arg Ile Lys Ile Phe Met Leu Val Thr Ala Val Val Leu Leu Cys
1               5                   10                  15

Cys Ser Gly Val Ala Thr Ala Ala Pro Lys Thr Tyr Cys Glu Glu Leu
            20                  25                  30

Lys Gly Thr Asp Thr Gly Gln Ala Cys Gln Ile Gln Met Ser Asp Pro
        35                  40                  45

Ala Tyr Asn Ile Asn Ile Ser Leu Pro Ser Tyr Tyr Pro Asp Gln Lys
    50                  55                  60

Ser Leu Glu Asn Tyr Ile Ala Gln Thr Arg Asp Lys Phe Leu Ser Ala
65                  70                  75                  80

Ala Thr Ser Ser Thr Pro Arg Glu Ala Pro Tyr Glu Leu Asn Ile Thr
                85                  90                  95

Ser Ala Thr Tyr Gln Ser Ala Ile Pro Pro Arg Gly Thr Gln Ala Val
            100                 105                 110

Val Leu Lys Val Tyr Gln Asn Ala Gly Gly Thr His Pro Thr Thr Thr
        115                 120                 125

Tyr Lys Ala Phe Asp Trp Asp Gln Ala Tyr Arg Lys Pro Ile Thr Tyr
    130                 135                 140

Asp Thr Leu Trp Gln Ala Asp Thr Asp Pro Leu Pro Val Val Phe Pro
145                 150                 155                 160

Ile Val Gln Gly Glu Leu Ser Lys Gln Thr Gly Gln Gln Val Ser Ile
                165                 170                 175

Ala Pro Asn Ala Gly Leu Asp Pro Val Asn Tyr Gln Asn Phe Ala Val
            180                 185                 190

Thr Asn Asp Gly Val Ile Phe Phe Phe Asn Pro Gly Glu Leu Leu Pro
        195                 200                 205

Glu Ala Ala Gly Pro Thr Gln Val Leu Val Pro Arg Ser Ala Ile Asp
    210                 215                 220
```

-continued

Ser Met Leu Ala
225

<210> SEQ ID NO 11
<211> LENGTH: 163
<212> TYPE: PRT
<213> ORGANISM: Mycobacterium tuberculosis

<400> SEQUENCE: 11

Asp Leu Ile Gly Arg Gly Cys Ala Gln Tyr Ala Ala Gln Asn Pro Thr
1 5 10 15

Gly Pro Gly Ser Val Ala Gly Met Ala Gln Asp Pro Val Ala Thr Ala
20 25 30

Ala Ser Asn Asn Pro Met Leu Ser Thr Leu Thr Ser Ala Leu Ser Gly
35 40 45

Lys Leu Asn Pro Asp Val Asn Leu Val Asp Thr Leu Asn Gly Gly Glu
50 55 60

Tyr Thr Val Phe Ala Pro Thr Asn Ala Ala Phe Asp Lys Leu Pro Ala
65 70 75 80

Ala Thr Ile Asp Gln Leu Lys Thr Asp Ala Lys Leu Leu Ser Ser Ile
85 90 95

Leu Thr Tyr His Val Ile Ala Gly Gln Ala Ser Pro Ser Arg Ile Asp
100 105 110

Gly Thr His Gln Thr Leu Gln Gly Ala Asp Leu Thr Val Ile Gly Ala
115 120 125

Arg Asp Asp Leu Met Val Asn Asn Ala Gly Leu Val Cys Gly Gly Val
130 135 140

His Thr Ala Asn Ala Thr Val Tyr Met Ile Asp Thr Val Leu Met Pro
145 150 155 160

Pro Ala Gln

<210> SEQ ID NO 12
<211> LENGTH: 220
<212> TYPE: PRT
<213> ORGANISM: Mycobacterium tuberculosis

<400> SEQUENCE: 12

Met Ile Asn Val Gln Ala Lys Pro Ala Ala Ala Ala Ser Leu Ala Ala
1 5 10 15

Ile Ala Ile Ala Phe Leu Ala Gly Cys Ser Ser Thr Lys Pro Val Ser
20 25 30

Gln Asp Thr Ser Pro Lys Pro Ala Thr Ser Pro Ala Ala Pro Val Thr
35 40 45

Thr Ala Ala Met Ala Asp Pro Ala Ala Asp Leu Ile Gly Arg Gly Cys
50 55 60

Ala Gln Tyr Ala Ala Gln Asn Pro Thr Gly Pro Gly Ser Val Ala Gly
65 70 75 80

Met Ala Gln Asp Pro Val Ala Thr Ala Ala Ser Asn Asn Pro Met Leu
85 90 95

Ser Thr Leu Thr Ser Ala Leu Ser Gly Lys Leu Asn Pro Asp Val Asn
100 105 110

Leu Val Asp Thr Leu Asn Gly Gly Glu Tyr Thr Val Phe Ala Pro Thr
115 120 125

Asn Ala Ala Phe Asp Lys Leu Pro Ala Ala Thr Ile Asp Gln Leu Lys
130 135 140

```
Thr Asp Ala Lys Leu Leu Ser Ser Ile Leu Thr Tyr His Val Ile Ala
145                 150                 155                 160

Gly Gln Ala Ser Pro Ser Arg Ile Asp Gly Thr His Gln Thr Leu Gln
                165                 170                 175

Gly Ala Asp Leu Thr Val Ile Gly Ala Arg Asp Asp Leu Met Val Asn
            180                 185                 190

Asn Ala Gly Leu Val Cys Gly Gly Val His Thr Ala Asn Ala Thr Val
        195                 200                 205

Tyr Met Ile Asp Thr Val Leu Met Pro Pro Ala Gln
    210                 215                 220


<210> SEQ ID NO 13
<211> LENGTH: 97
<212> TYPE: PRT
<213> ORGANISM: Mycobacterium tuberculosis

<400> SEQUENCE: 13

Met Ser Leu Leu Asp Ala His Ile Pro Gln Leu Val Ala Ser Gln Ser
1               5                   10                  15

Ala Phe Ala Ala Lys Ala Gly Leu Met Arg His Thr Ile Gly Gln Ala
            20                  25                  30

Glu Gln Ala Ala Met Ser Ala Gln Ala Phe His Gln Gly Glu Ser Ser
        35                  40                  45

Ala Ala Phe Gln Ala Ala His Ala Arg Phe Val Ala Ala Ala Ala Lys
    50                  55                  60

Val Asn Thr Leu Leu Asp Val Ala Gln Ala Asn Leu Gly Glu Ala Ala
65                  70                  75                  80

Gly Thr Tyr Val Ala Ala Asp Ala Ala Ala Ala Ser Thr Tyr Thr Gly
                85                  90                  95

Phe


<210> SEQ ID NO 14
<211> LENGTH: 96
<212> TYPE: PRT
<213> ORGANISM: Mycobacterium tuberculosis

<400> SEQUENCE: 14

Met Ser Gln Ile Met Tyr Asn Tyr Pro Ala Met Leu Gly His Ala Gly
1               5                   10                  15

Asp Met Ala Gly Tyr Ala Gly Thr Leu Gln Ser Leu Gly Ala Glu Ile
            20                  25                  30

Ala Val Glu Gln Ala Ala Leu Gln Ser Ala Trp Gln Gly Asp Thr Gly
        35                  40                  45

Ile Thr Tyr Gln Ala Trp Gln Ala Gln Trp Asn Gln Ala Met Glu Asp
    50                  55                  60

Leu Val Arg Ala Tyr His Ala Met Ser Ser Thr His Glu Ala Asn Thr
65                  70                  75                  80

Met Ala Met Met Ala Arg Asp Thr Ala Glu Ala Ala Lys Trp Gly Gly
                85                  90                  95


<210> SEQ ID NO 15
<211> LENGTH: 194
<212> TYPE: PRT
<213> ORGANISM: Mycobacterium tuberculosis

<400> SEQUENCE: 15

Met His Phe Glu Ala Tyr Pro Pro Glu Val Asn Ser Ala Asn Ile Tyr
1               5                   10                  15
```

-continued

```
Ala Gly Pro Gly Pro Asp Ser Met Leu Ala Ala Ala Arg Ala Trp Arg
            20                  25                  30

Ser Leu Asp Val Glu Met Thr Ala Val Gln Arg Ser Phe Asn Arg Thr
        35                  40                  45

Leu Leu Ser Leu Met Asp Ala Trp Ala Gly Pro Val Val Met Gln Leu
    50                  55                  60

Met Glu Ala Ala Lys Pro Phe Val Arg Trp Leu Thr Asp Leu Cys Val
65                  70                  75                  80

Gln Leu Ser Glu Val Glu Arg Gln Ile His Glu Ile Val Arg Ala Tyr
                85                  90                  95

Glu Trp Ala His His Asp Met Val Pro Leu Ala Gln Ile Tyr Asn Asn
            100                 105                 110

Arg Ala Glu Arg Gln Ile Leu Ile Asp Asn Asn Ala Leu Gly Gln Phe
        115                 120                 125

Thr Ala Gln Ile Ala Asp Leu Asp Gln Glu Tyr Asp Asp Phe Trp Asp
    130                 135                 140

Glu Asp Gly Glu Val Met Arg Asp Tyr Arg Leu Arg Val Ser Asp Ala
145                 150                 155                 160

Leu Ser Lys Leu Thr Pro Trp Lys Ala Pro Pro Pro Ile Ala His Ser
                165                 170                 175

Thr Val Leu Val Ala Pro Val Ser Pro Ser Thr Ala Ser Ser Arg Thr
            180                 185                 190

Asp Thr


<210> SEQ ID NO 16
<211> LENGTH: 99
<212> TYPE: PRT
<213> ORGANISM: Mycobacterium tuberculosis

<400> SEQUENCE: 16

Met Ser Phe Val Ile Thr Asn Pro Glu Ala Leu Thr Val Ala Ala Thr
1               5                   10                  15

Glu Val Arg Arg Ile Arg Asp Arg Ala Ile Gln Ser Asp Ala Gln Val
            20                  25                  30

Ala Pro Met Thr Thr Ala Val Arg Pro Pro Ala Ala Asp Leu Val Ser
        35                  40                  45

Glu Lys Ala Ala Thr Phe Leu Val Glu Tyr Ala Arg Lys Tyr Arg Gln
    50                  55                  60

Thr Ile Ala Ala Ala Ala Val Val Leu Glu Glu Phe Ala His Ala Leu
65                  70                  75                  80

Thr Thr Gly Ala Asp Lys Tyr Ala Thr Ala Glu Ala Asp Asn Ile Lys
                85                  90                  95

Thr Phe Ser


<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Ser Pro Gly Ile Ser Gly Gly Gly Gly Gly Ile Leu Glu
1               5                   10
```

<210> SEQ ID NO 18
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Met Ile Ile Thr Ser Leu Tyr Ala Thr Phe Gly Thr Ile Ala Asp Gly
1               5                   10                  15

Arg Arg Thr Ser Gly Gly Lys Thr Met Ile Arg Thr Asn Ala Val Ala
            20                  25                  30

Ala Leu Val Phe Ala Val Ala Thr Ser Ala Leu Ala
        35                  40
```

<210> SEQ ID NO 19
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Met Lys Lys Ile Trp Leu Ala Leu Ala Gly Leu Val Leu Ala Phe Ser
1               5                   10                  15

Ala Ser Ala
```

<210> SEQ ID NO 20
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Met Lys Lys Ile Trp Leu Ala Leu Ala Gly Leu Val Leu Ala Phe Ser
1               5                   10                  15

Ala Ser Ala
```

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

```
Met Lys Lys Val Ala Ala Phe Val Ala Leu Ser Leu Leu Met Ala Gly
1               5                   10                  15

Cys
```

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

```
Ala Gln Asp Pro
```

1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 23

Val Ser Asp Pro
1

<210> SEQ ID NO 24
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 24

```
Met Lys Lys Ile Trp Leu Ala Leu Ala Gly Leu Val Leu Ala Phe Ser
1               5                   10                  15

Ala Ser Ala Ala Gln Asp Pro
            20
```

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 25

```
Val Asp Lys Leu Ala Ala Ala Leu Glu
1               5
```

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 26

```
Gly Gly Gly Gly Ser Ser Ser Val Asp Lys Leu Ala Ala Ala Leu Glu
1               5                   10                  15
```

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 27

```
Val Asp Lys Leu Ala Ala Ala Leu Glu His His His His His
1               5                   10
```

<210> SEQ ID NO 28
<211> LENGTH: 22
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 28

Gly Gly Gly Gly Ser Ser Ser Val Asp Lys Leu Ala Ala Ala Leu Glu
1               5                   10                  15

His His His His His His
            20


<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Met Lys Lys Val Ala Ala Phe Val Ala Leu Ser Leu Leu Met Ala Gly
1               5                   10                  15

Cys


<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 30

His His His His His His
1               5


<210> SEQ ID NO 31
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Met Asn Ser Lys Lys Leu Cys Cys Ile Cys Val Leu Phe Ser Leu Leu
1               5                   10                  15

Ala Gly Cys Ala Ser
            20


<210> SEQ ID NO 32
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Met Arg Tyr Ser Lys Leu Thr Met Leu Ile Pro Cys Ala Leu Leu Leu
1               5                   10                  15

Ser Ala Cys


<210> SEQ ID NO 33
<211> LENGTH: 24
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Met Phe Val Thr Ser Lys Lys Met Thr Ala Ala Val Leu Ala Ile Thr
1               5                   10                  15

Leu Ala Met Ser Leu Ser Ala Cys
            20

<210> SEQ ID NO 34
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Met Ile Lys Arg Val Leu Val Val Ser Met Val Gly Leu Ser Leu Val
1               5                   10                  15

Gly Cys

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Gly Gly Gly Ser Ser Ser
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Thr Asp Pro Asn Ser Ser Ser
1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Arg or Leu
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (6)..(6)
<223> OTHER INFORMATION: Tyr or Trp -continued

<400> SEQUENCE: 37

Asp Xaa Ala Xaa Pro Xaa
1 5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(3)
<223> OTHER INFORMATION: Arg or Leu
<220> FEATURE:
<221> NAME/KEY: MOD_RES
<222> LOCATION: (5)..(5)
<223> OTHER INFORMATION: Ser or Thr
<220> FEATURE:
<221> NAME/KEY: MOD_RES
<222> LOCATION: (7)..(7)
<223> OTHER INFORMATION: Tyr or Trp

<400> SEQUENCE: 38

Cys Asp Xaa Ala Xaa Pro Xaa Cys Gly
1 5

<210> SEQ ID NO 39
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 39

Met Ala Pro Phe Glu Pro Leu Ala Ser Gly Ile Leu Leu Leu Leu Trp
1 5 10 15

Leu Ile Ala Pro Ser Arg Ala
20

<210> SEQ ID NO 40
<211> LENGTH: 5
<212> TYPE: PRT
<213> ORGANISM: Unknown
<220> FEATURE:
<223> OTHER INFORMATION: Description of Unknown:
sortase recognition sequence
<220> FEATURE:
<221> NAME/KEY: MOD_RES
<222> LOCATION: (3)..(3)
<223> OTHER INFORMATION: Any amino acid

<400> SEQUENCE: 40

Leu Pro Xaa Thr Gly
1 5

<210> SEQ ID NO 41
<211> LENGTH: 3
<212> TYPE: PRT
<213> ORGANISM: Unknown
<220> FEATURE:
<223> OTHER INFORMATION: Description of Unknown:
exosortase sequence

<400> SEQUENCE: 41

Pro Glu Pro
1

<210> SEQ ID NO 42
<211> LENGTH: 24
<212> TYPE: PRT
<213> ORGANISM: Listeria monocytogenes

<400> SEQUENCE: 42

```
Met Lys Lys Ile Met Leu Val Ile Thr Leu Ile Leu Val Ser Pro Ile
1               5                   10                  15

Ala Gln Gln Thr Glu Ala Lys Asp
            20
```

<210> SEQ ID NO 43
<211> LENGTH: 29
<212> TYPE: PRT
<213> ORGANISM: Lactococcus lactis

<400> SEQUENCE: 43

```
Met Lys Lys Lys Ile Ile Ser Ala Ile Leu Met Ser Thr Val Ile Leu
1               5                   10                  15

Ser Ala Ala Ala Pro Leu Ser Gly Val Tyr Ala Asp Thr
            20                  25
```

<210> SEQ ID NO 44
<211> LENGTH: 31
<212> TYPE: PRT
<213> ORGANISM: Bacillus anthracis

<400> SEQUENCE: 44

```
Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala Glu Val
            20                  25                  30
```

<210> SEQ ID NO 45
<211> LENGTH: 29
<212> TYPE: PRT
<213> ORGANISM: Listeria monocytogenes

<400> SEQUENCE: 45

```
Met Asn Met Lys Lys Ala Thr Ile Ala Ala Thr Ala Gly Ile Ala Val
1               5                   10                  15

Thr Ala Phe Ala Ala Pro Thr Ile Ala Ser Ala Ser Thr
            20                  25
```

<210> SEQ ID NO 46
<211> LENGTH: 54
<212> TYPE: PRT
<213> ORGANISM: Listeria monocytogenes

<400> SEQUENCE: 46

```
Met Gln Lys Thr Arg Lys Glu Arg Ile Leu Glu Ala Leu Gln Glu Glu
1               5                   10                  15

Lys Lys Asn Lys Lys Ser Lys Lys Phe Lys Thr Gly Ala Thr Ile Ala
            20                  25                  30

Gly Val Thr Ala Ile Ala Thr Ser Ile Thr Val Pro Gly Ile Glu Val
        35                  40                  45

Ile Val Ser Ala Asp Glu
    50
```

<210> SEQ ID NO 47

<211> LENGTH: 28
<212> TYPE: PRT
<213> ORGANISM: Bacillus anthracis

<400> SEQUENCE: 47

Met Lys Lys Leu Lys Met Ala Ser Cys Ala Leu Val Ala Gly Leu Met
1 5 10 15

Phe Ser Gly Leu Thr Pro Asn Ala Phe Ala Glu Asp
20 25

<210> SEQ ID NO 48
<211> LENGTH: 31
<212> TYPE: PRT
<213> ORGANISM: Staphylococcus aureus

<400> SEQUENCE: 48

Met Ala Lys Lys Phe Asn Tyr Lys Leu Pro Ser Met Val Ala Leu Thr
1 5 10 15

Leu Val Gly Ser Ala Val Thr Ala His Gln Val Gln Ala Ala Glu
20 25 30

<210> SEQ ID NO 49
<211> LENGTH: 59
<212> TYPE: PRT
<213> ORGANISM: Listeria monocytogenes

<400> SEQUENCE: 49

Met Thr Asp Lys Lys Ser Glu Asn Gln Thr Glu Lys Thr Glu Thr Lys
1 5 10 15

Glu Asn Lys Gly Met Thr Arg Arg Glu Met Leu Lys Leu Ser Ala Val
20 25 30

Ala Gly Thr Gly Ile Ala Val Gly Ala Thr Gly Leu Gly Thr Ile Leu
35 40 45

Asn Val Val Asp Gln Val Asp Lys Ala Leu Thr
50 55

<210> SEQ ID NO 50
<211> LENGTH: 53
<212> TYPE: PRT
<213> ORGANISM: Bacillus subtillis

<400> SEQUENCE: 50

Met Ala Tyr Asp Ser Arg Phe Asp Glu Trp Val Gln Lys Leu Lys Glu
1 5 10 15

Glu Ser Phe Gln Asn Asn Thr Phe Asp Arg Arg Lys Phe Ile Gln Gly
20 25 30

Ala Gly Lys Ile Ala Gly Leu Gly Leu Gly Leu Thr Ile Ala Gln Ser
35 40 45

Val Gly Ala Phe Gly
50

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 51

Lys Leu Gly Ser
1

-continued

```
<210> SEQ ID NO 52
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Ser
1


<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Lys Leu Gly Gly Ser
1               5


<210> SEQ ID NO 54
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ala Ala Ala
1
```